US010584323B2

(12) United States Patent
Torres Pazmino et al.

(10) Patent No.: US 10,584,323 B2
(45) Date of Patent: Mar. 10, 2020

(54) GLUCOAMYLASE VARIANTS

(71) Applicant: Danisco US Inc., Palo Alto, CA (US)

(72) Inventors: Daniel Esteban Torres Pazmino, Leiden (NL); Viktor Yuryevich Alekseyev, Palo Alto, CA (US); Casper Willem Vroemen, Palo Alto, CA (US); David A. Estell, San Francisco, CA (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 15/037,040

(22) PCT Filed: Dec. 3, 2014

(86) PCT No.: PCT/US2014/068293
§ 371 (c)(1),
(2) Date: May 16, 2016

(87) PCT Pub. No.: WO2015/084920
PCT Pub. Date: Jun. 11, 2015

(65) Prior Publication Data

US 2016/0272958 A1 Sep. 22, 2016

Related U.S. Application Data

(60) Provisional application No. 61/911,760, filed on Dec. 4, 2013.

(51) Int. Cl.

| | |
|---|---|
| ***C12N 9/26*** | (2006.01) |
| ***C12N 9/30*** | (2006.01) |
| ***C12P 19/14*** | (2006.01) |
| ***C12N 1/21*** | (2006.01) |
| ***C12N 15/56*** | (2006.01) |
| ***C12N 9/34*** | (2006.01) |

(52) U.S. Cl.
CPC ............ *C12N 9/2428* (2013.01); *C12P 19/14* (2013.01); *C12Y 302/01003* (2013.01)

(58) Field of Classification Search
None
See application file for complete search history.

(56) References Cited

U.S. PATENT DOCUMENTS

| | | | |
|---|---|---|---|
| 4,247,637 A | 1/1981 | Tamura et al. | |
| 4,618,579 A | 10/1986 | Dwiggins et al. | |
| 4,794,175 A | 12/1988 | Nunberg et al. | |
| 4,863,864 A | 9/1989 | Ashikari et al. | |
| 5,024,941 A | 6/1991 | Maine et al. | |
| 5,246,853 A | 9/1993 | Clarkson et al. | |
| 6,255,084 B1 | 7/2001 | Nielsen et al. | |
| 6,620,924 B2 | 9/2003 | Nielsen et al. | |
| 2005/0136525 A1* | 6/2005 | Baldwin | C12N 1/14 435/204 |
| 2010/0267114 A1* | 10/2010 | Aehle | C12N 9/2428 435/200 |
| 2011/0014681 A1 | 1/2011 | Aehle et al. | |
| 2011/0020899 A1 | 1/2011 | Aehle et al. | |

FOREIGN PATENT DOCUMENTS

| | | |
|---|---|---|
| WO | 2000/004136 A1 | 1/2000 |
| WO | 2009/048487 A1 | 4/2009 |
| WO | 2009/048488 A1 | 4/2009 |
| WO | 2009/067218 A2 | 5/2009 |
| WO | 2011/022465 A1 | 2/2011 |
| WO | 2013/181760 A1 | 12/2013 |

OTHER PUBLICATIONS

UniProt Accession No. Q12623, Glucoamylase, Berka, M., et al., Direct Submission, Nucleotide Sequence, Nov. 1, 1996.
UniProt Accession No. G2WZT6, Glucoamylase, Klosterman, S.J., et al., "Comparative genomics yields insights into niche adaption of plant vascular wilt pathogens," Nov. 16, 2011.
PCT International Search Report and the Written Opinion of the International Searching Authority for International Application No. PCT/US14/068293; ISA/EP; dated Jul. 13, 2015.
Nunberg et al., "Molecular Cloning and Characterization of the Glucoamylase Gene of Aspergillus awamori." Mol. Cell. Biol., 1984, vol. 4, No. 11, pp. 2306-2315.
Mitsuishi et al., "Site-directed mutagenesis of the putative catalytic residues of Trichoderma reesei cellobiohydrolase I and endoglucanase I," FEBS, 1990, vol. 275, pp. 135-138.
International Preliminary Report on Patentability for International Application No. PCT/US14/068293; Moon Kihwan, Authorized Officer, dated Jun. 7, 2016.
Hayashida et al., "Molecular Cloning of the Glucoamylase I Gene of *Aspergillus awamori* var. *kawachi* for Localization of the Raw-starch affinity Site," Agric. Biol. Chem., 1989, vol. 53, pp. 923-929.
Boer et al., "The relationship between thermal stabilitly and pH optimum studied with wild-type and mutant Trichoderma reesei cellobiohydrolse Cel7A," Eur. J. Biochem., 2003, vol. 270, pp. 841-848.
Bhikhabhai et al., "Isolation of Cellulolytic Enzymes from Trichoderma reesei QM 9414," J. Appl. Biochem. 1984, vol. 6, pp. 336-345.
Becker et al., "Engineering of a glycosidase Family 7 cellobiohydrolase to more alkaline pH optimum: the pH behaviour of Trichoderma reesei Cel7A and its E223S/A224H/L225V/T226A/D262G mutant," Biochem J., 2001, vol. 356, pp. 19-30.
Ashikari et al., "Rhizopus Raw-Starch-Degrading Glucoamylase: Its Cloning and Expression in Yeast," Agric. Biol. Chem., 1986, vol. 50, No. 4, pp. 957-964.
Aleshin et al., "Refined crystal structures of glucoamylase from *Aspergillus awamori* var. X100," J. Mol. Biol., 1994, vol. 238: pp. 575-591.

* cited by examiner

*Primary Examiner* — Robert B Mondesi
*Assistant Examiner* — Todd M Epstein

(57) ABSTRACT

Aspects of the present disclosure include glucoamylase (GA) variants having at least one improved property over a parent GA, compositions containing the GA variants, nucleic acids encoding the GA variants, and methods for producing and using the same. In some aspects, the GA variant is a variant of a parent GA from *Humicola grisea*.

9 Claims, 5 Drawing Sheets

Specification includes a Sequence Listing.

FIG. 1A

Top: SEQ ID NO:2
Bottom: SEQ ID NO:3
Signal Sequence: Underlined

```
(1)     atgcataccttctccaagctcctcgttcttggatctgccgtccagtctgccctcggacgg
(1)      M  H  T  F  S  K  L  L  V  L  G  S  A  V  Q  S  A  L  G  R

(61)    cctcacggctcttcgcgtctccaggaacgcgctgccgttgatacattcatcaacaccgag
(21)     P  H  G  S  S  R  L  Q  E  R  A  A  V  D  T  F  I  N  T  E

(121)   aagcccattgcatggaacaagctgcttgccaacatcggccctaacggcaaggccgctccc
(41)     K  P  I  A  W  N  K  L  L  A  N  I  G  P  N  G  K  A  A  P

(181)   ggtgccgccgccggtgttgtcattgccagcccttccaggacggacccccccttacttcttt
(61)     G  A  A  A  G  V  V  I  A  S  P  S  R  T  D  P  P  Y  F  F

(241)   acctggactcgcgatgccgctctggtcctcaccggcatcatcgagtcccttggccacaac
(81)     T  W  T  R  D  A  A  L  V  L  T  G  I  I  E  S  L  G  H  N

(301)   tacaacaccacgctgcagaccgtcatccagaactacgtcgcgtctcaagcaaagctgcag
(101)    Y  N  T  T  L  Q  T  V  I  Q  N  Y  V  A  S  Q  A  K  L  Q

(361)   caggtgtctaaccccagcggaacgttcgccgacggttctggtctcggtgaagccaagttc
(121)    Q  V  S  N  P  S  G  T  F  A  D  G  S  G  L  G  E  A  K  F

(421)   aatgtcgacttgactgctttcactggcgaatggggtcgccctcagcgagacggcccgccc
(141)    N  V  D  L  T  A  F  T  G  E  W  G  R  P  Q  R  D  G  P  P

(481)   ctgcgcgccatcgctctcatccagtacgccaagtggctgatcgccaacggttacaagagc
(161)    L  R  A  I  A  L  I  Q  Y  A  K  W  L  I  A  N  G  Y  K  S

(541)   acggccaagagcgtcgtctggccagtcgtcaagaacgatctcgcctatacggcacaatac
(181)    T  A  K  S  V  V  W  P  V  V  K  N  D  L  A  Y  T  A  Q  Y

(601)   tggaacgagaccggctttgatctctgggaggaggtccccggcagctccttctttacaatc
(201)    W  N  E  T  G  F  D  L  W  E  E  V  P  G  S  S  F  F  T  I

(661)   gctagctctcacagggctctgactgagggtgcttacctcgccgctcagctcgacaccgag
(221)    A  S  S  H  R  A  L  T  E  G  A  Y  L  A  A  Q  L  D  T  E

(721)   tgccgcgcttgcacgaccgtcgcccctcaggttctgtgcttccagcaggccttctggaat
(241)    C  R  A  C  T  T  V  A  P  Q  V  L  C  F  Q  Q  A  F  W  N

(781)   tccaagggcaactatgtcgtctcgaatatcaacggcggcgagtatcgctccggaaaggac
(261)    S  K  G  N  Y  V  V  S  N  I  N  G  G  E  Y  R  S  G  K  D

(841)   gccaactcgatccttgcgtctatccacaacttcgaccctgaggcaggctgtgacaacctg
(281)    A  N  S  I  L  A  S  I  H  N  F  D  P  E  A  G  C  D  N  L
```

FIG. 1B

```
(901)   accttccagccctgcagcgaacgcgccctggccaaccacaaggcttatgtcgactcgttc
(301)    T  F  Q  P  C  S  E  R  A  L  A  N  H  K  A  Y  V  D  S  F

(961)   cggaacctctacgccattaacaagggcatcgcccagggcaaggctgttgccgtcggacgc
(321)    R  N  L  Y  A  I  N  K  G  I  A  Q  G  K  A  V  A  V  G  R

(1021)  tactcggaggatgtctactacaacggcaacccgtggtatcttgccaactttgccgccgca
(341)    Y  S  E  D  V  Y  Y  N  G  N  P  W  Y  L  A  N  F  A  A  A

(1081)  gaacaactctacgacgccatctacgtttggaataagcaaggctccatcacagtgacctcc
(361)    E  Q  L  Y  D  A  I  Y  V  W  N  K  Q  G  S  I  T  V  T  S

(1141)  gtctccttgcccttttttcagggacttggtctcgagcgtcagcaccggcacttacagcaag
(381)    V  S  L  P  F  F  R  D  L  V  S  S  V  S  T  G  T  Y  S  K

(1201)  agcagcagcacgttcaccaacattgtcaacgccgtcaaggcatacgccgacggcttcatt
(401)    S  S  S  T  F  T  N  I  V  N  A  V  K  A  Y  A  D  G  F  I

(1261)  gaggtggcggccaagtacaccccgtccaacggcgcgctcgccgagcagtacgaccgtaac
(421)    E  V  A  A  K  Y  T  P  S  N  G  A  L  A  E  Q  Y  D  R  N

(1321)  acgggcaagcccgactcggccgctgacctgacttggtcgtactctgccttcctctctgcc
(441)    T  G  K  P  D  S  A  A  D  L  T  W  S  Y  S  A  F  L  S  A

(1381)  attgaccgacgagcaggtctcgtcccccccatcctggcgggccagcgttgccaagagccag
(461)    I  D  R  R  A  G  L  V  P  P  S  W  R  A  S  V  A  K  S  Q

(1441)  ctgccatccacatgttctcgcatcgaggtcgcaggcacatatgtcgccgccacgagcacc
(481)    L  P  S  T  C  S  R  I  E  V  A  G  T  Y  V  A  A  T  S  T

(1501)  tcgtttccgtccaagcaaaccccaaacccctccgcggcgccctccccgtccccctacccg
(501)    S  F  P  S  K  Q  T  P  N  P  S  A  A  P  S  P  S  P  Y  P

(1561)  accgcttgcgcggacgctagcgaggtctacgttaccttcaacgagcgagtgtcgaccgcg
(521)    T  A  C  A  D  A  S  E  V  Y  V  T  F  N  E  R  V  S  T  A

(1621)  tggggcgagactatcaaggtggtgggcaacgtgccggcgttgggaaactgggacacgtcc
(541)    W  G  E  T  I  K  V  V  G  N  V  P  A  L  G  N  W  D  T  S

(1681)  aaggcggtgaccctgtccgccagcggatacaagtcgaatgatcccctctggagcatcacg
(561)    K  A  V  T  L  S  A  S  G  Y  K  S  N  D  P  L  W  S  I  T

(1741)  gtgcccatcaaggctacgggctccgccgtgcagtacaagtatattaaggtcggcacaaac
(581)    V  P  I  K  A  T  G  S  A  V  Q  Y  K  Y  I  K  V  G  T  N

(1801)  ggtaagattacttgggagtccgaccccaataggagcattaccctgcagacggcgtcgagc
(601)    G  K  I  T  W  E  S  D  P  N  R  S  I  T  L  Q  T  A  S  S

(1861)  gctggcaagtgcgcagcgcagacggtgaatgattcgtggcgttga
(621)    A  G  K  C  A  A  Q  T  V  N  D  S  W  R  -
```

GLUCOAMYLASE VARIANTS

CROSS REFERENCE TO RELATED APPLICATIONS

This application is a U.S. National Phase Application of International Application No. PCT/US2014/068293, filed 03 Dec. 2014, claims benefit of priority from the U.S. Provisional application Ser. No. 61/911,760 filed 04 Dec. 2013 and are incorporated by reference in their entirety.

SEQUENCE LISTING

The sequence listing submitted via EFS, in compliance with 37 C.F.R. § 1.52(e), is incorporated herein by reference. The sequence listing text file submitted via EFS contains the file "NB40437USPCT_SEQ_LIST.txt" created on May 13, 2016, which is 20,480 bytes in size.

FIELD OF THE INVENTION

The present disclosure generally relates to amylase enzyme variants, particularly variants of glucoamylase (GA). Nucleic acids encoding the GA variants, compositions including the GA variants, methods of producing the GA variants, and methods of using the GA variants are also described.

BACKGROUND OF THE INVENTION

Industrial fermentations predominately use glucose as a feedstock for the production of a multitude of proteins, enzymes, alcohols, and other chemical end products. Typically, glucose is the product of starch processing, which is conventionally a two-step, enzymatic process that catalyzes the breakdown of starch, involving liquefaction and saccharification. During liquefaction, insoluble granular starch is slurried in water, gelatinized with heat, and hydrolyzed by a thermostable alpha-amylase. During saccharification, the soluble dextrins produced in liquefaction are further hydrolyzed by glucoamylases, producing a high glucose syrup containing greater than 95% glucose.

Glucoamylases are exo-acting carbohydrases, capable of hydrolyzing both the linear and branched glucosidic linkages of starch (e.g., amylose and amylopectin) to produce fermentable sugars from starch (e.g., an enzyme-liquefied starch substrate). The fermentable sugars, e.g., low molecular weight sugars, such as glucose, may then be converted to fructose by other enzymes (e.g., glucose isomerases); crystallized; or used in fermentations to produce numerous end products (e.g., alcohols, monosodium glutamate, succinic acid, vitamins, amino acids, 1,3-propanediol, and lactic acid).

In view of the central role glucoamylases play in generating glucose from starch, it would be an advantage in the art to provide glucoamylase (GA) variants with improved properties for this conversion. Examples of improved properties of variant GA include, but are not limited to: solubility, hydrolytic activity, thermostability, pH activity, pH stability, reduced reversion product activity, and chemical stability.

SUMMARY OF THE INVENTION

The present disclosure describes isolated variant glucoamylase (GA) enzymes having starch hydrolysis activity, nucleic acids encoding such GA enzymes, host cells containing GA enzyme-encoding polynucleotides (e.g., host cells that express the GA enzymes), compositions containing the GA enzyme, and methods for producing and using the same.

As such, aspects of the present invention provide variants of a parent GA enzyme, where the variant has starch hydrolysis activity, has at least 60% (e.g., at least 80%) sequence identity to SEQ ID NO:4, and has at least one improved property over the parent GA enzyme selected from: (a) expression, (b) hydrolytic activity on DP2 substrate, (c) hydrolytic activity on DP7 substrate at pH 6.8, (d) hydrolytic activity on DP7 substrate at pH 5.5, (e) hydrolytic activity on panose substrate, (f) hydrolytic activity on pullulan substrate, (g) hydrolytic activity on granular corn starch (CS), (h) thermostability, (i) glucose inhibition, and (j) reversion activity.

In certain embodiments, a GA variant has at least two, at least three, at least four, at least five, at least six, at least seven, at least 8, at least 9, or more improved properties (selected from the list above) over the parent GA enzyme.

In certain embodiments, a GA variant has one amino acid substitution, deletion, or insertion as compared to the parent GA, whereas in other embodiments, the GA variant is a combinatorial variant having more than one amino acid substitution, deletion, or insertion as compared to the parent GA. A combinatorial GA variant may have 2, 3, 4, 5, 6, 7, 8, 9, 10, 11, 12, 13, 14, 15, 16, 17, 18, 19, 20, 21, 22, 23, 24, 25, 26, 27, 28, 29, 30 or more substitutions, deletions, and/or insertions.

In certain embodiments, a GA variant has a few mutations, where by "a few" is meant from 1 to 10 mutations (e.g., from 1 to 10 amino acid substitutions as compared to a parent GA enzyme).

In certain embodiments, a GA variant has one or more highly combinable substitutions that fall into Group A as defined herein (see Examples section below).

In certain embodiments, a GA variant has one or more highly combinable substitutions that fall into Group B as defined herein, where the variant further may have one or more amino acid substitutions that fall into Group A.

In certain embodiments, a GA variant has one or more highly combinable substitutions that fall into Group C as defined herein, where the variant further may have one or more amino acid substitutions that fall into Group A or Group B.

In certain embodiments, the GA variant has an amino acid substitution at at least one site that has a productivity score of 4 as defined herein (see Examples section below and Table 8).

In certain embodiments, the GA variant has an amino acid substitution at at least one site that has a productivity score of 3, where the variant further may have at least one additional substitution at a site that has a productivity score of 4.

In certain embodiments, the GA variant has an amino acid substitution at at least one site that has a productivity score of 2, where the variant further may have at least one additional substitution at a site that has a productivity score of 3 or 4.

In certain embodiments, the GA variant has an amino acid substitution at at least one site that has a productivity score of 1, where the variant further may have at least one additional substitution at a site that has a productivity score of 2 or 3 or 4.

In certain embodiments, the GA variant has at least one amino acid substitution that has a variant suitability score of +++++ as defined herein (see Examples section below and Table 8).

In certain embodiments, the GA variant has at least one amino acid substitution that has a variant suitability score of ++++, where the variant further may have at least one additional substitution that has a variant suitability score of +++++.

In certain embodiments, the GA variant has at least one amino acid substitution that has a variant suitability score of +++, where the variant further may have at least one additional substitution that has a variant suitability score of ++++ or +++++.

In certain embodiments, the GA variant has at least one amino acid substitution that has a variant suitability score of ++, where the variant further may have at least one additional substitution that has a variant suitability score of +++ or ++++ or +++++.

In certain embodiments, the GA variant has at least one amino acid substitution that has a variant suitability score of +, where the variant further may have at least one additional substitution that has a variant suitability score of ++ or +++ or ++++ or +++++.

In certain embodiments, the GA variant has at least one amino acid substitution that falls into one of the specific productivity score/variant suitability score categories A to T as set forth in Table 1 below:

TABLE 1

GA Variant Categories

| | | Variant Suitability Score | | | | |
|---|---|---|---|---|---|---|
| | | + | ++ | +++ | ++++ | +++++ |
| Productivity Score | 4 | E | D | C | B | A |
| | 3 | J | I | H | G | F |
| | 2 | O | N | M | L | K |
| | 1 | T | S | R | Q | P |

The specific amino acid positions and substitutions for each category can be readily identified in Table 8 of Example 3 herein. For example, a GA variant can have at least one substitution or a combination of substitutions (i.e., a combinatorial GA variant) selected from the following, each of which falls into category A (the numbering of the amino acids is based on the mature form of HgGA shown in SEQ ID NO:3; it is noted that corresponding positions in GAs from other organisms are contemplated, as discussed in further detail below): K41E; P60Q; L97C, H, I or N; N100A, L or R; T107C, D, E, M or N; T245F or W; L300A, C, D, E, F, G, H, P, Q, R, S, T, V, W or Y; R308V; K334A, E, F, R or Y; S342K, M, P, R or V; Y364H, I, L, M, N, S or V; G374A or Y; S402F, K or M; T406E; N410A or D; G466Q; L467A, F, S or V; V468D, G, H, I, K, L, M, N, P, Q, R, T or W; P470A, C, E, F, G, I, L, M, N, Q, R, V or W; S471A, H, I, N or V; V476I or W; A477V; Q480F; S483H or L; T484F, L or S; K505H or P; Q506C; A522C or D; T544R; G587R; T599Q or S; N600K; and T604F, G or L.

Examples of GA variants include, but are not limited to the following:

1. A variant of a parent GA enzyme, where the GA variant has starch hydrolysis activity; has at least 60% (e.g., at least 80%) sequence identity to amino acids SEQ ID NO:4; and has at least one improved property over the parent GA enzyme selected from: (a) expression, (b) hydrolytic activity on DP2 substrate, (c) hydrolytic activity on DP7 substrate at pH 6.8, (d) hydrolytic activity on DP7 substrate at pH 5.5, (e) hydrolytic activity on panose substrate, (f) hydrolytic activity on pullulan substrate, (g) hydrolytic activity on granular corn starch (CS), (h) thermostability, (i) glucose inhibition, and (j) reversion activity; where the GA variant has at least one amino acid substitution at a position selected from the group consisting of: T35, K41, P60, L97, N100, T107, A175, K183, E229, T245, G263, P293, E294, N299, L300, R308, K334, S342, Y364, I367, V369, Q373, G374, S382, V393, S394, T397, K400, S402, T406, N407, V409, N410, A411, A414, I461, G466, L467, V468, P469, P470, S471, V476, A477, K478, S479, Q480, S483, T484, P503, K505, Q506, A522, T544, N556, G587, A589, T599, N600, T604, S607, P609, A31, I37, N46, K57, D85, L105, K171, K179, S184, P213, A221, T239, Q250, L252, N260, S261, K262, N264, E274, A295, A325, K328, A366, Y368, N371, K372, I376, S380, V381, P384, R387, V390, S391, T395, G396, S399, S401, S403, F405, I408, A448, D462, W472, S475, S486, A491, S511, S515, A524, V537, S538, A540, W541, G542, V551, P552, K561, A562, T564, L565, N573, A585, V590, Q591, V597, G601, I603, D608, I613, T614, S620, S632, A32, V33, N38, T39, T74, H99, T104, N111, K118, Q121, I164, Q168, I174, G177, S180, T181, V190, K191, A198, L227, L233, Q236, D238, E240, A243, A248, V251, Q255, Y275, N290, F291, D292, G296, D298, T301, F302, A311, A315, S319, G329, A331, Q332, V345, A360, D365, W370, T379, F386, L389, S392, Y398, K413, A416, D417, S429, A434, K443, A460, R463, R464, A465, R473, L481, T493, S499, S501, V531, R536, V548, N550, A553, L554, G555, D558, T559, S560, S572, D574, S578, K584, S588, I595, K596, K602, W605, E606, R611, S612, S619, V629, D34, P42, I43, K47, A50, N55, A58, A62, A64, I68, S72, R73, D75, P77, T83, L90, S96, G98, Y101, T103, I109, Q110, V113, S115, V122, S123, S126, T128, F129, A146, T148, E150, A165, L166, Y169, A170, A182, V185, P188, L194, T197, F206, F218, S222, H224, A226, Y232, L237, P249, Q256, A257, F258, W259, Y265, V267, S268, G272, G273, S277, D280, A281, I284, A286, S287, Q303, S306, E307, H313, Y316, D318, N322, V336, A337, N348, A355, N356, A359, L363, S375, T377, V378, L383, F385, D388, T404, E421, V422, A424, K425, Y426, A432, N440, S446, T451, F457, R487, I488, V495, A496, A497, F502, S504, A513, P516, P520, T521, S527, V529, T532, N534, E535, T539, E543, I545, V547, G549, K571, L576, I579, I583, T586, Y592, Y594, G622, Q627, T628, N630, and D631, where the position of each amino acid substitution corresponds to SEQ ID NO:3.

2. The GA variant as set forth in 1 above where the at least one amino acid substitution is selected from Table 8.

3. The GA variant as set forth in any one of 1 to 2 above and having an amino acid substitution at position T35 selected from the group consisting of: A, P, C, F, K, L, Q, R, W, Y and H.

4. The GA variant as set forth in any one of 1 to 3 above and having an amino acid substitution at position K41 selected from the group consisting of: C, S, T, W, D, H, L, N, P, R and E.

5. The GA variant as set forth in any one of 1 to 4 above and having an amino acid substitution at position P60 selected from the group consisting of: V, G, H, M, R, I, W, F, T and Q.

6. The GA variant as set forth in any one of 1 to 5 above and having an amino acid substitution at position L97 selected from the group consisting of: A, G, Q, E, T, V, F, C, H, I and N.

7. The GA variant as set forth in any one of 1 to 6 above and having an amino acid substitution at position N100 selected from the group consisting of: P, E, V, C, I, M, Q, T, F, G, K, S, W, Y, A, L and R.

8. The GA variant as set forth in any one of 1 to 7 above and having an amino acid substitution at position T107 selected from the group consisting of: A, W, Y, H, G, I, S, V, K, C, D, E, M and N.

9. The GA variant as set forth in any one of 1 to 8 above and having an amino acid substitution at position A175 selected from the group consisting of: F, E, H, K, M, N, Q, R, S, T, V and C.

10. The GA variant as set forth in any one of 1 to 9 above and having an amino acid substitution at position K183 selected from the group consisting of: H, E, I, Q, R, V, Y, D, F, T and W.

11. The GA variant as set forth in any one of 1 to 10 above and having an amino acid substitution at position E229 selected from the group consisting of: A, D, G, M, T, W, I, L, Y, C, F, K and V.

12. The GA variant as set forth in any one of 1 to 11 above and having an amino acid substitution at position T245 selected from the group consisting of: L, C, I, R, H, M, Q, S, V, Y, F and W.

13. The GA variant as set forth in any one of 1 to 12 above and having an amino acid substitution at position G263 selected from the group consisting of: A, C, E, H, L, Q, R, S, T and Y.

14. The GA variant as set forth in any one of 1 to 13 above and having an amino acid substitution at position P293 selected from the group consisting of: T, A, C, E, F, G, H, L, R, S, Y and Q.

15. The GA variant as set forth in any one of 1 to 14 above and having an amino acid substitution at position E294 selected from the group consisting of: D, G, I, K, L, M, N, S, V, W, A and C.

16. The GA variant as set forth in any one of 1 to 15 above and having an amino acid substitution at position N299 selected from the group consisting of: A, C, E, G, L, Q, T, V, P, R and S.

17. The GA variant as set forth in any one of 1 to 16 above and having an amino acid substitution at position L300 selected from the group consisting of: I, K, N, A, C, D, E, F, G, H, P, Q, R, S, T, V, W and Y.

18. The GA variant as set forth in any one of 1 to 17 above and having an amino acid substitution at position R308 selected from the group consisting of: I, F, L, A, D, E, G, H, K, M, Q, T, W and V.

19. The GA variant as set forth in any one of 1 to 18 above and having an amino acid substitution at position K334 selected from the group consisting of: C, G, I, L, T, W, D, V, A, E, F, R and Y.

20. The GA variant as set forth in any one of 1 to 19 above and having an amino acid substitution at position S342 selected from the group consisting of: G, L, T, W, Y, C, E, F, N, Q, K, M, P, R and V.

21. The GA variant as set forth in any one of 1 to 20 above and having an amino acid substitution at position Y364 selected from the group consisting of: E, R, W, G, Q, H, I, L, M, N, S and V.

22. The GA variant as set forth in any one of 1 to 21 above and having an amino acid substitution at position I367 selected from the group consisting of: G, E, F, K, L, M, S, V, W and Y.

23. The GA variant as set forth in any one of 1 to 22 above and having an amino acid substitution at position V369 selected from the group consisting of: F, Q, C, I, K, L, N, S, T, Y, A, E, G and M.

24. The GA variant as set forth in any one of 1 to 23 above and having an amino acid substitution at position Q373 selected from the group consisting of: D, E, F, G, L, N, R, S, T, C, H, K and V.

25. The GA variant as set forth in any one of 1 to 24 above and having an amino acid substitution at position G374 selected from the group consisting of: D, E, F, K, R, T, V, W, C, L, M, P, S, A and Y.

26. The GA variant as set forth in any one of 1 to 25 above and having an amino acid substitution at position S382 selected from the group consisting of: D, H, C, P, Q, E, G, N, T and V.

27. The GA variant as set forth in any one of 1 to 26 above and having an amino acid substitution at position V393 selected from the group consisting of: A, W, E, G, T, Y, F, H, I, L and N.

28. The GA variant as set forth in any one of 1 to 27 above and having an amino acid substitution at position S394 selected from the group consisting of: F, G, H, I, N, A, C, D, L, M, P and Y.

29. The GA variant as set forth in any one of 1 to 28 above and having an amino acid substitution at position T397 selected from the group consisting of: A, G, F, L, Q, V, W, Y, K and R.

30. The GA variant as set forth in any one of 1 to 29 above and having an amino acid substitution at position K400 selected from the group consisting of: A, E, G, L, R, S, V, W, Y and P.

31. The GA variant as set forth in any one of 1 to 30 above and having an amino acid substitution at position S402 selected from the group consisting of: D, I, N, P, T, W, R, F, K and M.

32. The GA variant as set forth in any one of 1 to 31 above and having an amino acid substitution at position T406 selected from the group consisting of: C, A, D, G, H, I, L, N, P, R, S, V, W and E.

33. The GA variant as set forth in any one of 1 to 32 above and having an amino acid substitution at position N407 selected from the group consisting of: C, G, I, K, L, Q, R, A, P, S and W.

34. The GA variant as set forth in any one of 1 to 33 above and having an amino acid substitution at position V409 selected from the group consisting of: C, G, H, K, D, E, L, M, R, W and Y.

35. The GA variant as set forth in any one of 1 to 34 above and having an amino acid substitution at position N410 selected from the group consisting of: I, G, Q, Y, C, F, H, K, L, P, T, V, W, A and D.

36. The GA variant as set forth in any one of 1 to 35 above and having an amino acid substitution at position A411 selected from the group consisting of: P, G, I, L, N, Q, R, S, W and C.

37. The GA variant as set forth in any one of 1 to 36 above and having an amino acid substitution at position A414 selected from the group consisting of: C, F, G, I, P, Q, S, D, E, R, T and W.

38. The GA variant as set forth in any one of 1 to 37 above and having an amino acid substitution at position I461 selected from the group consisting of: C, F, G, K, M, S, T, V, Y, N, Q and R.

39. The GA variant as set forth in any one of 1 to 38 above and having an amino acid substitution at position G466 selected from the group consisting of: D, K, M, R, Y, C, P, T, W, A, E, F, H, L, N, S, I, V and Q.

40. The GA variant as set forth in any one of 1 to 39 above and having an amino acid substitution at position L467 selected from the group consisting of: C, G, Q, T, W, D, H, N, Y, A, F, S and V.

41. The GA variant as set forth in any one of 1 to 40 above and having an amino acid substitution at position V468 selected from the group consisting of: A, E, D, G, H, I, K, L, M, N, P, Q, R, T and W.

42. The GA variant as set forth in any one of 1 to 41 above and having an amino acid substitution at position P469 selected from the group consisting of: R, C, H, T, V, G, N, S, E, I, Q and W.

43. The GA variant as set forth in any one of 1 to 42 above and having an amino acid substitution at position P470 selected from the group consisting of: K, S, A, C, E, F, G, I, L, M, N, Q, R, V and W.

44. The GA variant as set forth in any one of 1 to 43 above and having an amino acid substitution at position S471 selected from the group consisting of: D, C, M, E, G, P, Q, L, A, H, I, N and V.

45. The GA variant as set forth in any one of 1 to 44 above and having an amino acid substitution at position V476 selected from the group consisting of: A, D, E, G, H, N, S, L, M, P, Q, Y, R, T, I and W.

46. The GA variant as set forth in any one of 1 to 45 above and having an amino acid substitution at position A477 selected from the group consisting of: D, E, I, K, Q, R, M, W, S and V.

47. The GA variant as set forth in any one of 1 to 46 above and having an amino acid substitution at position K478 selected from the group consisting of: E, I, P, R, S, T, Y, F, Q and V.

48. The GA variant as set forth in any one of 1 to 47 above and having an amino acid substitution at position S479 selected from the group consisting of: A, G, L, M, N, Q, R, T, Y, F, I and K.

49. The GA variant as set forth in any one of 1 to 48 above and having an amino acid substitution at position Q480 selected from the group consisting of: A, C, D, T, V, H, I, L, M and F.

50. The GA variant as set forth in any one of 1 to 49 above and having an amino acid substitution at position S483 selected from the group consisting of: F, P, W, Y, A, I, K, N, R, T, H and L.

51. The GA variant as set forth in any one of 1 to 50 above and having an amino acid substitution at position T484 selected from the group consisting of: I, M, V, K, P, Q, Y, F, L and S.

52. The GA variant as set forth in any one of 1 to 51 above and having an amino acid substitution at position P503 selected from the group consisting of: A, D, F, G, L, M, N, Q, R, S, T, V and Y.

53. The GA variant as set forth in any one of 1 to 52 above and having an amino acid substitution at position K505 selected from the group consisting of: D, E, G, N, T, M, S, V, H and P.

54. The GA variant as set forth in any one of 1 to 53 above and having an amino acid substitution at position Q506 selected from the group consisting of: A, F, L, N, P, S, E, M, T, V, Y and C.

55. The GA variant as set forth in any one of 1 to 54 above and having an amino acid substitution at position A522 selected from the group consisting of: E, P, N, T, V, Y, L, R, K, C and D.

56. The GA variant as set forth in any one of 1 to 55 above and having an amino acid substitution at position T544 selected from the group consisting of: P, A, I, L, M, N, S, Y, G, K, V and R.

57. The GA variant as set forth in any one of 1 to 56 above and having an amino acid substitution at position N556 selected from the group consisting of: P, A, G, H, I, M, S, T, W, D, E, L, V and Y.

58. The GA variant as set forth in any one of 1 to 57 above and having an amino acid substitution at position G587 selected from the group consisting of: D, F, I, N, Q, T, Y, C, P, L and R.

59. The GA variant as set forth in any one of 1 to 58 above and having an amino acid substitution at position A589 selected from the group consisting of: C, D, K, L, M, R, E, Q, T and V.

60. The GA variant as set forth in any one of 1 to 59 above and having an amino acid substitution at position T599 selected from the group consisting of: M, C, E, R, D, K, L, V, Y, A, F, P, Q and S.

61. The GA variant as set forth in any one of 1 to 60 above and having an amino acid substitution at position N600 selected from the group consisting of: A, E, M, Q, R, W, Y, P, V and K.

62. The GA variant as set forth in any one of 1 to 61 above and having an amino acid substitution at position T604 selected from the group consisting of: K, M, S, Y, A, D, H, I, Q, R, F, G and L.

63. The GA variant as set forth in any one of 1 to 62 above and having an amino acid substitution at position S607 selected from the group consisting of: W, L, Y, G, I, Q, V, A, H, M and N.

64. The GA variant as set forth in any one of 1 to 63 above and having an amino acid substitution at position P609 selected from the group consisting of: K, L, N, Q, R, T, V, Y, A, G and W.

65. The GA variant as set forth in any one of 1 to 64 above and having an amino acid substitution at position A31 selected from the group consisting of: I, T, Y, F, L and Q.

66. The GA variant as set forth in any one of 1 to 65 above and having an amino acid substitution at position I37 selected from the group consisting of: G, M, A, S, C and T.

67. The GA variant as set forth in any one of 1 to 66 above and having an amino acid substitution at position N46 selected from the group consisting of: D, E, P, V, C and S.

68. The GA variant as set forth in any one of 1 to 67 above and having an amino acid substitution at position K57 selected from the group consisting of: E, S, A, C, I, V, T, Q and R.

69. The GA variant as set forth in any one of 1 to 68 above and having an amino acid substitution at position D85 selected from the group consisting of: N, Y, L, S, C, G, M, E and V.

70. The GA variant as set forth in any one of 1 to 69 above and having an amino acid substitution at position L105 selected from the group consisting of: M, R, T, I, F and Y.

71. The GA variant as set forth in any one of 1 to 70 above and having an amino acid substitution at position K171 selected from the group consisting of: C, G, H, R, V and W.

72. The GA variant as set forth in any one of 1 to 71 above and having an amino acid substitution at position K179 selected from the group consisting of: D, P, H, L, Q, R and W.

73. The GA variant as set forth in any one of 1 to 72 above and having an amino acid substitution at position S184 selected from the group consisting of: A, I, M, L, C, F, V and R.

74. The GA variant as set forth in any one of 1 to 73 above and having an amino acid substitution at position P213 selected from the group consisting of: A, M, N, H, Q and R.

75. The GA variant as set forth in any one of 1 to 74 above and having an amino acid substitution at position A221 selected from the group consisting of: M, R, S, I, L and T.

76. The GA variant as set forth in any one of 1 to 75 above and having an amino acid substitution at position T239 selected from the group consisting of: A, C, F, M, V, I and R.

77. The GA variant as set forth in any one of 1 to 76 above and having an amino acid substitution at position Q250 selected from the group consisting of: D, F, H, M, Y and E.

78. The GA variant as set forth in any one of 1 to 77 above and having an amino acid substitution at position L252 selected from the group consisting of: H, A, I, N, S, M and V.

79. The GA variant as set forth in any one of 1 to 78 above and having an amino acid substitution at position N260 selected from the group consisting of: C, H, R, T, F, S and W.

80. The GA variant as set forth in any one of 1 to 79 above and having an amino acid substitution at position S261 selected from the group consisting of: E, F, K, T, W and Y.

81. The GA variant as set forth in any one of 1 to 80 above and having an amino acid substitution at position K262 selected from the group consisting of: H, M, P, R, V, W and C.

82. The GA variant as set forth in any one of 1 to 81 above and having an amino acid substitution at position N264 selected from the group consisting of: A, F, P, Q, V and E.

83. The GA variant as set forth in any one of 1 to 82 above and having an amino acid substitution at position E274 selected from the group consisting of: V, D, I, L, Q and F.

84. The GA variant as set forth in any one of 1 to 83 above and having an amino acid substitution at position A295 selected from the group consisting of: F, G, V, W, Y, D and N.

85. The GA variant as set forth in any one of 1 to 84 above and having an amino acid substitution at position A325 selected from the group consisting of: E, C, F, L, P and Q.

86. The GA variant as set forth in any one of 1 to 85 above and having an amino acid substitution at position K328 selected from the group consisting of: C, L, Q, W, E, F and R.

87. The GA variant as set forth in any one of 1 to 86 above and having an amino acid substitution at position A366 selected from the group consisting of: Q, C, M, V, G, S and T.

88. The GA variant as set forth in any one of 1 to 87 above and having an amino acid substitution at position Y368 selected from the group consisting of: E, H, K, T, W and M.

89. The GA variant as set forth in any one of 1 to 88 above and having an amino acid substitution at position N371 selected from the group consisting of: C, L, M, D, Q, R, Y and A.

90. The GA variant as set forth in any one of 1 to 89 above and having an amino acid substitution at position K372 selected from the group consisting of: C, D, F, S, L, N and Q.

91. The GA variant as set forth in any one of 1 to 90 above and having an amino acid substitution at position I376 selected from the group consisting of: C, T, V, Y, A, F, L and M.

92. The GA variant as set forth in any one of 1 to 91 above and having an amino acid substitution at position S380 selected from the group consisting of: A, F, K, L, Q, R, W and Y.

93. The GA variant as set forth in any one of 1 to 92 above and having an amino acid substitution at position V381 selected from the group consisting of: F, G, K, M, N, S, A, C and Q.

94. The GA variant as set forth in any one of 1 to 93 above and having an amino acid substitution at position P384 selected from the group consisting of: D, F, S, Y, E, T and V.

95. The GA variant as set forth in any one of 1 to 94 above and having an amino acid substitution at position R387 selected from the group consisting of: C, I, Q, Y, G, L and K.

96. The GA variant as set forth in any one of 1 to 95 above and having an amino acid substitution at position V390 selected from the group consisting of: H, I, K, Y, F, L and R.

97. The GA variant as set forth in any one of 1 to 96 above and having an amino acid substitution at position S391 selected from the group consisting of: N, H, L, F, I and R.

98. The GA variant as set forth in any one of 1 to 97 above and having an amino acid substitution at position T395 selected from the group consisting of: K, Q, R, V, Y, F and L.

99. The GA variant as set forth in any one of 1 to 98 above and having an amino acid substitution at position G396 selected from the group consisting of: E, L, Q, R, K and V.

100. The GA variant as set forth in any one of 1 to 99 above and having an amino acid substitution at position S399 selected from the group consisting of: Q, T, R, W, K and C.

101. The GA variant as set forth in any one of 1 to 100 above and having an amino acid substitution at position S401 selected from the group consisting of: H, T, A, Y, P and Q.

102. The GA variant as set forth in any one of 1 to 101 above and having an amino acid substitution at position S403 selected from the group consisting of: I, P, W, Y, A and V.

103. The GA variant as set forth in any one of 1 to 102 above and having an amino acid substitution at position F405 selected from the group consisting of: A, H, W, Y, N and S.

104. The GA variant as set forth in any one of 1 to 103 above and having an amino acid substitution at position I408 selected from the group consisting of: Q, A, T, V, S and Y.

105. The GA variant as set forth in any one of 1 to 104 above and having an amino acid substitution at position A448 selected from the group consisting of: F, P, T, N, I and Q.

106. The GA variant as set forth in any one of 1 to 105 above and having an amino acid substitution at position D462 selected from the group consisting of: H, A, E, F, I, L, S, M and T.

107. The GA variant as set forth in any one of 1 to 106 above and having an amino acid substitution at position W472 selected from the group consisting of: R, D, I, M, Q, S and Y.

108. The GA variant as set forth in any one of 1 to 107 above and having an amino acid substitution at position S475 selected from the group consisting of: K, N, Q, E, F, I, R and L.

109. The GA variant as set forth in any one of 1 to 108 above and having an amino acid substitution at position S486 selected from the group consisting of: V, T, Y, D, G, K, L, I and M.

110. The GA variant as set forth in any one of 1 to 109 above and having an amino acid substitution at position A491 selected from the group consisting of: H, I, L, M, Y, K, R and V.

111. The GA variant as set forth in any one of 1 to 110 above and having an amino acid substitution at position S511 selected from the group consisting of: I, W, H, K, L and N.

112. The GA variant as set forth in any one of 1 to 111 above and having an amino acid substitution at position S515 selected from the group consisting of: D, M, N, T, A, I, K and V.

113. The GA variant as set forth in any one of 1 to 112 above and having an amino acid substitution at position A524 selected from the group consisting of: F, L, N, Q, R, T, W, S and Y.

114. The GA variant as set forth in any one of 1 to 113 above and having an amino acid substitution at position V537 selected from the group consisting of: M, T, A, C, K and R.

115. The GA variant as set forth in any one of 1 to 114 above and having an amino acid substitution at position S538 selected from the group consisting of: G, A, C, K, Q, R, T and F.

116. The GA variant as set forth in any one of 1 to 115 above and having an amino acid substitution at position A540 selected from the group consisting of: Y, E, F, L, T, V, W and M.

117. The GA variant as set forth in any one of 1 to 116 above and having an amino acid substitution at position W541 selected from the group consisting of: A, I, L, R, V and Y.

118. The GA variant as set forth in any one of 1 to 117 above and having an amino acid substitution at position G542 selected from the group consisting of: D, A, M, N, K and R.

119. The GA variant as set forth in any one of 1 to 118 above and having an amino acid substitution at position V551 selected from the group consisting of: S, N, F, K, L, Q and Y.

120. The GA variant as set forth in any one of 1 to 119 above and having an amino acid substitution at position P552 selected from the group consisting of: A, G, I, K, M, N, Y and R.

121. The GA variant as set forth in any one of 1 to 120 above and having an amino acid substitution at position K561 selected from the group consisting of: D, E, G, I, L, N, P, Q and R.

122. The GA variant as set forth in any one of 1 to 121 above and having an amino acid substitution at position A562 selected from the group consisting of: I, K, L, Y, C, G, V and S.

123. The GA variant as set forth in any one of 1 to 122 above and having an amino acid substitution at position T564 selected from the group consisting of: N, L, M, S, K and R.

124. The GA variant as set forth in any one of 1 to 123 above and having an amino acid substitution at position L565 selected from the group consisting of: E, H, M, Q, S, T and V.

125. The GA variant as set forth in any one of 1 to 124 above and having an amino acid substitution at position N573 selected from the group consisting of: G, E, F, H, I, Y and A.

126. The GA variant as set forth in any one of 1 to 125 above and having an amino acid substitution at position A585 selected from the group consisting of: D, F, S, T, W, Y and N.

127. The GA variant as set forth in any one of 1 to 126 above and having an amino acid substitution at position V590 selected from the group consisting of: W, A, G, P, S, I and L.

128. The GA variant as set forth in any one of 1 to 127 above and having an amino acid substitution at position Q591 selected from the group consisting of: L, Y, C, R, P, S and T.

129. The GA variant as set forth in any one of 1 to 128 above and having an amino acid substitution at position V597 selected from the group consisting of: R, L, M, Q, S, W, F and K.

130. The GA variant as set forth in any one of 1 to 129 above and having an amino acid substitution at position G601 selected from the group consisting of: E, I, R, A, H, N, P, Q and M.

131. The GA variant as set forth in any one of 1 to 130 above and having an amino acid substitution at position I603 selected from the group consisting of: Q, T, Y, A, K, F, L, N and P.

132. The GA variant as set forth in any one of 1 to 131 above and having an amino acid substitution at position D608 selected from the group consisting of: L, P, R, T, E, F and I.

133. The GA variant as set forth in any one of 1 to 132 above and having an amino acid substitution at position I613 selected from the group consisting of: A, F, L, S, T and V.

134. The GA variant as set forth in any one of 1 to 133 above and having an amino acid substitution at position T614 selected from the group consisting of: L, M, Q, V, Y and S.

135. The GA variant as set forth in any one of 1 to 134 above and having an amino acid substitution at position S620 selected from the group consisting of: D, M, Q, E, H, P and R.

136. The GA variant as set forth in any one of 1 to 135 above and having an amino acid substitution at position S632 selected from the group consisting of: L, C, D, E, G and T.

137. The GA variant as set forth in any one of 1 to 136 above and having an amino acid substitution at position A32 selected from the group consisting of: S, T, E and Q.

138. The GA variant as set forth in any one of 1 to 137 above and having an amino acid substitution at position V33 selected from the group consisting of: L, P and I.

139. The GA variant as set forth in any one of 1 to 138 above and having an amino acid substitution at position N38 selected from the group consisting of: G, F, H, K and I.

140. The GA variant as set forth in any one of 1 to 139 above and having an amino acid substitution at position T39 selected from the group consisting of: E, K, L and Q.

141. The GA variant as set forth in any one of 1 to 140 above and having an amino acid substitution at position T74 selected from the group consisting of: D, I, K and V.

142. The GA variant as set forth in any one of 1 to 141 above and having an amino acid substitution at position H99 selected from the group consisting of: G, A, M, V and Y.

143. The GA variant as set forth in any one of 1 to 142 above and having an amino acid substitution at position T104 selected from the group consisting of: V, D and E.

144. The GA variant as set forth in any one of 1 to 143 above and having an amino acid substitution at position N111 selected from the group consisting of: F, M, D, Q and H.

145. The GA variant as set forth in any one of 1 to 144 above and having an amino acid substitution at position K118 selected from the group consisting of: M, L, F and Y.

146. The GA variant as set forth in any one of 1 to 145 above and having an amino acid substitution at position Q121 selected from the group consisting of: V, L and T.

147. The GA variant as set forth in any one of 1 to 146 above and having an amino acid substitution at position I164 selected from the group consisting of: K, V and A.

148. The GA variant as set forth in any one of 1 to 147 above and having an amino acid substitution at position Q168 selected from the group consisting of: H, A, L and Y.

149. The GA variant as set forth in any one of 1 to 148 above and having an amino acid substitution at position I174 selected from the group consisting of: V, F and Y.

150. The GA variant as set forth in any one of 1 to 149 above and having an amino acid substitution at position G177 selected from the group consisting of: D, H, K and S.

151. The GA variant as set forth in any one of 1 to 150 above and having an amino acid substitution at position S180 selected from the group consisting of: A, C and F.

152. The GA variant as set forth in any one of 1 to 151 above and having an amino acid substitution at position T181 selected from the group consisting of: A, S and W.

153. The GA variant as set forth in any one of 1 to 152 above and having an amino acid substitution at position V190 selected from the group consisting of: A, I, M and L.

154. The GA variant as set forth in any one of 1 to 153 above and having an amino acid substitution at position K191 selected from the group consisting of: V, W and R.

155. The GA variant as set forth in any one of 1 to 154 above and having an amino acid substitution at position A198 selected from the group consisting of: Y, C, G and S.

156. The GA variant as set forth in any one of 1 to 155 above and having an amino acid substitution at position L227 selected from the group consisting of: A, C and I.

157. The GA variant as set forth in any one of 1 to 156 above and having an amino acid substitution at position L233 selected from the group consisting of: T, V and M.

158. The GA variant as set forth in any one of 1 to 157 above and having an amino acid substitution at position Q236 selected from the group consisting of: W, F, D, N and Y.

159. The GA variant as set forth in any one of 1 to 158 above and having an amino acid substitution at position D238 selected from the group consisting of: L, Q and R.

160. The GA variant as set forth in any one of 1 to 159 above and having an amino acid substitution at position E240 selected from the group consisting of: Q, W and P.

161. The GA variant as set forth in any one of 1 to 160 above and having an amino acid substitution at position A243 selected from the group consisting of: G, H, R and P.

162. The GA variant as set forth in any one of 1 to 161 above and having an amino acid substitution at position A248 selected from the group consisting of: G, C and S.

163. The GA variant as set forth in any one of 1 to 162 above and having an amino acid substitution at position V251 selected from the group consisting of: L, Q and R.

164. The GA variant as set forth in any one of 1 to 163 above and having an amino acid substitution at position Q255 selected from the group consisting of: E, G, L and S.

165. The GA variant as set forth in any one of 1 to 164 above and having an amino acid substitution at position Y275 selected from the group consisting of: E, G, L and S.

166. The GA variant as set forth in any one of 1 to 165 above and having an amino acid substitution at position N290 selected from the group consisting of: E, I, Q and V.

167. The GA variant as set forth in any one of 1 to 166 above and having an amino acid substitution at position F291 selected from the group consisting of: Y, L and M.

168. The GA variant as set forth in any one of 1 to 167 above and having an amino acid substitution at position D292 selected from the group consisting of: F, C and S.

169. The GA variant as set forth in any one of 1 to 168 above and having an amino acid substitution at position G296 selected from the group consisting of: L, P, Q and V.

170. The GA variant as set forth in any one of 1 to 169 above and having an amino acid substitution at position D298 selected from the group consisting of: A, E, I and N.

171. The GA variant as set forth in any one of 1 to 170 above and having an amino acid substitution at position T301 selected from the group consisting of: A, I, C and L.

172. The GA variant as set forth in any one of 1 to 171 above and having an amino acid substitution at position F302 selected from the group consisting of: G, M and W.

173. The GA variant as set forth in any one of 1 to 172 above and having an amino acid substitution at position A311 selected from the group consisting of: R, C, G, M and V.

174. The GA variant as set forth in any one of 1 to 173 above and having an amino acid substitution at position A315 selected from the group consisting of: G, C, E, M and Q.

175. The GA variant as set forth in any one of 1 to 174 above and having an amino acid substitution at position S319 selected from the group consisting of: N, M and Q.

176. The GA variant as set forth in any one of 1 to 175 above and having an amino acid substitution at position G329 selected from the group consisting of: T, C and D.

177. The GA variant as set forth in any one of 1 to 176 above and having an amino acid substitution at position A331 selected from the group consisting of: V, K, L, R and M.

178. The GA variant as set forth in any one of 1 to 177 above and having an amino acid substitution at position Q332 selected from the group consisting of: V, W, E, L and P.

179. The GA variant as set forth in any one of 1 to 178 above and having an amino acid substitution at position V345 selected from the group consisting of: I, Q and K.

180. The GA variant as set forth in any one of 1 to 179 above and having an amino acid substitution at position A360 selected from the group consisting of: C, G and S.

181. The GA variant as set forth in any one of 1 to 180 above and having an amino acid substitution at position D365 selected from the group consisting of: A, E, Q and R.

182. The GA variant as set forth in any one of 1 to 181 above and having an amino acid substitution at position W370 selected from the group consisting of: S, T, V, F and M.

183. The GA variant as set forth in any one of 1 to 182 above and having an amino acid substitution at position T379 selected from the group consisting of: E, H, N, Q and R.

184. The GA variant as set forth in any one of 1 to 183 above and having an amino acid substitution at position F386 selected from the group consisting of: H, L, T, V and W.

185. The GA variant as set forth in any one of 1 to 184 above and having an amino acid substitution at position L389 selected from the group consisting of: A, Q, S and T.

186. The GA variant as set forth in any one of 1 to 185 above and having an amino acid substitution at position S392 selected from the group consisting of: Y, I and P.

187. The GA variant as set forth in any one of 1 to 186 above and having an amino acid substitution at position Y398 selected from the group consisting of: N, Q, F, L and H.

188. The GA variant as set forth in any one of 1 to 187 above and having an amino acid substitution at position K413 selected from the group consisting of: T, E, F, L and R.

189. The GA variant as set forth in any one of 1 to 188 above and having an amino acid substitution at position A416 selected from the group consisting of: C, G and S.

190. The GA variant as set forth in any one of 1 to 189 above and having an amino acid substitution at position D417 selected from the group consisting of: N, T, E and Q.

191. The GA variant as set forth in any one of 1 to 190 above and having an amino acid substitution at position S429 selected from the group consisting of: D, G, M, T and A.

192. The GA variant as set forth in any one of 1 to 191 above and having an amino acid substitution at position A434 selected from the group consisting of: F, S, W and Y.

193. The GA variant as set forth in any one of 1 to 192 above and having an amino acid substitution at position K443 selected from the group consisting of: I, M, L and H.

194. The GA variant as set forth in any one of 1 to 193 above and having an amino acid substitution at position A460 selected from the group consisting of: C, G, M and T.

195. The GA variant as set forth in any one of 1 to 194 above and having an amino acid substitution at position R463 selected from the group consisting of: A, K and M.

196. The GA variant as set forth in any one of 1 to 195 above and having an amino acid substitution at position R464 selected from the group consisting of: F, V, H and K.

197. The GA variant as set forth in any one of 1 to 196 above and having an amino acid substitution at position A465 selected from the group consisting of: I, W, M, R and Y.

198. The GA variant as set forth in any one of 1 to 197 above and having an amino acid substitution at position R473 selected from the group consisting of: T, C and M.

199. The GA variant as set forth in any one of 1 to 198 above and having an amino acid substitution at position L481 selected from the group consisting of: F, H, R and C.

200. The GA variant as set forth in any one of 1 to 199 above and having an amino acid substitution at position T493 selected from the group consisting of: C, S, V and Q.

201. The GA variant as set forth in any one of 1 to 200 above and having an amino acid substitution at position S499 selected from the group consisting of: A, C, H, N and M.

202. The GA variant as set forth in any one of 1 to 201 above and having an amino acid substitution at position S501 selected from the group consisting of: V, A, I and Q.

203. The GA variant as set forth in any one of 1 to 202 above and having an amino acid substitution at position V531 selected from the group consisting of: S, T, A and C.

204. The GA variant as set forth in any one of 1 to 203 above and having an amino acid substitution at position R536 selected from the group consisting of: C, Q, L, Y and H.

205. The GA variant as set forth in any one of 1 to 204 above and having an amino acid substitution at position V548 selected from the group consisting of: F, M and T.

206. The GA variant as set forth in any one of 1 to 205 above and having an amino acid substitution at position N550 selected from the group consisting of: C, G, M, S and T.

207. The GA variant as set forth in any one of 1 to 206 above and having an amino acid substitution at position A553 selected from the group consisting of: E, K, P, Q and Y.

208. The GA variant as set forth in any one of 1 to 207 above and having an amino acid substitution at position L554 selected from the group consisting of: M, V and T.

209. The GA variant as set forth in any one of 1 to 208 above and having an amino acid substitution at position G555 selected from the group consisting of: K, A and H.

210. The GA variant as set forth in any one of 1 to 209 above and having an amino acid substitution at position D558 selected from the group consisting of: F, L, Q and R.

211. The GA variant as set forth in any one of 1 to 210 above and having an amino acid substitution at position T559 selected from the group consisting of: E, G, I and L.

212. The GA variant as set forth in any one of 1 to 211 above and having an amino acid substitution at position S560 selected from the group consisting of: F, A, K, M and V.

213. The GA variant as set forth in any one of 1 to 212 above and having an amino acid substitution at position S572 selected from the group consisting of: P, E, L, V and K.

214. The GA variant as set forth in any one of 1 to 213 above and having an amino acid substitution at position D574 selected from the group consisting of: I, M, N and Y.

215. The GA variant as set forth in any one of 1 to 214 above and having an amino acid substitution at position S578 selected from the group consisting of: F, A and C.

216. The GA variant as set forth in any one of 1 to 215 above and having an amino acid substitution at position K584 selected from the group consisting of: F, T and V.

217. The GA variant as set forth in any one of 1 to 216 above and having an amino acid substitution at position S588 selected from the group consisting of: H, L, P and Y.

218. The GA variant as set forth in any one of 1 to 217 above and having an amino acid substitution at position I595 selected from the group consisting of: G, M, T and L.

219. The GA variant as set forth in any one of 1 to 218 above and having an amino acid substitution at position K596 selected from the group consisting of: D, E and N.

220. The GA variant as set forth in any one of 1 to 219 above and having an amino acid substitution at position K602 selected from the group consisting of: D, I, R and F.

221. The GA variant as set forth in any one of 1 to 220 above and having an amino acid substitution at position W605 selected from the group consisting of: T, Y and F.

222. The GA variant as set forth in any one of 1 to 221 above and having an amino acid substitution at position E606 selected from the group consisting of: G, K and Q.

223. The GA variant as set forth in any one of 1 to 222 above and having an amino acid substitution at position R611 selected from the group consisting of: S, N and H.

224. The GA variant as set forth in any one of 1 to 223 above and having an amino acid substitution at position S612 selected from the group consisting of: C, E, W, F and H.

225. The GA variant as set forth in any one of 1 to 224 above and having an amino acid substitution at position S619 selected from the group consisting of: L, E and Q.

226. The GA variant as set forth in any one of 1 to 225 above and having an amino acid substitution at position V629 selected from the group consisting of: C, S, I, M and Q.

227. The GA variant as set forth in any one of 1 to 226 above and having an amino acid substitution at position D34 of M.

228. The GA variant as set forth in any one of 1 to 227 above and having an amino acid substitution at position P42 selected from the group consisting of: C and Q.

229. The GA variant as set forth in any one of 1 to 228 above and having an amino acid substitution at position I43 of V.

230. The GA variant as set forth in any one of 1 to 229 above and having an amino acid substitution at position K47 of R.

231. The GA variant as set forth in any one of 1 to 230 above and having an amino acid substitution at position A50 selected from the group consisting of: D and N.

232. The GA variant as set forth in any one of 1 to 231 above and having an amino acid substitution at position N55 of D.

233. The GA variant as set forth in any one of 1 to 232 above and having an amino acid substitution at position A58 of C.

234. The GA variant as set forth in any one of 1 to 233 above and having an amino acid substitution at position A62 of H.

235. The GA variant as set forth in any one of 1 to 234 above and having an amino acid substitution at position A64 of P.

236. The GA variant as set forth in any one of 1 to 235 above and having an amino acid substitution at position I68 of V.

237. The GA variant as set forth in any one of 1 to 236 above and having an amino acid substitution at position S72 selected from the group consisting of: C and Q.

238. The GA variant as set forth in any one of 1 to 237 above and having an amino acid substitution at position R73 of M.

239. The GA variant as set forth in any one of 1 to 238 above and having an amino acid substitution at position D75 selected from the group consisting of: H and R.

240. The GA variant as set forth in any one of 1 to 239 above and having an amino acid substitution at position P77 of D.

241. The GA variant as set forth in any one of 1 to 240 above and having an amino acid substitution at position T83 of V.

242. The GA variant as set forth in any one of 1 to 241 above and having an amino acid substitution at position L90 selected from the group consisting of: I and P.

243. The GA variant as set forth in any one of 1 to 242 above and having an amino acid substitution at position S96 selected from the group consisting of: A and Y.

244. The GA variant as set forth in any one of 1 to 243 above and having an amino acid substitution at position G98 selected from the group consisting of: Y and F.

245. The GA variant as set forth in any one of 1 to 244 above and having an amino acid substitution at position Y101 of F.

246. The GA variant as set forth in any one of 1 to 245 above and having an amino acid substitution at position T103 selected from the group consisting of: Q and V.

247. The GA variant as set forth in any one of 1 to 246 above and having an amino acid substitution at position I109 selected from the group consisting of: T and A.

248. The GA variant as set forth in any one of 1 to 247 above and having an amino acid substitution at position Q110 selected from the group consisting of: E and C.

249. The GA variant as set forth in any one of 1 to 248 above and having an amino acid substitution at position V113 selected from the group consisting of: E and L.

250. The GA variant as set forth in any one of 1 to 249 above and having an amino acid substitution at position S115 of A.

251. The GA variant as set forth in any one of 1 to 250 above and having an amino acid substitution at position V122 of L.

252. The GA variant as set forth in any one of 1 to 251 above and having an amino acid substitution at position S123 selected from the group consisting of: A and P.

253. The GA variant as set forth in any one of 1 to 252 above and having an amino acid substitution at position S126 of A.

254. The GA variant as set forth in any one of 1 to 253 above and having an amino acid substitution at position T128 of V.

255. The GA variant as set forth in any one of 1 to 254 above and having an amino acid substitution at position F129 of L.

256. The GA variant as set forth in any one of 1 to 255 above and having an amino acid substitution at position A146 of P.

257. The GA variant as set forth in any one of 1 to 256 above and having an amino acid substitution at position T148 selected from the group consisting of: L and M.

258. The GA variant as set forth in any one of 1 to 257 above and having an amino acid substitution at position E150 selected from the group consisting of: P and R.

259. The GA variant as set forth in any one of 1 to 258 above and having an amino acid substitution at position A165 of S.

260. The GA variant as set forth in any one of 1 to 259 above and having an amino acid substitution at position L166 selected from the group consisting of: M and C.

261. The GA variant as set forth in any one of 1 to 260 above and having an amino acid substitution at position Y169 selected from the group consisting of: E and F.

262. The GA variant as set forth in any one of 1 to 261 above and having an amino acid substitution at position A170 selected from the group consisting of: C and I.

263. The GA variant as set forth in any one of 1 to 262 above and having an amino acid substitution at position A182 of V.

264. The GA variant as set forth in any one of 1 to 263 above and having an amino acid substitution at position V185 selected from the group consisting of: N and Q.

265. The GA variant as set forth in any one of 1 to 264 above and having an amino acid substitution at position P188 of K.

266. The GA variant as set forth in any one of 1 to 265 above and having an amino acid substitution at position L194 of I.

267. The GA variant as set forth in any one of 1 to 266 above and having an amino acid substitution at position T197 selected from the group consisting of: A and G.

268. The GA variant as set forth in any one of 1 to 267 above and having an amino acid substitution at position F206 of Y.

269. The GA variant as set forth in any one of 1 to 268 above and having an amino acid substitution at position F218 of W.

270. The GA variant as set forth in any one of 1 to 269 above and having an amino acid substitution at position S222 selected from the group consisting of: M and Q.

271. The GA variant as set forth in any one of 1 to 270 above and having an amino acid substitution at position H224 of A.

272. The GA variant as set forth in any one of 1 to 271 above and having an amino acid substitution at position A226 of S.

273. The GA variant as set forth in any one of 1 to 272 above and having an amino acid substitution at position Y232 of F.

274. The GA variant as set forth in any one of 1 to 273 above and having an amino acid substitution at position L237 of I.

275. The GA variant as set forth in any one of 1 to 274 above and having an amino acid substitution at position P249 of D.

276. The GA variant as set forth in any one of 1 to 275 above and having an amino acid substitution at position Q256 of F.

277. The GA variant as set forth in any one of 1 to 276 above and having an amino acid substitution at position A257 selected from the group consisting of: G and F.

278. The GA variant as set forth in any one of 1 to 277 above and having an amino acid substitution at position F258 of N.

279. The GA variant as set forth in any one of 1 to 278 above and having an amino acid substitution at position W259 of Y.

280. The GA variant as set forth in any one of 1 to 279 above and having an amino acid substitution at position Y265 of W.

281. The GA variant as set forth in any one of 1 to 280 above and having an amino acid substitution at position V267 selected from the group consisting of: K and R.

282. The GA variant as set forth in any one of 1 to 281 above and having an amino acid substitution at position S268 of C.

283. The GA variant as set forth in any one of 1 to 282 above and having an amino acid substitution at position G272 of C.

284. The GA variant as set forth in any one of 1 to 283 above and having an amino acid substitution at position G273 of H.

285. The GA variant as set forth in any one of 1 to 284 above and having an amino acid substitution at position S277 of T.

286. The GA variant as set forth in any one of 1 to 285 above and having an amino acid substitution at position D280 of V.

287. The GA variant as set forth in any one of 1 to 286 above and having an amino acid substitution at position A281 of L.

288. The GA variant as set forth in any one of 1 to 287 above and having an amino acid substitution at position I284 selected from the group consisting of: L and V.

289. The GA variant as set forth in any one of 1 to 288 above and having an amino acid substitution at position A286 selected from the group consisting of: L and T.

290. The GA variant as set forth in any one of 1 to 289 above and having an amino acid substitution at position S287 selected from the group consisting of: C and Q.

291. The GA variant as set forth in any one of 1 to 290 above and having an amino acid substitution at position Q303 of E.

292. The GA variant as set forth in any one of 1 to 291 above and having an amino acid substitution at position S306 of C.

293. The GA variant as set forth in any one of 1 to 292 above and having an amino acid substitution at position E307 selected from the group consisting of: D and P.

294. The GA variant as set forth in any one of 1 to 293 above and having an amino acid substitution at position H313 of Y.

295. The GA variant as set forth in any one of 1 to 294 above and having an amino acid substitution at position Y316 of W.

296. The GA variant as set forth in any one of 1 to 295 above and having an amino acid substitution at position D318 of M.

297. The GA variant as set forth in any one of 1 to 296 above and having an amino acid substitution at position N322 selected from the group consisting of: H and C.

298. The GA variant as set forth in any one of 1 to 297 above and having an amino acid substitution at position V336 selected from the group consisting of: C and I.

299. The GA variant as set forth in any one of 1 to 298 above and having an amino acid substitution at position A337 of S.

300. The GA variant as set forth in any one of 1 to 299 above and having an amino acid substitution at position N348 of G.

301. The GA variant as set forth in any one of 1 to 300 above and having an amino acid substitution at position A355 selected from the group consisting of: S and C.

302. The GA variant as set forth in any one of 1 to 301 above and having an amino acid substitution at position N356 of S.

303. The GA variant as set forth in any one of 1 to 302 above and having an amino acid substitution at position A359 selected from the group consisting of: G and S.

304. The GA variant as set forth in any one of 1 to 303 above and having an amino acid substitution at position L363 selected from the group consisting of: A and V.

305. The GA variant as set forth in any one of 1 to 304 above and having an amino acid substitution at position S375 selected from the group consisting of: A and L.

306. The GA variant as set forth in any one of 1 to 305 above and having an amino acid substitution at position T377 selected from the group consisting of: S and A.

307. The GA variant as set forth in any one of 1 to 306 above and having an amino acid substitution at position V378 selected from the group consisting of: L and T.

308. The GA variant as set forth in any one of 1 to 307 above and having an amino acid substitution at position L383 selected from the group consisting of: C and N.

309. The GA variant as set forth in any one of 1 to 308 above and having an amino acid substitution at position F385 of L.

310. The GA variant as set forth in any one of 1 to 309 above and having an amino acid substitution at position D388 selected from the group consisting of: A and C.

311. The GA variant as set forth in any one of 1 to 310 above and having an amino acid substitution at position T404 of Q.

312. The GA variant as set forth in any one of 1 to 311 above and having an amino acid substitution at position E421 selected from the group consisting of: C and Q.

313. The GA variant as set forth in any one of 1 to 312 above and having an amino acid substitution at position V422 of F.

314. The GA variant as set forth in any one of 1 to 313 above and having an amino acid substitution at position A424 selected from the group consisting of: C and Q.

315. The GA variant as set forth in any one of 1 to 314 above and having an amino acid substitution at position K425 selected from the group consisting of: M and R.

316. The GA variant as set forth in any one of 1 to 315 above and having an amino acid substitution at position Y426 of F.

317. The GA variant as set forth in any one of 1 to 316 above and having an amino acid substitution at position A432 selected from the group consisting of: D and S.

318. The GA variant as set forth in any one of 1 to 317 above and having an amino acid substitution at position N440 of D.

319. The GA variant as set forth in any one of 1 to 318 above and having an amino acid substitution at position S446 of G.

320. The GA variant as set forth in any one of 1 to 319 above and having an amino acid substitution at position T451 of S.

321. The GA variant as set forth in any one of 1 to 320 above and having an amino acid substitution at position F457 of A.

322. The GA variant as set forth in any one of 1 to 321 above and having an amino acid substitution at position R487 of S.

323. The GA variant as set forth in any one of 1 to 322 above and having an amino acid substitution at position I488 of V.

324. The GA variant as set forth in any one of 1 to 323 above and having an amino acid substitution at position V495 of I.

325. The GA variant as set forth in any one of 1 to 324 above and having an amino acid substitution at position A496 of P.

326. The GA variant as set forth in any one of 1 to 325 above and having an amino acid substitution at position A497 selected from the group consisting of: Q and S.

327. The GA variant as set forth in any one of 1 to 326 above and having an amino acid substitution at position F502 of I.

328. The GA variant as set forth in any one of 1 to 327 above and having an amino acid substitution at position S504 of T.

329. The GA variant as set forth in any one of 1 to 328 above and having an amino acid substitution at position A513 selected from the group consisting of: D and G.

330. The GA variant as set forth in any one of 1 to 329 above and having an amino acid substitution at position P516 selected from the group consisting of: E and A.

331. The GA variant as set forth in any one of 1 to 330 above and having an amino acid substitution at position P520 of V.

332. The GA variant as set forth in any one of 1 to 331 above and having an amino acid substitution at position T521 selected from the group consisting of: W and S.

333. The GA variant as set forth in any one of 1 to 332 above and having an amino acid substitution at position S527 of F.

334. The GA variant as set forth in any one of 1 to 333 above and having an amino acid substitution at position V529 of W.

335. The GA variant as set forth in any one of 1 to 334 above and having an amino acid substitution at position T532 selected from the group consisting of: W and Y.

336. The GA variant as set forth in any one of 1 to 335 above and having an amino acid substitution at position N534 selected from the group consisting of: D and E.

337. The GA variant as set forth in any one of 1 to 336 above and having an amino acid substitution at position E535 of Q.

338. The GA variant as set forth in any one of 1 to 337 above and having an amino acid substitution at position T539 of S.

339. The GA variant as set forth in any one of 1 to 338 above and having an amino acid substitution at position E543 selected from the group consisting of: C and I.

340. The GA variant as set forth in any one of 1 to 339 above and having an amino acid substitution at position I545 of V.

341. The GA variant as set forth in any one of 1 to 340 above and having an amino acid substitution at position V547 selected from the group consisting of: A and C.

342. The GA variant as set forth in any one of 1 to 341 above and having an amino acid substitution at position G549 of A.

343. The GA variant as set forth in any one of 1 to 342 above and having an amino acid substitution at position K571 selected from the group consisting of: R and T.

344. The GA variant as set forth in any one of 1 to 343 above and having an amino acid substitution at position L576 of K.

345. The GA variant as set forth in any one of 1 to 344 above and having an amino acid substitution at position I579 of M.

346. The GA variant as set forth in any one of 1 to 345 above and having an amino acid substitution at position I583 of M.

347. The GA variant as set forth in any one of 1 to 346 above and having an amino acid substitution at position T586 selected from the group consisting of: L and R.

348. The GA variant as set forth in any one of 1 to 347 above and having an amino acid substitution at position Y592 of H.

349. The GA variant as set forth in any one of 1 to 348 above and having an amino acid substitution at position Y594 selected from the group consisting of: M and H.

350. The GA variant as set forth in any one of 1 to 349 above and having an amino acid substitution at position G622 selected from the group consisting of: P and W.

351. The GA variant as set forth in any one of 1 to 350 above and having an amino acid substitution at position Q627 selected from the group consisting of: E and A.

352. The GA variant as set forth in any one of 1 to 351 above and having an amino acid substitution at position T628 of L.

353. The GA variant as set forth in any one of 1 to 352 above and having an amino acid substitution at position N630 of C.

354. The GA variant as set forth in any one of 1 to 353 above and having an amino acid substitution at position D631 selected from the group consisting of: Q, and S.

In some embodiments, the parent GA is a fungal GA, e.g., a filamentous fungal GA. In some embodiments, the parent glucoamylase is obtained from a *Trichoderma* strain (e.g., *T. reesei, T. longibrachiatum, T. strictipilis, T. asperellum, T. konilangbra, T. citrinoviride, T. pseudokoningii* and *T. harzianum*), an *Aspergillus* strain (e.g. *A. aculeatus, A. niger, A. nidulans, A. kawachi, A. awamori, A. clavatus, A. terreus, A. fumigates*, and *A. orzyae*), a *Talaromyces* strain (e.g. *T. emersonii, T. thermophilus*, and *T. duponti*), a *Trametes* strain (e.g., *Trametes cingulata*), a *Hypocrea* strain (e.g. *H. gelatinosa, H. orientalis, H. vinosa, H. jecorina, H. schweinitzii*, and *H. citrina*), a *Fusarium* strain (e.g., *F. oxysporum*, and *F. roseum*), a *Humicola* strain (e.g., *H. grisea, H. insolens* and *H. lanuginose*), a *Saccharomycopsis* strain (e.g., *S. fibuligera*), *Scytalidium thermophilum, Podospora anderina*, or their respective anamorph, teleomorph or holomorph counterpart forms. In certain embodiments, the parent GA has at least 90% sequence identity to SEQ ID NO:4, e.g., at least 95% sequence identity. In certain embodiments, the parent fungal GA is *Humicola grisea* GA (HgGA; SEQ ID NO:4 shows the mature form; see FIG. 1). Amino acid residues in a GA enzyme derived from any of the filamentous fungi above that correspond to amino acid residues in HgGA can be determined using alignment algorithms as set forth in the definitions section below.

In some embodiments, the parent glucoamylase is a bacterial glucoamylase. For example, the polypeptide can be obtained from a gram-positive bacterial strain such as *Bacillus* (e.g., *B. alkalophilus, B. amyloliquefaciens, B. lentus, B. licheniformis, B. stearothermophilus, B. subtilis* and *B. thuringiensis*) or a *Streptomyces* strain (e.g., *S. lividans*).

Aspects of the subject invention include an isolated polynucleotide comprising a polynucleotide sequence encoding a variant of a parent GA as described herein. The isolated polynucleotide may be present in a vector, e.g., an expression vector or a vector for propagation of the polynucleotide. The vector may be present in a host cell to propagate the vector and/or that expresses the encoded GA variant as described herein. The host cell can be any cell that finds use in propagation of the GA variant polynucleotide and/or expression of the encoded GA variant, e.g., a bacterial cell, a fungal cell, etc. Examples of suitable fungal cell types that can be employed include filamentous fungal cells, e.g., cells of *Trichoderma reesei, Trichoderma longibrachiatum, Trichoderma viride, Trichoderma koningii, Trichoderma harzianum, Penicillium, Humicola, Humicola insolens, Humicola grisea, Chrysosporium, Chrysosporium lucknowense, Myceliophthora thermophila, Gliocladium, Aspergillus, Fusarium, Neurospora, Hypocrea, Emericella, Aspergillus niger, Aspergillus awamori, Aspergillus aculeatus*, and *Aspergillus nidulans*. Alternatively, the fungal host cell can be a yeast cell, e.g., *Saccharomyces cervisiae, Saccharomycopsis fibuligera, Schizzosaccharomyces pombe, Schwanniomyces occidentalis, Kluveromyces lactus, Candida utilis, Candida albicans, Pichia stipitis, Pichia pastoris, Yarrowia lipolytica, Hansenula polymorpha, Phaffia rhodozyma, Arxula adeninivorans, Debaryomyces hansenii*, or *Debaryomyces polymorphus*. In a particular aspect, a suitable host cell may even be one that is an ethanologen microorganism, including, for example, an engineered *Zymomonas mobilis* or a yeast ethanologen.

Aspects of the present invention include methods of producing a variant GA that includes culturing a host cell that contains a polynucleotide encoding the GA variant in a suitable culture medium under suitable conditions to express (or produce) the GA variant from the polynucleotide, e.g., where the polynucleotide encoding the GA variant is present in an expression vector (i.e., where the GA variant-encoding polynucleotide is operably linked to a promoter that drives expression of the GA variant in the host cell). In certain embodiments, the method further includes isolating the produced GA variant.

Aspects of the present invention also include compositions containing a GA variant as described herein. Examples of suitable compositions include, but are not limited to compositions comprising a starch substrate (e.g., liquefied starch from corn, grain, wheat tapioca, etc.) and the GA variant.

Aspects of the present invention include methods for hydrolyzing a starch substrate comprising contacting the substrate with a variant GA as described herein. In certain embodiments, the GA variant is provided as a cell-free composition, whereas in other embodiments, the GA variant is provided as a host cell composition in which the host cell expresses the GA variant. Thus, certain embodiments of the methods for hydrolyzing a starch substrate include contacting the substrate with a host cell containing a GA variant expression vector. The method may be a starch conversion process, an alcohol fermentation process, a direct starch to glucose process, or a simultaneous saccharification and fermentation process.

Aspects of the present invention include cell culture supernatant compositions that contain a GA variant as described herein. For example, a cell culture supernatant obtained by culturing a host cell that contains a polynucleotide encoding the GA variant in a suitable culture medium under suitable conditions to express the GA variant from the polynucleotide and secrete the GA variant into the cell culture supernatant. Such a cell culture supernatant can include other proteins and/or enzymes produced by the host cell, including endogenously- and/or exogenously-expressed proteins and/or enzymes. Such supernatant of the culture medium can be used as is, with minimum or no post-production processing, which may typically include filtration to remove cell debris, cell-kill procedures, and/or ultrafiltration or other steps to enrich or concentrate the enzymes therein. Such supernatants are sometimes referred to herein as "whole broths" (or grammatical equivalent).

The GA variants can be produced by co-expression with one or more other enzymes or protein products, e.g., an alpha-amylase. Alternatively, the GA variants can be produced without other enzymes or protein products. In the latter case, the GA variant optionally can be physically mixed with one or more other enzymes or protein products to form an enzyme composition that is useful for a particular application, e.g., in hydrolyzing starch substrates to generate glucose.

Other compositions containing a desired variant GA, as well as methods for using such compositions, are also contemplated.

BRIEF DESCRIPTION OF THE DRAWINGS

FIGS. 1A and 1B show a recombinant cDNA sequence (top line) (SEQ ID NO:2) and wild type amino acid sequence (bottom line) (SEQ ID NO:3) of the full-length *Humicola grisea* glucoamylase (HgGA). The signal sequence is underlined.

DETAILED DESCRIPTION

Figure 2:
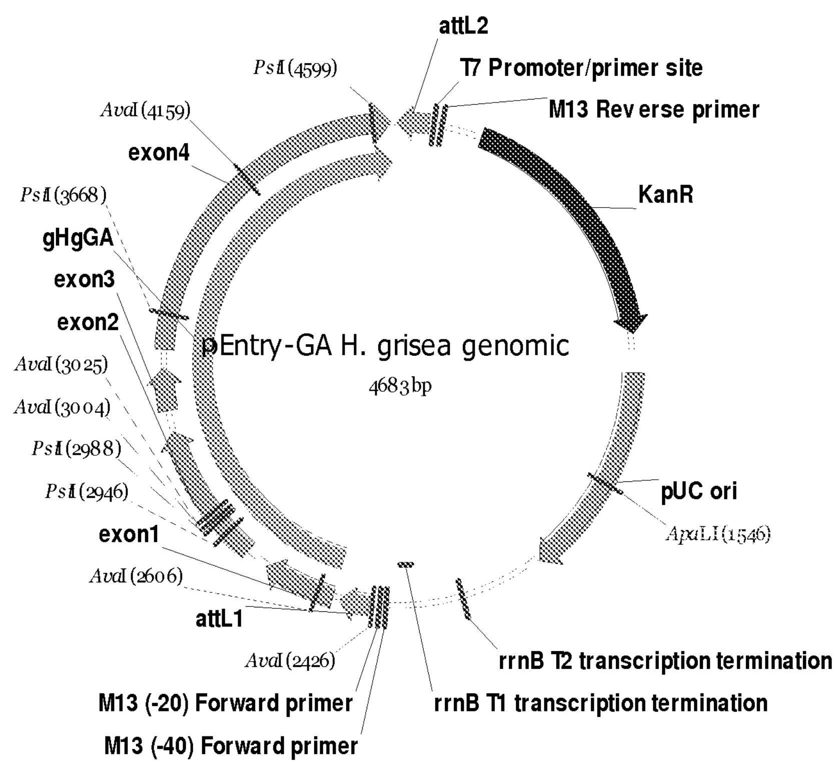
FIG. 2 is a schematic representation of the pEntry-HgGA genomic plasmid (see Example 2).

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., Dictionary of Microbiology and Molecular Biology, 3rd Ed., John Wiley and Sons, Ltd., New York (2007), and Hale & Marham, The Harper Collins Dictionary of Biology, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation. Practitioners are particularly directed to Green and Sambrook *Molecular Cloning: A Laboratory Manual* (Fourth Edition), *Cold Spring Harbor Laboratory Press* 2012, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Definitions

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. As such, the present invention contemplates every possible variant nucleotide sequence encoding GA or an amino acid variant thereof, all of which are possible given the degeneracy of the genetic code. Unless otherwise indicated, nucleic acid sequences are presented in 5'-to-3' orientation.

Nucleic acid and amino acid sequences that are referred to herein as "non-naturally occurring" are those that are not found in nature, i.e., are the product of human manipulation and/or synthesis.

"Glucoamylase" or "GA" or "GA enzyme" or "GA polypeptide," as used herein is defined as the amyloglucosidase class of enzymes (EC 3.2.1.3, glucoamylase, α-1, 4-D-glucan glucohydrolase). These are exo-acting enzymes that catalyze the release of D-glucose from the non-reducing ends of starch and related oligo- and polysaccharides. The enzymes are also capable of hydrolyzing α-1, 6 and α-1,3 linkages, although generally at much slower rates than the hydrolysis of α-1, 4 linkages.

A "variant" of an enzyme, protein, polypeptide, nucleic acid, or polynucleotide as used herein means that the variant is derived from a parent polypeptide or parent nucleic acid (e.g., native, wild-type or other defined parent polypeptide or nucleic acid) that includes at least one modification or alteration as compared to that parent. Thus, a variant may have a few mutations as compared to a parent, where by "a few" is meant from 1 to 10 mutations. For example, a variant having from 1 to 10 amino acid substitutions as compared to SEQ ID NO:4 can be referred to as a HgGA variant having a few substitutions. Alterations/modifications can include a substitution of an amino acid/nucleic acid residue in the parent for a different amino acid/nucleic acid residue at one or more sites, deletion of an amino acid/nucleic acid residue (or a series of amino acid/nucleic acid residues) in the parent at one or more sites, insertion of an amino acid/nucleic acid residue (or a series of amino acid/nucleic acid residues) in the parent at one or more sites, truncation of amino- and/or carboxy-terminal amino acid sequences or 5' and or 3' nucleic acid sequences, and any combination thereof. A variant HgGA enzyme according to aspects of the invention retains starch hydrolysis activity but may have an altered property in some specific aspect, e.g., an improved property. For example, a variant HgGA enzyme may have an altered pH optimum, improved thermostability, improved hydrolysis of one or more substrates (e.g., DP2 (e.g., maltose), DP7 (e.g., maltoheptaose), panose, and/or pullulan) or a combination thereof. In certain embodiments, the variant HgGA enzyme contains an amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:4, or an enzymatically active fragment thereof.

"Combinatorial variants" are variants comprising two or more mutations, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30 or more, substitutions, deletions, and/or insertions.

A "parent" or "parental" polynucleotide, polypeptide, or enzyme sequence (e.g., a "parent HgGA enzyme"), or equivalents thereto, as used herein refers to a polynucleotide, polypeptide, or enzyme sequence that was used as a starting point or template for designing a variant polynucleotide, polypeptide, or enzyme. It is further noted that the words "parent" and "parental" are used interchangeably in this context. A "parent HgGA enzyme" as used herein means a polypeptide that in its mature form comprises an amino acid sequence which has at least 60% identity with SEQ ID NO:4, including amino acid sequences having at least 60%, 70%, 80%, 81%, 82%, 83%, 84%, 85%, 86%, 870/0, 88%, 89%, 90%, 91%, 92%, 93%, 94%, 95%, 96%, 97%, 98%, 99%, or 100% identity with SEQ ID NO:4 (which provides the amino acid sequence of the mature form of wild type GA from *Humicola grisea*) or an allelic variant or a fragment thereof that has starch hydrolysis activity.

The term "wild-type" refers to a naturally-occurring polypeptide or nucleic acid sequence, i.e., one that does not include a human-made variation.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes, arranged to make a new functional nucleic acid, e.g., a promoter from one source and a coding region from another source. Similarly, a heterologous polypeptide will often refer to two or more subsequences that are not found in the same relationship to each other in nature (e.g., a fusion polypeptide).

The term "recombinant" when used with reference, e.g., to a cell, or nucleic acid, polypeptide, or vector, indicates that the cell, nucleic acid, polypeptide or vector, has been modified by the introduction of a heterologous nucleic acid or polypeptide or the alteration of a native nucleic acid or polypeptide, or that the cell is derived from a cell so modified. Thus, for example, recombinant cells express genes that are not found within the native (non-recombinant) form of the cell or express native genes that are otherwise abnormally expressed, under-expressed or not expressed at all. A "recombinant" composition requires manipulation by a human and therefore excludes products of nature.

The terms "isolated" or "purified" as used herein refer to a nucleic acid or polynucleotide that is removed from the environment in which it is naturally produced. In general, in an isolated or purified nucleic acid or polypeptide sample, the nucleic acid(s) or polypeptide(s) of interest are present at an increased absolute or relative concentration as compared to the environment in which they are naturally produced. In some instances, an isolated or purified nucleic acid or polynucleotide is synthetically generated.

The term "enriched" when describing a component or material in a composition (e.g., a polypeptide or polynucleotide) means that the component or material is present at a relatively increased concentration in that composition as compared to the starting composition from which the enriched composition was generated. For example, an enriched GA composition (or sample) is one in which the relative or absolute concentration of GA is increased as compared to the initial fermentation product from the host organism.

As used herein, the terms "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. A "constitutive" promoter is a promoter that is active under most environmental and developmental conditions. An "inducible" promoter is a promoter that is active under environmental or developmental regulation. An example of an inducible promoter useful in the present invention is the *T. reesei* (*H. jecorina*) cbh1 promoter which is deposited in GenBank under Accession Number D86235. In another aspect the promoter is a cbh II or xylanase promoter from *H. jecorina*. Examples of suitable promoters include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the *Mucor miehei* carboxyl protease gene, the *Hypocrea jecorina* glucoamylase I gene (Shoemaker, S. P. et al. (1984) European Patent Application No. EPO0137280A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45) the *A. nidulans* alcA gene (Lockington, R. A. et al. (1986) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell Biol. 3, 1430-1439), the *H. jecorina* xln1 gene, the *H. jecorina* cbh2 gene, the *H. jecorina* eg1 gene, the *H. jecorina* eg2 gene, the *H. jecorina* eg3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. Thus, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "signal sequence", "signal peptide", "secretory sequence", "secretory peptide", "secretory signal sequence", "secretory signal peptide" and the like denotes a peptide sequence that, as a component of a larger polypeptide, directs the larger polypeptide through a secretory pathway of a cell in which it is synthesized, as well as nucleic acids encoding such peptides. In general, the larger polypeptide (or protein) is commonly cleaved to remove the secretory/signal peptide during transit through the secretory pathway, where the cleaved form of the polypeptide (i.e., the form without the signal/secretory peptide) is often referred to herein as the "mature form" of the polypeptide. For example, SEQ ID NO:3 provides the amino acid sequence of GA from *H. grisea* (HgGA) with the signal peptide (i.e., full length HgGA) while SEQ ID NO:4 provides the amino acid sequence of HgGA without the signal peptide (i.e., mature HgGA).

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct that forms an extrachromosomal self-replicating genetic element when present in many bacteria and some eukaryotes. Plasmids may be employed for any of a number of different purposes, e.g., as cloning vectors, propagation vectors, expression vectors, etc.

As used herein, the term "selectable marker" refers to a nucleotide sequence or polypeptide encoded thereby which is capable of expression in cells and where expression of the selectable marker in cells confers the ability to be differentiated from cells that do not express the selectable marker. In certain embodiments, a selectable marker allows a cell expressing it to grow in the presence of a corresponding selective agent, or under corresponding selective growth conditions. In other embodiments, a selectable marker allows a cell expressing it to be identified and/or isolated from cells that do not express it by virtue of a physical characteristic, e.g., by differences in fluorescence, immunoreactivity, etc.

In general, nucleic acid molecules which encode the variant HgGA will hybridize, under moderate to high stringency conditions to the wild type sequence provided herein as SEQ ID NO:1 (native HgGA gene) or SEQ ID NO:2 (HgGA protein coding region). However, in some cases an HgGA-encoding nucleotide sequence is employed that possesses a substantially different codon usage, while the enzyme encoded by the HgGA-encoding nucleotide sequence has the same or substantially the same amino acid sequence as the native enzyme. For example, the coding sequence may be modified to facilitate faster expression of HgGA in a particular prokaryotic or eukaryotic expression system, in accordance with the frequency with which a particular codon is utilized by the host (commonly referred to as "codon optimization"). Te'o, et al. (2000), for example, describes the optimization of genes for expression in filamentous fungi. Such nucleic acid sequences are sometimes referred to as "degenerate" or "degenerated sequences".

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process generally includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

By the term "host cell" is meant a cell that contains a vector and supports the replication, and/or transcription and/or transcription and translation (expression) of the expression construct. Host cells for use in the present invention can be prokaryotic cells, such as *E. coli*, or eukaryotic cells such as yeast, plant, insect, amphibian, or mammalian cells. In certain embodiments, host cells are filamentous fungi.

When an amino acid position (or residue) in a first polypeptide is noted as being "equivalent" to an amino acid position in a second, related polypeptide, it means that the amino acid position of the first polypeptide corresponds to the position noted in the second, related polypeptide by one or more of (i) primary sequence alignment (see description of sequence alignment and sequence identity below); (ii) structural sequence homology; or (iii) analogous functional property. Thus, an amino acid position in a first GA enzyme (or a variant thereof) can be identified as "equivalent" (or "homologous") to an amino acid position in a second GA enzyme (or even multiple different GA enzymes).

Primary sequence alignment: Equivalent amino acid positions can be determined using primary amino acid sequence alignment methodologies, many of which are known in the art. For example, by aligning the primary amino acid sequences of two or more different GA enzymes, it is possible to designate an amino acid position number from one GA enzyme as equivalent to the position number of another one of the aligned GA enzymes. In this manner, the numbering system originating from the amino acid sequence of one GA enzyme (e.g., the HgGA enzyme denoted in SEQ ID NO: 3) can be used to identify equivalent (or homologous) amino acid residues in other GA enzymes.

Structural sequence homology: In addition to determining "equivalent" amino acid positions using primary sequence alignment methodologies, "equivalent" amino acid positions may also be defined by determining homology at the level of secondary and/or tertiary structure. For example, for a glucoamylase whose tertiary structure has been determined by x-ray crystallography, equivalent residues can be defined as those for which the atomic coordinates of two or more of the main chain atoms of a particular amino acid residue of the glucoamylase are within 0.13 nm and preferably 0.1 nm after alignment with HgGA (N on N, CA on CA, C on C, and O on O). Alignment is achieved after the best model has been oriented and positioned to give the maximum overlap of atomic coordinates of non-hydrogen protein atoms of the glucoamylase in question to HgGA. The best model is the crystallographic model that gives the highest resolution available. Where two or more different models have equal resolution, the model with the lowest R factor for experimental diffraction data, using the equation below, is used.

$$R \text{ factor} = \frac{\sum_h |Fo(h)| - |Fc(h)|}{\sum_h |Fo(h)|}$$

Analogous functional property: Equivalent amino acid residues in a first polypeptide which are functionally analogous to a specific residue of a second related polypeptide (e.g., a first glucoamylase and HgGA) are defined as those amino acids in the first polypeptide that adopt a conformation such that they alter, modify, or contribute to polypeptide structure, substrate binding, or catalysis in a manner defined and attributed to a specific residue of the second related polypeptide. When a tertiary structure has been obtained by x-ray crystallography for the first polypeptide, amino acid residues of the first polypeptide that are functionally analogous to the second polypeptide occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the second polypeptide.

The term "improved property" or "improved performance" and the like with respect to a variant enzyme (e.g., a GA variant) is defined herein as a characteristic or activity associated with a variant enzyme which is improved as compared to its respective parent enzyme. Improved properties include, but are not limited to, improved thermostability or altered temperature-dependent activity profile, improved activity or stability at a desired pH or pH range, improved substrate specificity, improved product specificity, and improved stability in the presence of a chemical or other component in a starch conversion process step, etc. Improved performance may be determined using a particular assay(s) including, but not limited to: (a) expression, (b) hydrolytic activity on DP2 substrate, (c) hydrolytic activity on DP7 substrate at pH 6.8, (d) hydrolytic activity on DP7 substrate at pH 5.5, (e) hydrolytic activity on panose substrate, (f) hydrolytic activity on pullulan substrate, (g) hydrolytic activity on granular corn starch (CS), (h) thermostability, (i) glucose inhibition, and (j) reversion activity.

The term "improved thermostability" with respect to a variant protein (e.g., a GA variant) is defined herein as a variant enzyme displaying retention of a greater fraction of enzymatic activity after a period of incubation at an elevated temperature relative to the parent enzyme. Such a variant may or may not display an altered thermal activity profile relative to the parent. For example, a variant may have an improved ability to refold following incubation at elevated temperature relative to the parent.

By "improved product specificity" is meant a variant enzyme displaying an altered product profile as compared to the parent enzyme, where the altered product profile of the variant is improved in a given application as compared to the parent. A "product profile" is defined herein as the chemical composition of the reaction products produced by the enzyme of interest.

By "improved substrate specificity" is meant a variant enzyme that targets a specific substrate (or class of substrate) for hydrolysis in a manner different than the parent enzyme, such that the variant has improved performance in a given application as compared to the parent.

By "improved chemical stability" is meant that a variant enzyme displays retention of enzymatic activity after a period of incubation in the presence of a chemical or chemicals that reduce the enzymatic activity of the parent enzyme under the same conditions. Variants with improved chemical stability are better able to catalyze a reaction in the presence of such chemicals as compared to the parent enzyme.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

As used herein, "starch" refers to any material comprised of the complex polysaccharide carbohydrates of plants, comprised of amylose and amylopectin with the formula $(C_6H_{10}O_5)_x$, wherein "X" can be any number. In particular, the term refers to any plant-based material including but not limited to grains, grasses, tubers and roots and more specifically wheat, barley, corn, rye, rice, sorghum, brans, cassava, millet, potato, sweet potato, and tapioca. "Granular starch" refers to uncooked (raw) starch, which has not been subject to gelatinization, where "starch gelatinization" means solubilization of a starch molecule to form a viscous suspension.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. DP7 denotes polymers with seven anhydroglucopyranose units.

As used herein, "hydrolysis of starch" and the like refers to the cleavage of glucosidic bonds with the addition of water molecules. Thus, enzymes having "starch hydrolysis activity" catalyze the cleavage of glucosidic bonds with the addition of water molecules As used herein, "fermentable sugars" refer to saccharides that are capable of being metabolized under fermentation conditions. These sugars typically refer to glucose, maltose, and maltotriose (DP1, DP2 and DP3).

As used herein, "total sugar content" refers to the total sugar content present in a starch composition.

"Percent sequence identity" or grammatical equivalents means that a particular sequence has at least a certain percentage of amino acid residues identical to those in a specified reference sequence using an alignment algorithm. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (<www(dot)ncbi(dot)nlm(dot)nih(dot)gov>). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

Alignment algorithms can also be employed to identify an amino acid residue (or residues) in a first amino acid sequence (e.g., HgGA) that correspond to an amino acid residue (or residues) in a second aminbo acid sequence (e.g., homologous GA enzymes from other species, e.g., *T. reesei* GA).

When questions of percent sequence identity or corresponding amino acid residues between two sequences arise, alignment using the CLUSTAL W algorithm with default parameters will govern. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

II. Molecular biology

Embodiments of the subject invention provide for the expression of a desired glucoamylase enzyme (or combination of glucoamylase enzymes) from glucoamylase-encoding nucleic acids under control of a promoter functional in a host cell of interest, e.g., a filamentous fungus. Therefore, this invention relies on a number of routine techniques in the field of recombinant genetics. Basic texts disclosing examples of suitable recombinant genetics methods are noted above.

Any method known in the art that can introduce mutations into a parent nucleic acid/polypeptide is contemplated by the present invention.

The present invention relates to the expression, purification and/or isolation and use of variant GA enzymes. These enzymes may be prepared by recombinant methods utilizing any of a number of glucoamylase genes known in the art (e.g., the *H. grisea* glucoamylase gene comprising SEQ ID NO:1 or recombinant sequence shown in SEQ ID NO:2). Any convenient method for introducing mutations may be employed, including site directed mutagenesis. As indicated above, mutations (or variations) include substitutions, additions, deletions or truncations that will correspond to one or more amino acid changes in the expressed GA variant. Again, site directed mutagenesis and other methods of incorporating amino acid changes in expressed proteins at the DNA level can be found in numerous references, e.g., Green and Sambrook, et al. 2012 and Ausubel, et al.

DNA encoding an amino acid sequence variant of a parent GA is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the parent GA enzyme.

Site-directed mutagenesis is one method that can be employed in preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the parent GA. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a desired glucoamylase can be determined, and a nucleic acid sequence encoding such amino acid sequence variant can be generated synthetically.

The desired glucoamylase(s) so prepared may be subjected to further modifications, oftentimes depending on the intended use of the glucoamylase. Such modifications may involve further alteration of the amino acid sequence, fusion to heterologous polypeptide(s) and/or covalent modifications.

III. Variant GA Polypeptides and Nucleic Acids Encoding Same

Glucoamylases (GAs) are produced by numerous strains of bacteria, fungi, yeast and plants. Many fungal glucoamylases are secreted from the cell, for example from strains of *Aspergillus* (Svensson et al., Carlsberg Res. Commun. 48: 529-544 (1983); Boel et al., EMBO J. 3: 1097-1102 (1984); Hayashida et al., Agric. Biol. Chem. 53: 923-929 (1989); U.S. Pat. No. 5,024,941; U.S. Pat. No. 4,794,175 and WO 88/09795); *Talaromyces* (U.S. Pat. No. 4,247,637; U.S. Pat. No. 6,255,084; and U.S. Pat. No. 6,620,924); *Rhizopus* (Ashikari et al., Agric. Biol. Chem. 50: 957-964 (1986); Ashikari et al., App. Microbio. Biotech. 32: 129-133 (1989) and U.S. Pat. No. 4,863,864); *Humicola* (WO 05/052148 and U.S. Pat. No. 4,618,579); and *Mucor* (Houghton-Larsen et al., Appl. Microbiol. Biotechnol. 62: 210-217 (2003)). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States. In general, glucoamylases may be, and commonly are, used with alpha-amylases in starch hydrolyzing processes to hydrolyze starch to dextrins and then glucose. The glucose may be used directly; be converted to fructose by other enzymes (e.g., glucose isomerases); crystallized; or used in fermentations to produce numerous end products (e.g., ethanol, citric acid, succinic acid, ascorbic acid intermediates, glutamic acid, glycerol, 1,3-propanediol and lactic acid).

Glucoamylases consist of as many as three distinct structural domains, a catalytic domain of approximately 450 residues that is structurally conserved in all glucoamylases, generally followed by a linker region consisting of between 30 and 80 residues that are connected to a starch binding domain (SBD) of approximately 100 residues (also referred to as a carbohydrate binding domain, or CBD). The structure of the *Trichoderma reesei* glucoamylase (TrGA) with all three regions intact was determined to 1.8 Angstrom resolution. See WO 2009/048488 and WO 2009/048487, incorporated herein by reference. Using the determined coordinates, the structure was aligned with the coordinates of the catalytic domain of the glucoamylase from *Aspergillus awamori* strain X100 that was determined previously (Aleshin, A. E., Hoffman, C., Firsov, L. M., and Honzatko, R. B. Refined crystal structures of glucoamylase from *Aspergillus awamori* var. X100. J. Mol. Biol. 238: 575-591 (1994)). The structure of the catalytic domains of these two glucoamylases overlap very closely, and it is possible to identify equivalent residues based on this structural superposition. It is further believed that all glucoamylases share the basic structure.

Given the well-known structure and function relationship of glucoamylases, glucoamylase variants having altered properties have been successfully created and characterized. Certain variants display improved properties as compared to the parent glucoamylases. Examples of improved properties include increased thermostability and increased specific activity. Methods for making and characterizing *T. reesei* GA variants with altered properties have been described in WO 2009/067218 (incorporated herein by reference).

Variant GA enzymes are described herein. The variant GA enzymes have one or more mutations, as set forth herein, with respect to a parent GA enzyme, where the parent GA enzyme has at least 60% (i.e., 60% or greater) amino acid sequence identity to SEQ ID NO:4, including at least 61%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, up to and including 100% amino acid sequence identity to SEQ ID NO:4. Variant GA enzymes (i.e., having one or more mutations) may have at least 60% (i.e., 60% or greater) amino acid sequence identity to SEQ ID NO:4, including at least 61%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4. In certain embodiments, the parent GA is selected from: a *Trichoderma* strain (e.g., *T. reesei, T. longibrachiatum, T. strictipilis, T. asperellum, T. konilangbra, T. citrinoviride, T. pseudokoningii* and *T. hazianum*), an *Aspergillus* strain (e.g. *A. aculeatus, A. niger, A. nidulans, A. kawachi, A. awamori, A. clavatus, A. terreus, A. fumigates*, and *A. orzyae*), a *Talaromyces* strain (e.g. *T. emersonii, T. thermophilus*, and *T. duponti*), a *Trametes* strain (e.g., *Trametes cingulata*), a *Hypocrea* strain (e.g. *H. gelatinosa, H. orientalis, H. vinosa, H. jecorina, H. schweinitzii*, and *H. citrina*), a *Fusarium* strain (e.g., *F. oxysporum*, and *F. roseum*), a *Humicola* strain (e.g., *H. grisea, H. insolens* and *H. lanuginose*), a *Saccharomycopsis* strain (e.g., *S. fibuligera*), *Scytalidium thermophilum, Podospora anderina*, or their respective anamorph, teleomorph or holomorph counterpart forms. In some cases the parent GA is *Humicola grisea* GA (HgGA). Further, the variant GA enzyme has starch hydrolysis activity (or is a variant GA fragment having starch hydrolysis activity) where, in certain embodiments, the variant GA has an improved property as compared to the parent GA (as detailed herein). The amino acid sequence for the wild type full-length (SEQ ID NO:3) and mature form (SEQ ID NO:4) of HgGA is shown in FIG. 1.

Aspects of the present invention provide variants of a parent GA enzyme, where the variant has starch hydrolysis activity, has at least 60% (e.g., at least 80%) sequence identity to SEQ ID NO:4, and has at least one improved property over the parent GA enzyme selected from: (a) expression, (b) hydrolytic activity on DP2 substrate, (c) hydrolytic activity on DP7 substrate at pH 6.8, (d) hydrolytic activity on DP7 substrate at pH 5.5, (e) hydrolytic activity on panose substrate, (f) hydrolytic activity on pullulan substrate, (g) hydrolytic activity on granular corn starch (CS), (h) thermostability, (i) glucose inhibition, and (j) reversion activity.

In certain embodiments, a GA variant has at least two, at least three, at least four, at least five, at least six, at least seven, at least 8, at least 9, or more improved properties (selected from the list above) over the parent GA enzyme. In certain embodiments, a variant GA enzyme comprises an amino acid mutation at one or more amino acid positions in HgGA (as denoted in SEQ ID NO:3). Because certain parent GA enzymes according to aspects of the invention may not have the same amino acid as wild type HgGA, amino acid positions corresponding to the residues noted above may also be designated either by the position number alone (e.g., amino acid position 35, as denoted in Table 8) or with an "X"

prefix (e.g., amino acid position X35). It is noted here that all three ways of designating the amino acid positions corresponding to a specific amino acid residue in HgGA are interchangeable (i.e., X35, T35, and amino acid 35).

Alignment of amino acid sequences to determine homology can be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada. See also the description of "percent sequence identity" provided in the Definitions section above.

In certain embodiments, a variant GA enzyme contains an amino acid substitution at one or more site corresponding to the sites shown in Table 8 for HgGA (see Example 3; amino acid numbering is based on the amino acid sequence of full-length HgGA shown in SEQ ID NO:3). All possible combinations of the substitutions shown in Table 8 at the indicated sites are contemplated embodiments of the invention. Variants include, but are not limited to, the following:

1. A GA variant as described above (i.e., a GA variant that has starch hydrolysis activity, has at least 60% (e.g., at least 80%) sequence identity to amino acids SEQ ID NO:4, and has at least one improved property over the parent GA enzyme selected from (a) to (j) above) where the GA variant has at least one amino acid substitution at a position selected from the group consisting of: T35, K41, P60, L97, N100, T107, A175, K183, E229, T245, G263, P293, E294, N299, L300, R308, K334, S342, Y364, I367, V369, Q373, G374, S382, V393, S394, T397, K400, S402, T406, N407, V409, N410, A411, A414, I461, G466, L467, V468, P469, P470, S471, V476, A477, K478, S479, Q480, S483, T484, P503, K505, Q506, A522, T544, N556, G587, A589, T599, N600, T604, S607, P609, A31, I37, N46, K57, D85, L105, K171, K179, S184, P213, A221, T239, Q250, L252, N260, S261, K262, N264, E274, A295, A325, K328, A366, Y368, N371, K372, I376, S380, V381, P384, R387, V390, S391, T395, G396, S399, S401, S403, F405, I408, A448, D462, W472, S475, S486, A491, S511, S515, A524, V537, S538, A540, W541, G542, V551, P552, K561, A562, T564, L565, N573, A585, V590, Q591, V597, G601, I603, D608, I613, T614, S620, S632, A32, V33, N38, T39, T74, H99, T104, N111, K118, Q121, I164, Q168, I174, G177, S180, T181, V190, K191, A198, L227, L233, Q236, D238, E240, A243, A248, V251, Q255, Y275, N290, F291, D292, G296, D298, T301, F302, A311, A315, S319, G329, A331, Q332, V345, A360, D365, W370, T379, F386, L389, S392, Y398, K413, A416, D417, S429, A434, K443, A460, R463, R464, A465, R473, L481, T493, S499, S501, V531, R536, V548, N550, A553, L554, G555, D558, T559, S560, S572, D574, S578, K584, S588, I595, K596, K602, W605, E606, R611, S612, S619, V629, D34, P42, I43, K47, A50, N55, A58, A62, A64, I68, S72, R73, D75, P77, T83, L90, S96, G98, Y101, T103, I109, Q110, V113, S115, V122, S123, S126, T128, F129, A146, T148, E150, A165, L166, Y169, A170, A182, V185, P188, L194, T197, F206, F218, S222, H224, A226, Y232, L237, P249, Q256, A257, F258, W259, Y265, V267, S268, G272, G273, S277, D280, A281, I284, A286, S287, Q303, S306, E307, H313, Y316, D318, N322, V336, A337, N348, A355, N356, A359, L363, S375, T377, V378, L383, F385, D388, T404, E421, V422, A424, K425, Y426, A432, N440, S446, T451, F457, R487, I488, V495, A496, A497, F502, S504, A513, P516, P520, T521, S527, V529, T532, N534, E535, T539, E543, I545, V547, G549, K571, L576, I579, I583, T586, Y592, Y594, G622, Q627, T628, N630, and D631 (where the position of each amino acid substitution corresponds to SEQ ID NO:3).

2. The GA variant of 1 above and having a T35A substitution.

3. The GA variant of 1 above and having a T35P substitution.

4. The GA variant of 1 above and having a T35C substitution.

5. The GA variant of 1 above and having a T35F substitution.

6. The GA variant of 1 above and having a T35K substitution.

7. The GA variant of 1 above and having a T35L substitution.

8. The GA variant of 1 above and having a T35Q substitution.

9. The GA variant of 1 above and having a T35R substitution.

10. The GA variant of 1 above and having a T35W substitution.

11. The GA variant of 1 above and having a T35Y substitution.

12. The GA variant of 1 above and having a T35H substitution.

13. The GA variant of any one of 1 to 12 above and having a K41C substitution.

14. The GA variant of any one of 1 to 12 above and having a K41S substitution.

15. The GA variant of any one of 1 to 12 above and having a K41T substitution.

16. The GA variant of any one of 1 to 12 above and having a K41W substitution.

17. The GA variant of any one of 1 to 12 above and having a K41D substitution.

18. The GA variant of any one of 1 to 12 above and having a K41H substitution.

19. The GA variant of any one of 1 to 12 above and having a K41L substitution.

20. The GA variant of any one of 1 to 12 above and having a K41N substitution.

21. The GA variant of any one of 1 to 12 above and having a K41P substitution.

22. The GA variant of any one of 1 to 12 above and having a K41R substitution.

23. The GA variant of any one of 1 to 12 above and having a K41E substitution.

24. The GA variant of any one of 1 to 23 above and having a P60V substitution.

25. The GA variant of any one of 1 to 23 above and having a P60G substitution.

26. The GA variant of any one of 1 to 23 above and having a P60H substitution.

27. The GA variant of any one of 1 to 23 above and having a P60M substitution.

28. The GA variant of any one of 1 to 23 above and having a P60R substitution.

29. The GA variant of any one of 1 to 23 above and having a P60I substitution.

30. The GA variant of any one of 1 to 23 above and having a P60W substitution.

31. The GA variant of any one of 1 to 23 above and having a P60F substitution.

32. The GA variant of any one of 1 to 23 above and having a P60T substitution.

33. The GA variant of any one of 1 to 23 above and having a P60Q substitution.

34. The GA variant of any one of 1 to 33 above and having a L97A substitution.

35. The GA variant of any one of 1 to 33 above and having a L97G substitution.

36. The GA variant of any one of 1 to 33 above and having a L97Q substitution.

37. The GA variant of any one of 1 to 33 above and having a L97E substitution.

38. The GA variant of any one of 1 to 33 above and having a L97T substitution.

39. The GA variant of any one of 1 to 33 above and having a L97V substitution.

40. The GA variant of any one of 1 to 33 above and having a L97F substitution.

41. The GA variant of any one of 1 to 33 above and having a L97C substitution.

42. The GA variant of any one of 1 to 33 above and having a L97H substitution.

43. The GA variant of any one of 1 to 33 above and having a L97I substitution.

44. The GA variant of any one of 1 to 33 above and having a L97N substitution.

45. The GA variant of any one of 1 to 44 above and having a N100P substitution.

46. The GA variant of any one of 1 to 44 above and having a N100E substitution.

47. The GA variant of any one of 1 to 44 above and having a N100V substitution.

48. The GA variant of any one of 1 to 44 above and having a N100C substitution.

49. The GA variant of any one of 1 to 44 above and having a N100I substitution.

50. The GA variant of any one of 1 to 44 above and having a N100M substitution.

51. The GA variant of any one of 1 to 44 above and having a N100Q substitution.

52. The GA variant of any one of 1 to 44 above and having a N100T substitution.

53. The GA variant of any one of 1 to 44 above and having a N100F substitution.

54. The GA variant of any one of 1 to 44 above and having a N100G substitution.

55. The GA variant of any one of 1 to 44 above and having a N100K substitution.

56. The GA variant of any one of 1 to 44 above and having a N100S substitution.

57. The GA variant of any one of 1 to 44 above and having a N100W substitution.

58. The GA variant of any one of 1 to 44 above and having a N100Y substitution.

59. The GA variant of any one of 1 to 44 above and having a N100A substitution.

60. The GA variant of any one of 1 to 44 above and having a N100L substitution.

61. The GA variant of any one of 1 to 44 above and having a N100R substitution.

62. The GA variant of any one of 1 to 61 above and having a T107A substitution.

63. The GA variant of any one of 1 to 61 above and having a T107W substitution.

64. The GA variant of any one of 1 to 61 above and having a T107Y substitution.

65. The GA variant of any one of 1 to 61 above and having a T107H substitution.

66. The GA variant of any one of 1 to 61 above and having a T107G substitution.

67. The GA variant of any one of 1 to 61 above and having a T107I substitution.

68. The GA variant of any one of 1 to 61 above and having a T107S substitution.

69. The GA variant of any one of 1 to 61 above and having a T107V substitution.

70. The GA variant of any one of 1 to 61 above and having a T107K substitution.

71. The GA variant of any one of 1 to 61 above and having a T107C substitution.

72. The GA variant of any one of 1 to 61 above and having a T107D substitution.

73. The GA variant of any one of 1 to 61 above and having a T107E substitution.

74. The GA variant of any one of 1 to 61 above and having a T107M substitution.

75. The GA variant of any one of 1 to 61 above and having a T107N substitution.

76. The GA variant of any one of 1 to 75 above and having an A175F substitution.

77. The GA variant of any one of 1 to 75 above and having an A175E substitution.

78. The GA variant of any one of 1 to 75 above and having an A175H substitution.

79. The GA variant of any one of 1 to 75 above and having an A175K substitution.

80. The GA variant of any one of 1 to 75 above and having an A175M substitution.

81. The GA variant of any one of 1 to 75 above and having an A175N substitution.

82. The GA variant of any one of 1 to 75 above and having an A175Q substitution.

83. The GA variant of any one of 1 to 75 above and having an A175R substitution.

84. The GA variant of any one of 1 to 75 above and having an A175S substitution.

85. The GA variant of any one of 1 to 75 above and having an A175T substitution.

86. The GA variant of any one of 1 to 75 above and having an A175V substitution.

87. The GA variant of any one of 1 to 75 above and having an A175C substitution.

88. The GA variant of any one of 1 to 87 above and having a K183H substitution.

89. The GA variant of any one of 1 to 87 above and having a K183E substitution.

90. The GA variant of any one of 1 to 87 above and having a K183I substitution.

91. The GA variant of any one of 1 to 87 above and having a K183Q substitution.

92. The GA variant of any one of 1 to 87 above and having a K183R substitution.

93. The GA variant of any one of 1 to 87 above and having a K183V substitution.

94. The GA variant of any one of 1 to 87 above and having a K183Y substitution.

95. The GA variant of any one of 1 to 87 above and having a K183D substitution.

96. The GA variant of any one of 1 to 87 above and having a K183F substitution.

97. The GA variant of any one of 1 to 87 above and having a K183T substitution.

98. The GA variant of any one of 1 to 87 above and having a K183W substitution.

99. The GA variant of any one of 1 to 98 above and having an E229A substitution.

100. The GA variant of any one of 1 to 98 above and having an E229D substitution.

101. The GA variant of any one of 1 to 98 above and having an E229G substitution.

102. The GA variant of any one of 1 to 98 above and having an E229M substitution.

103. The GA variant of any one of 1 to 98 above and having an E229T substitution.

104. The GA variant of any one of 1 to 98 above and having an E229W substitution.

105. The GA variant of any one of 1 to 98 above and having an E229I substitution.

106. The GA variant of any one of 1 to 98 above and having an E229L substitution.

107. The GA variant of any one of 1 to 98 above and having an E229Y substitution.

108. The GA variant of any one of 1 to 98 above and having an E229C substitution.

109. The GA variant of any one of 1 to 98 above and having an E229F substitution.

110. The GA variant of any one of 1 to 98 above and having an E229K substitution.

111. The GA variant of any one of 1 to 98 above and having an E229V substitution.

112. The GA variant of any one of 1 to 111 above and having a T245L substitution.

113. The GA variant of any one of 1 to 111 above and having a T245C substitution.

114. The GA variant of any one of 1 to 111 above and having a T245I substitution.

115. The GA variant of any one of 1 to 111 above and having a T245R substitution.

116. The GA variant of any one of 1 to 111 above and having a T245H substitution.

117. The GA variant of any one of 1 to 111 above and having a T245M substitution.

118. The GA variant of any one of 1 to 111 above and having a T245Q substitution.

119. The GA variant of any one of 1 to 111 above and having a T245S substitution.

120. The GA variant of any one of 1 to 111 above and having a T245V substitution.

121. The GA variant of any one of 1 to 111 above and having a T245Y substitution.

122. The GA variant of any one of 1 to 111 above and having a T245F substitution.

123. The GA variant of any one of 1 to 111 above and having a T245W substitution.

124. The GA variant of any one of 1 to 123 above and having a G263A substitution.

125. The GA variant of any one of 1 to 123 above and having a G263C substitution.

126. The GA variant of any one of 1 to 123 above and having a G263E substitution.

127. The GA variant of any one of 1 to 123 above and having a G263H substitution.

128. The GA variant of any one of 1 to 123 above and having a G263L substitution.

129. The GA variant of any one of 1 to 123 above and having a G263Q substitution.

130. The GA variant of any one of 1 to 123 above and having a G263R substitution.

131. The GA variant of any one of 1 to 123 above and having a G263S substitution.

132. The GA variant of any one of 1 to 123 above and having a G263T substitution.

133. The GA variant of any one of 1 to 123 above and having a G263Y substitution.

134. The GA variant of any one of 1 to 133 above and having a P293T substitution.

135. The GA variant of any one of 1 to 133 above and having a P293A substitution.

136. The GA variant of any one of 1 to 133 above and having a P293C substitution.

137. The GA variant of any one of 1 to 133 above and having a P293E substitution.

138. The GA variant of any one of 1 to 133 above and having a P293F substitution.

139. The GA variant of any one of 1 to 133 above and having a P293G substitution.

140. The GA variant of any one of 1 to 133 above and having a P293H substitution.

141. The GA variant of any one of 1 to 133 above and having a P293L substitution.

142. The GA variant of any one of 1 to 133 above and having a P293R substitution.

143. The GA variant of any one of 1 to 133 above and having a P293S substitution.

144. The GA variant of any one of 1 to 133 above and having a P293Y substitution.

145. The GA variant of any one of 1 to 133 above and having a P293Q substitution.

146. The GA variant of any one of 1 to 145 above and having an E294D substitution.

147. The GA variant of any one of 1 to 145 above and having an E294G substitution.

148. The GA variant of any one of 1 to 145 above and having an E294I substitution.

149. The GA variant of any one of 1 to 145 above and having an E294K substitution.

150. The GA variant of any one of 1 to 145 above and having an E294L substitution.

151. The GA variant of any one of 1 to 145 above and having an E294M substitution.

152. The GA variant of any one of 1 to 145 above and having an E294N substitution.

153. The GA variant of any one of 1 to 145 above and having an E294S substitution.

154. The GA variant of any one of 1 to 145 above and having an E294V substitution.

155. The GA variant of any one of 1 to 145 above and having an E294W substitution.

156. The GA variant of any one of 1 to 145 above and having an E294A substitution.

157. The GA variant of any one of 1 to 145 above and having an E294C substitution.

158. The GA variant of any one of 1 to 157 above and having a N299A substitution.

159. The GA variant of any one of 1 to 157 above and having a N299C substitution.

160. The GA variant of any one of 1 to 157 above and having a N299E substitution.

161. The GA variant of any one of 1 to 157 above and having a N299G substitution.

162. The GA variant of any one of 1 to 157 above and having a N299L substitution.

163. The GA variant of any one of 1 to 157 above and having a N299Q substitution.

164. The GA variant of any one of 1 to 157 above and having a N299T substitution.

165. The GA variant of any one of 1 to 157 above and having a N299V substitution.

166. The GA variant of any one of 1 to 157 above and having a N299P substitution.

167. The GA variant of any one of 1 to 157 above and having a N299R substitution.

168. The GA variant of any one of 1 to 157 above and having a N299S substitution.

169. The GA variant of any one of 1 to 168 above and having a L300I substitution.

170. The GA variant of any one of 1 to 168 above and having a L300K substitution.

171. The GA variant of any one of 1 to 168 above and having a L300N substitution.

172. The GA variant of any one of 1 to 168 above and having a L300A substitution.

173. The GA variant of any one of 1 to 168 above and having a L300C substitution.

174. The GA variant of any one of 1 to 168 above and having a L300D substitution.

175. The GA variant of any one of 1 to 168 above and having a L300E substitution.

176. The GA variant of any one of 1 to 168 above and having a L300F substitution.

177. The GA variant of any one of 1 to 168 above and having a L300G substitution.

178. The GA variant of any one of 1 to 168 above and having a L300H substitution.

179. The GA variant of any one of 1 to 168 above and having a L300P substitution.

180. The GA variant of any one of 1 to 168 above and having a L300Q substitution.

181. The GA variant of any one of 1 to 168 above and having a L300R substitution.

182. The GA variant of any one of 1 to 168 above and having a L300S substitution.

183. The GA variant of any one of 1 to 168 above and having a L300T substitution.

184. The GA variant of any one of 1 to 168 above and having a L300V substitution.

185. The GA variant of any one of 1 to 168 above and having a L300W substitution.

186. The GA variant of any one of 1 to 168 above and having a L300Y substitution.

187. The GA variant of any one of 1 to 186 above and having a R308I substitution.

188. The GA variant of any one of 1 to 186 above and having a R308F substitution.

189. The GA variant of any one of 1 to 186 above and having a R308L substitution.

190. The GA variant of any one of 1 to 186 above and having a R308A substitution.

191. The GA variant of any one of 1 to 186 above and having a R308D substitution.

192. The GA variant of any one of 1 to 186 above and having a R308E substitution.

193. The GA variant of any one of 1 to 186 above and having a R308G substitution.

194. The GA variant of any one of 1 to 186 above and having a R308H substitution.

195. The GA variant of any one of 1 to 186 above and having a R308K substitution.

196. The GA variant of any one of 1 to 186 above and having a R308M substitution.

197. The GA variant of any one of 1 to 186 above and having a R308Q substitution.

198. The GA variant of any one of 1 to 186 above and having a R308T substitution.

199. The GA variant of any one of 1 to 186 above and having a R308W substitution.

200. The GA variant of any one of 1 to 186 above and having a R308V substitution.

201. The GA variant of any one of 1 to 200 above and having a K334C substitution.

202. The GA variant of any one of 1 to 200 above and having a K334G substitution.

203. The GA variant of any one of 1 to 200 above and having a K334I substitution.

204. The GA variant of any one of 1 to 200 above and having a K334L substitution.

205. The GA variant of any one of 1 to 200 above and having a K334T substitution.

206. The GA variant of any one of 1 to 200 above and having a K334W substitution.

207. The GA variant of any one of 1 to 200 above and having a K334D substitution.

208. The GA variant of any one of 1 to 200 above and having a K334V substitution.

209. The GA variant of any one of 1 to 200 above and having a K334A substitution.

210. The GA variant of any one of 1 to 200 above and having a K334E substitution.

211. The GA variant of any one of 1 to 200 above and having a K334F substitution.

212. The GA variant of any one of 1 to 200 above and having a K334R substitution.

213. The GA variant of any one of 1 to 200 above and having a K334Y substitution.

214. The GA variant of any one of 1 to 213 above and having a S342G substitution.

215. The GA variant of any one of 1 to 213 above and having a S342L substitution.

216. The GA variant of any one of 1 to 213 above and having a S342T substitution.

217. The GA variant of any one of 1 to 213 above and having a S342W substitution.

218. The GA variant of any one of 1 to 213 above and having a S342Y substitution.

219. The GA variant of any one of 1 to 213 above and having a S342C substitution.

220. The GA variant of any one of 1 to 213 above and having a S342E substitution.

221. The GA variant of any one of 1 to 213 above and having a S342F substitution.

222. The GA variant of any one of 1 to 213 above and having a S342N substitution.

223. The GA variant of any one of 1 to 213 above and having a S342Q substitution.

224. The GA variant of any one of 1 to 213 above and having a S342K substitution.

225. The GA variant of any one of 1 to 213 above and having a S342M substitution.

226. The GA variant of any one of 1 to 213 above and having a S342P substitution.

227. The GA variant of any one of 1 to 213 above and having a S342R substitution.

228. The GA variant of any one of 1 to 213 above and having a S342V substitution.

229. The GA variant of any one of 1 to 228 above and having a Y364E substitution.

230. The GA variant of any one of 1 to 228 above and having a Y364R substitution.

231. The GA variant of any one of 1 to 228 above and having a Y364W substitution.

232. The GA variant of any one of 1 to 228 above and having a Y364G substitution.

233. The GA variant of any one of 1 to 228 above and having a Y364Q substitution.

234. The GA variant of any one of 1 to 228 above and having a Y364H substitution.

235. The GA variant of any one of 1 to 228 above and having a Y364I substitution.

236. The GA variant of any one of 1 to 228 above and having a Y364L substitution.

237. The GA variant of any one of 1 to 228 above and having a Y364M substitution.

238. The GA variant of any one of 1 to 228 above and having a Y364N substitution.

239. The GA variant of any one of 1 to 228 above and having a Y364S substitution.

240. The GA variant of any one of 1 to 228 above and having a Y364V substitution.

241. The GA variant of any one of 1 to 240 above and having an I367G substitution.

242. The GA variant of any one of 1 to 240 above and having an I367E substitution.

243. The GA variant of any one of 1 to 240 above and having an I367F substitution.

244. The GA variant of any one of 1 to 240 above and having an I367K substitution.

245. The GA variant of any one of 1 to 240 above and having an I367L substitution.

246. The GA variant of any one of 1 to 240 above and having an I367M substitution.

247. The GA variant of any one of 1 to 240 above and having an I367S substitution.

248. The GA variant of any one of 1 to 240 above and having an I367V substitution.

249. The GA variant of any one of 1 to 240 above and having an I367W substitution.

250. The GA variant of any one of 1 to 240 above and having an I367Y substitution.

251. The GA variant of any one of 1 to 250 above and having a V369F substitution.

252. The GA variant of any one of 1 to 250 above and having a V369Q substitution.

253. The GA variant of any one of 1 to 250 above and having a V369C substitution.

254. The GA variant of any one of 1 to 250 above and having a V369I substitution.

255. The GA variant of any one of 1 to 250 above and having a V369K substitution.

256. The GA variant of any one of 1 to 250 above and having a V369L substitution.

257. The GA variant of any one of 1 to 250 above and having a V369N substitution.

258. The GA variant of any one of 1 to 250 above and having a V369S substitution.

259. The GA variant of any one of 1 to 250 above and having a V369T substitution.

260. The GA variant of any one of 1 to 250 above and having a V369Y substitution.

261. The GA variant of any one of 1 to 250 above and having a V369A substitution.

262. The GA variant of any one of 1 to 250 above and having a V369E substitution.

263. The GA variant of any one of 1 to 250 above and having a V369G substitution.

264. The GA variant of any one of 1 to 250 above and having a V369M substitution.

265. The GA variant of any one of 1 to 264 above and having a Q373D substitution.

266. The GA variant of any one of 1 to 264 above and having a Q373E substitution.

267. The GA variant of any one of 1 to 264 above and having a Q373F substitution.

268. The GA variant of any one of 1 to 264 above and having a Q373G substitution.

269. The GA variant of any one of 1 to 264 above and having a Q373L substitution.

270. The GA variant of any one of 1 to 264 above and having a Q373N substitution.

271. The GA variant of any one of 1 to 264 above and having a Q373R substitution.

272. The GA variant of any one of 1 to 264 above and having a Q373S substitution.

273. The GA variant of any one of 1 to 264 above and having a Q373T substitution.

274. The GA variant of any one of 1 to 264 above and having a Q373C substitution.

275. The GA variant of any one of 1 to 264 above and having a Q373H substitution.

276. The GA variant of any one of 1 to 264 above and having a Q373K substitution.

277. The GA variant of any one of 1 to 264 above and having a Q373V substitution.

278. The GA variant of any one of 1 to 277 above and having a G374D substitution.

279. The GA variant of any one of 1 to 277 above and having a G374E substitution.

280. The GA variant of any one of 1 to 277 above and having a G374F substitution.

281. The GA variant of any one of 1 to 277 above and having a G374K substitution.

282. The GA variant of any one of 1 to 277 above and having a G374R substitution.

283. The GA variant of any one of 1 to 277 above and having a G374T substitution.

284. The GA variant of any one of 1 to 277 above and having a G374V substitution.

285. The GA variant of any one of 1 to 277 above and having a G374W substitution.

286. The GA variant of any one of 1 to 277 above and having a G374C substitution.

287. The GA variant of any one of 1 to 277 above and having a G374L substitution.

288. The GA variant of any one of 1 to 277 above and having a G374M substitution.

289. The GA variant of any one of 1 to 277 above and having a G374P substitution.

290. The GA variant of any one of 1 to 277 above and having a G374S substitution.

291. The GA variant of any one of 1 to 277 above and having a G374A substitution.

292. The GA variant of any one of 1 to 277 above and having a G374Y substitution.

293. The GA variant of any one of 1 to 292 above and having a S382D substitution.

294. The GA variant of any one of 1 to 292 above and having a S382H substitution.

295. The GA variant of any one of 1 to 292 above and having a S382C substitution.

296. The GA variant of any one of 1 to 292 above and having a S382P substitution.

297. The GA variant of any one of 1 to 292 above and having a S382Q substitution.

298. The GA variant of any one of 1 to 292 above and having a S382E substitution.

299. The GA variant of any one of 1 to 292 above and having a S382G substitution.

300. The GA variant of any one of 1 to 292 above and having a S382N substitution.

301. The GA variant of any one of 1 to 292 above and having a S382T substitution.

302. The GA variant of any one of 1 to 292 above and having a S382V substitution.

303. The GA variant of any one of 1 to 302 above and having a V393A substitution.

304. The GA variant of any one of 1 to 302 above and having a V393W substitution.

305. The GA variant of any one of 1 to 302 above and having a V393E substitution.

306. The GA variant of any one of 1 to 302 above and having a V393G substitution.

307. The GA variant of any one of 1 to 302 above and having a V393T substitution.

308. The GA variant of any one of 1 to 302 above and having a V393Y substitution.

309. The GA variant of any one of 1 to 302 above and having a V393F substitution.

310. The GA variant of any one of 1 to 302 above and having a V393H substitution.

311. The GA variant of any one of 1 to 302 above and having a V393I substitution.

312. The GA variant of any one of 1 to 302 above and having a V393L substitution.

313. The GA variant of any one of 1 to 302 above and having a V393N substitution.

314. The GA variant of any one of 1 to 313 above and having a S394F substitution.

315. The GA variant of any one of 1 to 313 above and having a S394G substitution.

316. The GA variant of any one of 1 to 313 above and having a S394H substitution.

317. The GA variant of any one of 1 to 313 above and having a S394I substitution.

318. The GA variant of any one of 1 to 313 above and having a S394N substitution.

319. The GA variant of any one of 1 to 313 above and having a S394A substitution.

320. The GA variant of any one of 1 to 313 above and having a S394C substitution.

321. The GA variant of any one of 1 to 313 above and having a S394D substitution.

322. The GA variant of any one of 1 to 313 above and having a S394L substitution.

323. The GA variant of any one of 1 to 313 above and having a S394M substitution.

324. The GA variant of any one of 1 to 313 above and having a S394P substitution.

325. The GA variant of any one of 1 to 313 above and having a S394Y substitution.

326. The GA variant of any one of 1 to 325 above and having a T397A substitution.

327. The GA variant of any one of 1 to 325 above and having a T397G substitution.

328. The GA variant of any one of 1 to 325 above and having a T397F substitution.

329. The GA variant of any one of 1 to 325 above and having a T397L substitution.

330. The GA variant of any one of 1 to 325 above and having a T397Q substitution.

331. The GA variant of any one of 1 to 325 above and having a T397V substitution.

332. The GA variant of any one of 1 to 325 above and having a T397W substitution.

333. The GA variant of any one of 1 to 325 above and having a T397Y substitution.

334. The GA variant of any one of 1 to 325 above and having a T397K substitution.

335. The GA variant of any one of 1 to 325 above and having a T397R substitution.

336. The GA variant of any one of 1 to 335 above and having a K400A substitution.

337. The GA variant of any one of 1 to 335 above and having a K400E substitution.

338. The GA variant of any one of 1 to 335 above and having a K400G substitution.

339. The GA variant of any one of 1 to 335 above and having a K400L substitution.

340. The GA variant of any one of 1 to 335 above and having a K400R substitution.

341. The GA variant of any one of 1 to 335 above and having a K400S substitution.

342. The GA variant of any one of 1 to 335 above and having a K400V substitution.

343. The GA variant of any one of 1 to 335 above and having a K400W substitution.

344. The GA variant of any one of 1 to 335 above and having a K400Y substitution.

345. The GA variant of any one of 1 to 335 above and having a K400P substitution.

346. The GA variant of any one of 1 to 345 above and having a S402D substitution.

347. The GA variant of any one of 1 to 345 above and having a S402I substitution.

348. The GA variant of any one of 1 to 345 above and having a S402N substitution.

349. The GA variant of any one of 1 to 345 above and having a S402P substitution.

350. The GA variant of any one of 1 to 345 above and having a S402T substitution.

351. The GA variant of any one of 1 to 345 above and having a S402W substitution.

352. The GA variant of any one of 1 to 345 above and having a S402R substitution.

353. The GA variant of any one of 1 to 345 above and having a S402F substitution.

354. The GA variant of any one of 1 to 345 above and having a S402K substitution.

355. The GA variant of any one of 1 to 345 above and having a S402M substitution.

356. The GA variant of any one of 1 to 355 above and having a T406C substitution.

357. The GA variant of any one of 1 to 355 above and having a T406A substitution.

358. The GA variant of any one of 1 to 355 above and having a T406D substitution.

359. The GA variant of any one of 1 to 355 above and having a T406G substitution.

360. The GA variant of any one of 1 to 355 above and having a T406H substitution.

361. The GA variant of any one of 1 to 355 above and having a T406I substitution.

362. The GA variant of any one of 1 to 355 above and having a T406L substitution.

363. The GA variant of any one of 1 to 355 above and having a T406N substitution.

364. The GA variant of any one of 1 to 355 above and having a T406P substitution.

365. The GA variant of any one of 1 to 355 above and having a T406R substitution.

366. The GA variant of any one of 1 to 355 above and having a T406S substitution.

367. The GA variant of any one of 1 to 355 above and having a T406V substitution.

368. The GA variant of any one of 1 to 355 above and having a T406W substitution.

369. The GA variant of any one of 1 to 355 above and having a T406E substitution.

370. The GA variant of any one of 1 to 369 above and having a N407C substitution.

371. The GA variant of any one of 1 to 369 above and having a N407G substitution.

372. The GA variant of any one of 1 to 369 above and having a N407I substitution.

373. The GA variant of any one of 1 to 369 above and having a N407K substitution.

374. The GA variant of any one of 1 to 369 above and having a N407L substitution.

375. The GA variant of any one of 1 to 369 above and having a N407Q substitution.

376. The GA variant of any one of 1 to 369 above and having a N407R substitution.

377. The GA variant of any one of 1 to 369 above and having a N407A substitution.

378. The GA variant of any one of 1 to 369 above and having a N407P substitution.

379. The GA variant of any one of 1 to 369 above and having a N407S substitution.

380. The GA variant of any one of 1 to 369 above and having a N407W substitution.

381. The GA variant of any one of 1 to 380 above and having a V409C substitution.

382. The GA variant of any one of 1 to 380 above and having a V409G substitution.

383. The GA variant of any one of 1 to 380 above and having a V409H substitution.

384. The GA variant of any one of 1 to 380 above and having a V409K substitution.

385. The GA variant of any one of 1 to 380 above and having a V409D substitution.

386. The GA variant of any one of 1 to 380 above and having a V409E substitution.

387. The GA variant of any one of 1 to 380 above and having a V409L substitution.

388. The GA variant of any one of 1 to 380 above and having a V409M substitution.

389. The GA variant of any one of 1 to 380 above and having a V409R substitution.

390. The GA variant of any one of 1 to 380 above and having a V409W substitution.

391. The GA variant of any one of 1 to 380 above and having a V409Y substitution.

392. The GA variant of any one of 1 to 391 above and having a N410I substitution.

393. The GA variant of any one of 1 to 391 above and having a N410G substitution.

394. The GA variant of any one of 1 to 391 above and having a N410Q substitution.

395. The GA variant of any one of 1 to 391 above and having a N410Y substitution.

396. The GA variant of any one of 1 to 391 above and having a N410C substitution.

397. The GA variant of any one of 1 to 391 above and having a N410F substitution.

398. The GA variant of any one of 1 to 391 above and having a N410H substitution.

399. The GA variant of any one of 1 to 391 above and having a N410K substitution.

400. The GA variant of any one of 1 to 391 above and having a N410L substitution.

401. The GA variant of any one of 1 to 391 above and having a N410P substitution.

402. The GA variant of any one of 1 to 391 above and having a N410T substitution.

403. The GA variant of any one of 1 to 391 above and having a N410V substitution.

404. The GA variant of any one of 1 to 391 above and having a N410W substitution.

405. The GA variant of any one of 1 to 391 above and having a N410A substitution.

406. The GA variant of any one of 1 to 391 above and having a N410D substitution.

407. The GA variant of any one of 1 to 406 above and having an A411P substitution.

408. The GA variant of any one of 1 to 406 above and having an A411G substitution.

409. The GA variant of any one of 1 to 406 above and having an A411I substitution.

410. The GA variant of any one of 1 to 406 above and having an A411L substitution.

411. The GA variant of any one of 1 to 406 above and having an A411N substitution.

412. The GA variant of any one of 1 to 406 above and having an A411Q substitution.

413. The GA variant of any one of 1 to 406 above and having an A411R substitution.

414. The GA variant of any one of 1 to 406 above and having an A411S substitution.

415. The GA variant of any one of 1 to 406 above and having an A411W substitution.

416. The GA variant of any one of 1 to 406 above and having an A411C substitution.

417. The GA variant of any one of 1 to 416 above and having an A414C substitution.

418. The GA variant of any one of 1 to 416 above and having an A414F substitution.

419. The GA variant of any one of 1 to 416 above and having an A414G substitution.

420. The GA variant of any one of 1 to 416 above and having an A414I substitution.

421. The GA variant of any one of 1 to 416 above and having an A414P substitution.

422. The GA variant of any one of 1 to 416 above and having an A414Q substitution.

423. The GA variant of any one of 1 to 416 above and having an A414S substitution.

424. The GA variant of any one of 1 to 416 above and having an A414D substitution.

425. The GA variant of any one of 1 to 416 above and having an A414E substitution.

426. The GA variant of any one of 1 to 416 above and having an A414R substitution.

427. The GA variant of any one of 1 to 416 above and having an A414T substitution.

428. The GA variant of any one of 1 to 416 above and having an A414W substitution.

429. The GA variant of any one of 1 to 428 above and having an I461C substitution.

430. The GA variant of any one of 1 to 428 above and having an I461F substitution.

431. The GA variant of any one of 1 to 428 above and having an I461G substitution.

432. The GA variant of any one of 1 to 428 above and having an I461K substitution.

433. The GA variant of any one of 1 to 428 above and having an I461M substitution.

434. The GA variant of any one of 1 to 428 above and having an I461S substitution.

435. The GA variant of any one of 1 to 428 above and having an I461T substitution.

436. The GA variant of any one of 1 to 428 above and having an I461V substitution.

437. The GA variant of any one of 1 to 428 above and having an I461Y substitution.

438. The GA variant of any one of 1 to 428 above and having an I461N substitution.

439. The GA variant of any one of 1 to 428 above and having an I461Q substitution.

440. The GA variant of any one of 1 to 428 above and having an I461R substitution.

441. The GA variant of any one of 1 to 440 above and having a G466D substitution.

442. The GA variant of any one of 1 to 440 above and having a G466K substitution.

443. The GA variant of any one of 1 to 440 above and having a G466M substitution.

444. The GA variant of any one of 1 to 440 above and having a G466R substitution.

445. The GA variant of any one of 1 to 440 above and having a G466Y substitution.

446. The GA variant of any one of 1 to 440 above and having a G466C substitution.

447. The GA variant of any one of 1 to 440 above and having a G466P substitution.

448. The GA variant of any one of 1 to 440 above and having a G466T substitution.

449. The GA variant of any one of 1 to 440 above and having a G466W substitution.

450. The GA variant of any one of 1 to 440 above and having a G466A substitution.

451. The GA variant of any one of 1 to 440 above and having a G466E substitution.

452. The GA variant of any one of 1 to 440 above and having a G466F substitution.

453. The GA variant of any one of 1 to 440 above and having a G466H substitution.

454. The GA variant of any one of 1 to 440 above and having a G466L substitution.

455. The GA variant of any one of 1 to 440 above and having a G466N substitution.

456. The GA variant of any one of 1 to 440 above and having a G466S substitution.

457. The GA variant of any one of 1 to 440 above and having a G466I substitution.

458. The GA variant of any one of 1 to 440 above and having a G466V substitution.

459. The GA variant of any one of 1 to 440 above and having a G466Q substitution.

460. The GA variant of any one of 1 to 459 above and having a L467C substitution.

461. The GA variant of any one of 1 to 459 above and having a L467G substitution.

462. The GA variant of any one of 1 to 459 above and having a L467Q substitution.

463. The GA variant of any one of 1 to 459 above and having a L467T substitution.

464. The GA variant of any one of 1 to 459 above and having a L467W substitution.

465. The GA variant of any one of 1 to 459 above and having a L467D substitution.

466. The GA variant of any one of 1 to 459 above and having a L467H substitution.

467. The GA variant of any one of 1 to 459 above and having a L467N substitution.

468. The GA variant of any one of 1 to 459 above and having a L467Y substitution.

469. The GA variant of any one of 1 to 459 above and having a L467A substitution.

470. The GA variant of any one of 1 to 459 above and having a L467F substitution.

471. The GA variant of any one of 1 to 459 above and having a L467S substitution.

472. The GA variant of any one of 1 to 459 above and having a L467V substitution.

473. The GA variant of any one of 1 to 472 above and having a V468A substitution.

474. The GA variant of any one of 1 to 472 above and having a V468E substitution.

475. The GA variant of any one of 1 to 472 above and having a V468D substitution.

476. The GA variant of any one of 1 to 472 above and having a V468G substitution.

477. The GA variant of any one of 1 to 472 above and having a V468H substitution.

478. The GA variant of any one of 1 to 472 above and having a V468I substitution.

479. The GA variant of any one of 1 to 472 above and having a V468K substitution.

480. The GA variant of any one of 1 to 472 above and having a V468L substitution.

481. The GA variant of any one of 1 to 472 above and having a V468M substitution.

482. The GA variant of any one of 1 to 472 above and having a V468N substitution.

483. The GA variant of any one of 1 to 472 above and having a V468P substitution.

484. The GA variant of any one of 1 to 472 above and having a V468Q substitution.

485. The GA variant of any one of 1 to 472 above and having a V468R substitution.

486. The GA variant of any one of 1 to 472 above and having a V468T substitution.

487. The GA variant of any one of 1 to 472 above and having a V468W substitution.

488. The GA variant of any one of 1 to 487 above and having a P469R substitution.

489. The GA variant of any one of 1 to 487 above and having a P469C substitution.

490. The GA variant of any one of 1 to 487 above and having a P469H substitution.

491. The GA variant of any one of 1 to 487 above and having a P469T substitution.

492. The GA variant of any one of 1 to 487 above and having a P469V substitution.

493. The GA variant of any one of 1 to 487 above and having a P469G substitution.

494. The GA variant of any one of 1 to 487 above and having a P469N substitution.

495. The GA variant of any one of 1 to 487 above and having a P469S substitution.

496. The GA variant of any one of 1 to 487 above and having a P469E substitution.

497. The GA variant of any one of 1 to 487 above and having a P469I substitution.

498. The GA variant of any one of 1 to 487 above and having a P469Q substitution.

499. The GA variant of any one of 1 to 487 above and having a P469W substitution.

500. The GA variant of any one of 1 to 499 above and having a P470K substitution.

501. The GA variant of any one of 1 to 499 above and having a P470S substitution.

502. The GA variant of any one of 1 to 499 above and having a P470A substitution.

503. The GA variant of any one of 1 to 499 above and having a P470C substitution.

504. The GA variant of any one of 1 to 499 above and having a P470E substitution.

505. The GA variant of any one of 1 to 499 above and having a P470F substitution.

506. The GA variant of any one of 1 to 499 above and having a P470G substitution.

507. The GA variant of any one of 1 to 499 above and having a P470I substitution.

508. The GA variant of any one of 1 to 499 above and having a P470L substitution.

509. The GA variant of any one of 1 to 499 above and having a P470M substitution.

510. The GA variant of any one of 1 to 499 above and having a P470N substitution.

511. The GA variant of any one of 1 to 499 above and having a P470Q substitution.

512. The GA variant of any one of 1 to 499 above and having a P470R substitution.

513. The GA variant of any one of 1 to 499 above and having a P470V substitution.

514. The GA variant of any one of 1 to 499 above and having a P470W substitution.

515. The GA variant of any one of 1 to 514 above and having a S471D substitution.

516. The GA variant of any one of 1 to 514 above and having a S471C substitution.

517. The GA variant of any one of 1 to 514 above and having a S471M substitution.

518. The GA variant of any one of 1 to 514 above and having a S471E substitution.

519. The GA variant of any one of 1 to 514 above and having a S471G substitution.

520. The GA variant of any one of 1 to 514 above and having a S471P substitution.

521. The GA variant of any one of 1 to 514 above and having a S471Q substitution.

522. The GA variant of any one of 1 to 514 above and having a S471L substitution.

523. The GA variant of any one of 1 to 514 above and having a S471A substitution.

524. The GA variant of any one of 1 to 514 above and having a S471H substitution.

525. The GA variant of any one of 1 to 514 above and having a S471I substitution.

526. The GA variant of any one of 1 to 514 above and having a S471N substitution.

527. The GA variant of any one of 1 to 514 above and having a S471V substitution.

528. The GA variant of any one of 1 to 527 above and having a V476A substitution.

529. The GA variant of any one of 1 to 527 above and having a V476D substitution.

530. The GA variant of any one of 1 to 527 above and having a V476E substitution.

531. The GA variant of any one of 1 to 527 above and having a V476G substitution.

532. The GA variant of any one of 1 to 527 above and having a V476H substitution.

533. The GA variant of any one of 1 to 527 above and having a V476N substitution.

534. The GA variant of any one of 1 to 527 above and having a V476S substitution.

535. The GA variant of any one of 1 to 527 above and having a V476L substitution.

536. The GA variant of any one of 1 to 527 above and having a V476M substitution.

537. The GA variant of any one of 1 to 527 above and having a V476P substitution.

538. The GA variant of any one of 1 to 527 above and having a V476Q substitution.

539. The GA variant of any one of 1 to 527 above and having a V476Y substitution.

540. The GA variant of any one of 1 to 527 above and having a V476R substitution.

541. The GA variant of any one of 1 to 527 above and having a V476T substitution.

542. The GA variant of any one of 1 to 527 above and having a V476I substitution.

543. The GA variant of any one of 1 to 527 above and having a V476W substitution.

544. The GA variant of any one of 1 to 543 above and having an A477D substitution.

545. The GA variant of any one of 1 to 543 above and having an A477E substitution.

546. The GA variant of any one of 1 to 543 above and having an A477I substitution.

547. The GA variant of any one of 1 to 543 above and having an A477K substitution.

548. The GA variant of any one of 1 to 543 above and having an A477Q substitution.

549. The GA variant of any one of 1 to 543 above and having an A477R substitution.

550. The GA variant of any one of 1 to 543 above and having an A477M substitution.

551. The GA variant of any one of 1 to 543 above and having an A477W substitution.

552. The GA variant of any one of 1 to 543 above and having an A477S substitution.

553. The GA variant of any one of 1 to 543 above and having an A477V substitution.

554. The GA variant of any one of 1 to 553 above and having a K478E substitution.

555. The GA variant of any one of 1 to 553 above and having a K478I substitution.

556. The GA variant of any one of 1 to 553 above and having a K478P substitution.

557. The GA variant of any one of 1 to 553 above and having a K478R substitution.

558. The GA variant of any one of 1 to 553 above and having a K478S substitution.

559. The GA variant of any one of 1 to 553 above and having a K478T substitution.

560. The GA variant of any one of 1 to 553 above and having a K478Y substitution.

561. The GA variant of any one of 1 to 553 above and having a K478F substitution.

562. The GA variant of any one of 1 to 553 above and having a K478Q substitution.

563. The GA variant of any one of 1 to 553 above and having a K478V substitution.

564. The GA variant of any one of 1 to 563 above and having a S479A substitution.

565. The GA variant of any one of 1 to 563 above and having a S479G substitution.

566. The GA variant of any one of 1 to 563 above and having a S479L substitution.

567. The GA variant of any one of 1 to 563 above and having a S479M substitution.

568. The GA variant of any one of 1 to 563 above and having a S479N substitution.

569. The GA variant of any one of 1 to 563 above and having a S479Q substitution.

570. The GA variant of any one of 1 to 563 above and having a S479R substitution.

571. The GA variant of any one of 1 to 563 above and having a S479T substitution.

572. The GA variant of any one of 1 to 563 above and having a S479Y substitution.

573. The GA variant of any one of 1 to 563 above and having a S479F substitution.

574. The GA variant of any one of 1 to 563 above and having a S479I substitution.

575. The GA variant of any one of 1 to 563 above and having a S479K substitution.

576. The GA variant of any one of 1 to 575 above and having a Q480A substitution.

577. The GA variant of any one of 1 to 575 above and having a Q480C substitution.

578. The GA variant of any one of 1 to 575 above and having a Q480D substitution.

579. The GA variant of any one of 1 to 575 above and having a Q480T substitution.

580. The GA variant of any one of 1 to 575 above and having a Q480V substitution.

581. The GA variant of any one of 1 to 575 above and having a Q480H substitution.

582. The GA variant of any one of 1 to 575 above and having a Q480I substitution.

583. The GA variant of any one of 1 to 575 above and having a Q480L substitution.

584. The GA variant of any one of 1 to 575 above and having a Q480M substitution.

585. The GA variant of any one of 1 to 575 above and having a Q480F substitution.

586. The GA variant of any one of 1 to 585 above and having a S483F substitution.

587. The GA variant of any one of 1 to 585 above and having a S483P substitution.

588. The GA variant of any one of 1 to 585 above and having a S483W substitution.

589. The GA variant of any one of 1 to 585 above and having a S483Y substitution.

590. The GA variant of any one of 1 to 585 above and having a S483A substitution.

591. The GA variant of any one of 1 to 585 above and having a S483I substitution.

592. The GA variant of any one of 1 to 585 above and having a S483K substitution.

593. The GA variant of any one of 1 to 585 above and having a S483N substitution.

594. The GA variant of any one of 1 to 585 above and having a S483R substitution.

595. The GA variant of any one of 1 to 585 above and having a S483T substitution.

596. The GA variant of any one of 1 to 585 above and having a S483H substitution.

597. The GA variant of any one of 1 to 585 above and having a S483L substitution.

598. The GA variant of any one of 1 to 597 above and having a T484I substitution.

599. The GA variant of any one of 1 to 597 above and having a T484M substitution.

600. The GA variant of any one of 1 to 597 above and having a T484V substitution.

601. The GA variant of any one of 1 to 597 above and having a T484K substitution.

602. The GA variant of any one of 1 to 597 above and having a T484P substitution.

603. The GA variant of any one of 1 to 597 above and having a T484Q substitution.

604. The GA variant of any one of 1 to 597 above and having a T484Y substitution.

605. The GA variant of any one of 1 to 597 above and having a T484F substitution.

606. The GA variant of any one of 1 to 597 above and having a T484L substitution.

607. The GA variant of any one of 1 to 597 above and having a T484S substitution.

608. The GA variant of any one of 1 to 607 above and having a P503A substitution.

609. The GA variant of any one of 1 to 607 above and having a P503D substitution.

610. The GA variant of any one of 1 to 607 above and having a P503F substitution.

611. The GA variant of any one of 1 to 607 above and having a P503G substitution.

612. The GA variant of any one of 1 to 607 above and having a P503L substitution.

613. The GA variant of any one of 1 to 607 above and having a P503M substitution.

614. The GA variant of any one of 1 to 607 above and having a P503N substitution.

615. The GA variant of any one of 1 to 607 above and having a P503Q substitution.

616. The GA variant of any one of 1 to 607 above and having a P503R substitution.

617. The GA variant of any one of 1 to 607 above and having a P503S substitution.

618. The GA variant of any one of 1 to 607 above and having a P503T substitution.

619. The GA variant of any one of 1 to 607 above and having a P503V substitution.

620. The GA variant of any one of 1 to 607 above and having a P503Y substitution.

621. The GA variant of any one of 1 to 620 above and having a K505D substitution.

622. The GA variant of any one of 1 to 620 above and having a K505E substitution.

623. The GA variant of any one of 1 to 620 above and having a K505G substitution.

624. The GA variant of any one of 1 to 620 above and having a K505N substitution.

625. The GA variant of any one of 1 to 620 above and having a K505T substitution.

626. The GA variant of any one of 1 to 620 above and having a K505M substitution.

627. The GA variant of any one of 1 to 620 above and having a K505S substitution.

628. The GA variant of any one of 1 to 620 above and having a K505V substitution.

629. The GA variant of any one of 1 to 620 above and having a K505H substitution.

630. The GA variant of any one of 1 to 620 above and having a K505P substitution.

631. The GA variant of any one of 1 to 630 above and having a Q506A substitution.

632. The GA variant of any one of 1 to 630 above and having a Q506F substitution.

633. The GA variant of any one of 1 to 630 above and having a Q506L substitution.

634. The GA variant of any one of 1 to 630 above and having a Q506N substitution.

635. The GA variant of any one of 1 to 630 above and having a Q506P substitution.

636. The GA variant of any one of 1 to 630 above and having a Q506S substitution.

637. The GA variant of any one of 1 to 630 above and having a Q506E substitution.

638. The GA variant of any one of 1 to 630 above and having a Q506M substitution.

639. The GA variant of any one of 1 to 630 above and having a Q506T substitution.

640. The GA variant of any one of 1 to 630 above and having a Q506V substitution.

641. The GA variant of any one of 1 to 630 above and having a Q506Y substitution.

642. The GA variant of any one of 1 to 630 above and having a Q506C substitution.

643. The GA variant of any one of 1 to 642 above and having an A522E substitution.

644. The GA variant of any one of 1 to 642 above and having an A522P substitution.

645. The GA variant of any one of 1 to 642 above and having an A522N substitution.

646. The GA variant of any one of 1 to 642 above and having an A522T substitution.

647. The GA variant of any one of 1 to 642 above and having an A522V substitution.

648. The GA variant of any one of 1 to 642 above and having an A522Y substitution.

649. The GA variant of any one of 1 to 642 above and having an A522L substitution.

650. The GA variant of any one of 1 to 642 above and having an A522R substitution.

651. The GA variant of any one of 1 to 642 above and having an A522K substitution.

652. The GA variant of any one of 1 to 642 above and having an A522C substitution.

653. The GA variant of any one of 1 to 642 above and having an A522D substitution.

654. The GA variant of any one of 1 to 653 above and having a T544P substitution.

655. The GA variant of any one of 1 to 653 above and having a T544A substitution.

656. The GA variant of any one of 1 to 653 above and having a T544I substitution.

657. The GA variant of any one of 1 to 653 above and having a T544L substitution.

658. The GA variant of any one of 1 to 653 above and having a T544M substitution.

659. The GA variant of any one of 1 to 653 above and having a T544N substitution.

660. The GA variant of any one of 1 to 653 above and having a T544S substitution.

661. The GA variant of any one of 1 to 653 above and having a T544Y substitution.

662. The GA variant of any one of 1 to 653 above and having a T544G substitution.

663. The GA variant of any one of 1 to 653 above and having a T544K substitution.

664. The GA variant of any one of 1 to 653 above and having a T544V substitution.

665. The GA variant of any one of 1 to 653 above and having a T544R substitution.

666. The GA variant of any one of 1 to 665 above and having a N556P substitution.

667. The GA variant of any one of 1 to 665 above and having a N556A substitution.

668. The GA variant of any one of 1 to 665 above and having a N556G substitution.

669. The GA variant of any one of 1 to 665 above and having a N556H substitution.

670. The GA variant of any one of 1 to 665 above and having a N556I substitution.

671. The GA variant of any one of 1 to 665 above and having a N556M substitution.

672. The GA variant of any one of 1 to 665 above and having a N556S substitution.

673. The GA variant of any one of 1 to 665 above and having a N556T substitution.

674. The GA variant of any one of 1 to 665 above and having a N556W substitution.

675. The GA variant of any one of 1 to 665 above and having a N556D substitution.

676. The GA variant of any one of 1 to 665 above and having a N556E substitution.

677. The GA variant of any one of 1 to 665 above and having a N556L substitution.

678. The GA variant of any one of 1 to 665 above and having a N556V substitution.

679. The GA variant of any one of 1 to 665 above and having a N556Y substitution.

680. The GA variant of any one of 1 to 679 above and having a G587D substitution.

681. The GA variant of any one of 1 to 679 above and having a G587F substitution.

682. The GA variant of any one of 1 to 679 above and having a G587I substitution.

683. The GA variant of any one of 1 to 679 above and having a G587N substitution.

684. The GA variant of any one of 1 to 679 above and having a G587Q substitution.

685. The GA variant of any one of 1 to 679 above and having a G587T substitution.

686. The GA variant of any one of 1 to 679 above and having a G587Y substitution.

687. The GA variant of any one of 1 to 679 above and having a G587C substitution.

688. The GA variant of any one of 1 to 679 above and having a G587P substitution.

689. The GA variant of any one of 1 to 679 above and having a G587L substitution.

690. The GA variant of any one of 1 to 679 above and having a G587R substitution.

691. The GA variant of any one of 1 to 690 above and having an A589C substitution.

692. The GA variant of any one of 1 to 690 above and having an A589D substitution.

693. The GA variant of any one of 1 to 690 above and having an A589K substitution.

694. The GA variant of any one of 1 to 690 above and having an A589L substitution.

695. The GA variant of any one of 1 to 690 above and having an A589M substitution.

696. The GA variant of any one of 1 to 690 above and having an A589R substitution.

697. The GA variant of any one of 1 to 690 above and having an A589E substitution.

698. The GA variant of any one of 1 to 690 above and having an A589Q substitution.

699. The GA variant of any one of 1 to 690 above and having an A589T substitution.

700. The GA variant of any one of 1 to 690 above and having an A589V substitution.

701. The GA variant of any one of 1 to 700 above and having a T599M substitution.

702. The GA variant of any one of 1 to 700 above and having a T599C substitution.

703. The GA variant of any one of 1 to 700 above and having a T599E substitution.

704. The GA variant of any one of 1 to 700 above and having a T599R substitution.

705. The GA variant of any one of 1 to 700 above and having a T599D substitution.

706. The GA variant of any one of 1 to 700 above and having a T599K substitution.

707. The GA variant of any one of 1 to 700 above and having a T599L substitution.

708. The GA variant of any one of 1 to 700 above and having a T599V substitution.

709. The GA variant of any one of 1 to 700 above and having a T599Y substitution.

710. The GA variant of any one of 1 to 700 above and having a T599A substitution.

711. The GA variant of any one of 1 to 700 above and having a T599F substitution.

712. The GA variant of any one of 1 to 700 above and having a T599P substitution.

713. The GA variant of any one of 1 to 700 above and having a T599Q substitution.

714. The GA variant of any one of 1 to 700 above and having a T599S substitution.

715. The GA variant of any one of 1 to 714 above and having a N600A substitution.

716. The GA variant of any one of 1 to 714 above and having a N600E substitution.

717. The GA variant of any one of 1 to 714 above and having a N600M substitution.

718. The GA variant of any one of 1 to 714 above and having a N600Q substitution.

719. The GA variant of any one of 1 to 714 above and having a N600R substitution.

720. The GA variant of any one of 1 to 714 above and having a N600W substitution.

721. The GA variant of any one of 1 to 714 above and having a N600Y substitution.

722. The GA variant of any one of 1 to 714 above and having a N600P substitution.

723. The GA variant of any one of 1 to 714 above and having a N600V substitution.

724. The GA variant of any one of 1 to 714 above and having a N600K substitution.

725. The GA variant of any one of 1 to 724 above and having a T604K substitution.

726. The GA variant of any one of 1 to 724 above and having a T604M substitution.

727. The GA variant of any one of 1 to 724 above and having a T604S substitution.

728. The GA variant of any one of 1 to 724 above and having a T604Y substitution.

729. The GA variant of any one of 1 to 724 above and having a T604A substitution.

730. The GA variant of any one of 1 to 724 above and having a T604D substitution.

731. The GA variant of any one of 1 to 724 above and having a T604H substitution.

732. The GA variant of any one of 1 to 724 above and having a T604I substitution.

733. The GA variant of any one of 1 to 724 above and having a T604Q substitution.

734. The GA variant of any one of 1 to 724 above and having a T604R substitution.

735. The GA variant of any one of 1 to 724 above and having a T604F substitution.

736. The GA variant of any one of 1 to 724 above and having a T604G substitution.

737. The GA variant of any one of 1 to 724 above and having a T604L substitution.

738. The GA variant of any one of 1 to 737 above and having a S607W substitution.

739. The GA variant of any one of 1 to 737 above and having a S607L substitution.

740. The GA variant of any one of 1 to 737 above and having a S607Y substitution.

741. The GA variant of any one of 1 to 737 above and having a S607G substitution.

742. The GA variant of any one of 1 to 737 above and having a S607I substitution.

743. The GA variant of any one of 1 to 737 above and having a S607Q substitution.

744. The GA variant of any one of 1 to 737 above and having a S607V substitution.

745. The GA variant of any one of 1 to 737 above and having a S607A substitution.

746. The GA variant of any one of 1 to 737 above and having a S607H substitution.

747. The GA variant of any one of 1 to 737 above and having a S607M substitution.

748. The GA variant of any one of 1 to 737 above and having a S607N substitution.

749. The GA variant of any one of 1 to 748 above and having a P609K substitution.

750. The GA variant of any one of 1 to 748 above and having a P609L substitution.

751. The GA variant of any one of 1 to 748 above and having a P609N substitution.

752. The GA variant of any one of 1 to 748 above and having a P609Q substitution.

753. The GA variant of any one of 1 to 748 above and having a P609R substitution.

754. The GA variant of any one of 1 to 748 above and having a P609T substitution.

755. The GA variant of any one of 1 to 748 above and having a P609V substitution.

756. The GA variant of any one of 1 to 748 above and having a P609Y substitution.

757. The GA variant of any one of 1 to 748 above and having a P609A substitution.

758. The GA variant of any one of 1 to 748 above and having a P609G substitution.

759. The GA variant of any one of 1 to 748 above and having a P609W substitution.

760. The GA variant of any one of 1 to 759 above and having an A31I substitution.

761. The GA variant of any one of 1 to 759 above and having an A31T substitution.

762. The GA variant of any one of 1 to 759 above and having an A31Y substitution.

763. The GA variant of any one of 1 to 759 above and having an A31F substitution.

764. The GA variant of any one of 1 to 759 above and having an A31L substitution.

765. The GA variant of any one of 1 to 759 above and having an A31Q substitution.

766. The GA variant of any one of 1 to 765 above and having an I37G substitution.

767. The GA variant of any one of 1 to 765 above and having an I37M substitution.

768. The GA variant of any one of 1 to 765 above and having an I37A substitution.

769. The GA variant of any one of 1 to 765 above and having an I37S substitution.

770. The GA variant of any one of 1 to 765 above and having an I37C substitution.

771. The GA variant of any one of 1 to 765 above and having an I37T substitution.

772. The GA variant of any one of 1 to 771 above and having a N46D substitution.

773. The GA variant of any one of 1 to 771 above and having a N46E substitution.

774. The GA variant of any one of 1 to 771 above and having a N46P substitution.

775. The GA variant of any one of 1 to 771 above and having a N46V substitution.

776. The GA variant of any one of 1 to 771 above and having a N46C substitution.

777. The GA variant of any one of 1 to 771 above and having a N46S substitution.

778. The GA variant of any one of 1 to 777 above and having a K57E substitution.

779. The GA variant of any one of 1 to 777 above and having a K57S substitution.

780. The GA variant of any one of 1 to 777 above and having a K57A substitution.

781. The GA variant of any one of 1 to 777 above and having a K57C substitution.

782. The GA variant of any one of 1 to 777 above and having a K57I substitution.

783. The GA variant of any one of 1 to 777 above and having a K57V substitution.

784. The GA variant of any one of 1 to 777 above and having a K57T substitution.

785. The GA variant of any one of 1 to 777 above and having a K57Q substitution.

786. The GA variant of any one of 1 to 777 above and having a K57R substitution.

787. The GA variant of any one of 1 to 786 above and having a D85N substitution.

788. The GA variant of any one of 1 to 786 above and having a D85Y substitution.

789. The GA variant of any one of 1 to 786 above and having a D85L substitution.

790. The GA variant of any one of 1 to 786 above and having a D85S substitution.

791. The GA variant of any one of 1 to 786 above and having a D85C substitution.

792. The GA variant of any one of 1 to 786 above and having a D85G substitution.

793. The GA variant of any one of 1 to 786 above and having a D85M substitution.

794. The GA variant of any one of 1 to 786 above and having a D85E substitution.

795. The GA variant of any one of 1 to 786 above and having a D85V substitution.

796. The GA variant of any one of 1 to 795 above and having a L105M substitution.

797. The GA variant of any one of 1 to 795 above and having a L105R substitution.

798. The GA variant of any one of 1 to 795 above and having a L105T substitution.

799. The GA variant of any one of 1 to 795 above and having a L105I substitution.

800. The GA variant of any one of 1 to 795 above and having a L105F substitution.

801. The GA variant of any one of 1 to 795 above and having a L105Y substitution.

802. The GA variant of any one of 1 to 801 above and having a K171C substitution.

803. The GA variant of any one of 1 to 801 above and having a K171G substitution.

804. The GA variant of any one of 1 to 801 above and having a K171H substitution.

805. The GA variant of any one of 1 to 801 above and having a K171R substitution.

806. The GA variant of any one of 1 to 801 above and having a K171V substitution.

807. The GA variant of any one of 1 to 801 above and having a K171W substitution.

808. The GA variant of any one of 1 to 807 above and having a K179D substitution.

809. The GA variant of any one of 1 to 807 above and having a K179P substitution.

810. The GA variant of any one of 1 to 807 above and having a K179H substitution.

811. The GA variant of any one of 1 to 807 above and having a K179L substitution.

812. The GA variant of any one of 1 to 807 above and having a K179Q substitution.

813. The GA variant of any one of 1 to 807 above and having a K179R substitution.

814. The GA variant of any one of 1 to 807 above and having a K179W substitution.

815. The GA variant of any one of 1 to 814 above and having a S184A substitution.

816. The GA variant of any one of 1 to 814 above and having a S184I substitution.

817. The GA variant of any one of 1 to 814 above and having a S184M substitution.

818. The GA variant of any one of 1 to 814 above and having a S184L substitution.

819. The GA variant of any one of 1 to 814 above and having a S184C substitution.

820. The GA variant of any one of 1 to 814 above and having a S184F substitution.

821. The GA variant of any one of 1 to 814 above and having a S184V substitution.

822. The GA variant of any one of 1 to 814 above and having a S184R substitution.

823. The GA variant of any one of 1 to 822 above and having a P213A substitution.

824. The GA variant of any one of 1 to 822 above and having a P213M substitution.

825. The GA variant of any one of 1 to 822 above and having a P213N substitution.

826. The GA variant of any one of 1 to 822 above and having a P213H substitution.

827. The GA variant of any one of 1 to 822 above and having a P213Q substitution.

828. The GA variant of any one of 1 to 822 above and having a P213R substitution.

829. The GA variant of any one of 1 to 828 above and having an A221M substitution.

830. The GA variant of any one of 1 to 828 above and having an A221R substitution.

831. The GA variant of any one of 1 to 828 above and having an A221S substitution.

832. The GA variant of any one of 1 to 828 above and having an A221I substitution.

833. The GA variant of any one of 1 to 828 above and having an A221L substitution.

834. The GA variant of any one of 1 to 828 above and having an A221T substitution.

835. The GA variant of any one of 1 to 834 above and having a T239A substitution.

836. The GA variant of any one of 1 to 834 above and having a T239C substitution.

837. The GA variant of any one of 1 to 834 above and having a T239F substitution.

838. The GA variant of any one of 1 to 834 above and having a T239M substitution.

839. The GA variant of any one of 1 to 834 above and having a T239V substitution.

840. The GA variant of any one of 1 to 834 above and having a T239I substitution.

841. The GA variant of any one of 1 to 834 above and having a T239R substitution.

842. The GA variant of any one of 1 to 841 above and having a Q250D substitution.

843. The GA variant of any one of 1 to 841 above and having a Q250F substitution.

844. The GA variant of any one of 1 to 841 above and having a Q250H substitution.

845. The GA variant of any one of 1 to 841 above and having a Q250M substitution.

846. The GA variant of any one of 1 to 841 above and having a Q250Y substitution.

847. The GA variant of any one of 1 to 841 above and having a Q250E substitution.

848. The GA variant of any one of 1 to 847 above and having a L252H substitution.

849. The GA variant of any one of 1 to 847 above and having a L252A substitution.

850. The GA variant of any one of 1 to 847 above and having a L252I substitution.

851. The GA variant of any one of 1 to 847 above and having a L252N substitution.

852. The GA variant of any one of 1 to 847 above and having a L252S substitution.

853. The GA variant of any one of 1 to 847 above and having a L252M substitution.

854. The GA variant of any one of 1 to 847 above and having a L252V substitution.

855. The GA variant of any one of 1 to 854 above and having a N260C substitution.

856. The GA variant of any one of 1 to 854 above and having a N260H substitution.

857. The GA variant of any one of 1 to 854 above and having a N260R substitution.

858. The GA variant of any one of 1 to 854 above and having a N260T substitution.

859. The GA variant of any one of 1 to 854 above and having a N260F substitution.

860. The GA variant of any one of 1 to 854 above and having a N260S substitution.

861. The GA variant of any one of 1 to 854 above and having a N260W substitution.

862. The GA variant of any one of 1 to 861 above and having a S261E substitution.

863. The GA variant of any one of 1 to 861 above and having a S261F substitution.

864. The GA variant of any one of 1 to 861 above and having a S261K substitution.

865. The GA variant of any one of 1 to 861 above and having a S261T substitution.

866. The GA variant of any one of 1 to 861 above and having a S261W substitution.

867. The GA variant of any one of 1 to 861 above and having a S261Y substitution.

868. The GA variant of any one of 1 to 867 above and having a K262H substitution.

869. The GA variant of any one of 1 to 867 above and having a K262M substitution.

870. The GA variant of any one of 1 to 867 above and having a K262P substitution.

871. The GA variant of any one of 1 to 867 above and having a K262R substitution.

872. The GA variant of any one of 1 to 867 above and having a K262V substitution.

873. The GA variant of any one of 1 to 867 above and having a K262W substitution.

874. The GA variant of any one of 1 to 867 above and having a K262C substitution.

875. The GA variant of any one of 1 to 874 above and having a N264A substitution.

876. The GA variant of any one of 1 to 874 above and having a N264F substitution.

877. The GA variant of any one of 1 to 874 above and having a N264P substitution.

878. The GA variant of any one of 1 to 874 above and having a N264Q substitution.

879. The GA variant of any one of 1 to 874 above and having a N264V substitution.

880. The GA variant of any one of 1 to 874 above and having a N264E substitution.

881. The GA variant of any one of 1 to 880 above and having an E274V substitution.

882. The GA variant of any one of 1 to 880 above and having an E274D substitution.

883. The GA variant of any one of 1 to 880 above and having an E274I substitution.

884. The GA variant of any one of 1 to 880 above and having an E274L substitution.

885. The GA variant of any one of 1 to 880 above and having an E274Q substitution.

886. The GA variant of any one of 1 to 880 above and having an E274F substitution.

887. The GA variant of any one of 1 to 886 above and having an A295F substitution.

888. The GA variant of any one of 1 to 886 above and having an A295G substitution.

889. The GA variant of any one of 1 to 886 above and having an A295V substitution.

890. The GA variant of any one of 1 to 886 above and having an A295W substitution.

891. The GA variant of any one of 1 to 886 above and having an A295Y substitution.

892. The GA variant of any one of 1 to 886 above and having an A295D substitution.

893. The GA variant of any one of 1 to 886 above and having an A295N substitution.

894. The GA variant of any one of 1 to 893 above and having an A325E substitution.

895. The GA variant of any one of 1 to 893 above and having an A325C substitution.

896. The GA variant of any one of 1 to 893 above and having an A325F substitution.

897. The GA variant of any one of 1 to 893 above and having an A325L substitution.

898. The GA variant of any one of 1 to 893 above and having an A325P substitution.

899. The GA variant of any one of 1 to 893 above and having an A325Q substitution.

900. The GA variant of any one of 1 to 899 above and having a K328C substitution.

901. The GA variant of any one of 1 to 899 above and having a K328L substitution.

902. The GA variant of any one of 1 to 899 above and having a K328Q substitution.

903. The GA variant of any one of 1 to 899 above and having a K328W substitution.

904. The GA variant of any one of 1 to 899 above and having a K328E substitution.

905. The GA variant of any one of 1 to 899 above and having a K328F substitution.

906. The GA variant of any one of 1 to 899 above and having a K328R substitution.

907. The GA variant of any one of 1 to 906 above and having an A366Q substitution.

908. The GA variant of any one of 1 to 906 above and having an A366C substitution.

909. The GA variant of any one of 1 to 906 above and having an A366M substitution.

910. The GA variant of any one of 1 to 906 above and having an A366V substitution.

911. The GA variant of any one of 1 to 906 above and having an A366G substitution.

912. The GA variant of any one of 1 to 906 above and having an A366S substitution.

913. The GA variant of any one of 1 to 906 above and having an A366T substitution.

914. The GA variant of any one of 1 to 913 above and having a Y368E substitution.

915. The GA variant of any one of 1 to 913 above and having a Y368H substitution.

916. The GA variant of any one of 1 to 913 above and having a Y368K substitution.

917. The GA variant of any one of 1 to 913 above and having a Y368T substitution.

918. The GA variant of any one of 1 to 913 above and having a Y368W substitution.

919. The GA variant of any one of 1 to 913 above and having a Y368M substitution.

920. The GA variant of any one of 1 to 919 above and having a N371C substitution.

921. The GA variant of any one of 1 to 919 above and having a N371L substitution.

922. The GA variant of any one of 1 to 919 above and having a N371M substitution.

923. The GA variant of any one of 1 to 919 above and having a N371D substitution.

924. The GA variant of any one of 1 to 919 above and having a N371Q substitution.

925. The GA variant of any one of 1 to 919 above and having a N371R substitution.

926. The GA variant of any one of 1 to 919 above and having a N371Y substitution.

927. The GA variant of any one of 1 to 919 above and having a N371A substitution.

928. The GA variant of any one of 1 to 927 above and having a K372C substitution.

929. The GA variant of any one of 1 to 927 above and having a K372D substitution.

930. The GA variant of any one of 1 to 927 above and having a K372F substitution.

931. The GA variant of any one of 1 to 927 above and having a K372S substitution.

932. The GA variant of any one of 1 to 927 above and having a K372L substitution.

933. The GA variant of any one of 1 to 927 above and having a K372N substitution.

934. The GA variant of any one of 1 to 927 above and having a K372Q substitution.

935. The GA variant of any one of 1 to 934 above and having an I376C substitution.

936. The GA variant of any one of 1 to 934 above and having an I376T substitution.

937. The GA variant of any one of 1 to 934 above and having an I376V substitution.

938. The GA variant of any one of 1 to 934 above and having an I376Y substitution.

939. The GA variant of any one of 1 to 934 above and having an I376A substitution.

940. The GA variant of any one of 1 to 934 above and having an I376F substitution.

941. The GA variant of any one of 1 to 934 above and having an I376L substitution.

942. The GA variant of any one of 1 to 934 above and having an I376M substitution.

943. The GA variant of any one of 1 to 942 above and having a S380A substitution.

944. The GA variant of any one of 1 to 942 above and having a S380F substitution.

945. The GA variant of any one of 1 to 942 above and having a S380K substitution.

946. The GA variant of any one of 1 to 942 above and having a S380L substitution.

947. The GA variant of any one of 1 to 942 above and having a S380Q substitution.

948. The GA variant of any one of 1 to 942 above and having a S380R substitution.

949. The GA variant of any one of 1 to 942 above and having a S380W substitution.

950. The GA variant of any one of 1 to 942 above and having a S380Y substitution.

951. The GA variant of any one of 1 to 950 above and having a V381F substitution.

952. The GA variant of any one of 1 to 950 above and having a V381G substitution.

953. The GA variant of any one of 1 to 950 above and having a V381K substitution.

954. The GA variant of any one of 1 to 950 above and having a V381M substitution.

955. The GA variant of any one of 1 to 950 above and having a V381N substitution.

956. The GA variant of any one of 1 to 950 above and having a V381S substitution.

957. The GA variant of any one of 1 to 950 above and having a V381A substitution.

958. The GA variant of any one of 1 to 950 above and having a V381C substitution.

959. The GA variant of any one of 1 to 950 above and having a V381Q substitution.

960. The GA variant of any one of 1 to 959 above and having a P384D substitution.

961. The GA variant of any one of 1 to 959 above and having a P384F substitution.

962. The GA variant of any one of 1 to 959 above and having a P384S substitution.

963. The GA variant of any one of 1 to 959 above and having a P384Y substitution.

964. The GA variant of any one of 1 to 959 above and having a P384E substitution.

965. The GA variant of any one of 1 to 959 above and having a P384T substitution.

966. The GA variant of any one of 1 to 959 above and having a P384V substitution.

967. The GA variant of any one of 1 to 966 above and having a R387C substitution.

968. The GA variant of any one of 1 to 966 above and having a R387I substitution.

969. The GA variant of any one of 1 to 966 above and having a R387Q substitution.

970. The GA variant of any one of 1 to 966 above and having a R387Y substitution.

971. The GA variant of any one of 1 to 966 above and having a R387G substitution.

972. The GA variant of any one of 1 to 966 above and having a R387L substitution.

973. The GA variant of any one of 1 to 966 above and having a R387K substitution.

974. The GA variant of any one of 1 to 973 above and having a V390H substitution.

975. The GA variant of any one of 1 to 973 above and having a V390I substitution.

976. The GA variant of any one of 1 to 973 above and having a V390K substitution.

977. The GA variant of any one of 1 to 973 above and having a V390Y substitution.

978. The GA variant of any one of 1 to 973 above and having a V390F substitution.

979. The GA variant of any one of 1 to 973 above and having a V390L substitution.

980. The GA variant of any one of 1 to 973 above and having a V390R substitution.

981. The GA variant of any one of 1 to 980 above and having a S391N substitution.

982. The GA variant of any one of 1 to 980 above and having a S391H substitution.

983. The GA variant of any one of 1 to 980 above and having a S391L substitution.

984. The GA variant of any one of 1 to 980 above and having a S391F substitution.

985. The GA variant of any one of 1 to 980 above and having a S391I substitution.

986. The GA variant of any one of 1 to 980 above and having a S391R substitution.

987. The GA variant of any one of 1 to 986 above and having a T395K substitution.

988. The GA variant of any one of 1 to 986 above and having a T395Q substitution.

989. The GA variant of any one of 1 to 986 above and having a T395R substitution.

990. The GA variant of any one of 1 to 986 above and having a T395V substitution.

991. The GA variant of any one of 1 to 986 above and having a T395Y substitution.

992. The GA variant of any one of 1 to 986 above and having a T395F substitution.

993. The GA variant of any one of 1 to 986 above and having a T395L substitution.

994. The GA variant of any one of 1 to 993 above and having a G396E substitution.

995. The GA variant of any one of 1 to 993 above and having a G396L substitution.

996. The GA variant of any one of 1 to 993 above and having a G396Q substitution.

997. The GA variant of any one of 1 to 993 above and having a G396R substitution.

998. The GA variant of any one of 1 to 993 above and having a G396K substitution.

999. The GA variant of any one of 1 to 993 above and having a G396V substitution.

1000. The GA variant of any one of 1 to 999 above and having a S399Q substitution.

1001. The GA variant of any one of 1 to 999 above and having a S399T substitution.

1002. The GA variant of any one of 1 to 999 above and having a S399R substitution.

1003. The GA variant of any one of 1 to 999 above and having a S399W substitution.

1004. The GA variant of any one of 1 to 999 above and having a S399K substitution.

1005. The GA variant of any one of 1 to 999 above and having a S399C substitution.

1006. The GA variant of any one of 1 to 1005 above and having a S401H substitution.

1007. The GA variant of any one of 1 to 1005 above and having a S401T substitution.

1008. The GA variant of any one of 1 to 1005 above and having a S401A substitution.

1009. The GA variant of any one of 1 to 1005 above and having a S401Y substitution.

1010. The GA variant of any one of 1 to 1005 above and having a S401P substitution.

1011. The GA variant of any one of 1 to 1005 above and having a S401Q substitution.

1012. The GA variant of any one of 1 to 1011 above and having a S403I substitution.

1013. The GA variant of any one of 1 to 1011 above and having a S403P substitution.

1014. The GA variant of any one of 1 to 1011 above and having a S403W substitution.

1015. The GA variant of any one of 1 to 1011 above and having a S403Y substitution.

1016. The GA variant of any one of 1 to 1011 above and having a S403A substitution.

1017. The GA variant of any one of 1 to 1011 above and having a S403V substitution.

1018. The GA variant of any one of 1 to 1017 above and having a F405A substitution.

1019. The GA variant of any one of 1 to 1017 above and having a F405H substitution.

1020. The GA variant of any one of 1 to 1017 above and having a F405W substitution.

1021. The GA variant of any one of 1 to 1017 above and having a F405Y substitution.

1022. The GA variant of any one of 1 to 1017 above and having a F405N substitution.

1023. The GA variant of any one of 1 to 1017 above and having a F405S substitution.

1024. The GA variant of any one of 1 to 1023 above and having an I408Q substitution.

1025. The GA variant of any one of 1 to 1023 above and having an I408A substitution.

1026. The GA variant of any one of 1 to 1023 above and having an I408T substitution.

1027. The GA variant of any one of 1 to 1023 above and having an I408V substitution.

1028. The GA variant of any one of 1 to 1023 above and having an I408S substitution.

1029. The GA variant of any one of 1 to 1023 above and having an I408Y substitution.

1030. The GA variant of any one of 1 to 1029 above and having an A448F substitution.

1031. The GA variant of any one of 1 to 1029 above and having an A448P substitution.

1032. The GA variant of any one of 1 to 1029 above and having an A448T substitution.

1033. The GA variant of any one of 1 to 1029 above and having an A448N substitution.

1034. The GA variant of any one of 1 to 1029 above and having an A448I substitution.

1035. The GA variant of any one of 1 to 1029 above and having an A448Q substitution.

1036. The GA variant of any one of 1 to 1035 above and having a D462H substitution.

1037. The GA variant of any one of 1 to 1035 above and having a D462A substitution.

1038. The GA variant of any one of 1 to 1035 above and having a D462E substitution.

1039. The GA variant of any one of 1 to 1035 above and having a D462F substitution.

1040. The GA variant of any one of 1 to 1035 above and having a D462I substitution.

1041. The GA variant of any one of 1 to 1035 above and having a D462L substitution.

1042. The GA variant of any one of 1 to 1035 above and having a D462S substitution.

1043. The GA variant of any one of 1 to 1035 above and having a D462M substitution.

1044. The GA variant of any one of 1 to 1035 above and having a D462T substitution.

1045. The GA variant of any one of 1 to 1044 above and having a W472R substitution.

1046. The GA variant of any one of 1 to 1044 above and having a W472D substitution.

1047. The GA variant of any one of 1 to 1044 above and having a W472I substitution.

1048. The GA variant of any one of 1 to 1044 above and having a W472M substitution.

1049. The GA variant of any one of 1 to 1044 above and having a W472Q substitution.

1050. The GA variant of any one of 1 to 1044 above and having a W472S substitution.

1051. The GA variant of any one of 1 to 1044 above and having a W472Y substitution.

1052. The GA variant of any one of 1 to 1051 above and having a S475K substitution.

1053. The GA variant of any one of 1 to 1051 above and having a S475N substitution.

1054. The GA variant of any one of 1 to 1051 above and having a S475Q substitution.

1055. The GA variant of any one of 1 to 1051 above and having a S475E substitution.

1056. The GA variant of any one of 1 to 1051 above and having a S475F substitution.

1057. The GA variant of any one of 1 to 1051 above and having a S475I substitution.

1058. The GA variant of any one of 1 to 1051 above and having a S475R substitution.

1059. The GA variant of any one of 1 to 1051 above and having a S475L substitution.

1060. The GA variant of any one of 1 to 1059 above and having a S486V substitution.

1061. The GA variant of any one of 1 to 1059 above and having a S486T substitution.

1062. The GA variant of any one of 1 to 1059 above and having a S486Y substitution.

1063. The GA variant of any one of 1 to 1059 above and having a S486D substitution.

1064. The GA variant of any one of 1 to 1059 above and having a S486G substitution.

1065. The GA variant of any one of 1 to 1059 above and having a S486K substitution.

1066. The GA variant of any one of 1 to 1059 above and having a S486L substitution.

1067. The GA variant of any one of 1 to 1059 above and having a S486I substitution.

1068. The GA variant of any one of 1 to 1059 above and having a S486M substitution.

1069. The GA variant of any one of 1 to 1068 above and having an A491H substitution.

1070. The GA variant of any one of 1 to 1068 above and having an A491I substitution.

1071. The GA variant of any one of 1 to 1068 above and having an A491L substitution.

1072. The GA variant of any one of 1 to 1068 above and having an A491M substitution.

1073. The GA variant of any one of 1 to 1068 above and having an A491Y substitution.

1074. The GA variant of any one of 1 to 1068 above and having an A491K substitution.

1075. The GA variant of any one of 1 to 1068 above and having an A491R substitution.

1076. The GA variant of any one of 1 to 1068 above and having an A491V substitution.

1077. The GA variant of any one of 1 to 1076 above and having a S511I substitution.

1078. The GA variant of any one of 1 to 1076 above and having a S511W substitution.

1079. The GA variant of any one of 1 to 1076 above and having a S511H substitution.

1080. The GA variant of any one of 1 to 1076 above and having a S511K substitution.

1081. The GA variant of any one of 1 to 1076 above and having a S511L substitution.

1082. The GA variant of any one of 1 to 1076 above and having a S511N substitution.

1083. The GA variant of any one of 1 to 1082 above and having a S515D substitution.

1084. The GA variant of any one of 1 to 1082 above and having a S515M substitution.

1085. The GA variant of any one of 1 to 1082 above and having a S515N substitution.

1086. The GA variant of any one of 1 to 1082 above and having a S515T substitution.

1087. The GA variant of any one of 1 to 1082 above and having a S515A substitution.

1088. The GA variant of any one of 1 to 1082 above and having a S515I substitution.

1089. The GA variant of any one of 1 to 1082 above and having a S515K substitution.

1090. The GA variant of any one of 1 to 1082 above and having a S515V substitution.

1091. The GA variant of any one of 1 to 1090 above and having an A524F substitution.

1092. The GA variant of any one of 1 to 1090 above and having an A524L substitution.

1093. The GA variant of any one of 1 to 1090 above and having an A524N substitution.

1094. The GA variant of any one of 1 to 1090 above and having an A524Q substitution.

1095. The GA variant of any one of 1 to 1090 above and having an A524R substitution.

1096. The GA variant of any one of 1 to 1090 above and having an A524T substitution.

1097. The GA variant of any one of 1 to 1090 above and having an A524W substitution.

1098. The GA variant of any one of 1 to 1090 above and having an A524S substitution.

1099. The GA variant of any one of 1 to 1090 above and having an A524Y substitution.

1100. The GA variant of any one of 1 to 1099 above and having a V537M substitution.

1101. The GA variant of any one of 1 to 1099 above and having a V537T substitution.

1102. The GA variant of any one of 1 to 1099 above and having a V537A substitution.

1103. The GA variant of any one of 1 to 1099 above and having a V537C substitution.

1104. The GA variant of any one of 1 to 1099 above and having a V537K substitution.

1105. The GA variant of any one of 1 to 1099 above and having a V537R substitution.

1106. The GA variant of any one of 1 to 1105 above and having a S538G substitution.

1107. The GA variant of any one of 1 to 1105 above and having a S538A substitution.

1108. The GA variant of any one of 1 to 1105 above and having a S538C substitution.

1109. The GA variant of any one of 1 to 1105 above and having a S538K substitution.

1110. The GA variant of any one of 1 to 1105 above and having a S538Q substitution.

1111. The GA variant of any one of 1 to 1105 above and having a S538R substitution.

1112. The GA variant of any one of 1 to 1105 above and having a S538T substitution.

1113. The GA variant of any one of 1 to 1105 above and having a S538F substitution.

1114. The GA variant of any one of 1 to 1113 above and having an A540Y substitution.

1115. The GA variant of any one of 1 to 1113 above and having an A540E substitution.

1116. The GA variant of any one of 1 to 1113 above and having an A540F substitution.

1117. The GA variant of any one of 1 to 1113 above and having an A540L substitution.

1118. The GA variant of any one of 1 to 1113 above and having an A540T substitution.

1119. The GA variant of any one of 1 to 1113 above and having an A540V substitution.

1120. The GA variant of any one of 1 to 1113 above and having an A540W substitution.

1121. The GA variant of any one of 1 to 1113 above and having an A540M substitution.

1122. The GA variant of any one of 1 to 1121 above and having a W541A substitution.

1123. The GA variant of any one of 1 to 1121 above and having a W541I substitution.

1124. The GA variant of any one of 1 to 1121 above and having a W541L substitution.

1125. The GA variant of any one of 1 to 1121 above and having a W541R substitution.

1126. The GA variant of any one of 1 to 1121 above and having a W541V substitution.

1127. The GA variant of any one of 1 to 1121 above and having a W541Y substitution.

1128. The GA variant of any one of 1 to 1127 above and having a G542D substitution.

1129. The GA variant of any one of 1 to 1127 above and having a G542A substitution.

1130. The GA variant of any one of 1 to 1127 above and having a G542M substitution.

1131. The GA variant of any one of 1 to 1127 above and having a G542N substitution.

1132. The GA variant of any one of 1 to 1127 above and having a G542K substitution.

1133. The GA variant of any one of 1 to 1127 above and having a G542R substitution.

1134. The GA variant of any one of 1 to 1133 above and having a V551S substitution.

1135. The GA variant of any one of 1 to 1133 above and having a V551N substitution.

1136. The GA variant of any one of 1 to 1133 above and having a V551F substitution.

1137. The GA variant of any one of 1 to 1133 above and having a V551K substitution.

1138. The GA variant of any one of 1 to 1133 above and having a V551L substitution.

1139. The GA variant of any one of 1 to 1133 above and having a V551Q substitution.

1140. The GA variant of any one of 1 to 1133 above and having a V551Y substitution.

1141. The GA variant of any one of 1 to 1140 above and having a P552A substitution.

1142. The GA variant of any one of 1 to 1140 above and having a P552G substitution.

1143. The GA variant of any one of 1 to 1140 above and having a P552I substitution.

1144. The GA variant of any one of 1 to 1140 above and having a P552K substitution.

1145. The GA variant of any one of 1 to 1140 above and having a P552M substitution.

1146. The GA variant of any one of 1 to 1140 above and having a P552N substitution.

1147. The GA variant of any one of 1 to 1140 above and having a P552Y substitution.

1148. The GA variant of any one of 1 to 1140 above and having a P552R substitution.

1149. The GA variant of any one of 1 to 1148 above and having a K561D substitution.

1150. The GA variant of any one of 1 to 1148 above and having a K561E substitution.

1151. The GA variant of any one of 1 to 1148 above and having a K561G substitution.

1152. The GA variant of any one of 1 to 1148 above and having a K561I substitution.

1153. The GA variant of any one of 1 to 1148 above and having a K561L substitution.

1154. The GA variant of any one of 1 to 1148 above and having a K561N substitution.

1155. The GA variant of any one of 1 to 1148 above and having a K561P substitution.

1156. The GA variant of any one of 1 to 1148 above and having a K561Q substitution.

1157. The GA variant of any one of 1 to 1148 above and having a K561R substitution.

1158. The GA variant of any one of 1 to 1157 above and having an A562I substitution.

1159. The GA variant of any one of 1 to 1157 above and having an A562K substitution.

1160. The GA variant of any one of 1 to 1157 above and having an A562L substitution.

1161. The GA variant of any one of 1 to 1157 above and having an A562Y substitution.

1162. The GA variant of any one of 1 to 1157 above and having an A562C substitution.

1163. The GA variant of any one of 1 to 1157 above and having an A562G substitution.

1164. The GA variant of any one of 1 to 1157 above and having an A562V substitution.

1165. The GA variant of any one of 1 to 1157 above and having an A562S substitution.

1166. The GA variant of any one of 1 to 1165 above and having a T564N substitution.

1167. The GA variant of any one of 1 to 1165 above and having a T564L substitution.

1168. The GA variant of any one of 1 to 1165 above and having a T564M substitution.

1169. The GA variant of any one of 1 to 1165 above and having a T564S substitution.

1170. The GA variant of any one of 1 to 1165 above and having a T564K substitution.

1171. The GA variant of any one of 1 to 1165 above and having a T564R substitution.

1172. The GA variant of any one of 1 to 1171 above and having a L565E substitution.

1173. The GA variant of any one of 1 to 1171 above and having a L565H substitution.

1174. The GA variant of any one of 1 to 1171 above and having a L565M substitution.

1175. The GA variant of any one of 1 to 1171 above and having a L565Q substitution.

1176. The GA variant of any one of 1 to 1171 above and having a L565S substitution.

1177. The GA variant of any one of 1 to 1171 above and having a L565T substitution.

1178. The GA variant of any one of 1 to 1171 above and having a L565V substitution.

1179. The GA variant of any one of 1 to 1178 above and having a N573G substitution.

1180. The GA variant of any one of 1 to 1178 above and having a N573E substitution.

1181. The GA variant of any one of 1 to 1178 above and having a N573F substitution.

1182. The GA variant of any one of 1 to 1178 above and having a N573H substitution.

1183. The GA variant of any one of 1 to 1178 above and having a N5731 substitution.

1184. The GA variant of any one of 1 to 1178 above and having a N573Y substitution.

1185. The GA variant of any one of 1 to 1178 above and having a N573A substitution.

1186. The GA variant of any one of 1 to 1185 above and having an A585D substitution.

1187. The GA variant of any one of 1 to 1185 above and having an A585F substitution.

1188. The GA variant of any one of 1 to 1185 above and having an A585S substitution.

1189. The GA variant of any one of 1 to 1185 above and having an A585T substitution.

1190. The GA variant of any one of 1 to 1185 above and having an A585W substitution.

1191. The GA variant of any one of 1 to 1185 above and having an A585Y substitution.

1192. The GA variant of any one of 1 to 1185 above and having an A585N substitution.

1193. The GA variant of any one of 1 to 1192 above and having a V590W substitution.

1194. The GA variant of any one of 1 to 1192 above and having a V590A substitution.

1195. The GA variant of any one of 1 to 1192 above and having a V590G substitution.

1196. The GA variant of any one of 1 to 1192 above and having a V590P substitution.

1197. The GA variant of any one of 1 to 1192 above and having a V590S substitution.

1198. The GA variant of any one of 1 to 1192 above and having a V590I substitution.

1199. The GA variant of any one of 1 to 1192 above and having a V590L substitution.

1200. The GA variant of any one of 1 to 1199 above and having a Q591L substitution.

1201. The GA variant of any one of 1 to 1199 above and having a Q591Y substitution.

1202. The GA variant of any one of 1 to 1199 above and having a Q591C substitution.

1203. The GA variant of any one of 1 to 1199 above and having a Q591R substitution.

1204. The GA variant of any one of 1 to 1199 above and having a Q591P substitution.

1205. The GA variant of any one of 1 to 1199 above and having a Q591S substitution.

1206. The GA variant of any one of 1 to 1199 above and having a Q591T substitution.

1207. The GA variant of any one of 1 to 1206 above and having a V597R substitution.

1208. The GA variant of any one of 1 to 1206 above and having a V597L substitution.

1209. The GA variant of any one of 1 to 1206 above and having a V597M substitution.

1210. The GA variant of any one of 1 to 1206 above and having a V597Q substitution.

1211. The GA variant of any one of 1 to 1206 above and having a V597S substitution.

1212. The GA variant of any one of 1 to 1206 above and having a V597W substitution.

1213. The GA variant of any one of 1 to 1206 above and having a V597F substitution.

1214. The GA variant of any one of 1 to 1206 above and having a V597K substitution.

1215. The GA variant of any one of 1 to 1214 above and having a G601E substitution.

1216. The GA variant of any one of 1 to 1214 above and having a G601I substitution.

1217. The GA variant of any one of 1 to 1214 above and having a G601R substitution.

1218. The GA variant of any one of 1 to 1214 above and having a G601A substitution.

1219. The GA variant of any one of 1 to 1214 above and having a G601H substitution.

1220. The GA variant of any one of 1 to 1214 above and having a G601N substitution.

1221. The GA variant of any one of 1 to 1214 above and having a G601P substitution.

1222. The GA variant of any one of 1 to 1214 above and having a G601Q substitution.

1223. The GA variant of any one of 1 to 1214 above and having a G601M substitution.

1224. The GA variant of any one of 1 to 1223 above and having an I603Q substitution.

1225. The GA variant of any one of 1 to 1223 above and having an I603T substitution.

1226. The GA variant of any one of 1 to 1223 above and having an I603Y substitution.

1227. The GA variant of any one of 1 to 1223 above and having an I603A substitution.

1228. The GA variant of any one of 1 to 1223 above and having an I603K substitution.

1229. The GA variant of any one of 1 to 1223 above and having an I603F substitution.

1230. The GA variant of any one of 1 to 1223 above and having an I603L substitution.

1231. The GA variant of any one of 1 to 1223 above and having an I603N substitution.

1232. The GA variant of any one of 1 to 1223 above and having an I603P substitution.

1233. The GA variant of any one of 1 to 1232 above and having a D608L substitution.

1234. The GA variant of any one of 1 to 1232 above and having a D608P substitution.

1235. The GA variant of any one of 1 to 1232 above and having a D608R substitution.

1236. The GA variant of any one of 1 to 1232 above and having a D608T substitution.

1237. The GA variant of any one of 1 to 1232 above and having a D608E substitution.

1238. The GA variant of any one of 1 to 1232 above and having a D608F substitution.

1239. The GA variant of any one of 1 to 1232 above and having a D6081 substitution.

1240. The GA variant of any one of 1 to 1239 above and having an I613A substitution.

1241. The GA variant of any one of 1 to 1239 above and having an I613F substitution.

1242. The GA variant of any one of 1 to 1239 above and having an I613L substitution.

1243. The GA variant of any one of 1 to 1239 above and having an I613S substitution.

1244. The GA variant of any one of 1 to 1239 above and having an I613T substitution.

1245. The GA variant of any one of 1 to 1239 above and having an I613V substitution.

1246. The GA variant of any one of 1 to 1245 above and having a T614L substitution.

1247. The GA variant of any one of 1 to 1245 above and having a T614M substitution.

1248. The GA variant of any one of 1 to 1245 above and having a T614Q substitution.

1249. The GA variant of any one of 1 to 1245 above and having a T614V substitution.

1250. The GA variant of any one of 1 to 1245 above and having a T614Y substitution.

1251. The GA variant of any one of 1 to 1245 above and having a T614S substitution.

1252. The GA variant of any one of 1 to 1251 above and having a S620D substitution.

1253. The GA variant of any one of 1 to 1251 above and having a S620M substitution.

1254. The GA variant of any one of 1 to 1251 above and having a S620Q substitution.

1255. The GA variant of any one of 1 to 1251 above and having a S620E substitution.

1256. The GA variant of any one of 1 to 1251 above and having a S620H substitution.

1257. The GA variant of any one of 1 to 1251 above and having a S620P substitution.

1258. The GA variant of any one of 1 to 1251 above and having a S620R substitution.

1259. The GA variant of any one of 1 to 1258 above and having a S632L substitution.

1260. The GA variant of any one of 1 to 1258 above and having a S632C substitution.

1261. The GA variant of any one of 1 to 1258 above and having a S632D substitution.

1262. The GA variant of any one of 1 to 1258 above and having a S632E substitution.

1263. The GA variant of any one of 1 to 1258 above and having a S632G substitution.

1264. The GA variant of any one of 1 to 1258 above and having a S632T substitution.

1265. The GA variant of any one of 1 to 1264 above and having an A32S substitution.

1266. The GA variant of any one of 1 to 1264 above and having an A32T substitution.

1267. The GA variant of any one of 1 to 1264 above and having an A32E substitution.

1268. The GA variant of any one of 1 to 1264 above and having an A32Q substitution.

1269. The GA variant of any one of 1 to 1268 above and having a V33L substitution.

1270. The GA variant of any one of 1 to 1268 above and having a V33P substitution.

1271. The GA variant of any one of 1 to 1268 above and having a V33I substitution.

1272. The GA variant of any one of 1 to 1271 above and having a N38G substitution.

1273. The GA variant of any one of 1 to 1271 above and having a N38F substitution.

1274. The GA variant of any one of 1 to 1271 above and having a N38H substitution.

1275. The GA variant of any one of 1 to 1271 above and having a N38K substitution.

1276. The GA variant of any one of 1 to 1271 above and having a N38I substitution.

1277. The GA variant of any one of 1 to 1271 above and having a T39E substitution.

1278. The GA variant of any one of 1 to 1271 above and having a N38K substitution.

1279. The GA variant of any one of 1 to 1271 above and having a N38L substitution.

1280. The GA variant of any one of 1 to 1271 above and having a N38Q substitution.

1281. The GA variant of any one of 1 to 1280 above and having a T74D substitution.

1282. The GA variant of any one of 1 to 1280 above and having a T74I substitution.

1283. The GA variant of any one of 1 to 1280 above and having a T74K substitution.

1284. The GA variant of any one of 1 to 1280 above and having a T74V substitution.

1285. The GA variant of any one of 1 to 1284 above and having a H99G substitution.

1286. The GA variant of any one of 1 to 1284 above and having a H99A substitution.

1287. The GA variant of any one of 1 to 1284 above and having a H99M substitution.

1288. The GA variant of any one of 1 to 1284 above and having a H99V substitution.

1289. The GA variant of any one of 1 to 1284 above and having a H99Y substitution.

1290. The GA variant of any one of 1 to 1289 above and having a T104V substitution.

1291. The GA variant of any one of 1 to 1289 above and having a T104D substitution.

1292. The GA variant of any one of 1 to 1289 above and having a T104E substitution.

1293. The GA variant of any one of 1 to 1292 above and having a N111F substitution.

1294. The GA variant of any one of 1 to 1292 above and having a N111M substitution.

1295. The GA variant of any one of 1 to 1292 above and having a N111D substitution.

1296. The GA variant of any one of 1 to 1292 above and having a N111Q substitution.

1297. The GA variant of any one of 1 to 1292 above and having a N111H substitution.

1298. The GA variant of any one of 1 to 1297 above and having a K118M substitution.

1299. The GA variant of any one of 1 to 1297 above and having a K118L substitution.

1300. The GA variant of any one of 1 to 1297 above and having a K118F substitution.

1301. The GA variant of any one of 1 to 1297 above and having a K118Y substitution.

1302. The GA variant of any one of 1 to 1301 above and having a Q121V substitution.

1303. The GA variant of any one of 1 to 1301 above and having a Q121L substitution.

1304. The GA variant of any one of 1 to 1301 above and having a Q121T substitution.

1305. The GA variant of any one of 1 to 1304 above and having an I164K substitution.

1306. The GA variant of any one of 1 to 1304 above and having an I164V substitution.

1307. The GA variant of any one of 1 to 1304 above and having an I164A substitution.

1308. The GA variant of any one of 1 to 1307 above and having a Q168H substitution.

1309. The GA variant of any one of 1 to 1307 above and having a Q168A substitution.

1310. The GA variant of any one of 1 to 1307 above and having a Q168L substitution.

1311. The GA variant of any one of 1 to 1307 above and having a Q168Y substitution.

1312. The GA variant of any one of 1 to 1311 above and having an I174V substitution.

1313. The GA variant of any one of 1 to 1311 above and having an I174F substitution.

1314. The GA variant of any one of 1 to 1311 above and having an I174Y substitution.

1315. The GA variant of any one of 1 to 1314 above and having a G177D substitution.

1316. The GA variant of any one of 1 to 1314 above and having a G177H substitution.

1317. The GA variant of any one of 1 to 1314 above and having a G177K substitution.

1318. The GA variant of any one of 1 to 1314 above and having a G177S substitution.

1319. The GA variant of any one of 1 to 1318 above and having a S180A substitution.

1320. The GA variant of any one of 1 to 1318 above and having a S180C substitution.

1321. The GA variant of any one of 1 to 1318 above and having a S180F substitution.

1322. The GA variant of any one of 1 to 1321 above and having a T181A substitution.

1323. The GA variant of any one of 1 to 1321 above and having a T181S substitution.

1324. The GA variant of any one of 1 to 1321 above and having a T181W substitution.

1325. The GA variant of any one of 1 to 1324 above and having a V190A substitution.

1326. The GA variant of any one of 1 to 1324 above and having a V190I substitution.

1327. The GA variant of any one of 1 to 1324 above and having a V190M substitution.

1328. The GA variant of any one of 1 to 1324 above and having a V190L substitution.

1329. The GA variant of any one of 1 to 1328 above and having a K191V substitution.

1330. The GA variant of any one of 1 to 1328 above and having a K191W substitution.

1331. The GA variant of any one of 1 to 1328 above and having a K191R substitution.

1332. The GA variant of any one of 1 to 1331 above and having an A198Y substitution.

1333. The GA variant of any one of 1 to 1331 above and having an A198C substitution.

1334. The GA variant of any one of 1 to 1331 above and having an A198G substitution.

1335. The GA variant of any one of 1 to 1331 above and having an A198S substitution.

1336. The GA variant of any one of 1 to 1335 above and having a L227A substitution.

1337. The GA variant of any one of 1 to 1335 above and having a L227C substitution.

1338. The GA variant of any one of 1 to 1335 above and having a L227I substitution.

1339. The GA variant of any one of 1 to 1338 above and having a L233T substitution.

1340. The GA variant of any one of 1 to 1338 above and having a L233V substitution.

1341. The GA variant of any one of 1 to 1338 above and having a L233M substitution.

1342. The GA variant of any one of 1 to 1341 above and having a Q236W substitution.

1343. The GA variant of any one of 1 to 1341 above and having a Q236F substitution.

1344. The GA variant of any one of 1 to 1341 above and having a Q236D substitution.

1345. The GA variant of any one of 1 to 1341 above and having a Q236N substitution.

1346. The GA variant of any one of 1 to 1341 above and having a Q236Y substitution.

1347. The GA variant of any one of 1 to 1346 above and having a D238L substitution.

1348. The GA variant of any one of 1 to 1346 above and having a D238Q substitution.

1349. The GA variant of any one of 1 to 1346 above and having a D238R substitution.

1350. The GA variant of any one of 1 to 1349 above and having an E240Q substitution.

1351. The GA variant of any one of 1 to 1349 above and having an E240W substitution.

1352. The GA variant of any one of 1 to 1349 above and having an E240P substitution.

1353. The GA variant of any one of 1 to 1352 above and having an A243G substitution.

1354. The GA variant of any one of 1 to 1352 above and having an A243H substitution.

1355. The GA variant of any one of 1 to 1352 above and having an A243R substitution.

1356. The GA variant of any one of 1 to 1352 above and having an A243P substitution.

1357. The GA variant of any one of 1 to 1356 above and having an A248G substitution.

1358. The GA variant of any one of 1 to 1356 above and having an A248C substitution.

1359. The GA variant of any one of 1 to 1356 above and having an A248S substitution.

1360. The GA variant of any one of 1 to 1359 above and having a V251L substitution.

1361. The GA variant of any one of 1 to 1359 above and having a V251Q substitution.

1362. The GA variant of any one of 1 to 1359 above and having a V251R substitution.

1363. The GA variant of any one of 1 to 1362 above and having a Q255E substitution.

1364. The GA variant of any one of 1 to 1362 above and having a Q255G substitution.

1365. The GA variant of any one of 1 to 1362 above and having a Q255L substitution.

1366. The GA variant of any one of 1 to 1362 above and having a Q255S substitution.

1367. The GA variant of any one of 1 to 1366 above and having a Y275E substitution.

1368. The GA variant of any one of 1 to 1366 above and having a Y275G substitution.

1369. The GA variant of any one of 1 to 1366 above and having a Y275L substitution.

1370. The GA variant of any one of 1 to 1366 above and having a Y275S substitution.

1371. The GA variant of any one of 1 to 1369 above and having a N290E substitution.

1372. The GA variant of any one of 1 to 1369 above and having a N290I substitution.

1373. The GA variant of any one of 1 to 1369 above and having a N290Q substitution.

1374. The GA variant of any one of 1 to 1369 above and having a N290V substitution.

1375. The GA variant of any one of 1 to 1374 above and having a F291Y substitution.

1376. The GA variant of any one of 1 to 1374 above and having a F291L substitution.

1377. The GA variant of any one of 1 to 1374 above and having a F291M substitution.

1378. The GA variant of any one of 1 to 1377 above and having a D292F substitution.

1379. The GA variant of any one of 1 to 1377 above and having a D292C substitution.

1380. The GA variant of any one of 1 to 1377 above and having a D292S substitution.

1381. The GA variant of any one of 1 to 1380 above and having a G296L substitution.

1382. The GA variant of any one of 1 to 1380 above and having a G296P substitution.

1383. The GA variant of any one of 1 to 1380 above and having a G296Q substitution.

1384. The GA variant of any one of 1 to 1380 above and having a G296V substitution.

1385. The GA variant of any one of 1 to 1384 above and having a D298A substitution.

1386. The GA variant of any one of 1 to 1384 above and having a D298E substitution.

1387. The GA variant of any one of 1 to 1384 above and having a D298I substitution.

1388. The GA variant of any one of 1 to 1384 above and having a D298N substitution.

1389. The GA variant of any one of 1 to 1388 above and having a T301A substitution.

1390. The GA variant of any one of 1 to 1388 above and having a T301I substitution.

1391. The GA variant of any one of 1 to 1388 above and having a T301C substitution.

1392. The GA variant of any one of 1 to 1388 above and having a T301L substitution.

1393. The GA variant of any one of 1 to 1392 above and having a F302G substitution.

1394. The GA variant of any one of 1 to 1392 above and having a F302M substitution.

1395. The GA variant of any one of 1 to 1392 above and having a F302W substitution.

1396. The GA variant of any one of 1 to 1395 above and having an A311R substitution.

1397. The GA variant of any one of 1 to 1395 above and having an A311C substitution.

1398. The GA variant of any one of 1 to 1395 above and having an A311G substitution.

1399. The GA variant of any one of 1 to 1395 above and having an A311M substitution.

1400. The GA variant of any one of 1 to 1395 above and having an A311V substitution.

1401. The GA variant of any one of 1 to 1400 above and having an A315G substitution.

1402. The GA variant of any one of 1 to 1400 above and having an A315C substitution.

1403. The GA variant of any one of 1 to 1400 above and having an A315E substitution.

1404. The GA variant of any one of 1 to 1400 above and having an A315M substitution.

1405. The GA variant of any one of 1 to 1400 above and having an A315Q substitution.

1406. The GA variant of any one of 1 to 1405 above and having a S319N substitution.

1407. The GA variant of any one of 1 to 1405 above and having a S319M substitution.

1408. The GA variant of any one of 1 to 1405 above and having a S319Q substitution.

1409. The GA variant of any one of 1 to 1408 above and having a G329T substitution.

1410. The GA variant of any one of 1 to 1408 above and having a G329C substitution.

1411. The GA variant of any one of 1 to 1408 above and having a G329D substitution.

1412. The GA variant of any one of 1 to 1411 above and having an A331V substitution.

1413. The GA variant of any one of 1 to 1411 above and having an A331K substitution.

1414. The GA variant of any one of 1 to 1411 above and having an A331L substitution.

1415. The GA variant of any one of 1 to 1411 above and having an A331R substitution.

1416. The GA variant of any one of 1 to 1411 above and having an A331M substitution.

1417. The GA variant of any one of 1 to 1416 above and having a Q332V substitution.

1418. The GA variant of any one of 1 to 1416 above and having a Q332W substitution.

1419. The GA variant of any one of 1 to 1416 above and having a Q332E substitution.

1420. The GA variant of any one of 1 to 1416 above and having a Q332L substitution.

1421. The GA variant of any one of 1 to 1416 above and having a Q332P substitution.

1422. The GA variant of any one of 1 to 1421 above and having a V345I substitution.

1423. The GA variant of any one of 1 to 1421 above and having a V345Q substitution.

1424. The GA variant of any one of 1 to 1421 above and having a V345K substitution.

1425. The GA variant of any one of 1 to 1424 above and having an A360C substitution.

1426. The GA variant of any one of 1 to 1424 above and having an A360G substitution.

1427. The GA variant of any one of 1 to 1424 above and having an A360S substitution.

1428. The GA variant of any one of 1 to 1427 above and having a D365A substitution.

1429. The GA variant of any one of 1 to 1427 above and having a D365E substitution.

1430. The GA variant of any one of 1 to 1427 above and having a D365Q substitution.

1431. The GA variant of any one of 1 to 1427 above and having a D365R substitution.

1432. The GA variant of any one of 1 to 1431 above and having a W370S substitution.

1433. The GA variant of any one of 1 to 1431 above and having a W370T substitution.

1434. The GA variant of any one of 1 to 1431 above and having a W370V substitution.

1435. The GA variant of any one of 1 to 1431 above and having a W370F substitution.

1436. The GA variant of any one of 1 to 1431 above and having a W370M substitution.

1437. The GA variant of any one of 1 to 1436 above and having a T379E substitution.

1438. The GA variant of any one of 1 to 1436 above and having a T379H substitution.

1439. The GA variant of any one of 1 to 1436 above and having a T379N substitution.

1440. The GA variant of any one of 1 to 1436 above and having a T379Q substitution.

1441. The GA variant of any one of 1 to 1436 above and having a T379R substitution.

1442. The GA variant of any one of 1 to 1441 above and having a F386H substitution.

1443. The GA variant of any one of 1 to 1441 above and having a F386L substitution.

1444. The GA variant of any one of 1 to 1441 above and having a F386T substitution.

1445. The GA variant of any one of 1 to 1441 above and having a F386V substitution.

1446. The GA variant of any one of 1 to 1441 above and having a F386W substitution.

1447. The GA variant of any one of 1 to 1446 above and having a L389A substitution.

1448. The GA variant of any one of 1 to 1446 above and having a L389Q substitution.

1449. The GA variant of any one of 1 to 1446 above and having a L389S substitution.

1450. The GA variant of any one of 1 to 1446 above and having a L389T substitution.

1451. The GA variant of any one of 1 to 1450 above and having a S392Y substitution.

1452. The GA variant of any one of 1 to 1450 above and having a S3921 substitution.

1453. The GA variant of any one of 1 to 1450 above and having a S392P substitution.

1454. The GA variant of any one of 1 to 1453 above and having a Y398N substitution.

1455. The GA variant of any one of 1 to 1453 above and having a Y398Q substitution.

1456. The GA variant of any one of 1 to 1453 above and having a Y398F substitution.

1457. The GA variant of any one of 1 to 1453 above and having a Y398L substitution.

1458. The GA variant of any one of 1 to 1453 above and having a Y398H substitution.

1459. The GA variant of any one of 1 to 1458 above and having a K413T substitution.

1460. The GA variant of any one of 1 to 1458 above and having a K413E substitution.

1461. The GA variant of any one of 1 to 1458 above and having a K413F substitution.

1462. The GA variant of any one of 1 to 1458 above and having a K413L substitution.

1463. The GA variant of any one of 1 to 1458 above and having a K413R substitution.

1464. The GA variant of any one of 1 to 1463 above and having an A416C substitution.

1465. The GA variant of any one of 1 to 1463 above and having an A416G substitution.

1466. The GA variant of any one of 1 to 1463 above and having an A416S substitution.

1467. The GA variant of any one of 1 to 1466 above and having a D417N substitution.

1468. The GA variant of any one of 1 to 1466 above and having a D417T substitution.

1469. The GA variant of any one of 1 to 1466 above and having a D417E substitution.

1470. The GA variant of any one of 1 to 1466 above and having a D417Q substitution.

1471. The GA variant of any one of 1 to 1470 above and having a S429D substitution.

1472. The GA variant of any one of 1 to 1470 above and having a S429G substitution.

1473. The GA variant of any one of 1 to 1470 above and having a S429M substitution.

1474. The GA variant of any one of 1 to 1470 above and having a S429T substitution.

1475. The GA variant of any one of 1 to 1470 above and having a S429A substitution.

1476. The GA variant of any one of 1 to 1475 above and having an A434F substitution.

1477. The GA variant of any one of 1 to 1475 above and having an A434S substitution.

1478. The GA variant of any one of 1 to 1475 above and having an A434W substitution.

1479. The GA variant of any one of 1 to 1475 above and having an A434Y substitution.

1480. The GA variant of any one of 1 to 1479 above and having a K443I substitution.

1481. The GA variant of any one of 1 to 1479 above and having a K443M substitution.

1482. The GA variant of any one of 1 to 1479 above and having a K443L substitution.

1483. The GA variant of any one of 1 to 1479 above and having a K443H substitution.

1484. The GA variant of any one of 1 to 1483 above and having an A460C substitution.
1485. The GA variant of any one of 1 to 1483 above and having an A460G substitution.
1486. The GA variant of any one of 1 to 1483 above and having an A460M substitution.
1487. The GA variant of any one of 1 to 1483 above and having an A460T substitution.
1488. The GA variant of any one of 1 to 1487 above and having a R463A substitution.
1489. The GA variant of any one of 1 to 1487 above and having a R463K substitution.
1490. The GA variant of any one of 1 to 1487 above and having a R463M substitution.
1491. The GA variant of any one of 1 to 1490 above and having a R464F substitution.
1492. The GA variant of any one of 1 to 1490 above and having a R464V substitution.
1493. The GA variant of any one of 1 to 1490 above and having a R464H substitution.
1494. The GA variant of any one of 1 to 1490 above and having a R464K substitution.
1495. The GA variant of any one of 1 to 1494 above and having an A4651 substitution.
1496. The GA variant of any one of 1 to 1494 above and having an A465W substitution.
1497. The GA variant of any one of 1 to 1494 above and having an A465M substitution.
1498. The GA variant of any one of 1 to 1494 above and having an A465R substitution.
1499. The GA variant of any one of 1 to 1494 above and having an A465Y substitution.
1500. The GA variant of any one of 1 to 1499 above and having a R473T substitution.
1501. The GA variant of any one of 1 to 1499 above and having a R473C substitution.
1502. The GA variant of any one of 1 to 1499 above and having a R473M substitution.
1503. The GA variant of any one of 1 to 1502 above and having a L481F substitution.
1504. The GA variant of any one of 1 to 1502 above and having a L481H substitution.
1505. The GA variant of any one of 1 to 1502 above and having a L481R substitution.
1506. The GA variant of any one of 1 to 1502 above and having a L481C substitution.
1507. The GA variant of any one of 1 to 1506 above and having a T493C substitution.
1508. The GA variant of any one of 1 to 1506 above and having a T493S substitution.
1509. The GA variant of any one of 1 to 1506 above and having a T493V substitution.
1510. The GA variant of any one of 1 to 1506 above and having a T493Q substitution.
1511. The GA variant of any one of 1 to 1510 above and having a S499A substitution.
1512. The GA variant of any one of 1 to 1510 above and having a S499C substitution.
1513. The GA variant of any one of 1 to 1510 above and having a S499H substitution.
1514. The GA variant of any one of 1 to 1510 above and having a S499N substitution.
1515. The GA variant of any one of 1 to 1510 above and having a S499M substitution.
1516. The GA variant of any one of 1 to 1515 above and having a S501V substitution.
1517. The GA variant of any one of 1 to 1515 above and having a S501A substitution.
1518. The GA variant of any one of 1 to 1515 above and having a S501I substitution.
1519. The GA variant of any one of 1 to 1515 above and having a S501Q substitution.
1520. The GA variant of any one of 1 to 1519 above and having a V531S substitution.
1521. The GA variant of any one of 1 to 1519 above and having a V531T substitution.
1522. The GA variant of any one of 1 to 1519 above and having a V531A substitution.
1523. The GA variant of any one of 1 to 1519 above and having a V531C substitution.
1524. The GA variant of any one of 1 to 1523 above and having a R536C substitution.
1525. The GA variant of any one of 1 to 1523 above and having a R536Q substitution.
1526. The GA variant of any one of 1 to 1523 above and having a R536L substitution.
1527. The GA variant of any one of 1 to 1523 above and having a R536Y substitution.
1528. The GA variant of any one of 1 to 1523 above and having a R536H substitution.
1529. The GA variant of any one of 1 to 1528 above and having a V548F substitution.
1530. The GA variant of any one of 1 to 1528 above and having a V548M substitution.
1531. The GA variant of any one of 1 to 1528 above and having a V548T substitution.
1532. The GA variant of any one of 1 to 1531 above and having a N550C substitution.
1533. The GA variant of any one of 1 to 1531 above and having a N550G substitution.
1534. The GA variant of any one of 1 to 1531 above and having a N550M substitution.
1535. The GA variant of any one of 1 to 1531 above and having a N550S substitution.
1536. The GA variant of any one of 1 to 1531 above and having a N550T substitution.
1537. The GA variant of any one of 1 to 1536 above and having an A553E substitution.
1538. The GA variant of any one of 1 to 1536 above and having an A553K substitution.
1539. The GA variant of any one of 1 to 1536 above and having an A553P substitution.
1540. The GA variant of any one of 1 to 1536 above and having an A553Q substitution.
1541. The GA variant of any one of 1 to 1536 above and having an A553Y substitution.
1542. The GA variant of any one of 1 to 1541 above and having a L554M substitution.
1543. The GA variant of any one of 1 to 1541 above and having a L554V substitution.
1544. The GA variant of any one of 1 to 1541 above and having a L554T substitution.
1545. The GA variant of any one of 1 to 1544 above and having a G555K substitution.
1546. The GA variant of any one of 1 to 1544 above and having a G555A substitution.
1547. The GA variant of any one of 1 to 1544 above and having a G555H substitution.
1548. The GA variant of any one of 1 to 1547 above and having a D558F substitution.
1549. The GA variant of any one of 1 to 1547 above and having a D558L substitution.

1550. The GA variant of any one of 1 to 1547 above and having a D558Q substitution.

1551. The GA variant of any one of 1 to 1547 above and having a D558R substitution.

1552. The GA variant of any one of 1 to 1551 above and having a T559E substitution.

1553. The GA variant of any one of 1 to 1551 above and having a T559G substitution.

1554. The GA variant of any one of 1 to 1551 above and having a T559I substitution.

1555. The GA variant of any one of 1 to 1551 above and having a T559L substitution.

1556. The GA variant of any one of 1 to 1555 above and having a S560F substitution.

1557. The GA variant of any one of 1 to 1555 above and having a S560A substitution.

1558. The GA variant of any one of 1 to 1555 above and having a S560K substitution.

1559. The GA variant of any one of 1 to 1555 above and having a S560M substitution.

1560. The GA variant of any one of 1 to 1555 above and having a S560V substitution.

1561. The GA variant of any one of 1 to 1560 above and having a S572P substitution.

1562. The GA variant of any one of 1 to 1560 above and having a S572E substitution.

1563. The GA variant of any one of 1 to 1560 above and having a S572L substitution.

1564. The GA variant of any one of 1 to 1560 above and having a S572V substitution.

1565. The GA variant of any one of 1 to 1560 above and having a S572K substitution.

1566. The GA variant of any one of 1 to 1565 above and having a D574I substitution.

1567. The GA variant of any one of 1 to 1565 above and having a D574M substitution.

1568. The GA variant of any one of 1 to 1565 above and having a D574N substitution.

1569. The GA variant of any one of 1 to 1565 above and having a D574Y substitution.

1570. The GA variant of any one of 1 to 1569 above and having a S578F substitution.

1571. The GA variant of any one of 1 to 1569 above and having a S578A substitution.

1572. The GA variant of any one of 1 to 1569 above and having a S578C substitution.

1573. The GA variant of any one of 1 to 1572 above and having a K584F substitution.

1574. The GA variant of any one of 1 to 1572 above and having a K584T substitution.

1575. The GA variant of any one of 1 to 1572 above and having a K584V substitution.

1576. The GA variant of any one of 1 to 1575 above and having a S588H substitution.

1577. The GA variant of any one of 1 to 1575 above and having a S588L substitution.

1578. The GA variant of any one of 1 to 1575 above and having a S588P substitution.

1579. The GA variant of any one of 1 to 1575 above and having a S588Y substitution.

1580. The GA variant of any one of 1 to 1579 above and having an I595G substitution.

1581. The GA variant of any one of 1 to 1579 above and having an I595M substitution.

1582. The GA variant of any one of 1 to 1579 above and having an I595T substitution.

1583. The GA variant of any one of 1 to 1579 above and having an I595L substitution.

1584. The GA variant of any one of 1 to 1583 above and having a K596D substitution.

1585. The GA variant of any one of 1 to 1583 above and having a K596E substitution.

1586. The GA variant of any one of 1 to 1583 above and having a K596N substitution.

1587. The GA variant of any one of 1 to 1586 above and having a K602D substitution.

1588. The GA variant of any one of 1 to 1586 above and having a K602I substitution.

1589. The GA variant of any one of 1 to 1586 above and having a K602R substitution.

1590. The GA variant of any one of 1 to 1586 above and having a K602F substitution.

1591. The GA variant of any one of 1 to 1590 above and having a W605T substitution.

1592. The GA variant of any one of 1 to 1590 above and having a W605Y substitution.

1593. The GA variant of any one of 1 to 1590 above and having a W605F substitution.

1594. The GA variant of any one of 1 to 1593 above and having an E606G substitution.

1595. The GA variant of any one of 1 to 1593 above and having an E606K substitution.

1596. The GA variant of any one of 1 to 1593 above and having an E606Q substitution.

1597. The GA variant of any one of 1 to 1596 above and having a R611S substitution.

1598. The GA variant of any one of 1 to 1596 above and having a R611N substitution.

1599. The GA variant of any one of 1 to 1596 above and having a R611H substitution.

1600. The GA variant of any one of 1 to 1599 above and having a S612C substitution.

1601. The GA variant of any one of 1 to 1599 above and having a S612E substitution.

1602. The GA variant of any one of 1 to 1599 above and having a S612W substitution.

1603. The GA variant of any one of 1 to 1599 above and having a S612F substitution.

1604. The GA variant of any one of 1 to 1599 above and having a S612H substitution.

1605. The GA variant of any one of 1 to 1604 above and having a S619L substitution.

1606. The GA variant of any one of 1 to 1604 above and having a S619E substitution.

1607. The GA variant of any one of 1 to 1604 above and having a S619Q substitution.

1608. The GA variant of any one of 1 to 1607 above and having a V629C substitution.

1609. The GA variant of any one of 1 to 1607 above and having a V629S substitution.

1610. The GA variant of any one of 1 to 1607 above and having a V629I substitution.

1611. The GA variant of any one of 1 to 1607 above and having a V629M substitution.

1612. The GA variant of any one of 1 to 1607 above and having a V629Q substitution.

1613. The GA variant of any one of 1 to 1612 above and having a D34M substitution.

1614. The GA variant of any one of 1 to 1613 above and having a P42C substitution.

1615. The GA variant of any one of 1 to 1613 above and having a P42Q substitution.

1616. The GA variant of any one of 1 to 1615 above and having an 143V substitution.

1617. The GA variant of any one of 1 to 1616 above and having a K47R substitution.

1618. The GA variant of any one of 1 to 1617 above and having an A50D substitution.

1619. The GA variant of any one of 1 to 1617 above and having an A50N substitution.

1620. The GA variant of any one of 1 to 1619 above and having a N55D substitution.

1621. The GA variant of any one of 1 to 1620 above and having an A58C substitution.

1622. The GA variant of any one of 1 to 1621 above and having an A62H substitution.

1623. The GA variant of any one of 1 to 1622 above and having an A64P substitution.

1624. The GA variant of any one of 1 to 1623 above and having an I68V substitution.

1625. The GA variant of any one of 1 to 1624 above and having a S72C substitution.

1626. The GA variant of any one of 1 to 1624 above and having a S72Q substitution.

1627. The GA variant of any one of 1 to 1626 above and having a R73M substitution.

1628. The GA variant of any one of 1 to 1627 above and having a D75H substitution.

1629. The GA variant of any one of 1 to 1627 above and having a D75R substitution.

1630. The GA variant of any one of 1 to 1629 above and having a P77D substitution.

1631. The GA variant of any one of 1 to 1630 above and having a T83V substitution.

1632. The GA variant of any one of 1 to 1631 above and having a L90I substitution.

1633. The GA variant of any one of 1 to 1631 above and having a L90P substitution.

1634. The GA variant of any one of 1 to 1633 above and having a S96A substitution.

1635. The GA variant of any one of 1 to 1633 above and having a S96Y substitution.

1636. The GA variant of any one of 1 to 1635 above and having a G98Y substitution.

1637. The GA variant of any one of 1 to 1635 above and having a G98F substitution.

1638. The GA variant of any one of 1 to 1637 above and having a Y101F substitution.

1639. The GA variant of any one of 1 to 1638 above and having a T103Q substitution.

1640. The GA variant of any one of 1 to 1638 above and having a T103V substitution.

1641. The GA variant of any one of 1 to 1640 above and having an I109T substitution.

1642. The GA variant of any one of 1 to 1640 above and having an I109A substitution.

1643. The GA variant of any one of 1 to 1642 above and having a Q110E substitution.

1644. The GA variant of any one of 1 to 1642 above and having a Q110C substitution.

1645. The GA variant of any one of 1 to 1644 above and having a V113E substitution.

1646. The GA variant of any one of 1 to 1644 above and having a V113L substitution.

1647. The GA variant of any one of 1 to 1646 above and having a S115A substitution.

1648. The GA variant of any one of 1 to 1647 above and having a V122L substitution.

1649. The GA variant of any one of 1 to 1648 above and having a S123A substitution.

1650. The GA variant of any one of 1 to 1648 above and having a S123P substitution.

1651. The GA variant of any one of 1 to 1650 above and having a S126A substitution.

1652. The GA variant of any one of 1 to 1651 above and having a T128V substitution.

1653. The GA variant of any one of 1 to 1652 above and having a F129L substitution.

1654. The GA variant of any one of 1 to 1653 above and having an A146P substitution.

1655. The GA variant of any one of 1 to 1654 above and having a T148L substitution.

1656. The GA variant of any one of 1 to 1654 above and having a T148M substitution.

1657. The GA variant of any one of 1 to 1656 above and having an E150P substitution.

1658. The GA variant of any one of 1 to 1656 above and having an E150R substitution.

1659. The GA variant of any one of 1 to 1658 above and having an A165S substitution.

1660. The GA variant of any one of 1 to 1659 above and having a L166M substitution.

1661. The GA variant of any one of 1 to 1660 above and having a L166C substitution.

1662. The GA variant of any one of 1 to 1661 above and having a Y169E substitution.

1663. The GA variant of any one of 1 to 1661 above and having a Y169F substitution.

1664. The GA variant of any one of 1 to 1663 above and having an A170C substitution.

1665. The GA variant of any one of 1 to 1663 above and having an A170I substitution.

1666. The GA variant of any one of 1 to 1665 above and having an A182V substitution.

1667. The GA variant of any one of 1 to 1666 above and having a V185N substitution.

1668. The GA variant of any one of 1 to 1666 above and having a V185Q substitution.

1669. The GA variant of any one of 1 to 1668 above and having a P188K substitution.

1670. The GA variant of any one of 1 to 1669 above and having a L194I substitution.

1671. The GA variant of any one of 1 to 1670 above and having a T197A substitution.

1672. The GA variant of any one of 1 to 1670 above and having a T197G substitution.

1673. The GA variant of any one of 1 to 1672 above and having a F206Y substitution.

1674. The GA variant of any one of 1 to 1673 above and having a F218W substitution.

1675. The GA variant of any one of 1 to 1674 above and having a S222M substitution.

1676. The GA variant of any one of 1 to 1674 above and having a S222Q substitution.

1677. The GA variant of any one of 1 to 1676 above and having a H224A substitution.

1678. The GA variant of any one of 1 to 1677 above and having an A226S substitution.

1679. The GA variant of any one of 1 to 1678 above and having a Y232F substitution.

1680. The GA variant of any one of 1 to 1679 above and having a L237I substitution.

1681. The GA variant of any one of 1 to 1680 above and having a P249D substitution.

1682. The GA variant of any one of 1 to 1681 above and having a Q256F substitution.

1683. The GA variant of any one of 1 to 1682 above and having an A257G substitution.

1684. The GA variant of any one of 1 to 1682 above and having an A257F substitution.

1685. The GA variant of any one of 1 to 1684 above and having a F258N substitution.

1686. The GA variant of any one of 1 to 1685 above and having a W259Y substitution.

1687. The GA variant of any one of 1 to 1686 above and having a Y265W substitution.

1688. The GA variant of any one of 1 to 1687 above and having a V267K substitution.

1689. The GA variant of any one of 1 to 1687 above and having a V267R substitution.

1690. The GA variant of any one of 1 to 1689 above and having a S268C substitution.

1691. The GA variant of any one of 1 to 1690 above and having a G272C substitution.

1692. The GA variant of any one of 1 to 1691 above and having a G273H substitution.

1693. The GA variant of any one of 1 to 1692 above and having a S277T substitution.

1694. The GA variant of any one of 1 to 1693 above and having a D280V substitution.

1695. The GA variant of any one of 1 to 1694 above and having an A281L substitution.

1696. The GA variant of any one of 1 to 1695 above and having an I284L substitution.

1697. The GA variant of any one of 1 to 1695 above and having an I284V substitution.

1698. The GA variant of any one of 1 to 1697 above and having an A286L substitution.

1699. The GA variant of any one of 1 to 1697 above and having an A286T substitution.

1700. The GA variant of any one of 1 to 1699 above and having a S287C substitution.

1701. The GA variant of any one of 1 to 1699 above and having a S287Q substitution.

1702. The GA variant of any one of 1 to 1701 above and having a Q303E substitution.

1703. The GA variant of any one of 1 to 1702 above and having a S306C substitution.

1704. The GA variant of any one of 1 to 1703 above and having an E307D substitution.

1705. The GA variant of any one of 1 to 1703 above and having an E307P substitution.

1706. The GA variant of any one of 1 to 1705 above and having a H313Y substitution.

1707. The GA variant of any one of 1 to 1706 above and having a Y316W substitution.

1708. The GA variant of any one of 1 to 1707 above and having a D318M substitution.

1709. The GA variant of any one of 1 to 1708 above and having a N322H substitution.

1710. The GA variant of any one of 1 to 1708 above and having a N322C substitution.

1711. The GA variant of any one of 1 to 1709 above and having a V336C substitution.

1712. The GA variant of any one of 1 to 1709 above and having a V336I substitution.

1713. The GA variant of any one of 1 to 1712 above and having an A337S substitution.

1714. The GA variant of any one of 1 to 1713 above and having a N348G substitution.

1715. The GA variant of any one of 1 to 1714 above and having an A355S substitution.

1716. The GA variant of any one of 1 to 1714 above and having an A355C substitution.

1717. The GA variant of any one of 1 to 1716 above and having a N356S substitution.

1718. The GA variant of any one of 1 to 1717 above and having an A359G substitution.

1719. The GA variant of any one of 1 to 1717 above and having an A359S substitution.

1720. The GA variant of any one of 1 to 1719 above and having a L363A substitution.

1721. The GA variant of any one of 1 to 1719 above and having a L363V substitution.

1722. The GA variant of any one of 1 to 1721 above and having a S375A substitution.

1723. The GA variant of any one of 1 to 1721 above and having a S375L substitution.

1724. The GA variant of any one of 1 to 1723 above and having a T377S substitution.

1725. The GA variant of any one of 1 to 1723 above and having a T377A substitution.

1726. The GA variant of any one of 1 to 1725 above and having a V378L substitution.

1727. The GA variant of any one of 1 to 1725 above and having a V378T substitution.

1728. The GA variant of any one of 1 to 1727 above and having a L383C substitution.

1729. The GA variant of any one of 1 to 1727 above and having a L383N substitution.

1730. The GA variant of any one of 1 to 1729 above and having a F385L substitution.

1731. The GA variant of any one of 1 to 1730 above and having a D388A substitution.

1732. The GA variant of any one of 1 to 1730 above and having a D388C substitution.

1733. The GA variant of any one of 1 to 1732 above and having a T404Q substitution.

1734. The GA variant of any one of 1 to 1733 above and having an E421C substitution.

1735. The GA variant of any one of 1 to 1733 above and having an E421Q substitution.

1736. The GA variant of any one of 1 to 1735 above and having a V422F substitution.

1737. The GA variant of any one of 1 to 1736 above and having an A424C substitution.

1738. The GA variant of any one of 1 to 1736 above and having an A424Q substitution.

1739. The GA variant of any one of 1 to 1738 above and having a K425M substitution.

1740. The GA variant of any one of 1 to 1738 above and having a K425R substitution.

1741. The GA variant of any one of 1 to 1740 above and having a Y426F substitution.

1742. The GA variant of any one of 1 to 1741 above and having an A432D substitution.

1743. The GA variant of any one of 1 to 1741 above and having an A432S substitution.

1744. The GA variant of any one of 1 to 1743 above and having a N440D substitution.

1745. The GA variant of any one of 1 to 1744 above and having a S446G substitution.

1746. The GA variant of any one of 1 to 1745 above and having a T451S substitution.

1747. The GA variant of any one of 1 to 1746 above and having a F457A substitution.

1748. The GA variant of any one of 1 to 1747 above and having a R487S substitution.

1749. The GA variant of any one of 1 to 1748 above and having an I488V substitution.

1750. The GA variant of any one of 1 to 1749 above and having a V495I substitution.

1751. The GA variant of any one of 1 to 1750 above and having an A496P substitution.

1752. The GA variant of any one of 1 to 1751 above and having an A497Q substitution.

1753. The GA variant of any one of 1 to 1751 above and having an A497S substitution.

1754. The GA variant of any one of 1 to 1753 above and having a F502I substitution.

1755. The GA variant of any one of 1 to 1754 above and having a S504T substitution.

1756. The GA variant of any one of 1 to 1755 above and having an A513D substitution.

1757. The GA variant of any one of 1 to 1755 above and having an A513G substitution.

1758. The GA variant of any one of 1 to 1757 above and having a P516E substitution.

1759. The GA variant of any one of 1 to 1757 above and having a P516A substitution.

1760. The GA variant of any one of 1 to 1759 above and having a P520V substitution.

1761. The GA variant of any one of 1 to 1760 above and having a T521W substitution.

1762. The GA variant of any one of 1 to 1760 above and having a T521S substitution.

1763. The GA variant of any one of 1 to 1762 above and having a S527F substitution.

1764. The GA variant of any one of 1 to 1763 above and having a V529W substitution.

1765. The GA variant of any one of 1 to 1764 above and having a T532W substitution.

1766. The GA variant of any one of 1 to 1764 above and having a T532Y substitution.

1767. The GA variant of any one of 1 to 1766 above and having a N534D substitution.

1768. The GA variant of any one of 1 to 1766 above and having a N534E substitution.

1769. The GA variant of any one of 1 to 1768 above and having an E535Q substitution.

1770. The GA variant of any one of 1 to 1769 above and having a T539S substitution.

1771. The GA variant of any one of 1 to 1770 above and having an E543C substitution.

1772. The GA variant of any one of 1 to 1770 above and having an E543I substitution.

1773. The GA variant of any one of 1 to 1772 above and having an I545V substitution.

1774. The GA variant of any one of 1 to 1773 above and having a V547A substitution.

1775. The GA variant of any one of 1 to 1773 above and having a V547C substitution.

1776. The GA variant of any one of 1 to 1775 above and having a G549A substitution.

1777. The GA variant of any one of 1 to 1776 above and having a K571R substitution.

1778. The GA variant of any one of 1 to 1776 above and having a K571T substitution.

1779. The GA variant of any one of 1 to 1778 above and having a L576K substitution.

1780. The GA variant of any one of 1 to 1779 above and having an I579M substitution.

1781. The GA variant of any one of 1 to 1780 above and having an I583M substitution.

1782. The GA variant of any one of 1 to 1781 above and having a T586L substitution.

1783. The GA variant of any one of 1 to 1781 above and having a T586R substitution.

1784. The GA variant of any one of 1 to 1783 above and having a Y592H substitution.

1785. The GA variant of any one of 1 to 1784 above and having a Y594M substitution.

1786. The GA variant of any one of 1 to 1784 above and having a Y594H substitution.

1787. The GA variant of any one of 1 to 1786 above and having a G622P substitution.

1788. The GA variant of any one of 1 to 1786 above and having a G622W substitution.

1789. The GA variant of any one of 1 to 1788 above and having a Q627E substitution.

1790. The GA variant of any one of 1 to 1788 above and having a Q627A substitution.

1791. The GA variant of any one of 1 to 1790 above and having a T628L substitution.

1792. The GA variant of any one of 1 to 1791 above and having a N630C substitution.

1793. The GA variant of any one of 1 to 1792 above and having a D631Q substitution.

1794. The GA variant of any one of 1 to 1792 above and having a D631S substitution.

In certain embodiments, a variant GA enzyme contains one or more amino acid substitution(s) corresponding to the HgGA substitutions as set forth in SEL Cohorts 1 to 10 as shown in Example 3. SEL Cohorts 1 to 10 are classified as follows (each variant is not listed here; they are listed in Example 3):

SEL Cohort 1—HgGA variants having improved Performance Index (PI) in expression (PI≥1.2);

SEL Cohort 2—HgGA variants having improved PI in thermostability (Residual DP7 hydrolysis activity after 63.5° C. for 5 min./Initial DP7 hydrolysis activity) (PI≥1.2);

SEL Cohort 3—HgGA variants having improved PI in a DP7 hydrolysis assay at pH 5.5 (PI≥1.2);

SEL Cohort 4—HgGA variants having improved PI in a DP7 hydrolysis assay at pH 6.8 (PI≥1.2);

SEL Cohort 5—HgGA variants having improved PI in a DP2 hydrolysis assay (PI≥1.2 in either $K_m$ assay or $V_{max}$ assay);

SEL Cohort 6—HgGA variants having improved PI in a pullulan hydrolysis assay (PI≥1.2);

SEL Cohort 7—HgGA variants having improved PI in a panose hydrolysis assay (PI≥1.2);

SEL Cohort 8—HgGA variants having improved PI in a corn starch hydrolysis assay (PI≥1.2);

SEL Cohort 9—HgGA variants having improved PI for glucose inhibition of enzyme activity [higher ratio of (inhibition sample)/(no inhibition sample) as compared to WT] (PI≥1.2); and SEL Cohort 10—HgGA variants having improved PI for glucose reversion to DP2+ products (less reversion, higher PI) (PI≥1.2).

Certain amino acid substitutions fall into more than one SEL Cohort, and thus provide improvements in more than one property (i.e., by demonstrating an improved outcome in two or more of assays (a) to (j) above). Therefore, aspects of the invention include substitutions in a GA corresponding to HgGA substitutions that fall into more than one of SEL Cohorts 1 to 10 above, including at least two SEL Cohorts, at least three SEL Cohorts, at least four SEL Cohorts, at least five SEL Cohorts, at least six SEL Cohorts, at least seven SEL Cohorts, at least eight SEL Cohorts, or at least nine SEL Cohorts. A review of the HgGA variant members of the SEL Cohorts listed in Example 3 clearly identifies the variants that fall into multiple SEL Cohorts, and thus have more than one improved property.

Tables 2 to 5 below show the possible functional class of GA variants that belong to two, three, four or five SEL Cohorts. Each of the functional classes listed in Tables 2 to 5 is named for the numbers of the SEL Cohorts to which each GA variant of the functional class belongs. For example, the functional class named "2.5.8" is one whose GA variant members belong to SEL Cohorts 2, 5 and 8 (and possibly more) and as such, each member of this functional class has (at least) the three improved properties that define SEL Cohorts 2, 5 and 8 (i.e., improved thermostability, improved DP2 hydrolysis, and improved corn starch hydrolysis). As noted above, the listing of the GA variants that belong to each SEL Cohort that is shown in Example 3 can be used to clearly identify which variant(s) belong to which functional class listed in Tables 2 to 5 (as well as functional classes of GA variants that belong to six, seven, eight, or nine SEL Cohorts, which can be readily derived from Example 3). Note that in the Tables 2 to 5, columns and rows that would have listed only duplicate SEL Cohort combinations (i.e., combinations that are listed elsewhere in the table) are not shown.

TABLE 2

Functional Classes of Combinations of Two SEL Cohorts

| SEL Cohort | 1 | 2 | 3 | 4 | 5 | 6 | 7 | 8 | 9 |
|---|---|---|---|---|---|---|---|---|---|
| 2 | 1.2 | — | — | — | — | — | — | — | — |
| 3 | 1.3 | 2.3 | — | — | — | — | — | — | — |
| 4 | 1.4 | 2.4 | 3.4 | — | — | — | — | — | — |
| 5 | 1.5 | 2.5 | 3.5 | 4.5 | — | — | — | — | — |
| 6 | 1.6 | 2.6 | 3.6 | 4.6 | 5.6 | — | — | — | — |
| 7 | 1.7 | 2.7 | 3.7 | 4.7 | 5.7 | 6.7 | — | — | — |
| 8 | 1.8 | 2.8 | 3.8 | 4.8 | 5.8 | 6.8 | 7.8 | — | — |
| 9 | 1.9 | 2.9 | 3.9 | 4.9 | 5.9 | 6.9 | 7.9 | 8.9 | — |
| 10 | 1.10 | 2.10 | 3.10 | 4.10 | 5.10 | 6.10 | 7.10 | 8.10 | 9.10 |

TABLE 3

Functional Classes of Combinations of Three SEL Cohorts (the left column lists combinations of two from previous table)

| SEL Cohort(s) | 1 | 2 | 3 | 4 | 5 | 6 | 7 | 8 |
|---|---|---|---|---|---|---|---|---|
| 2.3 | 1.2.3 | — | — | — | — | — | — | — |
| 2.4 | 1.2.4 | — | — | — | — | — | — | — |
| 2.5 | 1.2.5 | — | — | — | — | — | — | — |
| 2.6 | 1.2.6 | — | — | — | — | — | — | — |
| 2.7 | 1.2.7 | — | — | — | — | — | — | — |
| 2.8 | 1.2.8 | — | — | — | — | — | — | — |
| 2.9 | 1.2.9 | — | — | — | — | — | — | — |
| 2.10 | 1.2.10 | — | — | — | — | — | — | — |
| 3.4 | 1.3.4 | 2.3.4 | — | — | — | — | — | — |
| 3.5 | 1.3.5 | 2.3.5 | — | — | — | — | — | — |
| 3.6 | 1.3.6 | 2.3.6 | — | — | — | — | — | — |
| 3.7 | 1.3.7 | 2.3.7 | — | — | — | — | — | — |
| 3.8 | 1.3.8 | 2.3.8 | — | — | — | — | — | — |
| 3.9 | 1.3.9 | 2.3.9 | — | — | — | — | — | — |
| 3.10 | 1.3.10 | 2.3.10 | — | — | — | — | — | — |
| 4.5 | 1.4.5 | 2.4.5 | 3.4.5 | — | — | — | — | — |
| 4.6 | 1.4.6 | 2.4.6 | 3.4.6 | — | — | — | — | — |
| 4.7 | 1.4.7 | 2.4.7 | 3.4.7 | — | — | — | — | — |
| 4.8 | 1.4.8 | 2.4.8 | 3.4.8 | — | — | — | — | — |
| 4.9 | 1.4.9 | 2.4.9 | 3.4.9 | — | — | — | — | — |
| 4.10 | 1.4.10 | 2.4.10 | 3.4.10 | — | — | — | — | — |
| 5.6 | 1.5.6 | 2.5.6 | 3.5.6 | 4.5.6 | — | — | — | — |
| 5.7 | 1.5.7 | 2.5.7 | 3.5.7 | 4.5.7 | — | — | — | — |
| 5.8 | 1.5.8 | 2.5.8 | 3.5.8 | 4.5.8 | — | — | — | — |
| 5.9 | 1.5.9 | 2.5.9 | 3.5.9 | 4.5.9 | — | — | — | — |
| 5.10 | 1.5.10 | 2.5.10 | 3.5.10 | 4.5.10 | — | — | — | — |
| 6.7 | 1.6.7 | 2.6.7 | 3.6.7 | 4.6.7 | 5.6.7 | — | — | — |
| 6.8 | 1.6.8 | 2.6.8 | 3.6.8 | 4.6.8 | 5.6.8 | — | — | — |
| 6.9 | 1.6.9 | 2.6.9 | 3.6.9 | 4.6.9 | 5.6.9 | — | — | — |
| 6.10 | 1.6.10 | 2.6.10 | 3.6.10 | 4.6.10 | 5.6.10 | — | — | — |
| 7.8 | 1.7.8 | 2.7.8 | 3.7.8 | 4.7.8 | 5.7.8 | 6.7.8 | — | — |
| 7.9 | 1.7.9 | 2.7.9 | 3.7.9 | 4.7.9 | 5.7.9 | 6.7.9 | — | — |
| 7.10 | 1.7.10 | 2.7.10 | 3.7.10 | 4.7.10 | 5.7.10 | 6.7.10 | — | — |
| 8.9 | 1.8.9 | 2.8.9 | 3.8.9 | 4.8.9 | 5.8.9 | 6.8.9 | 7.8.9 | — |
| 8.10 | 1.8.10 | 2.8.10 | 3.8.10 | 4.8.10 | 5.8.10 | 6.8.10 | 7.8.10 | — |
| 9.10 | 1.9.10 | 2.9.10 | 3.9.10 | 4.9.10 | 5.9.10 | 6.9.10 | 7.9.10 | 8.9.10 |

TABLE 4

Functional Classes of Combinations of Four SEL Cohorts
(the left column lists combinations of three from previous table)

| SEL Cohort(s) | 1 | 2 | 3 | 4 | 5 | 6 | 7 |
|---|---|---|---|---|---|---|---|
| 2.3.4 | 1.2.3.4 | — | — | — | — | — | — |
| 2.3.5 | 1.2.3.5 | — | — | — | — | — | — |
| 2.3.6 | 1.2.3.6 | — | — | — | — | — | — |
| 2.3.7 | 1.2.3.7 | — | — | — | — | — | — |
| 2.3.8 | 1.2.3.8 | — | — | — | — | — | — |
| 2.3.9 | 1.2.3.9 | — | — | — | — | — | — |
| 2.3.10 | 1.2.3.10 | — | — | — | — | — | — |
| 2.4.5 | 1.2.4.5 | — | — | — | — | — | — |
| 2.4.6 | 1.2.4.6 | — | — | — | — | — | — |
| 2.4.7 | 1.2.4.7 | — | — | — | — | — | — |
| 2.4.8 | 1.2.4.8 | — | — | — | — | — | — |
| 2.4.9 | 1.2.4.9 | — | — | — | — | — | — |
| 2.4.10 | 1.2.4.10 | — | — | — | — | — | — |
| 2.5.6 | 1.2.5.6 | — | — | — | — | — | — |
| 2.5.7 | 1.2.5.7 | — | — | — | — | — | — |
| 2.5.8 | 1.2.5.8 | — | — | — | — | — | — |
| 2.5.9 | 1.2.5.9 | — | — | — | — | — | — |
| 2.5.10 | 1.2.5.10 | — | — | — | — | — | — |
| 2.6.7 | 1.2.6.7 | — | — | — | — | — | — |
| 2.6.8 | 1.2.6.8 | — | — | — | — | — | — |
| 2.6.9 | 1.2.6.9 | — | — | — | — | — | — |
| 2.6.10 | 1.2.6.10 | — | — | — | — | — | — |
| 2.7.8 | 1.2.7.8 | — | — | — | — | — | — |
| 2.7.9 | 1.2.7.9 | — | — | — | — | — | — |
| 2.7.10 | 1.2.7.10 | — | — | — | — | — | — |
| 2.8.9 | 1.2.8.9 | — | — | — | — | — | — |
| 2.8.10 | 1.2.8.10 | — | — | — | — | — | — |
| 2.9.10 | 1.2.9.10 | — | — | — | — | — | — |
| 3.4.5 | 1.3.4.5 | 2.3.4.5 | — | — | — | — | — |
| 3.4.6 | 1.3.4.6 | 2.3.4.6 | — | — | — | — | — |
| 3.4.7 | 1.3.4.7 | 2.3.4.7 | — | — | — | — | — |
| 3.4.8 | 1.3.4.8 | 2.3.4.8 | — | — | — | — | — |
| 3.4.9 | 1.3.4.9 | 2.3.4.9 | — | — | — | — | — |
| 3.4.10 | 1.3.4.10 | 2.3.4.10 | — | — | — | — | — |
| 3.5.6 | 1.3.5.6 | 2.3.5.6 | — | — | — | — | — |
| 3.5.7 | 1.3.5.7 | 2.3.5.7 | — | — | — | — | — |
| 3.5.8 | 1.3.5.8 | 2.3.5.8 | — | — | — | — | — |
| 3.5.9 | 1.3.5.9 | 2.3.5.9 | — | — | — | — | — |
| 3.5.10 | 1.3.5.10 | 2.3.5.10 | — | — | — | — | — |
| 3.6.7 | 1.3.6.7 | 2.3.6.7 | — | — | — | — | — |
| 3.6.8 | 1.3.6.8 | 2.3.6.8 | — | — | — | — | — |
| 3.6.9 | 1.3.6.9 | 2.3.6.9 | — | — | — | — | — |
| 3.6.10 | 1.3.6.10 | 2.3.6.10 | — | — | — | — | — |
| 3.7.8 | 1.3.7.8 | 2.3.7.8 | — | — | — | — | — |
| 3.7.9 | 1.3.7.9 | 2.3.7.9 | — | — | — | — | — |
| 3.7.10 | 1.3.7.10 | 2.3.7.10 | — | — | — | — | — |
| 3.8.9 | 1.3.8.9 | 2.3.8.9 | — | — | — | — | — |
| 3.8.10 | 1.3.8.10 | 2.3.8.10 | — | — | — | — | — |
| 3.9.10 | 1.3.9.10 | 2.3.9.10 | — | — | — | — | — |
| 4.5.6 | 1.4.5.6 | 2.4.5.6 | 3.4.5.6 | — | — | — | — |
| 4.5.7 | 1.4.5.7 | 2.4.5.7 | 3.4.5.7 | — | — | — | — |
| 4.5.8 | 1.4.5.8 | 2.4.5.8 | 3.4.5.8 | — | — | — | — |
| 4.5.9 | 1.4.5.9 | 2.4.5.9 | 3.4.5.9 | — | — | — | — |
| 4.5.10 | 1.4.5.10 | 2.4.5.10 | 3.4.5.10 | — | — | — | — |
| 4.6.7 | 1.4.6.7 | 2.4.6.7 | 3.4.6.7 | — | — | — | — |
| 4.6.8 | 1.4.6.8 | 2.4.6.8 | 3.4.6.8 | — | — | — | — |
| 4.6.9 | 1.4.6.9 | 2.4.6.9 | 3.4.6.9 | — | — | — | — |
| 4.6.10 | 1.4.6.10 | 2.4.6.10 | 3.4.6.10 | — | — | — | — |
| 4.7.8 | 1.4.7.8 | 2.4.7.8 | 3.4.7.8 | — | — | — | — |
| 4.7.9 | 1.4.7.9 | 2.4.7.9 | 3.4.7.9 | — | — | — | — |
| 4.7.10 | 1.4.7.10 | 2.4.7.10 | 3.4.7.10 | — | — | — | — |
| 4.8.9 | 1.4.8.9 | 2.4.8.9 | 3.4.8.9 | — | — | — | — |
| 4.8.10 | 1.4.8.10 | 2.4.8.10 | 3.4.8.10 | — | — | — | — |
| 4.9.10 | 1.4.9.10 | 2.4.9.10 | 3.4.9.10 | — | — | — | — |
| 5.6.7 | 1.5.6.7 | 2.5.6.7 | 3.5.6.7 | 4.5.6.7 | — | — | — |
| 5.6.8 | 1.5.6.8 | 2.5.6.8 | 3.5.6.8 | 4.5.6.8 | — | — | — |
| 5.6.9 | 1.5.6.9 | 2.5.6.9 | 3.5.6.9 | 4.5.6.9 | — | — | — |
| 5.6.10 | 1.5.6.10 | 2.5.6.10 | 3.5.6.10 | 4.5.6.10 | — | — | — |
| 5.7.8 | 1.5.7.8 | 2.5.7.8 | 3.5.7.8 | 4.5.7.8 | — | — | — |
| 5.7.9 | 1.5.7.9 | 2.5.7.9 | 3.5.7.9 | 4.5.7.9 | — | — | — |
| 5.7.10 | 1.5.7.10 | 2.5.7.10 | 3.5.7.10 | 4.5.7.10 | — | — | — |
| 5.8.9 | 1.5.8.9 | 2.5.8.9 | 3.5.8.9 | 4.5.8.9 | — | — | — |
| 5.8.10 | 1.5.8.10 | 2.5.8.10 | 3.5.8.10 | 4.5.8.10 | — | — | — |
| 5.9.10 | 1.5.9.10 | 2.5.9.10 | 3.5.9.10 | 4.5.9.10 | — | — | — |

TABLE 4-continued

Functional Classes of Combinations of Four SEL Cohorts
(the left column lists combinations of three from previous table)

| SEL Cohort(s) | 1 | 2 | 3 | 4 | 5 | 6 | 7 |
|---|---|---|---|---|---|---|---|
| 6.7.8 | 1.6.7.8 | 2.6.7.8 | 3.6.7.8 | 4.6.7.8 | 5.6.7.8 | — | — |
| 6.7.9 | 1.6.7.9 | 2.6.7.9 | 3.6.7.9 | 4.6.7.9 | 5.6.7.9 | — | — |
| 6.7.10 | 1.6.7.10 | 2.6.7.10 | 3.6.7.10 | 4.6.7.10 | 5.6.7.10 | — | — |
| 6.8.9 | 1.6.8.9 | 2.6.8.9 | 3.6.8.9 | 4.6.8.9 | 5.6.8.9 | — | — |
| 6.8.10 | 1.6.8.10 | 2.6.8.10 | 3.6.8.10 | 4.6.8.10 | 5.6.8.10 | — | — |
| 6.9.10 | 1.6.9.10 | 2.6.9.10 | 3.6.9.10 | 4.6.9.10 | 5.6.9.10 | — | — |
| 7.8.9 | 1.7.8.9 | 2.7.8.9 | 3.7.8.9 | 4.7.8.9 | 5.7.8.9 | 6.7.8.9 | — |
| 7.8.10 | 1.7.8.10 | 2.7.8.10 | 3.7.8.10 | 4.7.8.10 | 5.7.8.10 | 6.7.8.10 | — |
| 7.9.10 | 1.7.9.10 | 2.7.9.10 | 3.7.9.10 | 4.7.9.10 | 5.7.9.10 | 6.7.9.10 | — |
| 8.9.10 | 1.8.9.10 | 2.8.9.10 | 3.8.9.10 | 4.8.9.10 | 5.8.9.10 | 6.8.9.10 | 7.8.9.10 |

TABLE 5

Functional Classes of Combinations of Five SEL Cohorts
(the left column lists combinations of four from previous table)

| SEL Cohort(s) | 1 | 2 | 3 | 4 | 5 | 6 |
|---|---|---|---|---|---|---|
| 2.3.4.5 | 1.2.3.4.5 | — | — | — | — | — |
| 2.3.4.6 | 1.2.3.4.6 | — | — | — | — | — |
| 2.3.4.7 | 1.2.3.4.7 | — | — | — | — | — |
| 2.3.4.8 | 1.2.3.4.8 | — | — | — | — | — |
| 2.3.4.9 | 1.2.3.4.9 | — | — | — | — | — |
| 2.3.4.10 | 1.2.3.4.10 | — | — | — | — | — |
| 2.3.5.6 | 1.2.3.5.6 | — | — | — | — | — |
| 2.3.5.7 | 1.2.3.5.7 | — | — | — | — | — |
| 2.3.5.8 | 1.2.3.5.8 | — | — | — | — | — |
| 2.3.5.9 | 1.2.3.5.9 | — | — | — | — | — |
| 2.3.5.10 | 1.2.3.5.10 | — | — | — | — | — |
| 2.3.6.7 | 1.2.3.6.7 | — | — | — | — | — |
| 2.3.6.8 | 1.2.3.6.8 | — | — | — | — | — |
| 2.3.6.9 | 1.2.3.6.9 | — | — | — | — | — |
| 2.3.6.10 | 1.2.3.6.10 | — | — | — | — | — |
| 2.3.7.8 | 1.2.3.7.8 | — | — | — | — | — |
| 2.3.7.9 | 1.2.3.7.9 | — | — | — | — | — |
| 2.3.7.10 | 1.2.3.7.10 | — | — | — | — | — |
| 2.3.8.9 | 1.2.3.8.9 | — | — | — | — | — |
| 2.3.8.10 | 1.2.3.8.10 | — | — | — | — | — |
| 2.3.9.10 | 1.2.3.9.10 | — | — | — | — | — |
| 2.4.5.6 | 1.2.4.5.6 | — | — | — | — | — |
| 2.4.5.7 | 1.2.4.5.7 | — | — | — | — | — |
| 2.4.5.8 | 1.2.4.5.8 | — | — | — | — | — |
| 2.4.5.9 | 1.2.4.5.9 | — | — | — | — | — |
| 2.4.5.10 | 1.2.4.5.10 | — | — | — | — | — |
| 2.4.6.7 | 1.2.4.6.7 | — | — | — | — | — |
| 2.4.6.8 | 1.2.4.6.8 | — | — | — | — | — |
| 2.4.6.9 | 1.2.4.6.9 | — | — | — | — | — |
| 2.4.6.10 | 1.2.4.6.10 | — | — | — | — | — |
| 2.4.7.8 | 1.2.4.7.8 | — | — | — | — | — |
| 2.4.7.9 | 1.2.4.7.9 | — | — | — | — | — |
| 2.4.7.10 | 1.2.4.7.10 | — | — | — | — | — |
| 2.4.8.9 | 1.2.4.8.9 | — | — | — | — | — |
| 2.4.8.10 | 1.2.4.8.10 | — | — | — | — | — |
| 2.4.9.10 | 1.2.4.9.10 | — | — | — | — | — |
| 2.5.6.7 | 1.2.5.6.7 | — | — | — | — | — |
| 2.5.6.8 | 1.2.5.6.8 | — | — | — | — | — |
| 2.5.6.9 | 1.2.5.6.9 | — | — | — | — | — |
| 2.5.6.10 | 1.2.5.6.10 | — | — | — | — | — |
| 2.5.7.8 | 1.2.5.7.8 | — | — | — | — | — |
| 2.5.7.9 | 1.2.5.7.9 | — | — | — | — | — |
| 2.5.7.10 | 1.2.5.7.10 | — | — | — | — | — |
| 2.5.8.9 | 1.2.5.8.9 | — | — | — | — | — |
| 2.5.8.10 | 1.2.5.8.10 | — | — | — | — | — |
| 2.5.9.10 | 1.2.5.9.10 | — | — | — | — | — |
| 2.6.7.8 | 1.2.6.7.8 | — | — | — | — | — |
| 2.6.7.9 | 1.2.6.7.9 | — | — | — | — | — |
| 2.6.7.10 | 1.2.6.7.10 | — | — | — | — | — |
| 2.6.8.9 | 1.2.6.8.9 | — | — | — | — | — |
| 2.6.8.10 | 1.2.6.8.10 | — | — | — | — | — |
| 2.6.9.10 | 1.2.6.9.10 | — | — | — | — | — |

TABLE 5-continued

Functional Classes of Combinations of Five SEL Cohorts
(the left column lists combinations of four from previous table)

| SEL Cohort(s) | 1 | 2 | 3 | 4 | 5 | 6 |
|---|---|---|---|---|---|---|
| 2.7.8.9 | 1.2.7.8.9 | — | — | — | — | — |
| 2.7.8.10 | 1.2.7.8.10 | — | — | — | — | — |
| 2.7.9.10 | 1.2.7.9.10 | — | — | — | — | — |
| 2.8.9.10 | 1.2.8.9.10 | — | — | — | — | — |
| 3.4.5.6 | 1.3.4.5.6 | 2.3.4.5.6 | — | — | — | — |
| 3.4.5.7 | 1.3.4.5.7 | 2.3.4.5.7 | — | — | — | — |
| 3.4.5.8 | 1.3.4.5.8 | 2.3.4.5.8 | — | — | — | — |
| 3.4.5.9 | 1.3.4.5.9 | 2.3.4.5.9 | — | — | — | — |
| 3.4.5.10 | 1.3.4.5.10 | 2.3.4.5.10 | — | — | — | — |
| 3.4.6.7 | 1.3.4.6.7 | 2.3.4.6.7 | — | — | — | — |
| 3.4.6.8 | 1.3.4.6.8 | 2.3.4.6.8 | — | — | — | — |
| 3.4.6.9 | 1.3.4.6.9 | 2.3.4.6.9 | — | — | — | — |
| 3.4.6.10 | 1.3.4.6.10 | 2.3.4.6.10 | — | — | — | — |
| 3.4.7.8 | 1.3.4.7.8 | 2.3.4.7.8 | — | — | — | — |
| 3.4.7.9 | 1.3.4.7.9 | 2.3.4.7.9 | — | — | — | — |
| 3.4.7.10 | 1.3.4.7.10 | 2.3.4.7.10 | — | — | — | — |
| 3.4.8.9 | 1.3.4.8.9 | 2.3.4.8.9 | — | — | — | — |
| 3.4.8.10 | 1.3.4.8.10 | 2.3.4.8.10 | — | — | — | — |
| 3.4.9.10 | 1.3.4.9.10 | 2.3.4.9.10 | — | — | — | — |
| 3.5.6.7 | 1.3.5.6.7 | 2.3.5.6.7 | — | — | — | — |
| 3.5.6.8 | 1.3.5.6.8 | 2.3.5.6.8 | — | — | — | — |
| 3.5.6.9 | 1.3.5.6.9 | 2.3.5.6.9 | — | — | — | — |
| 3.5.6.10 | 1.3.5.6.10 | 2.3.5.6.10 | — | — | — | — |
| 3.5.7.8 | 1.3.5.7.8 | 2.3.5.7.8 | — | — | — | — |
| 3.5.7.9 | 1.3.5.7.9 | 2.3.5.7.9 | — | — | — | — |
| 3.5.7.10 | 1.3.5.7.10 | 2.3.5.7.10 | — | — | — | — |
| 3.5.8.9 | 1.3.5.8.9 | 2.3.5.8.9 | — | — | — | — |
| 3.5.8.10 | 1.3.5.8.10 | 2.3.5.8.10 | — | — | — | — |
| 3.5.9.10 | 1.3.5.9.10 | 2.3.5.9.10 | — | — | — | — |
| 3.6.7.8 | 1.3.6.7.8 | 2.3.6.7.8 | — | — | — | — |
| 3.6.7.9 | 1.3.6.7.9 | 2.3.6.7.9 | — | — | — | — |
| 3.6.7.10 | 1.3.6.7.10 | 2.3.6.7.10 | — | — | — | — |
| 3.6.8.9 | 1.3.6.8.9 | 2.3.6.8.9 | — | — | — | — |
| 3.6.8.10 | 1.3.6.8.10 | 2.3.6.8.10 | — | — | — | — |
| 3.6.9.10 | 1.3.6.9.10 | 2.3.6.9.10 | — | — | — | — |
| 3.7.8.9 | 1.3.7.8.9 | 2.3.7.8.9 | — | — | — | — |
| 3.7.8.10 | 1.3.7.8.10 | 2.3.7.8.10 | — | — | — | — |
| 3.7.9.10 | 1.3.7.9.10 | 2.3.7.9.10 | — | — | — | — |
| 3.8.9.10 | 1.3.8.9.10 | 2.3.8.9.10 | — | — | — | — |
| 4.5.6.7 | 1.4.5.6.7 | 2.4.5.6.7 | 3.4.5.6.7 | — | — | — |
| 4.5.6.8 | 1.4.5.6.8 | 2.4.5.6.8 | 3.4.5.6.8 | — | — | — |
| 4.5.6.9 | 1.4.5.6.9 | 2.4.5.6.9 | 3.4.5.6.9 | — | — | — |
| 4.5.6.10 | 1.4.5.6.10 | 2.4.5.6.10 | 3.4.5.6.10 | — | — | — |
| 4.5.7.8 | 1.4.5.7.8 | 2.4.5.7.8 | 3.4.5.7.8 | — | — | — |
| 4.5.7.9 | 1.4.5.7.9 | 2.4.5.7.9 | 3.4.5.7.9 | — | — | — |
| 4.5.7.10 | 1.4.5.7.10 | 2.4.5.7.10 | 3.4.5.7.10 | — | — | — |
| 4.5.8.9 | 1.4.5.8.9 | 2.4.5.8.9 | 3.4.5.8.9 | — | — | — |
| 4.5.8.10 | 1.4.5.8.10 | 2.4.5.8.10 | 3.4.5.8.10 | — | — | — |
| 4.5.9.10 | 1.4.5.9.10 | 2.4.5.9.10 | 3.4.5.9.10 | — | — | — |
| 4.6.7.8 | 1.4.6.7.8 | 2.4.6.7.8 | 3.4.6.7.8 | — | — | — |
| 4.6.7.9 | 1.4.6.7.9 | 2.4.6.7.9 | 3.4.6.7.9 | — | — | — |
| 4.6.7.10 | 1.4.6.7.10 | 2.4.6.7.10 | 3.4.6.7.10 | — | — | — |
| 4.6.8.9 | 1.4.6.8.9 | 2.4.6.8.9 | 3.4.6.8.9 | — | — | — |
| 4.6.8.10 | 1.4.6.8.10 | 2.4.6.8.10 | 3.4.6.8.10 | — | — | — |
| 4.6.9.10 | 1.4.6.9.10 | 2.4.6.9.10 | 3.4.6.9.10 | — | — | — |
| 4.7.8.9 | 1.4.7.8.9 | 2.4.7.8.9 | 3.4.7.8.9 | — | — | — |
| 4.7.8.10 | 1.4.7.8.10 | 2.4.7.8.10 | 3.4.7.8.10 | — | — | — |
| 4.7.9.10 | 1.4.7.9.10 | 2.4.7.9.10 | 3.4.7.9.10 | — | — | — |
| 4.8.9.10 | 1.4.8.9.10 | 2.4.8.9.10 | 3.4.8.9.10 | — | — | — |
| 5.6.7.8 | 1.5.6.7.8 | 2.5.6.7.8 | 3.5.6.7.8 | 4.5.6.7.8 | — | — |
| 5.6.7.9 | 1.5.6.7.9 | 2.5.6.7.9 | 3.5.6.7.9 | 4.5.6.7.9 | — | — |
| 5.6.7.10 | 1.5.6.7.10 | 2.5.6.7.10 | 3.5.6.7.10 | 4.5.6.7.10 | — | — |
| 5.6.8.9 | 1.5.6.8.9 | 2.5.6.8.9 | 3.5.6.8.9 | 4.5.6.8.9 | — | — |
| 5.6.8.10 | 1.5.6.8.10 | 2.5.6.8.10 | 3.5.6.8.10 | 4.5.6.8.10 | — | — |
| 5.6.9.10 | 1.5.6.9.10 | 2.5.6.9.10 | 3.5.6.9.10 | 4.5.6.9.10 | — | — |
| 5.7.8.9 | 1.5.7.8.9 | 2.5.7.8.9 | 3.5.7.8.9 | 4.5.7.8.9 | — | — |
| 5.7.8.10 | 1.5.7.8.10 | 2.5.7.8.10 | 3.5.7.8.10 | 4.5.7.8.10 | — | — |
| 5.7.9.10 | 1.5.7.9.10 | 2.5.7.9.10 | 3.5.7.9.10 | 4.5.7.9.10 | — | — |
| 5.8.9.10 | 1.5.8.9.10 | 2.5.8.9.10 | 3.5.8.9.10 | 4.5.8.9.10 | — | — |

TABLE 5-continued

| Functional Classes of Combinations of Five SEL Cohorts (the left column lists combinations of four from previous table) | | | | | | |
|---|---|---|---|---|---|---|
| SEL Cohort(s) | 1 | 2 | 3 | 4 | 5 | 6 |
| 6.7.8.9 | 1.6.7.8.9 | 2.6.7.8.9 | 3.6.7.8.9 | 4.6.7.8.9 | 5.6.7.8.9 | — |
| 6.7.8.10 | 1.6.7.8.10 | 2.6.7.8.10 | 3.6.7.8.10 | 4.6.7.8.10 | 5.6.7.8.10 | — |
| 6.7.9.10 | 1.6.7.9.10 | 2.6.7.9.10 | 3.6.7.9.10 | 4.6.7.9.10 | 5.6.7.9.10 | — |
| 6.8.9.10 | 1.6.8.9.10 | 2.6.8.9.10 | 3.6.8.9.10 | 4.6.8.9.10 | 5.6.8.9.10 | — |
| 7.8.9.10 | 1.7.8.9.10 | 2.7.8.9.10 | 3.7.8.9.10 | 4.7.8.9.10 | 5.7.8.9.10 | 6.7.8.9.10 |

In addition to the SEL Cohorts and functional classes above, amino acid substitutions in HgGA that have a PI for all assays that is <1.2 and ≥0.9 were identified and categorized as SEL Cohort 11. In certain embodiments of the subject invention, one or a combination of substitutions in SEL Cohort 11 find use in generating combinatorial HgGA variants with one or more of the substitutions identified in any of the SEL Cohorts 1 to 10 above. In other embodiments, one or more of the substitutions in SEL Cohort 11 may be present in a variant GA without additional substitutions selected from SEL Cohorts 1 to 10.

As described in Example 3 below, a specific set of combinatorial variants of HgGA were assayed and categorized into Cohorts as follows:

Combinatorial SEL Cohort 1—Combinatorial HgGA variants having improved PI in expression (PI≥1.1): G92T-I164N-Y346W, G92T-E535W, P54D-K328Q, T35S-G92T-T239A-A448V-I461A-K571T, I43F-T239N-N271Q-E535T-K546S, P60Q-F206V, T35S-G92T-T239A, I43D-G92F-Y346W, G92F-E203A-S375D-P552I, A448V-I461A-E543H-A567R-K596I, P60Q-F79V-F206V, K139R-F147N-F206D, T74R-A448V-E535A-E543H-K571R, I43F-T239N-A448V-I461A-K546S-K596I, D75R-K571R, F79V-F147M-N534S-E535W, A448V-I461A-E543H-K571R-K596I, A448V-I461A-K571R-K596I, I43F-P54D-G92F-K328Q-S375D, I43F-P54D-T239N-K328Q-K546S, G92F-S375D, W577K-W605K, D75R-G92I-E203F-K571R, G92F-L144F-D462Q-A567R, D75R-G92I-K571R, P60Q-F79V-E203F-F206V, T35S-I43F-P54D-G92F-K328Q-Y346W, K139R-F147N-F206D-P213W-K571F, V422P-D449A-S568R-G569W, D75E-F79D-D449A-S568R, I43F-T239N-N271Q-A448V-I461A-E535T-E543H-K546S-K571R-K596I, and F79T-G92F-S96L-L144F-I164N;

Combinatorial SEL Cohort 2—Combinatorial HgGA variants having improved PI in thermostability (Residual DP7 hydrolysis activity after 63.5° C. for 5 min./Initial DP7 hydrolysis activity) (PI≥1.1): F79T-G92F-S96L-L144F-I164N, A448V-I461A-E543H-A567R-K596I, A448V-I461A-K571R-K596I, A448V-I461A-E543H-K571R-K596I, and T35S-G092T-T239A-A448V-I461A-K571T;

Combinatorial SEL Cohort 3—Combinatorial HgGA variants having improved PI in a DP7 hydrolysis assay at pH 5.5 (PI≥1.1): I43D-G92F-Y346W, T35S-I43F-P54D-G92F-K328Q-Y346W, G92T-I164N-Y346W, A448V-I461A-E543H-K571R-K596I, A448V-I461A-E543H-A567R-K596I, P60Q-F79V-E203F-F206V, T74R-A448V-E535A-E543H-K571R, and A448V-I461A-K571R-K596I;

Combinatorial SEL Cohort 4—HgGA variants having improved PI in a DP7 hydrolysis assay at pH 6.8 (PI≥1.1): I43D-G92F-Y346W, T35S-I43F-P54D-G92F-K328Q-Y346W, and A448V-I461A-E543H-K571R-K596I;

Combinatorial SEL Cohort 5—HgGA variants having improved PI in a DP2 hydrolysis assay (PI≥1.1 in either $K_m$ assay or $V_{max}$ assay): A448V-I461A-E543H-K571R-K596I, T74R-A448V-E535A-E543H-K571R, D75R-K571R, and G92F-L144F-D462Q-A567R;

Combinatorial SEL Cohort 6—HgGA variants having improved PI in a pullulan hydrolysis assay (PI≥1.1): A448V-I146A-E543H-K571R-K596I, I43F-P54D-T239N-K328Q-K546S, and A448V-I461A-K571R-K596I;

Combinatorial SEL Cohort 7—HgGA variants having improved PI in a panose hydrolysis assay (PI≥1.1): K139R-F147N-F206D-P213W-K571F, A448V-I461A-E543H-K571R-K596I, V422P-D449A-S568R-G569W, and T74R-A448V-E535A-E543H-K571R;

Combinatorial SEL Cohort 8—HgGA variants having improved PI in a corn starch hydrolysis assay (PI≥1.1): T35S-I43F-P54D-G92F-K328Q-Y346W, F79T-G92F-S096L-L144F-I164N, and I43F-P54D-T239N-K328Q-K546S;

Combinatorial SEL Cohort 9—HgGA variants having improved PI for glucose inhibition of enzyme activity [higher ratio of (inhibition sample)/(no inhibition sample) as compared to WT] (PI≥1.1): D75E-F79D-D449A-S568R, I43F-T239N-N271Q-E535T-K546S, I43F-T239N-N271Q-A448V-I461A-E535T-E543H-K546S-K571R-K596I, T35S-I43F-P54D-G92F-K328Q-Y346W, G92F-L144F-D462Q-A567R, T35S-G92T-T239A, T35S-G92T-T239A-T441L, G92F-E23A-S375D-P552I, P60Q-F79V-E203F-F206V; and Combinatorial SEL Cohort 10—HgGA variants having improved PI for glucose reversion to DP2+ products (less reversion, higher PI) (PI≥1.1): D75E-F79D-D449A-S568R, F79T-G92F-S96L-L144F-I164N, T35S-I43F-P54D-G92F-K328Q-Y346W, I43D-G92F-Y346W, V422P-D449A-S568R-G569W, F79V-F147M-N534S-E535W, G92T-I164N-Y346W, P60Q-F79V-E203F-F206V, G92F-L144F-D462Q-A567R, I43F-P54D-G92F-K328Q-S375D, D75R-G92I-E203F-K571R, P60Q-F79V-F206V, D75R-G92I-K571R, G92F-E203A-S375D-P552I, G92F-S375D, D75R-K571R, P60Q-F206V, and I43F-P54D-T239N-K328Q-K546S.

Certain combinatorial variants fall into more than one Combinatorial SEL Cohort, and thus provide improvements in more than one property (i.e., by demonstrating an improved outcome in two or more of assays (a) to (j) above). Therefore, aspects of the invention include combinatorial HgGA variants that fall into more than one of the Combinatorial SEL Cohorts 1 to 10 above, including at least two Combinatorial SEL Cohorts, at least three Combinatorial SEL Cohorts, at least four Combinatorial SEL Cohorts, at least five Combinatorial SEL Cohorts, at least six Combinatorial SEL Cohorts, at least seven Combinatorial SEL Cohorts, or at least eight Combinatorial SEL Cohorts. A review of the combinatorial SEL Cohorts listed above (and in Example 3) clearly identifies combinatorial variants that fall into multiple Combinatorial SEL Cohorts, and thus have more than one improved property.

In certain embodiments, a variant GA enzyme contains one or more amino acid substitution(s) corresponding to the HgGA substitutions as set forth in SEL Cohorts.

In some embodiments, a variant according to the disclosure will comprise a fragment or functional domain of a variant GA. For example, a variant GA according to aspects of the present invention can include a variant catalytic domain of a parent HgGA (e.g., from about amino acid 32 to about amino acid 466 of SEQ ID NO:3), a variant linker region of a parent HgGA (e.g., from about amino acid 467 to about amino acid 526 of SEQ ID NO:3), a variant starch binding domain of a parent HgGA (e.g., from about amino acid 527 to about amino acid 634 of SEQ ID NO:3), or variant domains that have at least 60% sequence identity to these domains (e.g., having at least 60%, at least 70%, at least 80%, at least 90%, at least 95%, at least 97%, or at least 99% sequence identity to one or more to these domains). Therefore, while the full sequence of a variant GA may not have at least 60% (or greater) sequence identity to SEQ ID NO:4, variant GAs in which the variant catalytic, variant linker, and/or variant starch binding domain has at least 60% (or greater) sequence identity to the relevant domain in SEQ ID NO:4 are encompassed in aspects of the present invention.

GA variants according to aspects of the present invention also include chimeric or hybrid GAs with, for example, a starch binding domain (SBD) from a first GA and a catalytic domain and/or linker from a second GA, where at least one of the domains is a variant domain of the respective parent GA.

Polynucleotides (or nucleic acids) encoding a variant GA enzyme having one or more mutations with respect to a parent GA enzyme (e.g., as described above) are also provided herein. In certain embodiments, the variant GA encoded by the subject polynucleotide has at least 60% (i.e., 60% or greater as specified above) amino acid sequence identity to HgGA (SEQ ID NO:4). In certain embodiments, the polynucleotide encoding a variant GA enzyme has at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1 (excluding the portion of the nucleic acid that encodes the signal sequence) or SEQ ID NO:2. It will be appreciated that due to the degeneracy of the genetic code, a plurality of nucleic acids may encode the same variant GA enzyme. Moreover, nucleic acids encoding a variant GA enzyme as described herein may be engineered to be codon optimized, e.g., to improve expression in a host cell of interest. Certain codon optimization techniques are known in the art.

In certain embodiments, the variant GA enzyme-encoding nucleic acid hybridizes under stringent conditions to a nucleic acid encoding (or complementary to a nucleic acid encoding) a GA having at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1 (excluding the portion of the nucleic acid that encodes the signal sequence) or SEQ ID NO:2.

Nucleic acids may encode a "full-length" ("fl" or "FL") variant GA enzyme, which includes a signal sequence (e.g., SEQ ID NO:3), only the mature form of a variant GA enzyme, which lacks the signal sequence (e.g., SEQ ID NO:4), or a truncated form of a variant GA enzyme, which lacks portions of the N and/or C-terminus of the mature form but that retains glucoamylase activity.

A nucleic acid that encodes a variant GA enzyme can be operably linked to various promoters and regulators in a vector suitable for expressing the variant GA enzyme in a host cell(s) of interest, as described below.

IV. Expression of Recombinant GA Variants

Aspects of the subject invention include methods and compositions related to the generation nucleic acids encoding GA variants, host cells containing such nucleic acids, the production of GA variants by such host cells, and the isolation, purification and/or use of the GA variants.

As such, embodiments of the invention provide host cells that have been transduced, transformed or transfected with an expression vector comprising a desired GA variant-encoding nucleic acid sequence. For example, a filamentous fungal cell or yeast cell is transfected with an expression vector having a promoter or biologically active promoter fragment or one or more (e.g., a series) of enhancers which functions in the host cell line, operably linked to a DNA segment encoding a desired GA variant, such that desired GA variant is expressed in the cell line.

A. Nucleic Acid Constructs/Expression Vectors.

Natural or synthetic polynucleotide fragments encoding a desired GA variant may be incorporated into heterologous nucleic acid constructs or vectors, capable of introduction into, and replication in, a host cell of interest (e.g., a filamentous fungal or yeast cell). The vectors and methods disclosed herein are suitable for use in host cells for the expression of a desired GA variant. Any vector may be used as long as it meets the desired replication/expression characteristics in the host cell(s) into which it is introduced (such characteristics generally being defined by the user). Large numbers of suitable vectors and promoters are known to those of skill in the art, some of which are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant host cells comprising the coding sequence for a desired GA variant may be produced by introducing a heterologous nucleic acid construct comprising the desired GA variant coding sequence into the desired host cells (e.g., as described in further detail below). For example, a desired GA variant coding sequence may be inserted into a suitable vector according to well-known recombinant techniques and used to transform a filamentous fungus capable of GA expression. As has been noted above, due to the inherent degeneracy of the genetic code, other nucleic acid sequences which encode substantially the same or a functionally equivalent amino acid sequence may be used to clone and express a desired GA variant. Therefore it is appreciated that such substitutions in the coding region fall within the sequence variants covered by the present invention.

The present invention also includes recombinant nucleic acid constructs comprising one or more of the desired GA variant-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a desired GA variant: (i) in isolation; (ii) in combination with additional coding sequences; such as fusion polypeptide or signal peptide coding sequences, where the desired GA variant coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the desired GA variant coding sequence is a heterologous gene.

In one aspect of the present invention, a heterologous nucleic acid construct is employed to transfer a desired GA variant-encoding nucleic acid sequence into a host cell in vitro, e.g., into established filamentous fungal and yeast lines. Long-term production of a desired GA variant can be achieved by generating a host cell that has stable expression of the GA variant. Thus, it follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Examples of suitable promoters include both constitutive promoters and inducible promoters, examples of which include a CMV promoter, an SV40 early promoter, an RSV promoter, an EF-1$\alpha$ promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular host cell for expression purposes. It is operably linked to DNA sequence encoding a variant GA polypeptide. Such linkage comprises positioning of the promoter with respect to the initiation codon of the DNA sequence encoding the variant GA polypeptide in the expression vector such that the promoter can drive transcription/translation of the GA variant-encoding sequence. The promoter sequence contains transcription and translation control sequences which mediate the expression of the variant GA polypeptide. Examples include the promoters from the *Aspergillus niger, A awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Additional examples of suitable selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina*, which encodes the enzyme acetamidase, allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Examples of suitable plasmids include pUC18, pBR322, pRAX and pUC100. The pRAX plasmid contains AMA1 sequences from *A. nidulans*, which make it possible to replicate in *A. niger.*

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991.

B. Host Cells and Culture Conditions for GA and Variant GA Enzyme Production

After DNA sequences that encode the GA variants have been cloned into DNA constructs, the DNA is used to transform microorganisms. The microorganism to be transformed for the purpose of expressing a variant GA according to the present invention can be chosen from a wide variety of host cells. The sections below are provided as examples of host cells/microorganisms and are not meant to limit the scope of host cells that can be employed in practicing aspects of the present invention.

(i) Filamentous Fungi

Aspects of the present invention include filamentous fungi which have been modified, selected and cultured in a manner effective to result in desired GA variant production or expression relative to the corresponding non-transformed parental filamentous fungi.

Examples of species of parental filamentous fungi that may be treated and/or modified for desired glyucoamylase expression include, but are not limited to *Trichoderma, Penicillium* sp., *Humicola* sp., including *Humicola insolens; Aspergillus* sp., including *Aspergillus niger, Chrysosporium* sp., *Myceliophthora* sp., *Fusarium* sp., *Hypocrea* sp., and *Emericella* sp.

Cells expressing a desired GA variant are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ.

Microbiol. 63:1298-1306, 1997. Standard culture conditions are known in the art, e.g., cultures are incubated at 28° C. in shaker cultures or fermenters until desired levels of desired GA variant expression are achieved.

Culture conditions for a given filamentous fungus can be found, for example, in the scientific literature and/or from the source of the fungi such as the American Type Culture Collection (ATCC). After fungal growth has been established, the cells are exposed to conditions effective to cause or permit the expression of a desired GA variant.

In cases where a desired GA variant coding sequence is under the control of an inducible promoter, the inducing agent, e.g., a sugar, metal salt or antibiotic, is added to the medium at a concentration effective to induce expression of the desired GA variant.

In one embodiment, the strain is an *Aspergillus niger* strain, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAPS-4 are known (Ward et al, 1993, Appl. Microbiol. Biotechnol. 39:738-743).

In another embodiment, the strain is a *Trichoderma reesei* strain, which is a useful strain for obtaining overexpressed protein. For example, RL-P37, described by Sheir-Neiss, et al., *Appl. Microbiol. Biotechnol.* 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in over-expressing variant GA.

Where it is desired to obtain a GA variant in the absence of potentially detrimental native glucoamylase activity, it is useful to obtain a host cell strain which has had one or more glucoamylase genes deleted prior to introduction of a DNA construct or plasmid containing the DNA fragment encoding the desired GA variant. Such strains may be prepared in any convenient manner, for example by the method disclosed in U.S. Pat. No. 5,246,853 and WO 92/06209, which disclosures are hereby incorporated by reference. By expressing a desired GA variant in a host microorganism that is missing one or more glucoamylase genes (e.g., the endogenous glucoamylase gene of a host cell), identification and subsequent purification procedures, where desired, are simplified.

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, for example from about 0.5 to about 2.0 kb, may remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

In certain embodiments, more than one copy of DNA encoding a desired GA variant may be present in a host strain to facilitate overexpression of the GA variant. For example, a host cell may have multiple copies of a desired GA variant integrated into the genome or, alternatively, include a plasmid vector that is capable of replicating autonomously in the host organism.

(ii) Yeast

The present invention also contemplates the use of yeast as a host cell for desired GA production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei* (Cummings and Fowler, 1996), a xylanase from *Aureobasdlium pullulans* (Li and Ljungdahl, 1996), an alpha-amylase from wheat (Rothstein et al., 1987), etc.

(iii) Other

It is further contemplated that in some embodiments, expression systems in host cells other than filamentous fungal cells or yeast cells may be employed, including insect cell or bacterial cell expression systems. Certain of the bacterial host cells can, for example, be one that is also an ethanologen, such as an engineered *Zymomonas moblis*, which is not only capable of expressing the enzyme(s)/variant(s) of interest but also capable of metabolizing certain monomeric and other fermentable sugars, turning them into ethanol. The selection of a host cell may be determined by the desires of the user of the GA variants described herein, and thus no limitation in that regard is intended.

C. Introduction of a Desired GA-Encoding Nucleic Acid Sequence into Host Cells.

The invention further provides cells and cell compositions which have been genetically modified to comprise an exogenously provided desired GA variant-encoding nucleic acid sequence. A parental cell or cell line may be genetically modified (e.g., transduced, transformed or transfected) with a cloning vector or an expression vector. The vector may be, for example, in the form of a plasmid, a viral particle, a phage, etc., as further described above.

The methods of transformation of the present invention may result in the stable integration of all or part of the transformation vector into the genome of the host cell. However, transformation resulting in the maintenance of a self-replicating extra-chromosomal transformation vector is also contemplated.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). In essence, the particular genetic engineering procedure used should be capable of successfully introducing a polynucleotide (e.g., an expression vector) into the host cell that is capable of expressing the desired GA variant.

Many standard transfection methods can be used to produce *Trichoderma reesei* cell lines that express large quantities of the heterologous polypeptide. Some of the published methods for the introduction of DNA constructs into strains of *Trichoderma* include: Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164; for *Aspergillus*: Yelton, Hamer and Timberlake, 1984, Proc. Natl. Acad. Sci. USA 81: 1470-1474; for *Fusarium*: Bajar, Podila and Kolattukudy, 1991, Proc. Natl. Acad. Sci. USA 88: 8202-8212; for *Streptomyces*: Hopwood et al., 1985, The John Innes Foundation, Norwich, UK and for *Bacillus*: Brigidi, DeRossi, Bertarini, Riccardi and Matteuzzi, 1990, FEMS Microbiol. Lett. 55: 135-138. An example of a suitable transformation process for *Asper-*

*gillus* sp. can be found in Campbell et al. Improved transformation efficiency of *A. niger* using homologous niaD gene for nitrate reductase. Curr. Genet. 16:53-56; 1989.

In addition, heterologous nucleic acid constructs comprising a desired glucoamylase-encoding nucleic acid sequence can be transcribed in vitro, and the resulting RNA introduced into the host cell by well-known methods, e.g., by injection.

D. Analysis for GA Nucleic Acid Coding Sequences and/or Protein Expression.

In order to evaluate the expression of a desired GA variant by a cell line that has been transformed with a desired GA variant-encoding nucleic acid construct, assays can be carried out at the protein level, the RNA level or by use of functional bioassays particular to glucoamylase activity and/or production.

In general, assays employed to analyze the expression of a desired GA variant include, but are not limited to, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a desired GA variant may be measured in a sample directly, for example, by assays for glucoamylase activity, expression and/or production. Such assays are described, for example, in Becker et al., Biochem J. (2001) 356:19-30 and Mitsuishi et al., FEBS (1990) 275:135-138, each of which is expressly incorporated by reference herein. The ability of a GA to hydrolyze isolated soluble and insoluble substrates can be measured using assays described in Srisodsuk et al., J. Biotech. (1997) 57:49-57 and Nidetzky and Claeyssens, Biotech. Bioeng. (1994) 44:961-966. Substrates useful for assaying glucoamylase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression may be evaluated by immunological methods, such as ELISA, competitive immunoassays, radioimmunoassays, Western blot, indirect immunofluorescent assays, and the like. Certain of these assays can be performed using commercially available reagents and/or kits designed for detecting GA enzymes. Such immunoassays can be used to qualitatively and/or quantitatively evaluate expression of a desired GA variant. The details of such methods are known to those of skill in the art and many reagents for practicing such methods are commercially available. In certain embodiments, an immunological reagent that is specific for a desired variant GA enzyme but not its parent GA may be employed, e.g., an antibody that is specific for a GA substitution or a fusion partner of the GA variant (e.g., an N or C terminal tag sequence, e.g., a hexa-Histidine tag or a FLAG tag). Thus, aspects of the present invention include using a purified form of a desired GA variant to produce either monoclonal or polyclonal antibodies specific to the expressed polypeptide for use in various immunoassays. (See, e.g., Hu et al., 1991).

V. Methods for Enrichment, Isolation and/or Purification of GA Variant Polypeptide In general, a desired GA variant polypeptide produced in a host cell culture is secreted into the medium (producing a culture supernatant containing the GA variant) and may be enriched, purified or isolated, e.g., by removing unwanted components from the cell culture medium. However, in some cases, a desired GA variant polypeptide may be produced in a cellular form (e.g., cytoplasmic, periplasmic, or otherwise associated with the cell) necessitating recovery from a cell lysate/homogenate. The desired GA variant polypeptide is harvested from the cells or cell supernatants in which it was produced using techniques routinely employed by those of skill in the art. Examples include, but are not limited to, filtration (e.g., ultra- or micro-filtration), centrifugation, density gradient fractionation (e.g., density gradient ultracentrifugation), affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

While enriched, isolated or purified GA variant polypeptide is sometimes desired, in some embodiments, a host cell expressing a GA variant polypeptide is employed directly in an process that requires glucoamylase activity. Thus, enrichment, isolation or purification of the desired GA variant polypeptide is not always required to obtain a GA variant polypeptide composition that finds use in a desired assay or process that requires, or would benefit from, glucoamylase activity. In one such example, GA variant-expressing yeast cells may be added directly into a fermentation process such that the yeast cell expresses the variant GA directly into the fermentation broth where its glucoamylase activity converts a non-fermentable substrate into fermentable sugars for the yeast cell to convert directly to a desired product, e.g., into ethanol (see, e.g., Ilmén et al., *High level secretion of cellobiohydrolases by Saccharomyces cerevisiae* Biotechnology for Biofuels 2011, 4:30).

VI. Compositions

Compositions that include a variant GA as disclosed herein are contemplated. The variant GAs described herein may be used in enzyme compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions. Further, the variant glucoamylases may be used in baking applications, such as bread and cake production, brewing, healthcare, textile, environmental waste conversion processes, biopulp processing, and biomass conversion applications.

In some embodiments, an enzyme composition including a variant GA encompassed by the disclosure (e.g., obtained in culture media or recovered and purified from the culture medium) will be used in combination with any one or a combination of the following enzymes: alpha amylases, proteases, pullulanases, isoamylases, cellulases, hemicellulases, xylanases, cyclodextrin glycotransferases, lipases, phytases, laccases, oxidases, esterases, cutinases, xylanases, granular starch hydrolyzing enzyme and other glucoamylases.

In some representative compositions, one or more variant GAs as described herein will be combined with an alpha amylase, such as fungal alpha amylases (e.g., derived from a *Trichoderma* sp.) or bacterial alpha amylases (e.g., derived from a *Bacillus* sp.), including variants, chimeras, and hybrids thereof. In certain embodiments the alpha amylase is an acid stable alpha amylase. In certain embodiments, the alpha amylase is a granular starch hydrolyzing enzyme (GSHE). Commercially available alpha amylases contemplated for use in the variant GA compositions as described herein are available (e.g., from Danisco US Inc. or Novozymes).

In other embodiments, one or more variant GAs as described herein can be combined with other GAs, either variant or native. In some embodiments, the GAs of the disclosure will be combined with one or more GAs derived from strains of *Aspergillus* or variants thereof, such as *A. oryzae, A. niger, A. kawachi*, and *A. awamori*; glucoamylases derived from strains of *Humicola* or variants thereof; glucoamylases derived from strains of *Talaromyces* or variants thereof, particularly *T. emersonii*; glucoamylases derived from strains of *Athelia* or variants thereof, particularly *A. rolfsii*; glucoamylases derived from strains of *Penicillium* or variants thereof, particularly *P. chrysogenum*; and glucoamylases derived from strains of *Trichoderma* or variants thereof, particularly *T. reesei.*

VII. Utility of GA Variants

As detailed above, GAs are very important commercial enzymes used in a wide variety of applications that require the hydrolysis of starch substrates to fermentable sugars (e.g., glucose, maltose, maltotriose, etc.). GAs are used in processes to produce high fructose corn sweeteners, which comprise over 50% of the sweetener market in the United States, as well as in processes for the direct production of glucose. In general, glucoamylases may be, and commonly are, used with alpha-amylases in starch hydrolyzing processes to hydrolyze starch to dextrins and then to glucose. The glucose may be used directly; be converted to fructose by other enzymes (e.g., glucose isomerases); crystallized; or used in fermentations to produce numerous end products (e.g., ethanol, citric acid, succinic acid, ascorbic acid intermediates, glutamic acid, glycerol, 1,3-propanediol and lactic acid).

Given the commercial importance of GAs, it can be appreciated that the desired GA variant-encoding nucleic acids, the desired GA variant polypeptides and compositions comprising the same find utility in a wide variety applications. The improved property or properties of the GA variants described herein can be exploited in many ways. For example, GA variants with improved performance under conditions of thermal stress can be used to increase starch hydrolysis activity in processes carried out at high temperatures (e.g., temperatures at which the parent GA would perform poorly), allowing a user to reduce the total amount of GA employed (as compared to using the parent GA). Other improved properties of GA variant polypeptides can be exploited, including GA variants having altered pH optima, increased stability or activity at a specific pH, increased specific activity for a substrate, and/or high level expression in a host cell of interest.

A starch hydrolysis composition containing a desired GA variant as described herein finds use in ethanol production. Ethanol from this process can be further used as an octane enhancer or directly as a fuel in lieu of gasoline, which is advantageous, because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Separate saccharification and fermentation is a process whereby starch present in a feedstock, e.g., corn, is converted to glucose and subsequently an ethanologen (e.g., a yeast strain) convert the glucose into ethanol. Simultaneous saccharification and fermentation (SSF) is a process whereby starch present in a feedstock is converted to glucose and, at the same time and in the same reactor, an ethanologen converts the glucose into ethanol. Thus, the GA variants of the invention find use in the both of these processes for the degradation of starch-containing feedstock to generate ethanol.

In some embodiments, a GA variant as described herein is expressed in an ethanologen whereby the enzymatic activity of the variant GA expressed by the ethanologen generates glucose that can be converted to ethanol by the ethanologen.

GA variants as described herein find use in generating host cells for producing biochemical products of interest. As such, aspects of the present disclosure include methods of producing a biochemical by obtaining a host cell expressing a GA variant as described herein and culturing the host cell under conditions to produce the biochemical of interest. The host cell may include additional modifications to promote production of the desired biochemical, e.g., to express homologous or heterologous genes, additional variant genes, and/or to delete or otherwise inactivate the expression of one or more endogenous genes. Biochemicals of interest include, but are not limited to alcohols (ethanol, methanol, butanol, etc.) and other organic compounds, including volatile organic molecules (e.g., isoprene).

It is noted that GA variants with decreased thermostability find use, for example, in areas where the enzyme activity is required to be neutralized at lower temperatures, so that other enzymes that may be present are left unaffected. In addition, the enzymes may find utility in the limited conversion of cellulosics, for example, in controlling the degree of crystallinity or of cellulosic chain-length. After reaching the desired extent of conversion, the saccharifying temperature can be raised above the survival temperature of the de-stabilized GA variant. As the GA activity is essential for hydrolysis of crystalline cellulose, conversion of crystalline cellulose will cease at the elevated temperature.

One aspect of the invention relates to the use of the GA variant polypeptide according to the invention in the production of a fermented beverage, such as a beer. As such, aspects of the present disclosure include a method of providing/producing a fermented beverage comprising the step of contacting a mash and/or a wort with a GA variant polypeptide as described herein. A further aspect relates to a method of providing a fermented beverage comprising the steps of: (a) preparing a mash, (b) filtering the mash to obtain a wort, and (c) fermenting the wort to obtain a fermented beverage, such as a beer, wherein a GA variant polypeptide is added to: (i) the mash of step (a) and/or (ii) the wort of step (b) and/or (iii) the wort of step (c).

According to yet another aspect, a fermented beverage, such as a beer, is produced or provided by a method comprising the step(s) of (1) contacting a mash and/or a wort with a GA variant polypeptide as described herein; and/or (2) (a) preparing a mash, (b) filtering the mash to obtain a wort, and (c) fermenting the wort to obtain a fermented beverage, such as a beer, wherein a GA variant polypeptide is added to: (i) the mash of step (a) and/or (ii) the wort of step (b) and/or (iii) the wort of step (c).

Aspects of the invention also include a fermented beverage, such as a beer, produced using a GA variant as described above.

The term "beer" is meant to include any fermented wort produced by fermentation/brewing of a starch-containing plant material. Often, beer is produced from malt or adjunct, or any combination of malt and adjunct as the starch-containing plant material.

As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, corn (maize), potato, tapioca, cassava and syrups, such as corn syrup, sugar cane syrup, inverted sugar syrup, barley and/or wheat syrups, and the like may be used as a source of starch.

As used herein, the term "mash" refers to an aqueous slurry of any starch and/or sugar containing plant material such as grist, e.g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing/producing a fermented beverage such as beer comprising mixing the polypeptide of the invention with malt or adjunct.

Examples of beers produced according to the uses and methods above (i.e., in which a GA variant as described herein is used) include, but are not limited to, the following: full malted beer, beer brewed under the "Reinheitsgebot", ale, India Pale Ale (IPA), lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g. citrus flavored, such as lemon-, orange-, lime-, or berry-flavored malt beverages, liquor flavored malt beverages, e.g., vodka-, rum-, or tequila-flavored malt liquor, or coffee flavored malt beverages, such as coffee-flavored malt liquor, and the like.

As seen from above, GA variant polypeptides (and the nucleic acids encoding them) with improved properties as compared to their parent GA enzymes find use in improving any of a number of assays and processes that employ cellobiohydrolases.

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

Example 1

I. Assays

The following assays were used in the examples described below. The HgGA SEL data derived from the assays described below was employed to calculate Performance Index (PI) values for each HgGA variant in each assay performed on that variant. The PI compares the performance or stability of the variant (measured value) and the standard enzyme (theoretical value, e.g., for non-variant HgGA) at the same polypeptide concentration. In addition, the theoretical values can be calculated using the parameters of the Langmuir equation of the standard enzyme. A dose response curve was generated for the wild-type HgGA by fitting the data with the Langmuir equation with intercept ($y=((x*a)/(x+b))+c$) and the activities of the HgGA variants were divided by a calculated activity of wild-type HgGA of the same plate to yield a PI. A PI that is greater than 1 (PI>1) indicates improved performance by a variant as compared to the standard (e.g., wild-type HgGA), while a PI of 1 (PI=1) identifies a variant that performs the same as the standard, and a PI that is less than 1 (PI<1) identifies a variant that has a lower performance as compared to the standard.

A. Expression

A.1. Bradford Protein Content Determination Assay

The Bradford dye reagent (Quick Start) assay was used to determine the protein concentration in samples on microtiter plate (MTP) scale. The chemical and reagent solutions used were: Quick Start Bradford Dye Reagent (BIO-RAD Catalog No. 500-0205), and dilution buffer (50 mM NaOAc pH5.0). The equipment used was a Biomek FX Robot (Beckman) and a SpectraMAX (type 340) MTP reader. The MTPs were from Greiner Bio-one (655101). Two hundred (200) μL Bradford dye reagent was pipetted into each well of an MTP, followed by 5 μL of filtered supernatant from each HgGA sample. After thorough mixing, the MTPs were incubated for 15 minutes at room temperature. OD of each well was read at 595 nm and 450 nm. The ratio of the OD values obtained provided a relative measure of the protein content in the samples. Variant concentrations were determined using the calibration curve generated by control HgGA samples (from 0 to 3500 ppm range).

A.2. Enzyme Purification and Normalization

Filtered supernatants of expressed HGA variants (approximately 500 μL) were transferred to filter MTP plates (Corning 3505) containing β-Cyclodextrin coupled Sepharose 6B beads (see below for protocol employed to make these beads). The filter MTPs were centrifuged to remove the liquid from the beads and the beads were washed with 200 μL of 50 mM NaOAc, pH 5.5 (100×g for 1 min.). HgGA bound to the β-cyclodextrin coupled beads was eluted by adding 200 μL of 50 mM NaOAc, pH 5.5+20 mM α-cyclodextrin+100 mM NaCl and collecting the eluent by centrifugation (1000×g for 1 min.) into collection MTPs. 210 μL of collected HgGA samples were dialyzed in dialysis MTPs (Harvard Apparatus, 10 kDa MWCO) using 50 mM NaOAc, pH 5.5 buffer to remove α-cyclodextrin and NaCl (4° C. overnight; 1:100 ratio of sample:buffer). Protein in the dialyzed samples was quantified by reading the absorbance at 280 nm wavelength. This protein quantification result was used to normalize samples (e.g., to 50 ppm) for use in certain assays described herein.

Making β-cyclodextrin coupled Sepharose 6B column (for 50 mL final volume of coupled beads):

Solutions and Equipment:

1. 15 g β-cyclodextrin (Sigma-Aldrich; CAS nr:68168-23-0) in 300 ml 0.1M NaOH
2. 125 mL 1M ethanolamine
3. 1.5 L 0.1 M Acetate buffer pH 4.0 with 0.5M NaCl
4. 1.5 L 0.1 M Tris-HCl pH 8 with 0.5M NaCl
5. 45 g Epoxy-activated Sepharose™ 6 B (GE Healthcare; Lot: 10021987)
6. 0.22 μm filter (GP Express PLUS Membrane Cat no: SCGPT05RE)
7. Vacuum pump
8. Demineralized water Epoxy-activated Sepharose was washed with 3 L demineralized water over the filter under a low flow. Sepharose was mixed with β-cyclodextrin solubilized in 300 ml 0.1 M NaOH at 45° C. for 24 hours with mild stirring. The reacted Sepharose was washed with 3 L demineralized water over the filter under a low flow. The remaining active groups were blocked with 125 mL 1M ethanolamine at 45° C. for 4 hours (or overnight at 40-50° C.) with mild stirring. The Sepharose was washed with 3 L demineralized water over 0.22 μm filter under a low flow. The Sepharose was then washed thoroughly with at least three cycles of 500 ml 0.1 M Acetate buffer pH 4.0 containing 0.5M NaCl followed by a wash with 500 ml 0.1 M Tris-HCl pH 8 containing 0.5M NaCl. After that, the Sepharose was washed with 500 mL demineralized water. The Sepharose was then washed with loading buffer and the slurry was poured into the column in one continuous motion, while minimizing the introduction of air bubbles. The remainder of the column was immediately filled with buffer. The adaptor was inserted at an angle into the column, ensuring that no air was trapped under the net.

A.3. HPLC Protein Content Determination

A fresh 96-well round-bottom MTP containing 100 μL of approximately 50 ppm normalized sample per well (as described in A.2 above) was used for the High Performance Liquid Chromatography (HPLC) protein determination method. An Agilent 1260 or 1290 (Hewlett Packard) HPLC equipped with an Acuity UPLC BEH 125 SEC (Waters) column was used to separate remaining contaminants. Sample was eluted from the column using 25 mM sodium phosphate buffer pH 6.8 containing 250 mM sodium chloride. Absorbance was measured at 220 nm, integrated using ChemStation software (Agilent Technologies) and the protein concentration of samples was determined based on a standard curve of purified wild type protein.

B. Hydrolytic Activity on DP2 Substrate Maltose: $V_{max}$ and $K_m$ Assays

Supernatants containing each HgGA enzyme (as described in A.2 above) were normalized to 50 ppm with 50 mM NaOAc pH 5.5.

$V_{max}$ assay: 20 μl of the normalized HgGA supernatant was combined with 40 μl of Reagent A (25 U/mL HRP (horseradish peroxidase); 62 U/mL OXYGO® (glucose oxidase; Genencor); 50 mM NaOAc, pH 5.5; 0.005% (v/v) TWEEN®-80) and 50 μl $V_{max}$ Reagent (50 mM NaAC, pH 5.5; 0.005% (v/v) TWEEN®-80; 3.24 mg/mL ABTS (2,2'-Azino-bis(3-Ethylbenzothiazoline-6-Sulfonic Acid)); 10 mM Maltose (DP2 substrate)) and mixed well. OD 405 (absorbance at 405 nm) was read immediately and continuously for 3.5 minutes in the kinetic mode. The rate of absorbance increase at 405 nm is proportional to the hydrolytic activity of the enzyme. Reactions were run in triplicate.

$K_m$ assay: 20 μl of the normalized HgGA supernatant was combined with 40 μl of Reagent A (25 U/mL HRP; 62 U/mL OXYGO® (glucose oxidase; Genencor); 50 mM NaAC, pH 5.5; 0.005% (v/v) TWEEN®-80) and 50 μl $K_m$ Reagent (50 mM NaAC, pH 5.5; 0.005% (v/v) TWEEN®-80; 3.24 mg/mL ABTS; 2 mM Maltose (DP2 substrate)) and mixed well. OD 405 (absorbance at 405 nm) was read immediately and continuously for 3.5 minutes in the kinetic mode. The rate of absorbance increase at 405 nm is proportional to the hydrolytic activity of the enzyme. Reactions were run in triplicate.

C. Hydrolytic Activity on DP7 (Maltoheptaose) Substrate at pH 6.8

Supernatants containing each HgGA enzyme (as described in A.2 above) were normalized to 50 ppm with 50 mM NaOAc pH 5.5. 6 μL of the normalized HgGA supernatant were combined with 40 μl of Reagent A (25 U/mL HRP; 62 U/mL OXYGO® (glucose oxidase; Genencor); 50 mM sodium-phosphate buffer, pH 6.8; 0.005% (v/v) TWEEN®-80) and 50 μL Reagent B (50 mM NaOAc, pH 5.5; 0.005% (v/v) TWEEN®-80; 3.24 mg/mL ABTS; 6 mM DP7 (substrate)) and mixed well. OD 405 (absorbance at 405 nm) was read immediately and continuously for 3.5 minutes in the kinetic mode. The rate of absorbance increase at 405 nm is proportional to the hydrolytic activity of the enzyme. Reactions were run in triplicate.

D. Hydrolytic Activity on DP7 (Maltoheptaose) Substrate at pH 5.5

Supernatants containing each HgGA enzyme (as described in A.2 above) were normalized to 50 ppm with 50 mM NaOAc pH 5.5. 6 μL of the normalized HgGA supernatant were combined with 40 μl of Reagent A (25 U/mL HRP; 62 U/mL OXYGO® (glucose oxidase; Genencor); 50 mM NaOAc, pH 5.5; 0.005% (v/v) TWEEN®-80) and 50 μL Reagent B (50 mM NaOAc, pH 5.5; 0.005% (v/v) TWEEN®-80; 3.24 mg/mL ABTS; 6 mM DP7 (substrate)) and mixed well. OD 405 (absorbance at 405 nm) was read immediately and continuously for 3.5 minutes in the kinetic mode. The rate of absorbance increase at 405 nm is proportional to the hydrolytic activity of the enzyme. Reactions were run in triplicate.

E. Hydrolytic Activity on Panose (PAN) Substrate

Supernatants containing each HgGA enzyme (as described in A.2 above) were normalized to 50 ppm with 50 mM NaOAc pH 5.5. 20 μL of the normalized HgGA supernatant were combined with 40 μl of Reagent A (25 U/mL HRP; 62 U/mL OXYGO® (glucose oxidase; Genencor); 50 mM NaOAc, pH 5.5; 0.005% (v/v) TWEEN®-80) and 50 μL Reagent B (50 mM NaOAc, pH 5.5; 0.005% (v/v) TWEEN®-80; 3.24 mg/mL ABTS; 100 mM panose (substrate)) and mixed well. OD 405 (absorbance at 405 nm) was read immediately and continuously for 3.5 minutes in the kinetic mode. The rate of absorbance increase at 405 nm is proportional to the hydrolytic activity of the enzyme. Reactions were run in triplicate.

F. Hydrolytic Activity on Pullulan (PUL) Substrate

Supernatants containing each HgGA enzyme (as described in A.2 above) were normalized to 50 ppm with 50 mM NaOAc pH 5.5. 10 μL of the normalized HgGA supernatant were combined with 40 μl of Reagent A (25 U/mL HRP; 62 U/mL OXYGO® (glucose oxidase; Genencor); 50 mM NaOAc, pH 5.5; 0.005% (v/v) TWEEN®-80) and 50 μL Reagent B (50 mM NaOAc, pH 5.5; 0.005% (v/v) TWEEN®-80; 3.24 mg/mL ABTS; 4% pullulan solution (substrate)) and mixed well. OD 405 (absorbance at 405 nm) was read immediately and continuously for 3.5 minutes in the kinetic mode. The rate of absorbance increase at 405 nm is proportional to the hydrolytic activity of the enzyme. Reactions were run in triplicate.

G. Hydrolytic Activity on Granular Corn Starch (CS)

Supernatants containing each HgGA enzyme (as described in A.2 above) were normalized to 50 ppm with 50 mM NaOAc pH 5.5. 8 μL of each of the normalized HgGA supernatant was combined with 80 μL 5% corn starch solution in a PCR MTP, sealed, and incubated in a Tetrad PCR machine at 55° C. for 10 minutes. At the end of the incubation the PCR plates were cooled down to 4° C. and the reactions were quenched with 20 μL 0.5 M NaOH. The plates are then centrifuged (3000 rpm for 3 minutes) and 10 μL of the obtained supernatant was combined with 90 μL of 50 mM NaOAc pH 5.5. 10 μL of the 10-fold diluted quenched solution was combined with 100 μL of BCA reagent in a new PCR MTP, sealed, and incubated in a Tetrad PCR machine at 95° C. for 2 minutes. After incubation, 80 μL of the reaction mixture was transferred to a transparent MTP and the OD at 560 nm was read immediately.

H. Thermostability Assay on DP7 (Maltoheptaose) Substrate

Supernatants containing each HgGA enzyme (as described in A.2 above) were normalized to 50 ppm with 50 mM NaOAc pH 5.5. 50 µL per well of the normalized HgGA supernatant were placed into a 96-well PCR MTP, sealed, and incubated in a Tetrad2 Peltier Thermal Cycler (Biorad) at 63.5° C. for 5 minutes. At the end of the incubation the PCR plates were cooled down to 4° C. The heat-incubated samples were analyzed for DP7 hydrolytic activity at pH 5.5, Maltoheptaose (DP7) as described in D above. Activity was compared to samples not incubated at 63.5° C. to determine the "residual" activity (i.e., activity remaining after the heat treatment).

I. Glucose Inhibition of p-nitrophenyl-glucopyranoside (p-NPG) Reaction

Supernatants containing each HgGA enzyme (as described in A.2 above) were normalized to 50 ppm with 50 mM NaOAc pH 5.5. Two different MTPs were prepared, with each of the two MTPs containing one of the following solutions: (1) 30 µl of 25 mM pNPG (no inhibition sample) and (2) 30 µl of 25 mM pNPG+840 mM glucose (DP1) (inhibition sample). 20 µl a 50 ppm normalized HgGA supernatant was added to a well of each of the MTP (final concentration in the pNPG assay is 20 ppm HgGA; final concentration of glucose in reaction (3) is 500 mM). The MTPs were incubated for 30 min at 50° C. with shaking at 900 rpm. The reaction was quenched by adding 65 µl of 0.2M borate stop solution and shaking for an additional 30 sec. The samples were analyzed by reading the OD at 405 nm ($OD_{405}$) at room temperature (RT) to detect p-nitrophenyl released by HgGA activity on the p-NPG substrate. Reactions were done in triplicate. The ratio of (inhibition sample)/(no inhibition sample) was determined. Variants having ratios higher than WT HgGA have a higher PI value (as described below).

J. Reversion Activity (Glucose Condensation)

Glucose condensation activity (reversion activity) for each HgGA enzyme was tested by combining 87.5 µL of 60% (w/v) glucose in 50 mM NaOAc, pH5.5 with 12.5 µL of each of the non-normalized purified HgGA samples (as described in A.2 above) in MTPs and incubated with shaking (200 rpm) at 55° C. for 66 hours. After further incubation of the MTPs at 20° C. for 1 hour (with shaking), 20 µL of each sample were added to a new MTP containing 180 µL of 100 mM $H_2SO_4$ solution. Glucose and reversion products (DP2, DP3, and DP4+) were quantitated by HPLC separation on a Rezex RFQ-Fast Acid H+ column pre-equilibrated with 0.01 N $H_2SO_4$ at 80° C. (Running buffer: 0.01 N $H_2SO_4$ (isocratic); Flow rate: 0.9 ml/min; Analysis time: 4 minutes; Temperature: 80° C. (column); Injection vol.: 5 µL). The expected retention times of the main components are: glucose (2.23 min), DP2 (1.79 min), DP3 (1.59 min), $H_2SO_4$/DP4+ (1.42 min).

Example 2

I. Generation of HgGA Variants

Plasmid and Library Construction

Figure 3:
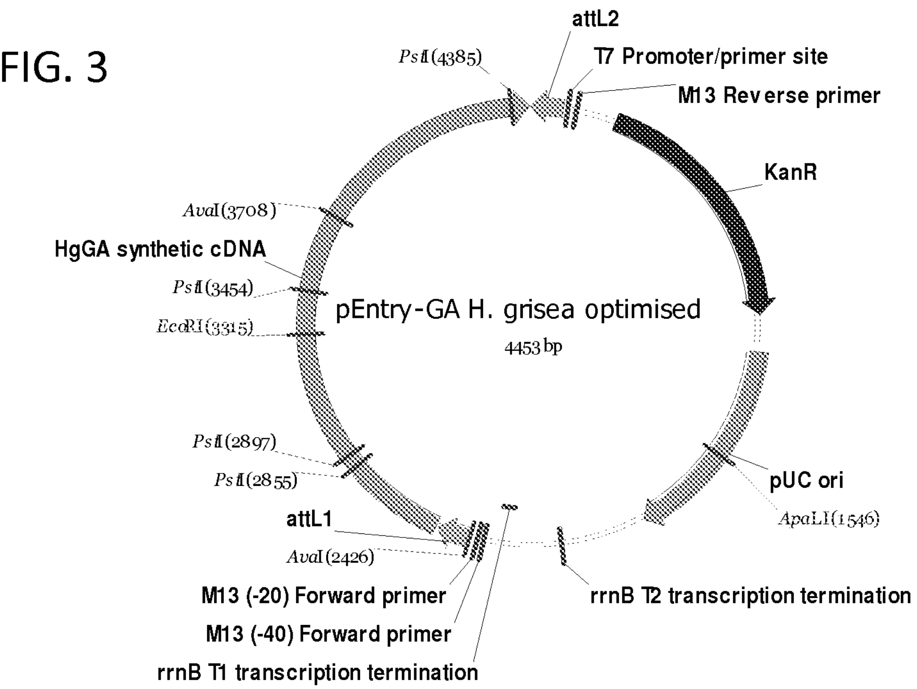
FIG. 3 is a schematic representation of the pEntry-HgGA synthetic optimized cDNA plasmid used to construct SEL libraries and combinatorial variants (see Example 2).
Figure 4:
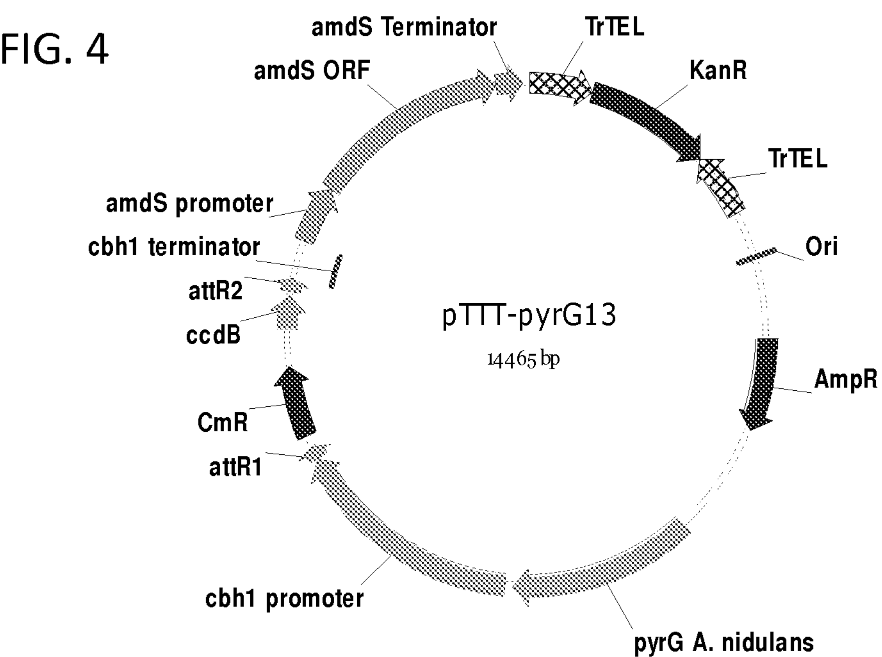
FIG. 4 is a schematic representation of the destination vector pTTTpyrG13 used with the Gateway® LR technology (see Example 2).
Figure 5:
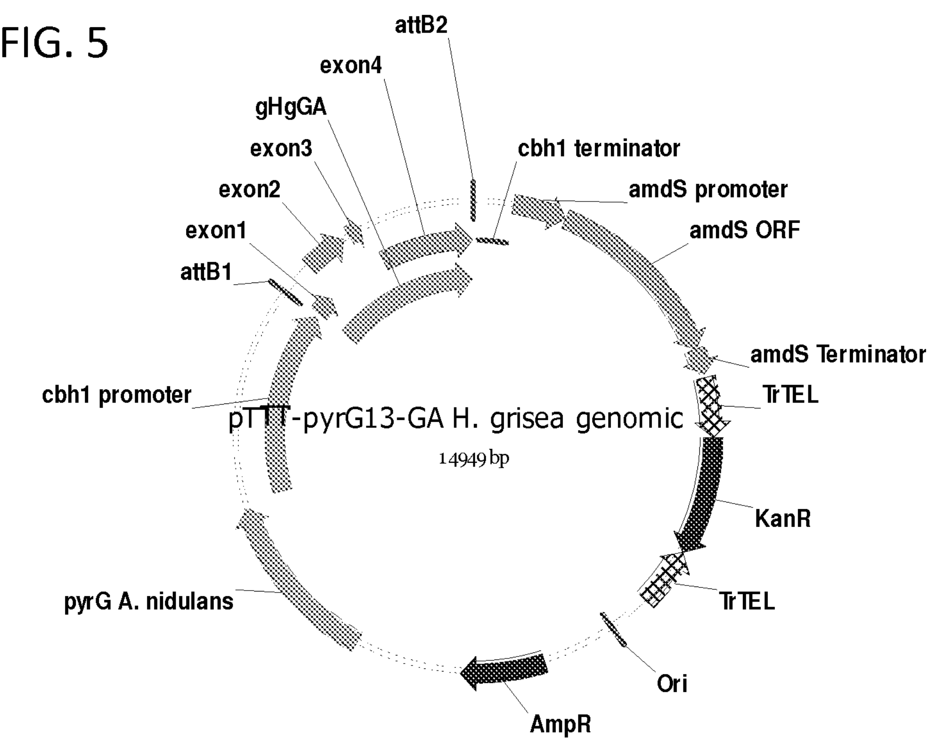
FIG. 5 is a schematic representation of the expression plasmid for genomic HgGA (pTTTpyrG13-HgGA) (see Example 2).
Figure 6:
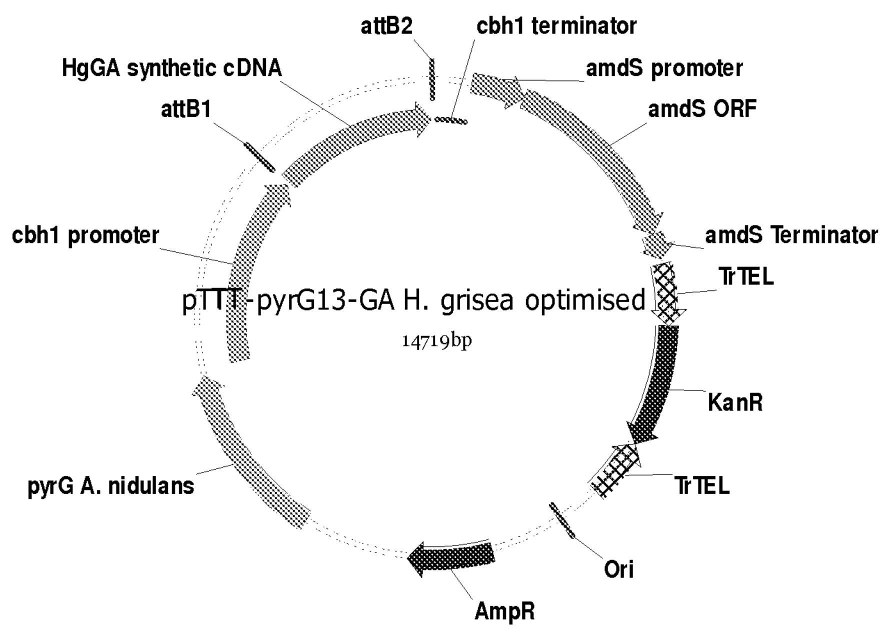
FIG. 6 is a schematic representation of the expression plasmid for synthetic optimized HgGA (pTTTpyrG13-HgGA) (see Example 2).

A DNA sequence containing the coding region for glucoamylase (GH15) from the filamentous fungus *H. grisea* strain 473N, ATCC #16453 was amplified from the genomic DNA with the gene specific primers extended with the attB1 and attB2 sites to allow for the Gateway® BP recombination cloning into the pDonor221 vector (Invitrogen, USA). Phusion DNA polymerase (Finnzymes OY, Finland) was used for PCR amplification to minimize sequence errors. The pEntry-HgGA genomic plasmid, as shown in FIG. 2, was verified by sequence analysis and used by vendors as a template for construction of site saturation libraries (SELs). In addition, a synthetic optimized cDNA sequence of HgGA was used to construct a few SEL libraries as well as 41 combinatorial variants (CVs) (FIG. 3). SELs were made for 580 of the 604 amino acid positions of the HgGA mature polypeptide. On average, the number of mutant variants per each SEL library varied, with some exceptions, between 14 and 19. All variants were recombined via the Gateway® LR technology with the destination vector pTTTpyrG13 (FIG. 4) resulting in final expression plasmids pTTTpyrG13-HgGA genomic (FIG. 5) and pTTTpyrG13-HgGA optimized (FIG. 6). Plasmids were generated in the *Escherichia coli* DH5a strain, purified, sequenced, arrayed individually in 96-well MTPs and used for fungal transformation as described further (see section II. below).

The expression vector contains the *T. reesei* cbh1 promoter and terminator regions allowing for a strong inducible expression of a gene of interest, the *Aspergillus nidulans* amdS and pyrG selective markers conferring growth of transformants on minimal medium with acetamide in the absence of uridine. The plasmids are maintained autonomously in the fungal cell due to *T. reesei* derived telomere regions. Usage of replicative plasmids results in increased frequencies of transformation and circumvents problems of locus-dependent expression observed with integrative fungal transformation.

Nucleotide sequence of genomic HgGA (SEQ ID NO:1; introns are in italic case and underlined):

ATGCATACCTTCTCCAAGCTCCTCGTCCTGGGCTCTGCCGTCCAGTCTGC

CCTCGGGCGGCCTCACGGCTCTTCGCGTCTCCAGGAACGCGCTGCCGTTG

ATACCTTCATCAACACCGAGAAGCCCATCGCATGGAACAAGCTGCTCGCC

AACATCGGCCCTAACGGCAAAGCCGCTCCCGGTGCCGCCGCCGGCGTTGT

GATTGCCAGCCCTTCCAGGACGGACCCTCCTT*GTACGTGGTGGCATGGAA*

*TGGACCCAAGAGACTGGTTTTAGATGAAAGAGAGTTTCTGCTAACCGCCA*

*CACCCAG*ACTTCTTCACCTGGACCCGCGATGCCGCCCTGGTCCTCACCGG

CATCATCGAGTCCCTTGGCCACAACTACAACACCACCCTGCAGACCGTCA

TCCAGAACTACGTCGCGTCGCAGGCCAAGCTGCAGCAGGTCTCGAACCCC

TCGGGAACCTTCGCCGACGGCTCGGGTCTCGGTGAGGCCAAGTTCAATGT

CGACCTCACTGCCTTCACTGGCGAATGGGGTCGCCCTCAGAGGGACGGCC

CGCCCCTGCGCGCCATCGCTCTCATCCAGTACGCCAAGTGGCTGATCGCC

AACGGCTACAAGAGCACGGCCAAGAGCGTCGTCTGGCCCGTCGTCAAGAA

CGATCTCGCCTACACGGCCCAGTACTGGAACGAGACCGGCTTCGATCTCT

GGGAGGAGGTCCCCGGCAGCTCGTTCTTTACCATCGCCAGCTCTCACAGG

G*GTGAGTCATTTATTGTTCAGTGTTTTCTCATTGAATAATTACCGGAATG*

*CCACTGACGCCAAACAG*CTCTGACTGAGGGTGCTTACCTCGCCGCTCAGC

TCGACACCGAGTGCCGCGCCTGCACGACCGTCGCCCCTCAGGTTCTGTGC

TTCCAGCAGGCCTTCTGGAACTCCAAGGGCAACTATGTCGTCTCCAACA*G*

*TAAGATCCCTACACCAACAAAAAAAATCGAAAAGGAACGTTAGCTGACCC*

*TTCTAG*TCAACGGCGGCGAGTATCGCTCCGGCAAGGACGCCAACTCGATC

CTGGCGTCCATCCACAACTTCGACCCTGAGGCCGGCTGCGACAACCTGAC

-continued

CTTCCAGCCCTGCAGCGAGCGCGCCCTGGCCAACCACAAGGCCTATGTCG
ACTCGTTCCGCAACCTCTACGCCATCAACAAGGGCATCGCCCAGGGCAAG
GCCGTTGCCGTCGGCCGCTACTCGGAGGATGTCTACTACAACGGCAACCC
GTGGTACCTGGCCAACTTTGCCGCCGCCGAGCAGCTCTACGACGCCATCT
ACGTGTGGAACAAGCAGGGCTCCATCACCGTGACCTCGGTCTCCCTGCCC
TTCTTCCGCGACCTTGTCTCGTCGGTCAGCACCGGCACCTACTCCAAGAG
CAGCTCGACCTTCACCAACATCGTCAACGCCGTCAAGGCCTACGCCGACG
GCTTCATCGAGGTGGCGGCCAAGTACACCCCGTCCAACGGCGCGCTCGCC
GAGCAGTACGACCGCAACACGGGCAAGCCCGACTCGGCCGCCGACCTGAC
GTGGTCGTACTCGGCCTTCCTCTCGGCCATCGACCGCCGCGCGGGTCTCG
TCCCCCCGAGCTGGCGGGCCAGCGTGGCCAAGAGCCAGCTGCCGTCCACC
TGCTCGCGCATCGAGGTCGCCGGCACCTACGTCGCCGCCACGAGCACCTC
GTTCCCGTCCAAGCAGACCCCGAACCCCTCCGCGGCGCCCTCCCCGTCCC
CCTACCCGACCGCCTGCGCGGACGCTAGCGAGGTGTACGTCACCTTCAAC
GAGCGCGTGTCGACCGCGTGGGGCGAGACCATCAAGGTGGTGGGCAACGT
GCCGGCGCTGGGGAACTGGGACACGTCCAAGGCGGTGACCCTGTCGGCCA
GCGGGTACAAGTCGAATGATCCCCTCTGGAGCATCACGGTGCCCATCAAG
GCGACGGGCTCGGCCGTGCAGTACAAGTATATCAAGGTCGGCACCAACGG
GAAGATTACTTGGGAGTCGGACCCCAACAGGAGCATTACCCTGCAGACGG
CGTCGTCTGCGGGCAAGTGCGCCGCGCAGACGGTGAATGATTCGTGGCGT
TAA

Nucleotide sequence of the synthetic optimized cDNA sequence of HgGA (SEQ ID NO:2):

ATGCATACCTTCTCCAAGCTCCTCGTTCTTGGATCTGCCGTCCAGTCTGC
CCTCGGACGGCCTCACGGCTCTTCGCGTCTCCAGGAACGCGCTGCCGTTG
ATACATTCATCAACACCGAGAAGCCCATTGCATGGAACAAGCTGCTTGCC
AACATCGGCCCTAACGGCAAGGCCGCTCCCGGTGCCGCCGCCGGTGTTGT
CATTGCCAGCCCTTCCAGGACGGACCCCCCTTACTTCTTTACCTGGACTC
GCGATGCCGCTCTGGTCCTCACCGGCATCATCGAGTCCCTTGGCCACAAC
TACAACACCACGCTGCAGACCGTCATCCAGAACTACGTCGCGTCTCAAGC
AAAGCTGCAGCAGGTGTCTAACCCCAGCGGAACGTTCGCCGACGGTTCTG
GTCTCGGTGAAGCCAAGTTCAATGTCGACTTGACTGCTTTCACTGGCGAA
TGGGGTCGCCCTCAGCGAGACGGCCCGCCCCTGCGCGCCATCGCTCTCAT
CCAGTACGCCAAGTGGCTGATCGCCAACGGTTACAAGAGCACGGCCAAGA
GCGTCGTCTGGCCAGTCGTCAAGAACGATCTCGCCTATACGGCACAATAC
TGGAACGAGACCGGCTTTGATCTCTGGGAGGAGGTCCCCGGCAGCTCCTT
CTTTACAATCGCTAGCTCTCACAGGGCTCTGACTGAGGGTGCTTACCTCG
CCGCTCAGCTCGACACCGAGTGCCGCGCTTGCACGACCGTCGCCCCTCAG
GTTCTGTGCTTCCAGCAGGCCTTCTGGAATTCCAAGGGCAACTATGTCGT
CTCGAATATCAACGGCGGCGAGTATCGCTCCGGAAAGGACGCCAACTCGA

-continued

TCCTTGCGTCTATCCACAACTTCGACCCTGAGGCAGGCTGTGACAACCTG
ACCTTCCAGCCCTGCAGCGAACGCGCCCTGGCCAACCACAAGGCTTATGT
CGACTCGTTCCGGAACCTCTACGCCATTAACAAGGGCATCGCCCAGGGCA
AGGCTGTTGCCGTCGGACGCTACTCGGAGGATGTCTACTACAACGGCAAC
CCGTGGTATCTTGCCAACTTTGCCGCCGCAGAACAACTCTACGACGCCAT
CTACGTTTGGAATAAGCAAGGCTCCATCACAGTGACCTCCGTCTCCTTGC
CCTTTTTCAGGGACTTGGTCTCGAGCGTCAGCACCGGCACTTACAGCAAG
AGCAGCAGCACGTTCACCAACATTGTCAACGCCGTCAAGGCATACGCCGA
CGGCTTCATTGAGGTGGCGGCCAAGTACACCCCGTCCAACGGCGCGCTCG
CCGAGCAGTACGACCGTAACACGGGCAAGCCCGACTCGGCCGCTGACCTG
ACTTGGTCGTACTCTGCCTTCCTCTCTGCCATTGACCGACGAGCAGGTCT
CGTCCCCCCATCCTGGCGGGCCAGCGTTGCCAAGAGCCAGCTGCCATCCA
CATGTTCTCGCATCGAGGTCGCAGGCACATATGTCGCCGCCACGAGCACC
TCGTTTCCGTCCAAGCAAACCCCAAACCCCTCCGCGGCGCCCTCCCCGTC
CCCCTACCCGACCGCTTGCGCGGACGCTAGCGAGGTCTACGTTACCTTCA
ACGAGCGAGTGTCGACCGCGTGGGGCGAGACTATCAAGGTGGTGGGCAAC
GTGCCGGCGTTGGGAAACTGGGACACGTCCAAGGCGGTGACCCTGTCCGC
CAGCGGATACAAGTCGAATGATCCCCTCTGGAGCATCACGGTGCCCATCA
AGGCTACGGGCTCCGCCGTGCAGTACAAGTATATTAAGGTCGGCACAAAC
GGTAAGATTACTTGGGAGTCCGACCCCAATAGGAGCATTACCCTGCAGAC
GGCGTCGAGCGCTGGCAAGTGCGCAGCGCAGACGGTGAATGATTCGTGGC
GTTGA

Amino acid sequence of full-length HgGA glycoamylase (SEQ ID NO:3; putative signal peptide is in bold):

MHTFSKLLVLGSAVQSALGRPHGSSRLQERAAVDTFINTEKPIAWNKLLA
NIGPNGKAAPGAAAGVVIASPSRTDPPYFFTWTRDAALVLTGIIESLGHN
YNTTLQTVIQNYVASQAKLQQVSNPSGTFADGSGLGEAKFNVDLTAFTGE
WGRPQRDGPPLRAIALIQYAKWLIANGYKSTAKSVVWPVVKNDLAYTAQY
WNETGFDLWEEVPGSSFFTIASSHRALTEGAYLAAQLDTECRACTTVAPQ
VLCFQQAFWNSKGNYVVSNINGGEYRSGKDANSILASIHNFDPEAGCDNL
TFQPCSERALANHKAYVDSFRNLYAINKGIAQGKAVAVGRYSEDVYYNGN
PWYLANFAAAEQLYDAIYVWNKQGSITVTSVSLPFFRDLVSSVSTGTYSK
SSSTFTNIVNAVKAYADGFIEVAAKYTPSNGALAEQYDRNTGKPDSAADL
TWSYSAFLSAIDRRAGLVPPSWRASVAKSQLPSTCSRIEVAGTYVAATST
SFPSKQTPNPSAAPSPSPYPTACADASEVYVTFNERVSTAWGETIKVVGN
VPALGNWDTSKAVTLSASGYKSNDPLWSITVPIKATGSAVQYKYIKVGTN
GKITWESDPNRSITLQTASSAGKCAAQTVNDSWR

Amino acid sequence of mature HgGA glycoamylase (SEQ ID NO:4):

AAVDTFINTEKPIAWNKLLANIGPNGKAAPGAAAGVVIASPSRTDPPYFF

TWTRDAALVLTGIIESLGHNYNTTLQTVIQNYVASQAKLQQVSNPSGTFA

DGSGLGEAKFNVDLTAFTGEWGRPQRDGPPLRAIALIQYAKWLIANGYKS

TAKSVVWPVVKNDLAYTAQYWNETGFDLWEEVPGSSFFTIASSHRALTEG

AYLAAQLDTECRACTTVAPQVLCFQQAFWNSKGNYVVSNINGGEYRSGKD

ANSILASIHNFDPEAGCDNLTFQPCSERALANHKAYVDSFRNLYAINKGI

AQGKAVAVGRYSEDVYYNGNPWYLANFAAAEQLYDAIYVWNKQGSITVTS

VSLPFFRDLVSSVSTGTYSKSSSTFTNIVNAVKAYADGFIEVAAKYTPSN

GALAEQYDRNTGKPDSAADLTWSYSAFLSAIDRRAGLVPPSWRASVAKSQ

LPSTCSRIEVAGTYVAATSTSFPSKQTPNPSAAPSPSPYPTACADASEVY

VTFNERVSTAWGETIKVVGNVPALGNWDTSKAVTLSASGYKSNDPLWSIT

VPIKATGSAVQYKYIKVGTNGKITWESDPNRSITLQTASSAGKCAAQTVN

DSWR

II. Production of HgGA Variant Polypeptides

Fungal Strains, Growth Media and Transformation

Using a PEG-Protoplast method, plasmids (5-10 ul) from SEL libraries and combinatorial variants (CVs) were transformed in a *T. reesei* strain deleted for major cellulases (Δcbh1, Δcbh2, Δegl1, Δegl2, Δegl3, ΔbglA, and pyr4−). All high throughput transformations were performed robotically in a 24 well MTP format using Biomek robots (Beckman Coulter, USA). Plasmids with variants were received from the vendors in 96 well MTPs arrayed according to a predetermined layout. Transformation mixtures containing approximately 1 μg of DNA and $5\times10^6$ protoplasts in a total volume of 50 μl were mixed with 200 ul of 25% PEG solution, diluted with equal volume of 1.2M sorbitol/10 mM Tris, pH7.5/10 mM $CaCl_2$ solution, rearranged robotically into 24 well MTPs and mixed with 1 ml of 3% agarose Minimal Medium (MM) {(20 g/L glucose, 15 g/L $KH_2PO_4$, 1 g/L $CaCl_2x2H_2O$, 1 g/L $MgSO_4x7H_2O$, pH 4.5, 2.5 ml/L of 400× *T. reesei* trace elements (175 g/L citric acid, 200 g/L $FeSO4x7H_2O$, 16 g/L $ZnSO4x7H_2O$, 3.2 g/L $CuSO4x5H_2O$, 1.4 g/L $MnSO4xH_2O$, 0.8 g/L boric acid)} containing 1M sorbitol and 10 mM NH4Cl. After growth of transformants, spores from each well were pooled and repatched on fresh 24 well MTPs with MM containing 10 mM acetamide for additional selective pressure. Once sporulated, spores were harvested and used for inoculation of liquid cultures either in a 24-well MTP format (for screening) or shake flasks (for validation studies) in the following production medium: 37 g/L glucose, 1 g/L sophorose, 9 g/L casamino acids, 10 g/L $(NH_4)_2SO_4$, 5 g/L $KH_2PO_4$, 1 g/L $CaCl_2x2H_2O$, 1 g/L $MgSO_4x7H_2O$, 33 g/L 1,4-Piperazine-bis (propanesulfonic acid), pH 5.5, 2.5 ml/L of 400× *T. reesei* trace elements). 1 ml of production medium was added to produce variants in 24 well MTPs. For shake flasks, volumes were scaled up.

Plates were grown for 6 days at 28° C. and 80% humidity with shaking at 200 rpm. Culture supernatants were harvested by filtration and GA variants were purified on b-cyclodextrin linked to epoxy-activated Sepharose 6B resin (GE Healthcare). Coupling of b-cylodextrin dissolved in 0.1 M NaOH to the matrix was performed for 24 h at 45 C with stirring followed by washing step to remove the excess of the substrate and blocking the remaining active groups with ethanolamine. For purification of GA samples, 96 well filter plates (Corning Art. No. 3505) containing 100 ul of β-cyclodextrin resin equilibrated with 25 mM Na-acetate buffer, pH 4.3, were loaded with 200-600 ul of culture samples, filtered, washed with 200 ul of the buffer and GA protein samples bound to the matrix were eluted in 100 ul of 10 mM a-cyclodextrin in the same buffer. To remove a-cyclodextrin, samples were desalted using Zeba™ Spin Desalting 96 well plates (ThemoScientific).

Purified HgGA enzyme samples were assayed for specific activity and thermostability as described elsewhere (see, e.g., US Patent Application publications US/2011/0020899 and US/2011/0014681).

Expression of certain variants was analyzed by SDS-PAGE.

Example 3

Expression, Activity and Performance of HgGA Variants

Performance index (PI) values were determined for all the HgGA variants tested using the following assays (described in Example 1): (a) expression, (b) hydrolytic activity on DP2 substrate, (c) hydrolytic activity on DP7 substrate at pH 6.8, (d) hydrolytic activity on DP7 substrate at pH 5.5, (e) hydrolytic activity on panose substrate, (f) hydrolytic activity on pullulan substrate, (g) hydrolytic activity on granular corn starch (CS), (h) thermostability, (i) glucose inhibition, and (j) reversion activity.

Below is a listing of HgGA substitution variants having an improved property over wild type HgGA in at least one of the assays performed. The HgGA variants fall into the following SEL Cohorts (the assay and PI cut-off is listed for each Cohort).

SEL Cohort 1—HgGA variants having improved PI in expression (PI≥1.2): A31T, A31Y, A31L, A31M, A31F, A31K, A31I, A31N, A31Q, A32Q, A32T, A32S, V33H, V33I, V33G, V33C, V33V, D34M, D34A, D34E, D34C, T35A, T35N, T35H, T35P, F36H, F36P, I37P, I37H, I37G, I37M, I37D, I37L, I37C, I37T, N38I, N38G, N38K, N38H, K41E, K41H, K41D, K41L, K41R, K41N, I43G, I43A, I43L, I43S, I43Y, I43I, A44G, A44N, A44L, A44F, A44V, W45Q, W45E, N46S, K47S, K47K, K47Q, L48N, L48Q, L49S, L49N, A50W, A50A, A50D, A50N, A50L, A50F, A50T, A50S, A50M, N51S, P54N, P54G, P54M, K57C, K57I, K57R, K57Q, K57A, K57V, K57W, K57T, K57L, P60H, A62I, A62V, A62T, A62A, A62C, A64A, V67P, I68I, A69C, A69E, S70A, S72C, S72D, S72K, S72Q, S72V, S72G, S72E, R73M, R73S, R73Q, R73N, R73P, T74D, T74L, D75H, D75R, P76P, P76G, P77S, P77C, P77W, Y78A, F79E, F79D, F80T, F80A, F80D, F80Q, F80W, F80R, F80M, F80H, F80F, T81A, T81C, W82N, W82Q, W82L, W82A, W82M, W82E, W82V, W82R, W82F, T83V, T83N, T83T, R84Q, R84C, R84H, R84L, R84P, R84E, D85C, D85N, D85E, D85G, D85P, D85V, D85Y, D85M, D85D, D85L, D85S, D85H, A86G, A87C, L88S, L88L, L88Q, L88W, L88G, V89D, L90A, L90N, L90I, L90P, T91G, I93A, I93Y, I93I, I93R, I93W, I94N, I94S, I94H, I94L, I94A, I94Q, I94I, I94M, I94G, I94V, I94P, I94D, E95I, S96A, L97V, L97R, L97G, L97I, L97C, L97Q, L97P, L97E, L97T, L97A, L97W, L97H, L97N, L97L, L97F, L97S, G98P, H99S, H99G, N100A, N100T, N100L, N100M, N100I, N100R, N100C, N100P, N100N, N100V, N100K, N100F, N100S, N100W, N100Y, N102T, N102Q, N102Y, N102H, N102V, N102A, N102F, N102C, N102I, N102G, N102S, N102K, T104R, T104H, T104V, T104S, T104L, T104G, T104A, L105T, L105R, L105A, L105F, L105M, L105E, L105P, L105Q, L105C, L105K, L105L, L105G, L105I, L105V, Q106K, Q106Y, Q106I, Q106W, T107W, T107S, T107T, T107N, T107E, T107A, T107Y, T107D, T107M, T107C, T107H, T107K, V108C, V108R, V108E, I109E, I109D, I109T, Q110Q, Q110E, Q110D, Q110G, N111D, N111F, N111N, N111M, N111P, N111Q, N111K, N111L, N111R, N111A, N111H, N111I, N111W, N111V, N111G, Y112W, Y112Y, Y112F, Y112C, V113E, V113L, A114P, A114F, A114M, A114K, A114L, S115G, S115A, S115L, S115E, S115D, S115S, S115R, K118N, K118L, K118M, K118S, K118Y, Q121P, Q121L, Q121V, Q121M, Q121T, Q121A, Q121K, Q121C, V122L, V122T, V122E, V122V, V122N, S123S, S123P, N124T, N124N, N124C, S126M, S126G, S126T, T128V, T128S, G132G, G134S, G134A, G136S, G136A, G136D, G136G, E137S, E137V, E137A, E137M, E137E, E137Q, E137T, E137D, A138N, A138W, A138F, A138C, A138E, A138Q, A138R, A138G, A138T, A138D, A138V, A138S, A138I, A138Y, K139Q, K139A, K139W, K139T, K139V, F140Y, N141Y, N141K, N141G, N141N, N141D, N141W, N141R, N141L, N141T, N141Q, V142P, T145L, F147T, T148N, T148A, E150G, E150S, E150Y, E150F, W151E, W151G, W151N, W151H, W151S, W151L, W151V, W151F, W151T, G152Y, G152I, R153I, R153Q, R153A, R153M, R153V, R153N, R153F, R153R, R153P, R153L, R153S, P154F, Q155L, Q155V, Q155K, Q155R, Q155P, Q155A, Q155M, Q155E, Q155I, Q155T, Q155F, D157A, D157S, D157T, P159C, L161D, I164Q, I164V, A165S, A165D, Y169F, Y169G, Y169E, Y169R, Y169L, Y169T, Y169I, Y169W, K171C, W172Q, W172Y, I174A, I174M, I174V, I174Y, Y178V, Y178R, S180L, S180C, S180F, S180N, S180A, S180D, T181Q, T181S, T181R, T181A, T181E, T181K, T181W, A182V, K183T, S184R, S184Q, S184V, S184I, S184G, S184M, S184F, S184A, V185F, V190A, V190V, V190L, V190I, V190T, K191E, K191L, K191A, K191W, K191I, K191M, K191Q, K191T, N192N, N192A, D193S, L194M, A195K, A195H, Y196G, T197E, T197T, T197A, T197V, A198A, A198V, Q199S, Q199G, Q199R, Y200R, Y200F, Y200H, Y200Q, W201W, W201S, W201I, W201A, N202Q, N202N, N202V, N202I, N202R, T204L, T204T, T204F, T204K, T204I, T204Q, T204E, T204H, T204N, G205E, G205Q, G205G, G205W, G205C, G205T, F206H, F206R, F206G, F206D, F206I, F206Q, F206T, F206A, F206K, F206E, F206P, F206S, D207G, D207C, D207L, D207A, L208F, L208W, L208S, L208V, L208G, L208M, L208P, L208N, L208E, W209A, E210R, E210E, E210H, E210K, E210Q, E210L, E211S, E211M, E211A, E211Y, E211N, E211T, V212I, G214V, G214S, G214M, G214N, G214I, G214E, S215Q, S215S, S215C, S215D, S215L, S216G, S216E, S216N, S216M, S216C, S216V, S216S, F217F, F218V, F218H, F218N, F218P, F218S, F218L, F218F, F218Y, T219R, T219I, T219E, T219N, I220I, I220K, I220T, I220H, I220S, I220A, A221L, A221S, A221M, S222F, S222L, S222Q, S222R, S222M, S222H, S223Y, S223M, S223V, S223N, S223T, S223I, S223C, T228F, T228S, T228Q, E229M, E229D, E229A, E229W, E229Y, E229G, E229L, E229T, E229H, E229S, E229I, E229F, A235T, Q236D, Q236S, Q236Y, Q236R, Q236L, Q236A, Q236K, Q236M, Q236Q, Q236N, T239R, R242Q, R242S, R242P, R242K, R242W, R242E, R242F, R242M, A243P, A243Q, A243G, A243L, A243R, A243A, A243N, A243D, A243C, A243V, A243K, T245S, T245T, T245M, T245L, T245V, T245H, T245G, T245Q, T245E, T246I, V247A, A248G, P249Y, Q250Q, Q250E, L252V, L252H, L252M, L252L, C253C, C253L, C253H, C253A, C253S, C253R, C253D, C253G, C253Q, C253F, F254E, Q255S, A257G, F258E, N260F, N260S, N260N, S261G, K262C, G263Y, N264E, V266A, V267Y, V267N, V267L, S268Q, S268R, S268T, N269L, N269E, N269W, N269M, N271A, N271T, N271L, N271G, N271P, N271F, N271Q, N271H, N271W, G272L, G273V, G273S, G273Y, G273P, G273C, G273H, E274F, E274V, Y275C, Y275F, Y275V, Y275E, Y275S, Y275L, R276P, S277W, S277F, S277G, S277N, S277L, G278H, G278Y, G278E, G278N, G278V, G278D, G278S, G278W, G278F, G278M, G278K, G278I, K279D, K279N, K279R, A281A, A281G, A281S, A281Y, A281T, A281F, N282I, N282T, N282P, N282E, N282N, N282H, S283E, S283T, S283F, S283Q, L285F, L285M, L285D, L285T, A286T, A286L, H289A, H289E, N290M, F291M, F291L, P293T, E294E, A295D, A295C, G296V, N299S, L300F, T301T, S306C, S306N, S306G, E307H, R308V, R308K, R308M, R308H, R308W, R308Q, R308A, R308I, R308E, R308T, R308G, A309L, A309H, A309C, A309I, L310L, A311R, A311A, A311L, A311K, A311F, N312N, N312T, N312L, N312I, A315G, Y316S, Y316L, Y316F, Y316Y, Y316W, Y316I, V317K, D318M, D318W, D318E, D318N, D318V, D318Q, D318S, D318L, S319N, S319A, S319M, S319V, S319Q, S319H, S319R, S319G, F320F, F320M, N322C, L323Y, L323D, A325E, I326V, N327D, K328C, K328T, K328F, K328R, K328E, G329L, I330W, A331M, A331V, A331P, Q332V, Q332W, Q332P, Q332L, G333P, A335C, A335G, A335S, A335T, A335D, A335E, A335M, A335W, V336D, V336T, V336G, V336R, V336N, V336Y, V336K, V336L, V336F, V336C, V336I, V336H, A337P, A337T, A337A, A337S, A337H, A337C, A337G, V338I, V338A, V338M, V338P, V338T, V338L, V338S, V338N, V338C, S342T, E343S, E343N, E343I, E343K, E343C, E343G, E343T, E343V, E343E, E343M, E343W, E343F, E343L, E343H, V345P, V345Q, V345C, V345K, V345I, V345M, V345Y, V345R, V345A, V345W, V345N, Y346F, Y346C, Y346E, Y346D, Y346Y, Y346K, Y346V, Y346A, Y346L, Y346M, Y346G, Y346T, Y347Y, Y347G, Y347A, N348L, N348A, P351A, W352Y, Y353L, Y353W, Y353F, Y353M, Y353Y, Y353I, Y353P, Y353E, Y353D, Y353T, Y353V, Y353A, Y353S, Y353N, L354E, L354T, L354M, L354I, A355G, A355S, A355A, N356V, N356S, F357H, F357E, F357L, F357M, A358M, A358W, A358N, A358Y, A358F, A358K, A358R, A359S, A359G, A359P, A359M, A359V, A359I, A359Q, A359L, A359N, A359E, A360G, A360V, A360M, A360P, A360C, A360F, A360L, A360N, A360I, E361H, E361N, E361M, E361C, E361G, E361V, E361D, E361A, E361Q, E361R, E361T, E361S, E361Y, L363M, L363A, Y364S, Y364I, Y364N, Y364W, Y364V, Y364H, Y364M, Y364L, Y364Q, Y364G, D365A, D365R, A366S, A366M, A366A, A366C, A366G, A366T, A366V, Y368M, V369I, V369Q, V369F, V369G, V369A, V369V, V369M, V369E, W370W, W370M, W370F, N371A, K372L, K372N, K372Q, Q373H, Q373K, Q373C, Q373Q, Q373V, Q373D, G374A, G374Y, G374G, G374M, G374L, G374C, G374P, G374S, S375A, S375W, I376M, I376F, I376A, I376T, I376C, I376V, I376L, T377S, T377A, S380Y, S380A, S380S, S380P, V381Q, V381V, V381C, V381A, V381F, S382D, S382S, S382V, S382H, S382T, S382E, S382N, S382G, S382C, S382L, L383N, L383S, L383C, P384S, P384E, P384V, P384T, F386M, F386W, F386F, F386V, R387Q, R387K, R387C, R387G, R387F, R387L, D388T, D388C, D388H, L389T, L389S, L389A, V390L, V390R, V390T, V390A, V390H, V390F, V390I, S391F, S391R, S391N, S391I, S391W, S391E, S392Y, S392P, S392S, V393A, V393C, V393L, V393I, V393V, V393H, V393F, V393N, S394A, S394Y, S394D, S394C, S394T, S394S, S394P, S394F, S394M, S394W, S394L, T395L, T395Q, T395A, T395N, T395S, T395I, T395F, T395K, G396M, T397G, T397R, T397A, S399Q, S399C, S399K, S399T, K400K, K400P, S401Q, S401E, S401A, S401Y, S401H, S401R, S401K, S401T, S401P, S402S, S402T, S402D, S402F, S402K, S402M, S402R, S402W, S402G, S402N, S402I, S403V, S403A, T406E, T406D, T406A, T406G, T406W, T406T, T406I, T406R, T406V, T406L, T406S, T406P, T406N, T406H, N407A, N407S, N407W, I408T, I408F, V409R, V409Y, V409G, N410D, N410A, N410T, N410I, N410K, N410F, N410V, N410N, N410L, N410C, N410P, N410W, N410H, N410M, A411C, K413T, A414W, A414D, A414R, A414T, A414E, A416S, D417E, D417Q, E421Y, V422E, V422L, V422F, A424G, A424V, A424L, A424F, A424Q, K425M, K425K, K425E, Y426I, Y426M, Y426E, Y426F, P428C, P428M, P428K, P428T, S429A, S429T, S429D, S429R, S429M, S429G, G431F, G431S, G431C, A432P, A432D, A434S, A434R, A434P, A434T, A434C, A434W, A434G, A434M, A434F, A434Y, A434D, A434K, A434E, A434A, R439G, N440A, N440M, N440Q, N440V, T441T, T441Y, T441E, K443I, K443N, K443H, K443M, K443V, P444V, P444G, P444Y, P444Q, P444W, P444E, P444S, S446C, S446A, A447A, A448R, A448W, A448Q, A448H, A448F, A448I, A448T, D449D, W452V, W452R, W452T, W452C, W452A, W452G, W452S, W452H, W452K, W452Y, W452M, Y454M, Y454N, Y454Q, Y454S, Y454T, Y454G, Y454L, Y454W, F457S, L458G, L458E, L458A, A460T, I461I, I461M, I461R, I461N, I461F, I461C, I46I, R464N, R464K, A465Y, A465R, A465K, A465I, A465W, G466S, G466A, G466M, G466K, G466G, G466Y, G466F, G466H, G466R, G466D, G466E, G466L, G466N, G466V, G466I, G466Q, G466C, L467S, L467A, L467F, L467L, L467V, L467D, L467H, L467Y, L467N, V468T, V468L, V468M, V468R, V468P, V468K, V468D, V468H, V468G, V468N, V468Q, V468W, V468I, V468A, P469R, P469N, P469S, P469G, P469C, P469H, P469W, P469I, P469Q, P469V, P469T, P470Q, P470E, P470G, P470I, P470C, P470W, P470M, P470R, P470N, P470F, P470L, P470V, P470A, P470K, S471I, S471Q, S471V, S471E, S471N, S471S, S471G, S471A, S471H, S471L, S471C, S471D, S471M, W472R, W472Y, W472H, W472G, W472M, W472S, W472T, W472N, W472L, R473M, R473C, R473T, A474A, S475L, S475S, S475W, S475R, S475G, S475N, S475Q, S475K, V476W, V476L, V476E, V476S, V476H, V476Y, V476I, V476D, V476A, V476N, V476V, V476Q, V476P, V476G, V476M, V476R, V476T, A477Q, A477E, A477S, A477K, A477R, A477I, A477D, A477V, A477T, A477M, A477Y, A477W, A477F, K478F, K478Q, K478V, S479F, S479I, S479K, Q480A, Q480H, Q480C, Q480D, Q480I, Q480M, Q480F, Q480K, Q480V, Q480W, Q480R, Q480S, Q480Q, Q480T, Q480P, L481C, L481D, P482L, P482E, P482W, P482F, P482K, P482V, S483H, S483L, S483Y, S483W, S483P, T484I, T484S, T484F, T484L, T484Q, T484P, T484Y, T484K, C485F, C485T, C485P, C485L, S486M, S486I, S486V, S486D, S486G, S486L, S486K, R487Q, I488I, I488C, I488T, I488W, I488G, I488R, I488V, E489M, E489P, E489H, E489W, E489L, E489T, E489R, E489F, E489K, E489D, A491P, A491K, A491G, A491L, A491I, A491Y, A491F, A491M, A491R, A491T, A491S, A491N, A491H, A491V, A491Q, A491E, G492C, G492H, T493C, T493V, T493S, T493E, T493R, T493F, T493M, T493Q, T493K, Y494F, Y494W, V495D, V495W, V495E, A496M, A496Y, A496P, A496L, A496I, A496C, A497C, A497S, A497W, A497T, A497F, A497H, A497R, A497Q, A497L, A497D, A497P, A497V, A497E, A497M, A497Y, T498W, T498R, T498T, S499M, T500N, T500Q, T500R, T500M, T500K, S501V, S501D, S501I, S501G, S501Q, F502A, F502I, F502S, F502N, F502K, F502E, F502P, F502R, F502Q, F502H, F502G, F502V, F502Y, F502D, P503L, P503S, P503Q, P503A, P503R, P503P, P503N, P503V, P503M, P503I, P503F, P503T, P503D, P503Y, P503G, P503E, P503W, S504T, S504S, K505W, K505H, K505P, K505Y, K505S, K505V, K505D, K505M, K505K, Q506K, Q506S, Q506N, Q506A, Q506C, Q506L, Q506D, Q506P, Q506T, Q506M, Q506W, Q506E, 506V, Q506G, Q506F, Q506Y, Q506R, T507H, T507P, T507C, T507Q, P508R, P510E, S511N, S511L, S511M, S511I, S511W, A512G, A513D, A513K, P514D, P514R, P514N, S515D, S515V, S515K, S515L, S515I, S515A, P516A, P516P, P516E, P516N, P516D, P516M, P516R, S517L, Y519E, Y519G, Y519L, Y519W, Y519C, P520V, P520Q, P520H, P520W, P520E, P520L, P520N, T521T, T521L, T521I, T521V, T521C, T521I, T521W, T521R, T521D, T521G, A522D, A522E, A522P, A522C, A522Y, A522K, A522N, A522V, A522H, C523S, C523H, C523T, C523Q, C523G, C523K, C523D, A524Y, A524F, A524V, A524S, A524N, A524D, A524T, A524W, A524Q, D525D, D525F, D525H, D525W, E528D, E528T, E528N, E528E, E528W, E528L, E528R, E528I, E528V, E528M, Y530Y, Y530C, Y530V, Y530R, Y530A, Y530D, V531C, V531E, V531V, V531S, T532T, T532K, T532W, T532M, T532D, R536H, R536C, V537M, V537L, V537R, V537K, V537T, V537G, S538C, S538F, S538G, S538K, S538Q, T539S, T539Q, T539R, T539C, T539T, T539D, T539N, A540A, A540Y, A540M, W541A, W541I, W541V, G542V, G542D, E543S, T544P, T544R, T544G, I545R, I545F, I545V, I545S, I545Q, I545N, I545W, I545P, K546Y, V547Q, V547A, V547C, V547F, V547V, V548F, V548M, V548T, G549A, G549K, G549C, G549V, G549R, N550M, N550W, N550G, N550C, V551S, V551N, V551Y, P552P, P552A, P552R, A553G, A553N, L554L, L554D, L554T, L554E, L554M, L554V, L554G, L554W, L554N, L554R, G555H, G555K, G555I, N556E, N556D, N556Y, N556L, N556V, N556P, W557M, W557F, T559Q, S560F, K561D, K561N, K561F, K561R, K561V, K561Y, K561E, K561I, K561L, K561G, K561Q, K561C, K561P, K561T, K561A, K561S, A562P, A562T, A562I, A562H, A562Q, A562V, A562C, A562L, A562G, A562K, A562Y, A562S, A562E, A562R, T564N, T564K, L565Q, L565N, L565C, L565P, L565H, L565M, L565F, L565G, L565I, L565S, L565V, L565T, L565E, L565W, L565L, S566L, S566C, S566K, S566M, S566A, S566S, S566E, S566G, S566T, S566D, S566I, S566V, S566Y, S566W, A567W, S568P, S568S, S568H, Y570N, K571D, K571A, K571C, S572K, N573G, D574M, D574N, D574I, D574S, D574L, D574Y, D574W, D574C, P575E, P575R, P575F, P575K, P575G, P575Y, P575P, P575Q, P575M, P575L, P575V, L576L, L576K, W577S, W577H, W577A, W577I, W577Q, S578A, S578W, S578C, S578E, S578F, S578N, S578L, S578I, I579K, I579R, I579I, T580Y, T580M, T580R, T580F, T580H, V581M, V581R, V581V, V581K, V581L, V581S, V581F, I583M, I583W, K584V, K584T, A585N, G587R, G587T, G587D, G587Y, G587I, G587F, G587L, G587Q, G587N, A589E, A589T, V590W, V590K, V590Y, V590R, V590S, V590I, V590C, V590P, V590L, V590A, V590G, Q591L, Q591P, Y592R, Y592H, Y592Q, Y592A, Y592S, Y592N, Y592P, K593E, K593G, K593T, K593K, K593W, K593S, K593R, K593M, K593A, Y594M, Y594W, Y594C, Y594H, Y594Y, Y594A, Y594N, Y594E, Y594Q, Y594G, I595T, I595L, I595G, I595M, I595Y, K596D, K596E, K596G, V597W, V597Q, V597E, V597R, V597K, V597V, V597F, T599K, T599S, T599L, T599M, T599Q, T599D, T599P, T599A, T599F, T599E, T599C, T599H, T599R, T599G, N600K, N600V, N600P, G601M, G601E, G601N, G601P, G601R, G601H, G601Q, G601I, K602D, K602F, K602W, I603Y, I603Q, I603N, I603P, I603T, I603I, I603M, I603E, I603F, I603L, T604S, T604F, T604L, T604T, T604G, T604H, T604, T604P, T604A, T604R, T604I, T604D, W605T, W605Y, W605K, W605P, W605H, W605E, W605L, W605D, W605A, W605, W605F, W605V, E606K, E606I, E606G, E606F, E606V, E606R, E606T, E606H, E606W, E606, E606E, S607V, S607W, S607, S607H, S607L, S607M, S607N, S607Y, S607A, D608R, D608L, D608P, D608T, P609V, P609D, P609Y, P609R, P609W, P609N, P609T, P609L, P609K, P609Q, R611S, R611E, R611D, R611A, R611Q, R611F, R611H, R611K, R611P, R611V, R611N, R611M, R611W, R611I, S612H, S612F, I613T, I613H, I613S, I613N, I613V, I613L, I613K, I613A, I613G, I613F, T614G, T614S, L615W, S619Q, S619S, S620P, S620S, S620E, G622W, G622P, G622K, G622H, G622G, A625D, A625A, A626T, Q627R, Q627A, V629Q, V629S, V629N, N630S, D631S, D631Q, D631N, D631T, D631P, S632L and S632G.

SEL Cohort 2—HgGA variants having improved PI in thermostability (Residual DP7 hydrolysis activity after 63.5° C. for 5 min./Initial DP7 hydrolysis activity) (PI≥1.2): N38D, K41P, N46E, N46D, N46C, A50D, N55D, K57A, K57E, K57S, A58C, A59G, P60V, P60Q, P60I, P60L, P60M, P60R, P60T, P60Y, P60H, A64P, G65K, G65R, G65F, V67K, V67D, I68V, A69E, A69K, A69H, A69L, A69D, A69R, A69F, S70W, S70Y, S72S, D75N, P77D, Y78W, Y78F, Y78K, Y78I, F80P, W82F, W82T, W82H, W82I, W82Q, W82R, W82M, W82G, W82V, W82P, W82L, W82C, W82N, W82E, W82A, T83V, R84W, R84H, R84P, R84S, R84T, R84C, R84V, R84L, R84F, R84D, R84E, A86Y, A86K, A86P, A86F, A86H, A87L, A87K, A87P, V89R, E95K, N100E, N102N, N102Y, N102M, N102G, N102R, N102F, N102W, N102T, N102L, L105I, T107E, T107K, N111D, V113Q, A114G, A114W, S115A, K118F, L119K, Q120W, V122D, S123P, S123D, N124E, N124R, N124H, S126L, S126C, G127P, G127I, F129L, A130E, G132D, G132Q, G132K, G132R, G132I, G132F, G132P, G132V, G132T, G132E, G132N, G134P, G134R, G134H, L135K, E137R, E137P, E137H, E137T, E137K, A138Y, A138L, A138A, K139G, F140P, A146P, T148W, E150P, W151K, W151A, W151C, W151Y, W151R, W151V, W151P, G152N, G152K, G152H, G152S, G152R, G152Q, G152M, G152Y, G152T, G152C, G152W, R153P, Q155S, Q155A, Q155Y, R156W, D157W, D157R, D157F, D157N, D157P, D157I, D157L, G158L, L161P, R162W, R162P, R162H, R162F, A163P, A163R, A165W, L166R, L166C, I167H, I167G, I167M, I167P, I167Q, I167S, A170D, A170N, A170Q, A170H, A170I, K171P, K171W, A175F, A175W, A175C, G177I, G177V, G177W, G177L, G177A, K179D, K179P, A182G, A182S, K183D, K183C, K183F, K183H, K183W, S184S, S184C, S184P, V186K, V186H, V186P, V186R, V186L, V186F, W187V, W187I, W187H, W187Y, W187Q, W187A, W187L, W187F, P188A, P188M, P188C, P188S, P188G, P188Q, P188H, P188K, V190S, V190G, V190F, V190T, V190A, V190C, V190M, D193H, A195A, G205P, F206G, D207F, D207D, D207K, D207I, D207R, D207Y, D207W, D207Q, D207V, D207H, L208R, W209K, W209V, W209C, W209P, W209G, W209S, E210F, E210D, E210L, E210K, E210C, E210M, E210S, E210Y, E210I, E210Q, E210W, E210T, P213R, P213H, P213L, P213V, P213Y, P213Q, P213C, P213M, P213N, S216R, F217N, I220N, R225P, L227A, L227C, L227S, L227T, L227G, L227I, G230E, L233D, L233E, L233S, L233T, L233A, L233Q, L233H, L233M, L233Y, L233W, L233F, A234M, A234G, A234S, Q236W, T239I, E240P, C241W, C241N, C241A, C241G, A243R, C244F, T245F, T245W, T245Y, T245M, T245H, V247C, A248C, A248D, P249E, P249R, F254F, Q255D, Q256C, A257D, S261C, K262I, K262C, N264C, S268C, G272C, G272T, E274F, E274Y, Y275G, D280M, D280T, D280P, A281R, A281L, A281K, I284R, I284V, I284E, L285P, L285L, A286T, N290K, F291G, E294C, E294A, A295L, C297P, C297S, D298P, D298W, D298F, L300K, L300N, T301I, T301V, T301A, F302A, Q303C, Q303P, Q303L, Q303S, Q303E, Q303T, P304G, P304C, P304S, S306K, S306I, S306W, S306N, S306E, S306T, S306Y, S306G, E307K, E307L, E307W, E307F, E307I, E307M, E307R, R308C, R308D, L310P, L310W, L310A, L310Q, L310F, L310S, L310C, A311I, A311S, Y316W, D318D, S319S, S319Q, Y324W, Q332N, V338R, V338W, G339F, G339K, G339P, G339I, G339Q, G339H, G339Y, G339V, G339D, G339N, G339R, G339L, G339E, G339W, G339T, G339C, R340F, R340W, S342P, D344H, D344F, D344M, V345T, N348G, N350I, N350P, N350V, N350W, P351K, P351H, P351R, P351D, P351Q, W352G, W352K, W352V, W352R, L354R, L354Y, L354D, A355C, N356R, N356K, L363Q, I367A, I367G, I367D, V369P, W370V, W370S, W370C, W370T, W370A, W370Q, W370H, N371P, N371L, N371C, N371M, Q373P, G374P, S375P, I376S, I376G, I376Y, I376N, I376H, I376T, I376C, T377V, V378Y, V378F, T379P, T379I, T379W, S382E, S382P, S382Q, F385Q, R387P, V393W, V393H, G396F, Y398R, Y398D, Y398G, Y398S, Y398N, Y398P, Y398Q, Y398K, K400N, S401D, T404A, F405R, F405D, F405K, F405E, F405L, F405T, F405I, F405P, F405Q, F405N, F405S, I408S, I408H, I408K, I408Y, I408G, I408Q, V409W, V409G, V409P, V409M, V409D, V409Y, V409I, V409K, V409R, V409L, V409E, V409H, V409C, V409V, A411P, A411A, A411H, G418F, G418G, F419R, P428I, P428G, G431R, G431L, A432S, A432A, A434Y, A447R, A448P, A448M, T451P, T451W, T451K, T451S, T451Y, T451F, T451L, T451R, W452D, W452A, W452G, W452P, S453R, S453K, S453L, S453I, S453M, S453W, S453Y, I461S, I461G, I461Q, R463M, R464Y, R464F, R464W, R464H, R464L, R464N, R464I, A465D, A465P, G466Q, G466P, G466W, G466V, G466R, G466C, G466I, G466T, G466L, G466K, G466D, G466F, G466H, G466A, G466E, G466Y, L467C, V468N, V468W, V468L, V468H, V468E, V468Q, V468D, V468M, V468K, V468R, V468P, V468I, V468G, P469M, P469E, P469G, P469N, P470V, P470Y, P470S, P470W, P470M, P470C, P470A, P470F, P470K, W472W, R473D, A474C, A474S, V476I, A522G, A522A, A522Q, A522T, A522K, A524M, A524L, A524A, A524R, E528K, S538Y, S538R, S538P, W541R, W541K, W541L, W541M, G542K, G542R, T544R, T544K, G555K, G555R, T564R, T564K, S572F, S572P, A589A, A589Q, A589V, Q591T, Q591Y, V597K, T599R, E606M, S619K, S619E, A626H, V629C and S632T.

SEL Cohort 3—HgGA variants having improved PI in a DP7 hydrolysis assay at pH 5.5 (PI≥1.2): P42M, N51F, P54K, A59Q, A59P, A59V, A59W, P60W, L90D, L90Y, G98F, N111I, N111V, N111K, S115K, S115E, S115N, S123A, P125A, L135T, L135V, F140W, L144H, L144N, Q168H, K191V, K191W, Y196T, Y196W, W201K, L208P, S216A, F218M, F218S, F218Q, T219A, T219M, T219V, T219Q, T219C, A221P, S222F, L227S, L227L, L227Y, L227A, L227G, L227T, E229A, E229K, G230W, G230I, G230L, G230Y, A231K, L233W, L233H, L233Q, L233Y, A234K, L237Q, E240K, E240I, E240L, C244K, C244D, C244P, C244T, C244S, T246F, T246T, T246V, V247G, L252P, F254P, D280P, D280Q, D280H, D280T, D280A, A281V, A281T, S287M, S287V, S287E, S287C, S287Y, H289H, F291G, D292F, D292H, D292L, E294H, A295N, C297Q, C297N, C297G, C297T, C297S, L300Y, Q303L, Q303P, Q303R, Q305S, I326R, I326A, N327P, N327F, N327L, N327V, N327Q, N327K, K328C, Q332C, G339A, E343I, E343G, G349N, A359L, A359V, A359Y, A359I, A359N, A360S, L363P, A366Q, P384L, F385G, F385S, F385T, F386Q, G396A, G396V, T397K, Y398V, Y398D, Y398G, Y398H, Y398P, I408K, D417R, A423W, D449K, D449V, D449R, D449I, D449Q, D462T, V468L, V468A, V468H, V468R, P470N, P470F, P470I, P470V, P470C, P470E, W472K, W472N, W472E, W472R, W472G, V476L, V476D, V476H, V476A, V476Q, V476G, V476R, V476P, V476W, V476Y, V476S, A491I, A491H, A491G, Y494V, Y494P, Y519A, A526Q, V529A, S538F, S538T, A540W, A540N, L576A, P609W, N610S, S619A, S619M, S619Q, S620Y, S620R, G622K, A626T and A626R.

SEL Cohort 4—HgGA variants having improved PI in a DP7 hydrolysis assay at pH 6.8 (PI≥1.2): P54W, A59Q, A59P, A59V, A59W, P60W, G98F, N111I, S115H, S123A, P125A, L135T, L144H, L144V, Q168H, K191V, K191W, Y196T, L208P, L227S, L227A, E229A, E229V, G230W, G230I, G230L, A231K, L233H, L233W, L233Y, A234K, E240K, C241F, C244P, C244D, C244K, C244T, P249T, Q256K, D280P, D280Q, D280H, D280T, D280M, D280A, D280Y, A281V, S287M, S287C, S287E, S287V, H289H, D292F, D292A, D292S, E294H, A295N, C297Q, C297N, C297S, C297G, C297T, C297P, L300Y, Q303L, Q303P, Q303R, E307P, D318G, I326R, I326A, I326K, N327P, N327F, N327V, N327L, G329C, G329T, Q332C, A359L, A359V, A359I, A359N, A360S, L363P, A366Q, P384L, F385G, F385S, F386Q, G396A, G396V, T397K, Y398D, Y398H, Y398G, Y398P, S399C, I408K, D449K, D449V, D449R, V468L, V468H, V468A, V468R, P470N, P470I, P470C, P470V, P470F, P470E, A474A, V476H, V476Q, V476A, V476D, V476G, A491I, A491H, Y494V, Y494P, Y519A, A526Q, A526R, A526P, V529A, S538F, A540W, A540N, L576A, P609W, S619A, S619M, S619Q, A626T and A626R.

SEL Cohort 5—HgGA variants having improved PI in a DP2 hydrolysis assay (PI≥1.2 in either $K_m$ assay or $V_{max}$ assay): G53A, G53S, A59Q, A59V, A59P, A59W, P60W, P60G, P60I, P60F, G61P, A62E, A62L, A63P, A63I, A63L, A64V, A64L, A64I, A64T, A64C, P71S, D75E, D75L, D75A, P77D, F79W, T81S, G92T, L97L, G98F, H99K, H99R, N100P, N100I, N100A, N100C, N100G, N100L, N100S, Y101A, N111L, N111I, N111R, N111K, N111A, N111M, S115I, S115P, S115R, S123A, P125A, L135T, L135Q, N141Q, N141N, L144V, L144F, G152D, Q168H, K191V, K191W, N192L, N192C, N192H, N192R, N192A, L194L, L194M, Y196T, T197G, T197A, Q199K, Q199H, L208P, F218W, F218G, S222M, S222V, S222N, S222H, S222Q, L227I, L227A, L227S, E229A, E229C, E229G, E229D, G230W, G230I, G230L, E240L, E240K, C244K, C244P, C244D, C244T, V247A, P249A, P249T, D280P, D280Y, H289H, F291G, D292F, D292A, D292S, D292C, D292H, P293Q, E294H, A295N, C297Q, C297N, C297S, C297G, C297T, C297P, L300Y, Q303P, Q303L, Q303R, D318G, I326R, I326A, I326Y, I326N, I326S, I326G, N327V, N327P, N327F, N327L, K328C, Q332C, E343E, Y353N, Y353W, Y353Y, Y353M, Y353V, Y353I, Y353D, Y353F, Y353T, Y353E, Y353K, N356V, A359L, A359V, A359N, A359I, A359M, A360S, L363P, A366Q, A366V, A366T, I376E, I376I, I376M, P384L, F385G, G396A, G396V, T397K, Y398G, Y398H, A434D, A434M, A434W, D438V, D438Q, A448K, D449K, D449R, D449G, T451A, T451S, F457Q, V468L, V468H, V468A, V468K, V468M, V468R, V468N, V468G, V468D, V468T, V468Q, V468P, P469G, P470I, P470N, P470C, P470F, P470R, P470V, P470L, P470E, P470W, P470A, P470K, P470G, P470Q, V476A, V476L, V476H, V476Q, V476G, V476W, V476D, V476S, V476Y, V476R, V476P, V476V, V476I, V476M, A491H, A491I, A491G, A491N, A491T, A491R, A491M, A491K, A491V, A491P, A491E, A491Y, Y494P, Y494Q, Y494V, Y494T, Y519A, A526Q, A526P, A526K, A526W, A526V, V529A, S538F, S538T, A540W, A540N, K561L, L565W, S572S, S572C, S572I, L576A, P609W, S619A, S619Q, S619H, S620R, S620H, S620D, G622K, A625D, A625N, A626R and T628L.

SEL Cohort 6—HgGA variants having improved PI in a pullulan hydrolysis assay (PI≥1.2): P54W, P54K, A59Q, A59P, A59V, A59W, P60W, G65S, V66Q, L90D, L90Y, G98F, N111I, S115K, S115P, S115H, S115E, S115R, S115N, Q116L, A117D, Q120T, Q120V, S123A, S123F, S123C, P125A, S133P, L135T, L135N, L135V, L135Q, L144H, L144V, L144N, E150N, Q168H, W187H, V189F, K191V, K191W, N192R, Y196T, L208P, L227G, L227S, L227A, L227N, E229A, E229V, E229M, E229C, G230W, G230I, G230L, G230Y, L233W, L233H, L233S, L233Q, L233Y, A234K, A234R, L237Q, L237T, E240K, E240L, C241F, C244K, C244D, C244P, C244T, C244S, T246W, V247G, P249T, P249A, L252P, F254P, Q256K, Y265T, D280P, D280Q, D280H, D280A, D280T, D280Y, D280M, D280W, L285N, S287M, S287C, S287E, S287V, S287R, H289H, F291G, D292F, D292H, D292S, D292C, D292L, E294H, A295N, C297Q, C297N, C297G, C297S, C297P, C297T, L300Y, Q303P, Q303L, Q303R, P304V, P304S, C305S, E307A, E307D, D318G, I326R, I326G, I326K, I326A, I326N, I326S, I326H, N327P, N327F, N327R, N327L, N327V, N327W, N327Q, K328C, G329T, G329C, G329A, G329M, G329I, G329S, I330Y, I330N, Q332C, E343F, G349W, G349P, G349I, G349Y, G349S, G349M, G349L, G349T, G349V, G349F, G349N, G349C, G349A, Y353K, A355H, A358P, A359L, A359V, A359I, A359N, A359Y, A360S, E361E, L363S, A366Q, A366V, P384L, F385G, F385S, F385T, F386Q, D388Q, G396A, G396V, T397K, Y398G, Y398P, Y398D, Y398H, Y398S, T404Y, I408K, I408, A423W, A434G, D449K, D449V, D449R, D449I, D449L, I461G, V468H, V468A, V468L, V468K, V468M, V468G, V468R, V468T, P470F, P470V, P470I, P470N, P470C, P470R, V476L, V476A, V476H, V476Q, V476D, V476G, V476W, V476S, V476P, V476M, V476R, V476V, V476Y, A491H, A491I, A491T, A491M, A491K, Y494V, Y494P, Y494G, Y494T, Y494Q, K505F, Y519A, P520S, V529A, S538F, A540W, A540N, A553A, S572S, L576A, D608A, P609W, S619A, S619M, S619G, S619Q, S619S and S619H.

SEL Cohort 7—HgGA variants having improved PI in a panose hydrolysis assay (PI≥1.2): L49A, L49S, L49W, L49F, L49R, A50R, I52K, I52G, I52S, I152T, A58K, A59Q, P60W, V66A, V66G, V67M, I68M, P71I, P71V, S72T, S72I, S72V, S72E, S72H, S72G, S72F, T81G, A86T, G92T, L97V, L97I, L97L, G98F, H99K, N100P, N100I, N100G, N100A, N100S, N100L, N100V, N100C, N100T, N100K, N111A, S115P, S115R, S115A, S115V, S115I, S115K, S115S, Q120V, S123A, N124V, P125A, L135T, L135N, L135Q, L135F, A138T, K139M, N141V, N141R, V142R, V142L, L144V, K191V, K191W, Y196T, W201K, F206I, L208P, L208Q, V212T, V212S, P213M, P213Y, P213V, P213A, P213Q, G214Y, F218W, F218G, F218Q, S222H, S222M, L227G, L227S, L227I, L227A, G230I, G230L, G230W, A234K, E240L, E240K, C244K, C244P, C244D, C244T, C244V, T246V, V247G, P249T, R276K, D280P, D280W, D280Q, S287M, S287E, S287V, S287C, N290V, F291G, D292F, D292A, D292S, E294H, A295N, C297Q, C297N, C297S, C297G, C297T, C297P, L300Y, Q303P, Q303L, Q303R, D318G, I326R, I326A, I326N, N327P, N327F, N327V, N327L, N327R, K328C, G329T, Q332C, Y341N, Y341H, E343I, E343F, E343G, E343L, E343C, E343K, E343V, E343Y, E343R, E343M, A359L, A359V, A359I, A359N, A360S, L363P, A366Q, P384L, F385G, F385S, G396A, G396V, T397K, Y398G, Y398D, Y398H, Y398P, Y398S, A423W, A434G, D449K, D449R, D449V, D449A, D449G, D449T, T451A, T451S, V468H, V468L, V468A, V468R, V468K, V468M, V468G, V468T, V468N, V468D, V468Q, P470N, P470I, P470F, P470V, P470C, P470R, P470E, P470L, P470A, P470K, P470W, P470Q, P470G, P470S, P470Y, P470M, V476A, V476L, V476H, V476Q, V476I, V476Y, V476G, V476W, V476D, V476S, V476R, V476V, A491H, A491P, A491N, A491I, A491T, A491G, A491R, A491M, A491K, A491Y, A491V, A491E, A491L, A491Q, Y494Q, Y494V, Y494P, A526Q, A526P, V529A, S538F, S538T, A540W, A540N, L576A, P609W, S619A, T628L and S632R.

SEL Cohort 8—HgGA variants having improved PI in a corn starch hydrolysis assay (PI≥1.2): N46P, N46F, N51P, G53K, G53E, G53W, G53V, G53Y, G53R, P54F, P54W, P54Y, P54R, P54P, N55R, N55N, N55K, A59Q, A59V, A59P, A59W, A59R, A59K, A59I, A59N, A59H, A59T, P60W, A62Y, A62Q, A62R, A62K, A64Y, A64L, A64P, G65S, V66Q, V66F, V67F, V67T, V67P, I68G, I68Y, D75L, Y78Y, F79R, F79S, A86T, G98F, Y101R, Y101L, N111E, S115W, Q116K, Q116L, Q116R, A117D, A117P, L119W, L119N, L119K, L119Y, Q120N, Q120V, Q120T, Q120G, Q120H, Q120F, Q120S, Q120I, Q120C, Q121D, N124Q, P125A, S126L, G127K, D131P, S133P, L135T, L135N, L135V, L135Q, L135G, L135K, A138P, D143F, L144H, L144R, P159E, P159V, L166K, L166W, A170H, W187H, W187V, W187Q, W187I, W187A, V189Y, V189F, V189R, K191V, K191W, N192R, N192K, D193N, A195V, Y196T, Y196W, T197H, A198Y, Q199W, Q199P, Q199H, L208P, A221D, S222F, H224K, H224Q, R225G, R225W, R225I, R225S, R225D, R225V, L227G, L227N, L227S, L227H, L227T, L227A, L227L, L227Y, E229C, E229V, E229F, E229A, G230W, G230I, G230L, G230Y, G230F, G230E, A231R, A231P, L233H, L233W, L233S, L233Q, L233E, L233Y, L233M, A234K, A234R, A234I, L237T, L237Q, L237W, L237S, L237V, E240K, E240L, C241V, C241W, C241S, C241G, C241N, C241A, C241F, C244K, C244D, C244P, C244Q, C244T, C244G, C244S, T245F, T246G, T246V, T246F, V247G, P249C, P249Y, V251D, L252P, C253P, C253D, C253I, C253Q, F254P, Q256K, N260W, N260V, S261R, N264R, Y265T, S277N, D280P, D280Q, D280Y, S283F, L285Y, L285G, L285N, L285W, S287R, S287E, S287C, H289H, F291G, F291P, D292L, D292F, E294H, A295N, G296E, C297Q, C297N, C297G, C297P, C297S, C297T, C297A, D298R, D298W, D298K, N299P, N299R, L300Y, Q303P, Q303L, Q303R, Q303K, P304V, Q305S, Q305H, Q305P, L310Q, H313R, D318H, I326G, I326H, I326W, I326Y, I326R, I326N, I326P, N327P, N327H, N327W, N327R, N327F, N327L, N327K, N327V, N327D, G329T, G329C, Q332C, A337F, A337W, G339S, G339A, S342Y, S342P, E343I, G349W, G349S, G349N, G349P, G349T, G349C, Y353R, Y353K, A355H, A358P, A358T, A359Y, A359L, A360S, E361E, L363P, A366Q, W370T, W370S, W370C, W370H, W370Q, Q373P, I376G, S382R, S382Y, P384L, F385G, F385S, F386Q, D388Q, D388E, D388R, L389E, L389P, L389L, T397D, T397N, T397K, Y398G, S399C, K400Q, S401V, S402V, S402W, T404Y, F405D, F405P, N407P, I408Q, I408K, V409P, A416F, A416R, A416P, A416Y, A416K, A423H, A423W, G431V, L433H, A434L, D438P, R439V, K443P, D449V, D449K, D449I, D449Q, T451Q, Y454R, F457T, D462T, D462M, D462H, R463D, R463E, R463F, V468A, V468E, P470N, P470I, P470L, P470V, P470R, P470K, P470S, P470G, P470W, P470Y, P470F, P470Q, P470C, S471D, V476L, S483F, S486E, A491I, A491H, A491V, A491Q, A491F, A491P, A491K, Y494V, Y494G, Y494P, Y494T, Y494Q, Y494C, Y494A, V495V, F502M, S504Q, K505F, K505C, Y519A, D525Y, A526Q, A526P, E528F, V529A, V529M, V531T, R536Q, S538F, A540W, A540N, V547D, S572Q, N573A, I579K, Q591S, V597D, S607E, D608A, P609W, I613A, L615S, S619A, S619M, S619D, S620S, A626G, A626T, A626W and Q627R.

SEL Cohort 9—HgGA variants having improved PI for glucose inhibition of enzyme activity [higher ratio of (inhibition sample)/(no inhibition sample) as compared to WT] (PI≥1.2): E40C, P42M, N51T, N51V, G53R, A58I, G65E, G65F, G65I, G65K, G65P, G65Q, G65R, G65S, G65V, V67K, I68D, A69G, A69P, A69T, T74P, D75P, P76A, P76E, P76G, P76H, P76K, P76L, P76M, P76S, P76T, P76V, F80A, F80D, F80G, F80L, F80P, F80Q, F80R, F80S, F80T, T83E, T83G, T83H, T83I, T83L, T83M, T83P, T83Q, T83V, A86C, A86E, A86M, A86N, A86Q, A86W, A87C, L88G, L88M, V89D, V89I, T91P, I93Y, I94K, Y112A, Y112C, Y112E, Y112G, Y112I, Y112L, Y112M, Y112P, Y112V, V113N, Q116Y, L119F, L119K, L119R, N124A, N124G, N124L, N124Q, N124V, P125F, P125K, P125L, P125N, P125Q, P125R, P125T, P125V, P125Y, S126D, S126F, S126G, S126H, S126K, S126P, S126T, S126W, G127A, G127C, G127D, G127F, G127I, G127K, G127L, G127M, G127N, G127P, G127Q, G127R, G127S, G127V, G127W, F129D, F129H, G132H, G132M, G132P, G134E, G134H, G134I, G134L, G134M, G134P, G134R, G134V, G134W, L135A, L135T, L135V, G136D, G136H, G136N, G136Q, G136S, G136T, G136V, E137F, E137H, A138C, A138E, A138F, A138G, A138I, A138L, A138Q, A138S, A138Y, K139A, K139C, K139E, K139P, K139Q, K139S, K139T, K139V, K139W, F140C, F140D, F140E, F140G, F140L, F140N, F140P, F140Q, F140W, F147A, F147G, F147L, F147N, F147P, F147Q, F147R, F147S, F147T, F147V, E150W, W151A, W151C, W151D, W151F, W151G, W151H, W151I, W151L, W151N, W151R, W151V, G152H, G152I, G152R, G152S, G152T, G152V, R153A, R153C, R153D, R153G, R153I, R153L, R153N, R153P, R153S, R153T, R153V, P154R, P154S, P154V, R156A, R156F, R156G, R156H, R156I, R156K, R156L, R156N, R156P, R156Q, R156S, R156T, R156V, R156Y, G158A, G158C, G158N, G158S, G158T, P160I, P160L, P160Q, P160V, P160Y, L161A, L161C, L161F, L161I, L161M, L161Q, L161S, L161T, L161V, L161W, L161Y, I164P, A165Y, L166A, L166D, L166E, L166G, L166I, L166S, L166T, L166V, Y169M, V186A, V186D, V186H, V186L, V186P, V186S, V186T, V186Y, D193A, D193H, D193T, L194V, Y196G, Y196W, T197H, T197L, T197M, Q199P, Y200A, Y200C, Y200E, Y200H, Y200I, Y200N, Y200Q, Y200T, Y200V, W201K, E203G, T204F, T204G, T204Y, G205E, G205F, G205I, G205K, G205L, G205, G205S, G205V, G205Y, F206A, F206C, F206D, F206E, F206L, F206M, F206Q, F206R, F206S, F206T, F206W, D207A, D207C, D207E, D207F, D207G, D207H, D207I, D207K, D207M, D207P, D207R, D207S, D207V, L208G, L208T, W209L, W209R, W209V, W209Y, E211C, E211F, E211G, E211H, E211I, E211L, E211M, E211W, E211Y, V212E, V212I, V212M, V212R, G214C, G214D, G214E, G214F, G214I, G214K, G214L, G214N, G214P, G214R, G214S, G214T, G214V, G214W, G214Y, S215C, S215E, S215I, S215K, S215L, S215Q, S215T, S215V, S215W, S215Y, S216C, S216E, S216G, S216L, S216M, S216N, S216Q, S216R, S216T, S216V, S216W, F217V, F218D, F218H, F218I, F218K, F218L, F218M, F218N, F218P, F218T, F218V, F218Y, T219C, T219D, T219E, T219G, T219I, T219L, T219M, T219N, T219P, T219V, T219W, T219Y, I220K, I220P, I220W, A221P, S223D, S223L, S223M, S223N, S223R, S223V, S223W, S223Y, A226Y, L227R, L227W, Y232R, E240N, C244F, C244H, C244R, V247K, V247W, P249C, P249G, P249Q, P249R, V251F, V251M, V251S, F258A, F258C, F258E, F258K, F258L, F258P, S268D, S268E, S268F, S268H, S268M, S268P, S268Q, S268R, S268Y, N269A, N269C, N269E, N269F, N269G, N269I, N269K, N269L, N269M, N269P, N269Q, N269S, N269T, N269V, N269W, N269Y, N271I, N271L, N271T, G272F, G272I, G272L, G272M, G272P, G272Q, G272R, G272V, G273A, G273C, G273D, G273E, G273I, G273L, G273M, G273N, G273P, G273V, G273Y, R276C, R276D, R276E, R276F, R276L, R276M, R276N, R276P, R276Q, R276S, R276T, R276V, R276W, R276Y, G278D, G278E, G278F, G278H, G278I, G278L, G278P, G278T, G278Y, A281F, A281I, A281V, A281W, A281Y, N282A, N282E, N282G, N282H, N282I, N282L, N282M, N282P, N282Q, N282S, N282V, S283R, I284R, I284W, L285A, L285D, L285F, L285R, A286C, A286D, A286H, A286L, A286N, A286Q, A286W, I288G, I288Y, H289F, H289W, S306W, N312R, N312W, F320K, F320P, Y324D, Y324E, Y324K, Y324P, Y324Q, Y324R, Y324W, N327R, K328Y, A337K, G339C, G339D, G339E, G339F, G339H, G339I, G339K, G339L, G339N, G339P, G339Q, G339R, G339V, G339W, R340A, R340C, R340D, R340F, R340G, R340H, R340I, R340K, R340L, R340P, R340T, R340V, R340W, Y341A, Y341G, Y341L, E343P, E343W, D344K, D344V, Y346P, Y347A, Y347G, Y347I, Y347N, Y347A, Y347R, Y347S, Y347T, Y347V, G349C, G349D, G349F, G349I, G349L, G349M, G349N, G349P, G349R, G349S, G349W, G349Y, N350K, N350L, N350V, P351L, W352M, L354E, L354P, L354S, L354W, A355W, F357R, A358E, A358F, A358I, A358K, A358L, A358M, A358W, A359F, A359F, A359W, A359W, A359Y, A359Y, A360R, A360R, E361F, E361F, R387F, Y398V, S401D, S401L, A414V, D417R, P428H, G431I, G431M, A434I, A434V, D449I, D449R, D449V, T451E, T451M, T451Q, Y454A, Y454E, L458P, A465D, A465E, K478L, A496C, A497T, T500N, Y519H, Y519Q, Y519V, S527H, F533K, P575C, Q591V, Y592K, T599H, E606I, T614E, T614F, S619R, S619W, A625K, V629N, N630F, N630G, N630Q, D631N, W633C, and W633F.

SEL Cohort 10—HgGA variants having improved PI for glucose reversion to DP2+ products (less reversion, higher PI) (PI≥1.2): A32Y, N51W, N51R, N51P, I52P, I52R, G53R, G53K, G53P, G53Q, G53W, G53V, G53I, G53D, G53L, G53T, G53Y, G53E, P54Y, P54W, A58I, A58P, A59G, A59P, A59W, A59R, A59K, A59H, A59Q, P60W, P60Y, P60D, G61R, A62H, A62K, A62R, A62N, A62Q, A62F, A62E, A62Y, A62P, G65R, G65L, G65F, G65K, G65T, G65I, G65M, G65V, G65D, G65Y, G65P, G65E, G65C, G65Q, G65W, G65A, V66R, V66H, V66K, V66Y, V66W, V66N, V66D, V66Q, V67H, V67K, V67D, V67G, V67Y, V67E, V67S, I68R, I68K, I68P, I68G, I68W, I68Y, I68A, I68F, I68Q, I68D, I68C, A69E, A69R, A69H, A69K, A69L, A69D, A69F, A69I, A69V, A69T, A69C, A69S, A69G, S70R, S70Y, S70Q, S70K, S70M, S70L, S70I, S70V, S70T, S70W, S70E, S70D, P71R, P71A, P71S, P71L, P71T, S72P, S72L, S72D, T74P, D75P, P76G, P76K, P76M, P76S, P76L, P76A, P76E, P76V, P76T, P76H, P77L, P77V, P77F, Y78A, Y78S, Y78N, Y78T, Y78W, Y78Q, Y78C, Y78K, Y78V, Y78F, Y78I, Y78L, Y78M, F79I, F79G, F79A, F79Q, F79P, F79T, F79C, F80P, F80H, F80I, F80V, F80R, F80L, F80T, F80W, F80S, F80D, T81R, T81W, T81P, T81G, W82E, W82V, W82M, W82Q, W82G, W82L, W82N, W82T, W82F, W82I, W82A, W82H, W82C, W82R, W82Y, T83W, T83R, T83Y, T83H, T83P, T83G, T83Q, R84W, R84Q, R84P, R84E, R84H, R84S, R84C, R84T, R84V, R84M, R84L, R84F, A86P, A86Y, A86K, A86L, A86V, A86I, A86M, A86W, A86D, A86Q, A87F, A87Y, A87L, A87E, L88P, L88C, L88H, L88G, V89R, V89K, V89I, V89D, L90R, I93P, I94K, E95G, L97G, N102Q, N102T, N102H, N102Y, N102F, N102A, N102V, N102I, N102G, N102C, N102S, N102K, N102N, N102R, N102E, N102M, N102W, N102L, Y112R, Y112P, Y112M, Y112C, S115W, S115F, Q116P, Q116F, Q116W, Q116R, Q116Y, Q116K, L119P, L119R, L119K, L119W, Q120K, Q120W, Q120L, Q120P, Q120R, Q120N, Q120G, Q120H, Q120T, Q120C, Q120V, Q120S, V122D, N124K, N124W, N124H, N124R, N124Y, N24I, N124F, N124L, N124M, N124Q, P125L, P125Y, P125S, P125C, P125H, P125T, S126L, S126P, S126K, S126R, S126H, S126I, S126W, S126E, S126F, S126V, S126D, G127P, G127I, G127R, G127K, G127V, G127N, G127Q, G127W, G127A, G127F, G127L, G127M, G127S, G127C, G127D, F129H, F129R, F129N, F129G, F129T, D131P, G132P, G132E, G132V, G132N, G132T, G132K, G132D, G132R, G132I, G132C, G132W, G132M, G132H, G132S, G132L, S133P, G134R, G134H, G134W, G134M, G134I, G134L, L135R, L135H, L135K, L135W, L135P, L135A, L135N, L135T, L135V, L135S, L135G, L135Q, G136L, G136F, G136I, G136R, G136W, G136K, G136V, G136M, G136T, G136P, G136H, G136Q, G136N, G136D, G136S, E137F, E137R, E137P, E137L, E137H, E137A, E137T, E137W, E137C, E137G, E137I, E137V, E137Q, E137S, E137M, E137K, A138R, A138W, A138D, A138Y, A138K, A138L, A138F, A138H, A138N, A138E, A138C, A138Q, A138I, A138G, K139G, K139P, K139E, F140P, F140E, F140G, F140Q, F140N, F140H, F140D, F140V, F140L, F140C, F140S, F140F, N141P, V142H, V142S, V142Q, V142W, D143P, L144P, L144H, L144W, T145P, A146W, A146Y, F147R, F147P, F147G, F147L, F147K, F147A, F147M, F147H, F147T, F147V, F147Q, F147C, F147I, F147N, G149I, G149V, G149T, G149Y, G149P, G149R, G149L, G149F, E150G, W151K, W151C, W151E, W151A, W151R, W151L, W151T, W151V, W151D, W151P, W151I, W151H, W151F, W151S, W151Y, W151N, W151G, G152H, G152K, G152N, G152D, G152R, R153K, R153H, R153W, R153T, R153C, R153V, R153I, R153S, R153F, R153Y, R153Q, R153N, R153L, R153M, R153G, R153P, R153A, R153D, P154N, P154L, P154Q, P154F, P154R, P154W, P154Y, P154M, P154H, P154K, P154I, P154E, P154T, P154V, P154S, P154C, P154D, Q155K, Q155R, Q155W, Q155P, Q155V, Q155F, Q155Y, Q155G, Q155I, Q155T, Q155L, Q155S, Q155M, Q155D, Q155A, Q155E, R156W, R156F, R156P, R156Y, D157A, D157T, D157S, D157Q, D157Y, D157H, D157L, D157I, D157V, D157N, D157F, D157P, D157M, D157R, D157W, G158H, G158F, G158K, G158R, G158Y, G158L, G158I, G158Q, G158P, G158T, G158V, G158N, G158C, G158A, P159W, P159K, P159R, P159I, P159L, P159M, P159Q, P159V, P159E, P160R, P160K, P160I, P160L, P160Q, P160E, P160Y, L161Y, L161W, R162P, R162H, R162F, R162W, R162K, R162D, R162T, R162I, R162G, A163P, A163R, A163K, A163H, I164K, A165W, A165C, A165Y, A165T, A165K, A165R, L166R, L166K, G177P, S180L, A182D, A182N, A182P, V185L, V186W, V186R, V186V, V186K, V186T, V186I, V186Y, V186M, V186F, V186L, V186A, V186H, V186S, V186E, V186C, V186G, V186N, V189Y, V189F, V189R, N192W, N192Y, N192F, N192R, D193V, D193I, D193M, D193W, D193Y, D193L, D193H, D193R, D193T, D193N, D193Q, D193E, L194T, L194V, Y196K, Y196I, Y196P, Y196M, Y196T, Y196H, T197R, T197Y, T197W, T197K, T197H, T197F, Q199W, Q199P, Q199I, N202W, E203P, G205W, G205P, G205K, G205R, G205L, G205F, G205V, G205E, G205Y, F206G, F206P, F206A, F206S, F206Q, F206R, F206K, F206C, D207K, D207L, D207W, D207F, D207Y, D207R, D207D, D207I, D207Q, D207A, D207V, D207H, D207M, D207S, D207P, D207G, D207C, L208W, L208R, L208F, L208K, L208N, L208G, L208T, L208S, W209P, W209Q, W209D, W209V, W209K, W209L, W209E, W209R, W209N, W209A, W209S, W209G, W209F, E210H, E210L, E210Q, E210K, E210R, E210T, E210Y, E210W, E210F, E210D, E210S, E210C, E210M, E210I, E211R, E211W, E211K, E211F, E211L, E211C, E211Y, E211V, E211G, E211A, E211I, E211N, E211S, E211T, E211M, V212P, V212G, G214P, S215E, S215C, S216R, S216K, S216D, S216M, S216W, S216L, F218E, T219R, T219I, T219W, T219Y, T219L, I220R, A221R, S223R, S223W, S223Y, A226W, A231L, Y232R, L233I, E240N, E240T, C241I, P249E, P249F, P249R, P249S, P249G, W259P, S261R, V266N, S268E, S268M, N269K, N269P, N269H, R276M, R276L, S277S, A281K, A281R, A281I, A281W, A281Y, N282F, N282Y, N282R, N282I, N282T, N282L, N282V, S283R, S283H, S283K, S283W, S283I, I284R, I284S, I284T, L285P, L285L, L285R, L285K, L285A, L285G, L285F, H289I, H289L, H289V, H289F, H289P, H289N, H289D, H289Q, H289E, D292R, E294H, L300M, L300H, L300K, L300D, L300T, L300V, L300G, L300N, L300W, L300E, L300S, L300R, L300F, L300A, L300Y, L300I, L300P, L300Q, L300L, L300C, N312R, N312K, Y316R, F320P, F320K, Y324K, Y324Q, Y324H, Y324E, Y324D, Y324T, Y324V, Y324L, Y324I, I326H, I326W, N327H, N327R, N327P, N327F, G329H, G329T, K334H, K334V, K334G, K334S, K334D, K334C, K334E, K334I, K334R, K334L, K334F, K334M, K334Y, K334P, K334A, K334T, K334K, K334W, A335Y, A337W, A337I, A337K, A337L, A337F, A337Y, V338K, V338W, V338R, V338F, G339V, G339W, G339Q, G339I, G339F, G339L, G339K, G339D, G339R, G339E, G339P, G339T, G339H, G339C, G339N, G339M, G339S, R340G, R340P, R340A, R340F, R340W, R340Y, R340H, R340V, R340I, R340C, R340T, R340D, R340L, R340K, Y341V, Y341H, Y341R, Y341G, Y341E, Y341K, Y341F, Y341L, Y341C, Y341T, Y341D, Y341M, Y341W, Y341Q, Y341S, Y341N, Y341A, Y341Y, S342C, S342K, S342Y, S342M, S342G, S342S, S342V, S342Q, S342D, S342W, S342E, S342N, S342P, S342T, S342L, S342F, S342R, D344M, D344W, D344I, D344T, D344V, D344L, D344K, D344H, D344Y, D344P, D344R, D344Q, D344E, D344F, D344G, D344N, D344C, D344S, V345P, Y346K, Y346P, Y346R, Y346G, Y346A, Y346T, Y346E, Y346V, Y346C, Y346S, Y346L, Y346H, Y346D, Y346I, Y346M, Y346F, Y347P, Y347N, Y347L, Y347R, Y347T, Y347H, Y347D, Y347S, Y347I, Y347G, Y347V, Y347Q, Y347C, Y347M, N348P, G349Q, G349I, G349Y, G349P, G349W, G349V, G349L, G349R, G349F, G349M, G349T, G349S, G349C, G349D, G349N, G349A, N350Y, N350W, N350P, N350V, N350I, N350T, N350F, N350K, N350L, N350A, N350C, N350S, N350H, N350M, N350D, N350E, N350G, P351W, P351R, P351H, P351K, P351D, P351L, P351N, P351Q, P351V, P351F, P351Y, P351M, P351T, P351E, W352R, W352H, W352K, W352E, W352S, W352N, W352G, W352I, W352Q, W352T, W352D, W352C, W352A, W352L, W352M, W352Y, Y353K, Y353R, L354R, L354W, L354Y, L354D, L354H, L354P, L354Q, L354E, L354S, L354T, L354N, L354V, A355R, A355K, A355W, A355P, N356W, N356R, N356K, N356F, N356L, F357R, A358P, A358R, A358A, A358T, A358W, A358S, A359R, A359W, A359F, A359Y, E361D, F386M, S391A, S401L, G418F, F419P, F419R, E421P, A423H, A423W, P428H, G431R, G431I, L433P, L433H, L433R, L433G, A434I, A434V, A434L, D438P, D438W, D438I, D438V, R439I, R439V, R439W, R439D, N440P, T441P, K443P, S446I, S446Q, S446K, S446E, S446V, S446P, S446R, S446W, S446C, S446F, S446T, S446D, S446A, S446Y, S446N, S446G, A447R, A447N, A447D, A447W, A447M, A447P, A447H, D449W, D449R, D449K, D449V, T451R, T451W, T451Y, T451F, T451P, T451K, T451L, T451M, T451V, T451I, T451D, T451C, W452R, W452H, W452K, W452T, W452S, W452D, W452G, W452P, W452A, W452Q, W452E, W452C, W452V, W452Y, W452M, S453K, S453Y, S453W, S453I, S453L, S453R, S453P, S453H, S453V, S453E, S453D, Y454A, Y454K, R463D, A465D, W472W, W472T, R473S, T484T, A491G, Y494I, Y494S, Y494A, Y494V, Y494Q, Y494T, Y494G, V495P, T500N, A513G, Y519Q, V529R, V529W, V531S, V531A, V531T, S538F, L554L, L554F, Y570G, S572F, P575C, I579G, T586P, S620W, A625K, A626H, A626F, A626E, N630G, N630Q, S632N and S632V.

It is noted that there are numerous HgGA variants that fall into more than one of SEL Cohorts 1 to 10 above. Thus, aspects of the present invention are drawn to HgGA variants that belong to any 2, 3, 4, 5, 6 or more of the SEL Cohorts above. For example, HgGA variant P470F belongs to SEL Cohorts 1 through 8 above.

In addition to the HgGA variants in SEL Cohorts 1 to 10 above (or combinations thereof), HgGA substitution variants were identified that had a PI for all assays that was less than 1.2 and greater than or equal to 0.90. These HgGA variants belong to SEL Cohort 11.

SEL Cohort 11:—HgGA variants in which the PI for all assays is <1.2 and ≥0.9: A32E, V33P, T35R, T35L, T35W, T35Y, F36F, N38F, T39Q, T39E, T39L, K41C, P42P, P42Q, P42C, W45W, K47R, N51N, G56G, T74K, F79F, R84R, E95E, G98Y, H99M, H99A, T103Q, T104E, T104D, L105Y, T107G, T107V, T107I, I109I, I109A, Q110C, P125P, D143D, F147F, T148M, T148L, Q155Q, P160P, I164I, I164A, L166M, K171R, K171G, I174I, I174F, G177D, G177S, G177G, Y178Y, K179L, K179R, K179Q, K179H, K179W, T181T, S184L, V185Q, W187W, V189V, K191R, L194I, A198C, A198S, L208L, H224H, R225R, A226A, A226S, A231A, Y232F, L233V, Q236F, L237I, L237L, D238R, D238Q, D238L, T239M, T239T, T239A, T239V, T239C, E240Q, E240W, R242R, A243H, C244C, T245C, T245R, T245I, A248S, P249P, P249D, Q250Y, Q250M, L252A, L252N, L252I, Q255E, Q255L, Q256Q, Q256F, A257A, A257F, N260C, S261Y, S261W, S261T, S261K, S261F, K262W, K262R, K262K, K262P, K262V, K262D, K262M, K262H, G263A, G263E, G263H, G263R, G263Q, G263T, N264N, N264P, N264F, N264V, N264A, Y265W, V267K, V267R, S268S, N271N, E274D, E274Q, R276R, S277T, I284I, I288I, N290Q, N290E, N290I, F291Y, F291F, D292D, P293R, P293H, P293F, P293Y, P293G, P293L, P293S, P293E, E294W, E294V, E294N, E294G, E294M, A295V, A295F, G296P, G296L, C297C, D298N, D298I, D298D, D298A, D298E, N299Q, T301L, F302W, Q303Q, E307E, A311V, A311C, A311M, H313Y, H313H, V317V, N322H, N322G, A325L, A325P, A325Q, A325C, A325F, K328W, I330I, D344D, Y364E, D365E, D365Q, I367S, I367L, I367K, I367Y, Y368H, Y368E, Y368W, Y368T, K372S, Q373R, Q373E, Q373L, Q373F, Q373N, Q373G, Q373A, G374E, G374K, G374D, G374F, G374T, G374R, G374V, G374W, V378L, T379H, T379R, T379N, T379T, S380W, V381S, V381K, L383L, P384Y, P384D, F385L, F386L, F386H, F386T, R387R, D388D, D388A, V390K, S394G, S394H, S394I, T395R, T395V, T395Y, G396R, G396E, G396Q, G396L, T397Q, T397W, T397V, T397F, T397Y, T397L, Y398F, Y398L, K400Y, K400V, K400W, S402P, S403W, S403I, S403P, T404Q, T404T, F405Y, F405W, F405F, F405H, N407G, N407I, N407K, N407Q, N407C, N407L, N407R, I408V, I408A, N410Q, N410Y, A411L, A411G, A411S, A411R, A411Q, A411I, A411N, A411W, K413E, K413P, A414I, A414A, A414Q, A414P, A414F, A414C, A414S, A416G, A416A, A416C, D417T, D417N, E421Q, E421C, K425R, G431G, L433L, D438D, R439R, N440N, K443L, T451T, F457F, D462A, R463K, R463R, R464R, L467Q, L467W, L467T, L467G, S471P, S475I, S475F, K478S, K478P, K478E, K478T, K478R, K478Y, S479G, S479N, S479M, S479Q, S479T, S479Y, S479R, Q480L, L481H, L481F, L481R, S483K, S483R, S483T, S483I, S483A, S483N, C485C, S486T, S486Y, R487R, T493T, Y494Y, V495I, S499C, S499H, S499A, K505G, K505N, K505T, K505E, T507T, N509N, S511H, A513A, S515M, S515S, S515T, S515N, Y519Y, T521S, A522R, A522L, T532Y, E535E, R536R, R536L, R536Y, V537V, V537C, V537A, S538A, A540T, A540E, A540V, A540L, W541Y, G542M, E543E, E543C, E543I, T544N, T544A, T544I, T544T, T544L, K546K, V548V, N550N, N550T, V551Q, V551K, V551F, V551L, P552G, P552K, P552N, P552I, P552M, P552Y, A553K, A553Q, A553Y, N556N, N556M, N556W, D558Q, D558R, D558F, D558L, S560K, S560M, S560A, T564L, T564S, T564T, T564M, K571T, S572L, N573E, N573Y, N573H, N573F, N573I, I579M, I583I, K584K, K584F, A585S, A585F, A585D, A585W, A585A, T586R, G587C, G587P, S588L, S588H, A589L, A589C, A589R, A589K, A589D, Q591C, Q591Q, Q591R, K596K, V597M, V597L, T599V, T599Y, N600R, N600E, N600Q, N600M, N600A, N600W, G601G, G601F, K602I, K602R, D608F, D608I, D608E, P609A, P609P, P609G, T614L, T614T, T614Y, T614Q, L615L, S619L, S620Q, S620M, Q627E, T628T, V629M, V629I, N630C, N630R, D631D, S632D, S632E and S632C.

In certain embodiments of the subject invention, one or a combination of substitutions in SEL Cohort 11 find use in generating combinatorial HgGA variants with one or more of the substitutions identified in any of the SEL Cohorts 1 to 10 above.

In addition to the analysis above, productive amino acid positions in HgGA were identified based on the results of the functional assays. Productive positions are described as those positions within a molecule that are most useful for making combinatorial variants exhibiting an improved characteristic, where the position itself allows for at least one combinable mutation. Highly combinable mutations are mutations at any amino acid position that can be used to make combinatorial variants. Highly combinable mutations improve at least one desired property of the molecule, while not significantly decreasing expression, activity, or stability. Highly combinable mutations can be grouped as follows:

Group A: A mutation that produces a variant wherein the minimum performance indices (PI) relative to a defined parent polypeptide for: (1) expression, (2) hydrolytic activity on DP2 substrate, (3) hydrolytic activity on DP7 substrate at pH 5.5, (4) hydrolytic activity on granular corn starch (CS), and (5) thermostability, are greater than or equal to 0.9, and, in addition, has a PI for any one of these tests that is greater than or equal to 1.0.

Group B: A mutation that produces a variant wherein the minimum performance indices (PI) relative to a defined parent polypeptide for: (1) expression, (2) hydrolytic activity on DP2 substrate, (3) hydrolytic activity on DP7 substrate at pH 5.5, (4) hydrolytic activity on granular corn starch (CS), and (5) thermostability, are greater than or equal to 0.8, and, in addition, has a PI for any one of these tests that is greater than or equal to 1.2.

Group C: A mutation that produces a variant wherein the minimum performance indices (PI) relative to a defined parent polypeptide for: (1) expression, (2) hydrolytic activity on DP2 substrate, (3) hydrolytic activity on DP7 substrate at pH 5.5, (4) hydrolytic activity on granular corn starch (CS), and (5) thermostability, are greater than or equal to 0.5, and, in addition, has a PI for any one of these tests that is greater than or equal to 1.5.

The properties of highly combinable mutations are summarized in the following Table.

TABLE 6

PI Properties for each Group of highly combinable mutations

| | Performance Index (PI) | | | |
|---|---|---|---|---|
| | Expression (1 above) | Activity (2, 3, and 4 above) | Thermostability (5 above) | Minimum PI in one or more tests |
| Group A | ≥0.9 | ≥0.9 | ≥0.9 | X ≥ 1.0 |
| Group B | ≥0.8 | ≥0.8 | ≥0.8 | X ≥ 1.2 |
| Group C | ≥0.5 | ≥0.5 | ≥0.5 | X ≥ 1.5 |

Preferred combinable mutations are at "productive positions," as described below. In the case of the present GA enzymes, "activity" refers to glucoamylase activity, which can be measured as described herein.

Productive positions are amino acid positions that are tolerant to substitution with different amino acid residues, wherein the resulting variants meet a set of performance criteria for combinability, as set forth above. Productive positions can be assigned a Productivity Score as follows:

- Positions where less than 15% of the substitutions at a given position fall within groups A, B, or C are given a Productivity Score of "1".
- Positions where less than 40%, but greater than, or equal to 15% of the substitutions at a given position fall within groups A, B, or C are given a Productivity Score of "2".
- Positions where less than 75%, but greater than, or equal to 40% of the substitutions at a given position fall within groups A, B, or C are given a Productivity Score of "3".
- Positions where 75% or more of the substitutions at a given position fall within groups A, B, or C are given a Productivity Score of "4".

Mutations at preferred productive positions are highly combinable.

Suitability score refers to the ability of one or more highly combinable mutations to be used to make combinatorial variants, based on the performance criteria for combinability, (i.e., A, B, and C, as set forth, above) in which each of the mutations fall. A higher suitability score indicates a mutation or mutations that are more suitable for use in making combinatorial variants.

Suitability scores are described in Table 7 below.

TABLE 7

Definitions of suitability scores

| Substitutions meet the criteria for Group(s) | Suitability Score |
|---|---|
| A, B and C | +++++ |
| A and B | ++++ |
| A or (B and C) | +++ |
| B | ++ |
| C | + |

Table 8 shows the Productivity Score (4, 3, 2, or 1) calculated for each position in the HgGA polypeptide. For each HgGA position, variants are listed according to the suitability score they received (+, ++, +++, ++++, or +++++). Position numbering is based on the full length HgGA polypeptide listed in SEQ ID NO: 3 (putative signal sequence is from amino acid 1 to 30, as noted above).

TABLE 8

Productivity and Suitability Scores for HgGA variant polypeptides

| POS (SEQ ID NO: 3) | Productivity score | + | ++ | +++ (WT AA listed first) | ++++ | +++++ |
|---|---|---|---|---|---|---|
| 35 | 4 | A | P | TCFKLQRWY | H | |
| 41 | 4 | | | KCSTW | DHLNPR | E |
| 60 | 4 | V | GHMR | PIW | FT | Q |
| 97 | 4 | AGQ | | LETV | F | CHIN |
| 100 | 4 | P | EV | NCIMQT | FGKSWY | ALR |
| 107 | 4 | AWY | H | TGISV | K | CDEMN |
| 175 | 4 | | F | AEHKMNQRST V | C | |
| 183 | 4 | | H | KEIQRVY | DFTW | |
| 229 | 4 | ADGMTW | I | ELY | CFKV | |
| 245 | 4 | | L | TCIR | HMQSVY | FW |
| 263 | 4 | | | GACEHLQRST | Y | |
| 293 | 4 | | T | PACEFGHLRSY | Q | |
| 294 | 4 | | | EDGIKLMNSVW | AC | |
| 299 | 4 | | | NACEGLQTV | PRS | |
| 300 | 4 | | | LIKN | | ACDEFGHPQRSTVW Y |
| 308 | 4 | | I | RFL | ADEGHKMQTW | V |
| 334 | 4 | CGILTW | | KDV | | AEFRY |
| 342 | 4 | GLTWY | | SCEFNQ | | KMPRV |
| 364 | 4 | | | YERW | GQ | HILMNSV |
| 367 | 4 | | G | IEFKLMSVWY | | |
| 369 | 4 | | FQ | VCIKLNSTY | AEGM | |
| 373 | 4 | | D | QEFGLNRST | CHKV | |
| 374 | 4 | | | GDEFKRTVW | CLMPS | AY |
| 382 | 4 | DH | CPQ | SEGNTV | | |
| 393 | 4 | | AW | VEGTY | FHILN | |
| 394 | 4 | | F | SGHIN | ACDLMPY | |
| 397 | 4 | | AG | TFLQVWY | KR | |
| 400 | 4 | | | KAEGLRSVWY | P | |
| 402 | 4 | D | IN | SPTW | R | FKM |
| 406 | 4 | | | TC | ADGHILNPRSV W | E |
| 407 | 4 | | | NCGIKLQR | APSW | |
| 409 | 4 | | CGHK | V | DELMRWY | |
| 410 | 4 | | I | NGQY | CFHKLPTVW | AD |
| 411 | 4 | | P | AGILNQRSW | C | |

TABLE 8-continued

Productivity and Suitability Scores for HgGA variant polypeptides

| POS (SEQ ID NO: 3) | Productivity score | + | ++ | +++ (WT AA listed first) | ++++ | +++++ |
|---|---|---|---|---|---|---|
| 414 | 4 | | | ACFGIPQS | DERTW | |
| 461 | 4 | | CFGKMS | ITVY | NQR | |
| 466 | 4 | DKMRY | CPTW | GAEFHLNS | IV | Q |
| 467 | 4 | | C | LGQTW | DHNY | AFSV |
| 468 | 4 | | | V | AE | DGHIKLMNPQRTW |
| 469 | 4 | R | CHTV | PGNS | EIQW | |
| 470 | 4 | | | P | KS | ACEFGILMNQRVW |
| 471 | 4 | D | CM | SEGPQ | L | AHINV |
| 476 | 4 | ADEGHNS | | VLMPQY | RT | IW |
| 477 | 4 | DEIKQR | MW | AS | | V |
| 478 | 4 | | | KEIPRSTY | FQV | |
| 479 | 4 | | | SAGLMNQRTY | FIK | |
| 480 | 4 | ACD | TV | QHILM | | F |
| 483 | 4 | | FPWY | SAIKNRT | | HL |
| 484 | 4 | | | TIMV | KPQY | FLS |
| 503 | 4 | ADFGLMNQRST VY | | P | | |
| 505 | 4 | | D | KEGNT | MSV | HP |
| 506 | 4 | AFLNPS | | QEMTVY | | C |
| 522 | 4 | EP | NTVY | ALR | K | CD |
| 544 | 4 | | P | TAILMNSY | GKV | R |
| 556 | 4 | | P | NAGHIMSTW | DELVY | |
| 587 | 4 | | DFINQTY | GCP | L | R |
| 589 | 4 | | | ACDKLMR | EQTV | |
| 599 | 4 | M | CER | TDKLVY | AFP | QS |
| 600 | 4 | | | NAEMQRWY | PV | K |
| 604 | 4 | | | TKMSY | ADHIQR | FGL |
| 607 | 4 | W | LY | SGIQV | AHMN | |
| 609 | 4 | | KLNQRTV Y | PAGW | | |
| 31 | 3 | | I | ATY | FLQ | |
| 37 | 3 | | GM | IAS | CT | |
| 46 | 3 | | DEP | NV | C | S |
| 57 | 3 | | ES | KACIV | T | QR |
| 85 | 3 | NY | LS | DCGM | | EV |
| 105 | 3 | MRT | I | LFY | | |
| 171 | 3 | | C | KGHRV | W | |

TABLE 8-continued

Productivity and Suitability Scores for HgGA variant polypeptides

| POS (SEQ ID NO: 3) | Productivity score | + | ++ | +++ (WT AA listed first) | ++++ | +++++ |
|---|---|---|---|---|---|---|
| 179 | 3 | | DP | KHLQRW | | |
| 184 | 3 | | AIM | SL | CFV | R |
| 213 | 3 | | AMN | P | HQ | R |
| 221 | 3 | | MRS | AILT | | |
| 239 | 3 | | | TACFMV | IR | |
| 250 | 3 | | | QDFHMY | E | |
| 252 | 3 | | H | LAINS | MV | |
| 260 | 3 | | | NCHRT | FSW | |
| 261 | 3 | | | SEFKTWY | | |
| 262 | 3 | | | KHMPRVW | C | |
| 264 | 3 | | | NAFPQV | E | |
| 274 | 3 | | V | EDILQ | F | |
| 295 | 3 | | | AFGVWY | DN | |
| 325 | 3 | | E | ACFLPQ | | |
| 328 | 3 | | C | KLQW | EFR | |
| 366 | 3 | Q | | ACM | V | GST |
| 368 | 3 | | | YEHKTW | M | |
| 371 | 3 | | CLM | NDQRY | A | |
| 372 | 3 | | | KCDFS | LNQ | |
| 376 | 3 | CTV | Y | IAFLM | | |
| 380 | 3 | | A | SFKLQRWY | | |
| 381 | 3 | | F | VGKMNS | ACQ | |
| 384 | 3 | | | PDFSY | ETV | |
| 387 | 3 | | C | RIQY | GL | K |
| 390 | 3 | | HI | VKY | FLR | |
| 391 | 3 | | N | SHL | FIR | |
| 395 | 3 | | KQ | TRVY | FL | |
| 396 | 3 | | | GELQR | KV | |
| 399 | 3 | Q | T | SRW | K | C |
| 401 | 3 | H | T | SAY | P | Q |
| 403 | 3 | | | SIPWY | AV | |
| 405 | 3 | | | FAHWY | NS | |
| 408 | 3 | Q | | IATV | SY | |
| 448 | 3 | | FPT | AN | IQ | |
| 462 | 3 | | H | DAEFILS | MT | |
| 472 | 3 | R | DIMQSY | W | | |
| 475 | 3 | | KNQ | SEFI | R | L |

TABLE 8-continued

| Productivity and Suitability Scores for HgGA variant polypeptides | | | | | | |
|---|---|---|---|---|---|---|
| POS (SEQ ID NO: 3) | Productivity score | + | ++ | +++ (WT AA listed first) | ++++ | +++++ |
| 486 | 3 | | V | STY | DGKL | IM |
| 491 | 3 | HILMY | | AKR | | V |
| 511 | 3 | | IW | SHK | LN | |
| 515 | 3 | | D | SMNT | AIKV | |
| 524 | 3 | | FLNQRTW | A | S | Y |
| 537 | 3 | | MT | VAC | KR | |
| 538 | 3 | | G | SA | CKQRT | F |
| 540 | 3 | | Y | AEFLTVW | M | |
| 541 | 3 | | AILRV | WY | | |
| 542 | 3 | | D | GAMN | KR | |
| 551 | 3 | S | N | VFKLQ | Y | |
| 552 | 3 | | A | PGIKMNY | R | |
| 561 | 3 | DEG | | KILNPQR | | |
| 562 | 3 | IKLY | | ACGV | | S |
| 564 | 3 | | N | TLMS | KR | |
| 565 | 3 | EHMQSTV | | L | | |
| 573 | 3 | | G | NEFHIY | A | |
| 585 | 3 | | | ADFSTWYN | | |
| 590 | 3 | W | AGPS | V | IL | |
| 591 | 3 | | LY | QCR | PST | |
| 597 | 3 | | R | VLMQSW | FK | |
| 601 | 3 | E | IR | GA | HNPQ | M |
| 603 | 3 | | QTY | IAK | FLNP | |
| 608 | 3 | | LPRT | DEFI | | |
| 613 | 3 | | AFLST | I | V | |
| 614 | 3 | | | TLMQVY | S | |
| 620 | 3 | | D | SMQ | EHPR | |
| 632 | 3 | | L | SCDE | GT | |
| 32 | 2 | | ST | AE | Q | |
| 33 | 2 | | | VLP | I | |
| 38 | 2 | | G | NF | HK | I |
| 39 | 2 | | | TEKLQ | | |
| 74 | 2 | | D | TIKV | | |
| 99 | 2 | | G | HAMVY | | |
| 104 | 2 | | V | TDE | | |
| 111 | 2 | FM | | NDQ | H | |

TABLE 8-continued

| Productivity and Suitability Scores for HgGA variant polypeptides | | | | | | |
|---|---|---|---|---|---|---|
| POS (SEQ ID NO: 3) | Productivity score | + | ++ | +++ (WT AA listed first) | ++++ | +++++ |
| 118 | 2 | M | | KL | FY | |
| 121 | 2 | | V | Q | LT | |
| 164 | 2 | K | V | IA | | |
| 168 | 2 | | H | QALY | | |
| 174 | 2 | | V | IF | Y | |
| 177 | 2 | | | GDHKS | | |
| 180 | 2 | | AC | S | F | |
| 181 | 2 | | ASW | T | | |
| 190 | 2 | A | IM | V | | L |
| 191 | 2 | VW | | KR | | |
| 198 | 2 | | Y | ACGS | | |
| 227 | 2 | AC | I | L | | |
| 233 | 2 | T | | LV | M | |
| 236 | 2 | | W | QF | DNY | |
| 238 | 2 | | | DLQR | | |
| 240 | 2 | | | EQW | P | |
| 243 | 2 | | G | AH | R | P |
| 248 | 2 | G | C | AS | | |
| 251 | 2 | | | VLQR | | |
| 255 | 2 | | | QEGL | S | |
| 275 | 2 | | EGLS | Y | | |
| 290 | 2 | | | NEIQ | V | |
| 291 | 2 | | | FY | L | M |
| 292 | 2 | F | CS | D | | |
| 296 | 2 | | | GLPQ | V | |
| 298 | 2 | | | DAEIN | | |
| 301 | 2 | | AI | TCL | | |
| 302 | 2 | | | FGMW | | |
| 311 | 2 | R | | ACGMV | | |
| 315 | 2 | | G | ACEMQ | | |
| 319 | 2 | N | | S | MQ | |
| 329 | 2 | T | | GCD | | |
| 331 | 2 | | V | AKLR | M | |
| 332 | 2 | | VW | QE | LP | |
| 345 | 2 | | I | VQ | K | |
| 360 | 2 | | | AC | | GS |
| 365 | 2 | | A | DEQ | R | |

TABLE 8-continued

Productivity and Suitability Scores for HgGA variant polypeptides

| POS (SEQ ID NO: 3) | Productivity score | + | ++ | +++ (WT AA listed first) | ++++ | +++++ |
|---|---|---|---|---|---|---|
| 370 | 2 | ST | V | W | FM | |
| 379 | 2 | | | TEHNQR | | |
| 386 | 2 | | | FHLT | VW | |
| 389 | 2 | | A | LQ | ST | |
| 392 | 2 | | Y | SI | P | |
| 398 | 2 | | NQ | YFL | H | |
| 413 | 2 | | T | KEFLR | | |
| 416 | 2 | | | ACG | | S |
| 417 | 2 | | | DNT | EQ | |
| 429 | 2 | | DGMT | S | A | |
| 434 | 2 | FSWY | | A | | |
| 443 | 2 | I | M | KL | H | |
| 460 | 2 | | | ACGM | T | |
| 463 | 2 | | | RAK | M | |
| 464 | 2 | | F | RV | HK | |
| 465 | 2 | | IW | AM | | RY |
| 473 | 2 | T | | RCM | | |
| 481 | 2 | | | LFHR | C | |
| 493 | 2 | CSV | Q | T | | |
| 499 | 2 | | | SACHN | M | |
| 501 | 2 | | V | SA | IQ | |
| 531 | 2 | ST | | VAC | | |
| 536 | 2 | | CQ | RLY | H | |
| 548 | 2 | | FM | V | T | |
| 550 | 2 | | CGM | NST | | |
| 553 | 2 | | | AEKPQY | | |
| 554 | 2 | M | V | LT | | |
| 555 | 2 | | K | GA | H | |
| 558 | 2 | | | DFLQR | | |
| 559 | 2 | | | TEGIL | | |
| 560 | 2 | | F | SAKMV | | |
| 572 | 2 | | P | SELV | | K |
| 574 | 2 | IMN | Y | D | | |
| 578 | 2 | | F | SA | C | |
| 584 | 2 | | | KF | TV | |
| 588 | 2 | | | SHLPY | | |

TABLE 8-continued

| Productivity and Suitability Scores for HgGA variant polypeptides | | | | | | |
|---|---|---|---|---|---|---|
| POS (SEQ ID NO: 3) | Productivity score | + | ++ | +++ (WT AA listed first) | ++++ | +++++ |
| 595 | 2 | G | M | IT | | L |
| 596 | 2 | | DE | KN | | |
| 602 | 2 | | D | KIR | F | |
| 605 | 2 | TY | F | W | | |
| 606 | 2 | GK | Q | E | | |
| 611 | 2 | S | N | R | H | |
| 612 | 2 | | | SCEW | FH | |
| 619 | 2 | | | SL | EQ | |
| 629 | 2 | | CS | VIM | Q | |
| 34 | 1 | M | | D | | |
| 42 | 1 | | | PCQ | | |
| 43 | 1 | | | IV | | |
| 47 | 1 | | | KR | | |
| 50 | 1 | | | A | DN | |
| 55 | 1 | | D | N | | |
| 58 | 1 | C | | A | | |
| 62 | 1 | H | | A | | |
| 64 | 1 | | P | A | | |
| 68 | 1 | | V | I | | |
| 72 | 1 | CQ | | S | | |
| 73 | 1 | | M | R | | |
| 75 | 1 | HR | | D | | |
| 77 | 1 | | D | P | | |
| 83 | 1 | V | | T | | |
| 90 | 1 | | I | L | P | |
| 96 | 1 | | A | SY | | |
| 98 | 1 | | | GY | | F |
| 101 | 1 | | | YF | | |
| 103 | 1 | | | TQV | | |
| 109 | 1 | | T | IA | | |
| 110 | 1 | | E | QC | | |
| 113 | 1 | | E | V | L | |
| 115 | 1 | | | SA | | |
| 122 | 1 | L | | V | | |
| 123 | 1 | | | S | AP | |
| 126 | 1 | | | SA | | |
| 128 | 1 | | V | T | | |

TABLE 8-continued

| Productivity and Suitability Scores for HgGA variant polypeptides | | | | | | |
|---|---|---|---|---|---|---|
| POS (SEQ ID NO: 3) | Productivity score | + | ++ | +++ (WT AA listed first) | ++++ | +++++ |
| 129 | 1 | | L | F | | |
| 146 | 1 | | P | A | | |
| 148 | 1 | | | TLM | | |
| 150 | 1 | P | | ER | | |
| 165 | 1 | | | AS | | |
| 166 | 1 | | | LM | C | |
| 169 | 1 | | | Y | EF | |
| 170 | 1 | | | AC | I | |
| 182 | 1 | | V | A | | |
| 185 | 1 | | | VNQ | | |
| 188 | 1 | | K | P | | |
| 194 | 1 | | | LI | | |
| 197 | 1 | | | T | AG | |
| 206 | 1 | | | FY | | |
| 218 | 1 | | | FW | | |
| 222 | 1 | | MQ | S | | |
| 224 | 1 | | | HA | | |
| 226 | 1 | | | AS | | |
| 232 | 1 | | | YF | | |
| 237 | 1 | | | LI | | |
| 249 | 1 | | | PD | | |
| 256 | 1 | | | QF | | |
| 257 | 1 | | G | AF | | |
| 258 | 1 | | | FN | | |
| 259 | 1 | | | WY | | |
| 265 | 1 | | | YW | | |
| 267 | 1 | | | VKR | | |
| 268 | 1 | | | SC | | |
| 272 | 1 | | | GC | | |
| 273 | 1 | | H | G | | |
| 277 | 1 | | | ST | | |
| 280 | 1 | | V | D | | |
| 281 | 1 | L | | A | | |
| 284 | 1 | | LV | I | | |
| 286 | 1 | | L | A | T | |
| 287 | 1 | | C | SQ | | |

TABLE 8-continued

| Productivity and Suitability Scores for HgGA variant polypeptides | | | | | | |
|---|---|---|---|---|---|---|
| POS (SEQ ID NO: 3) | Productivity score | + | ++ | +++ (WT AA listed first) | ++++ | +++++ |
| 303 | 1 | | E | Q | | |
| 306 | 1 | | C | S | | |
| 307 | 1 | | | E | DP | |
| 313 | 1 | | | HY | | |
| 316 | 1 | | W | Y | | |
| 318 | 1 | M | | D | | |
| 322 | 1 | | | NH | C | |
| 336 | 1 | | | V | CI | |
| 337 | 1 | S | | A | | |
| 348 | 1 | | | N | | G |
| 355 | 1 | S | C | A | | |
| 356 | 1 | | S | N | | |
| 359 | 1 | | | AGS | | |
| 363 | 1 | | A | LV | | |
| 375 | 1 | | A | SL | | |
| 377 | 1 | | | TS | A | |
| 378 | 1 | | | VLT | | |
| 383 | 1 | | C | LN | | |
| 385 | 1 | | | FL | | |
| 388 | 1 | | | DA | | C |
| 404 | 1 | | | TQ | | |
| 421 | 1 | | | ECQ | | |
| 422 | 1 | | F | V | | |
| 424 | 1 | | CQ | A | | |
| 425 | 1 | | | KMR | | |
| 426 | 1 | | | Y | F | |
| 432 | 1 | | D | A | S | |
| 440 | 1 | | | ND | | |
| 446 | 1 | G | | S | | |
| 451 | 1 | S | | T | | |
| 457 | 1 | | | FA | | |
| 487 | 1 | | | RS | | |
| 488 | 1 | | V | I | | |
| 495 | 1 | | | VI | | |
| 496 | 1 | | P | A | | |
| 497 | 1 | QS | | A | | |
| 502 | 1 | I | | F | | |

TABLE 8-continued

| Productivity and Suitability Scores for HgGA variant polypeptides | | | | | | |
|---|---|---|---|---|---|---|
| POS (SEQ ID NO: 3) | Productivity score | + | ++ | +++ (WT AA listed first) | ++++ | +++++ |
| 504 | 1 | | | S | T | |
| 513 | 1 | | D | A | | G |
| 516 | 1 | | E | PA | | |
| 520 | 1 | V | | P | | |
| 521 | 1 | | W | TS | | |
| 527 | 1 | | | SF | | |
| 529 | 1 | W | | V | | |
| 532 | 1 | | W | TY | | |
| 534 | 1 | | | NDE | | |
| 535 | 1 | | | EQ | | |
| 539 | 1 | | S | T | | |
| 543 | 1 | | | ECI | | |
| 545 | 1 | | V | I | | |
| 547 | 1 | | AC | V | | |
| 549 | 1 | | A | G | | |
| 571 | 1 | | | KRT | | |
| 576 | 1 | | | L | K | |
| 579 | 1 | | | IM | | |
| 583 | 1 | | | IM | | |
| 586 | 1 | | | TLR | | |
| 592 | 1 | H | | Y | | |
| 594 | 1 | M | H | Y | | |
| 622 | 1 | PW | | G | | |
| 627 | 1 | | | QE | A | |
| 628 | 1 | | L | T | | |
| 630 | 1 | | | NC | | |
| 631 | 1 | QS | | D | | |

As noted above, any combination of variants in Table 8 finds use in aspects of the present invention.

In addition to the HgGA variants having a single substitution, performance index (PI) values were determined for 41 specific combinatorial HgGA variants using the following assays (described in Example 1): (a) expression, (b) hydrolytic activity on DP2 substrate, (c) hydrolytic activity on DP7 substrate at pH 6.8, (d) hydrolytic activity on DP7 substrate at pH 5.5, (e) hydrolytic activity on panose substrate, (f) hydrolytic activity on pullulan substrate, (g) hydrolytic activity on granular corn starch (CS), (h) thermostability, (i) glucose inhibition, and (j) reversion activity.

Below is a listing of the combinatorial HgGA variants that have an improved property over wild type HgGA in at least one of the assays. The combinatorial HgGA variants fall into the following Combinatorial SEL Cohorts (the assay and PI cut-off is listed for each combinatorial Cohort).

Combinatorial SEL Cohort 1—Combinatorial HgGA variants having improved PI in expression (PI≥1.1): G92T-I164N-Y346W, G92T-E535W, P54D-K328Q, T35S-G92T-T239A-A448V-I461A-K571T, I43F-T239N-N271Q-E535T-K546S, P60Q-F206V, T35S-G92T-T239A, I43D-G92F-Y346W, G92F-E203A-S375D-P552I, A448V-I461A-E543H-A567R-K596I, P60Q-F79V-F206V, K139R-F147N-F206D, T74R-A448V-E535A-E543H-K571R, I43F-T239N-A448V-I461A-K546S-K596I, D75R-K571R, F79V-F147M-N534S-E535W, A448V-I146A-E543H-K571R-K596I, A448V-I461A-K571R-K596I, I43F-P54D-G92F-

K328Q-S375D, I43F-P54D-T239N-K328Q-K546S, G92F-S375D, W577K-W605K, D75R-G92I-E203F-K571R, G92F-L144F-D462Q-A567R, D75R-G92I-K571R, P60Q-F79V-E203F-F206V, T35S-I43F-P54D-G92F-K328Q-Y346W, K139R-F147N-F206D-P213W-K571F, V422P-D449A-S568R-G569W, D75E-F79D-D449A-S568R, I43F-T239N-N271Q-A448V-I461A-E535T-E543H-K546S-K571R-K596I, and F79T-G92F-S96L-L144F-I164N.

Combinatorial SEL Cohort 2—Combinatorial HgGA variants having improved PI in thermostability (Residual DP7 hydrolysis activity after 63.5° C. for 5 min./Initial DP7 hydrolysis activity) (PI≥1.1): F79T-G92F-S96L-L144F-I164N, A448V-I461A-E543H-A567R-K596I, A448V-I146A-K571R-K596I, A448V-I461A-E543H-K571R-K596I, and T35S-G092T-T239A-A448V-I461A-K571T.

Combinatorial SEL Cohort 3—Combinatorial HgGA variants having improved PI in a DP7 hydrolysis assay at pH 5.5 (PI≥1.1): I43D-G92F-Y346W, T35S-I43F-P54D-G92F-K328Q-Y346W, G92T-I164N-Y346W, A448V-I461A-E543H-K571R-K596I, A448V-I461A-E543H-A567R-K596I, P60Q-F79V-E203F-F206V, T74R-A448V-E535A-E543H-K571R, and A448V-I461A-K571R-K596I.

Combinatorial SEL Cohort 4—HgGA variants having improved PI in a DP7 hydrolysis assay at pH 6.8 (PI≥1.1): I43D-G92F-Y346W, T35S-I43F-P54D-G92F-K328Q-Y346W, and A448V-I461A-E543H-K571R-K596I.

Combinatorial SEL Cohort 5—HgGA variants having improved PI in a DP2 hydrolysis assay (PI≥1.1 in either $K_m$ assay or $V_{max}$ assay): A448V-I461A-E543H-K571R-K596I, T74R-A448V-E535A-E543H-K571R, D75R-K571R, and G92F-L144F-D462Q-A567R.

Combinatorial SEL Cohort 6—HgGA variants having improved PI in a pullulan hydrolysis assay (PI≥1.1): A448V-I461A-E543H-K571R-K596I, I43F-P54D-T239N-K328Q-K546S, and A448V-I461A-K571R-K596I.

Combinatorial SEL Cohort 7—HgGA variants having improved PI in a panose hydrolysis assay (PI≥1.1): K139R-F147N-F206D-P213W-K571F, A448V-I461A-E543H-K571R-K596I, V422P-D449A-S568R-G569W, and T74R-A448V-E535A-E543H-K571R.

Combinatorial SEL Cohort 8—HgGA variants having improved PI in a corn starch hydrolysis assay (PI≥1.1): T35S-I43F-P54D-G92F-K328Q-Y346W, F79T-G92F-S096L-L144F-I164N, and I43F-P54D-T239N-K328Q-K546S.

Combinatorial SEL Cohort 9—HgGA variants having improved PI for glucose inhibition of enzyme activity [higher ratio of (inhibition sample)/(no inhibition sample) as compared to WT] (PI≥1.1): D75E-F79D-D449A-S568R, I43F-T239N-N271Q-E535T-K546S, I43F-T239N-N271Q-A448V-I461A-E535T-E543H-K546S-K571R-K596I, T35S-I43F-P54D-G92F-K328Q-Y346W, G92F-L144F-D462Q-A567R, T35S-G92T-T239A, T35S-G92T-T239A-T441L, G92F-E23A-S375D-P552I, P60Q-F79V-E203F-F206V.

Combinatorial SEL Cohort 10—HgGA variants having improved PI for glucose reversion to DP2+ products (less reversion, higher PI) (PI≥1.1): D75E-F79D-D449A-S568R, F79T-G92F-S96L-L144F-I164N, T35S-I43F-P54D-G92F-K328Q-Y346W, I43D-G92F-Y346W, V422P-D449A-S568R-G569W, F79V-F147M-N534S-E535W, G92T-I164N-Y346W, P60Q-F79V-E203F-F206V, G92F-L144F-D462Q-A567R, I43F-P54D-G92F-K328Q-S375D, D75R-G92I-E203F-K571R, P60Q-F79V-F206V, D75R-G92I-K571R, G92F-E203A-S375D-P552I, G92F-S375D, D75R-K571R, P60Q-F206V, and I43F-P54D-T239N-K328Q-K546S.

It is noted that there are numerous combinatorial HgGA variants that fall into more than one of Combinatorial SEL Cohorts 1 to 10 above. Thus, aspects of the present invention are drawn to HgGA variants that belong to any 2, 3, 4, 5, 6 or more of the SEL Cohorts above. For example, combinatorial HgGA variant A448V-I461A-E543H-K571R-K596I belongs to SEL Cohorts 1 to 7 above.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Altschul, S. F., et al., J. Mol. Biol. 215:403-410, 1990.

Altschul, S. F., et al., Nucleic Acids Res. 25:3389-3402, 1997.

Aro, N., et al., J. Biol. Chem., 10.1074/M003624200, Apr. 13, 2001.

Aubert, et al., Ed., p 11 et seq., Academic Press, 1988.

Ausubel G. M., et al. CURRENT PROTOCOLS IN MOLECULAR BIOLOGY, John Wiley & Sons, New York, N.Y., 1993.

Baldwin, D., et al., Curr. Opin. Plant Biol. 2(2):96-103, 1999.

Baulcombe, D., Arch. Virol. Suppl. 15:189-201, 1999.

Bhikhabhai, R. et al., J. Appl. Biochem. 6:336, 1984.

Boer and Koivula, 2003, Eur. J. Biochem. 270: 841-848

Brumbauer, A. et al., Bioseparation 7:287-295, 1999.

Carter et al., Nucl. Acids Res. 13:4331, 1986.

Chen et al., Biochem. Biophys. Acta. 1121:54-60, 1992.

Coligan, J. E. et al., eds., CURRENT PROTOCOLS IN IMMUNOLOGY, 1991.

Collen, A., et al., Journal of Chromatography A 910:275-284, 2001.

Coughlan, et al., BIOCHEMISTRY AND GENETICS OF CELLULOSE DEGRADATION.

Cummings and Fowler, Curr. Genet. 29:227-233, 1996.

Dayhoff et al. in Atlas of Protein Sequence and Structure, Volume 5, Supplement 3, Chapter 22, pp. 345-352, 1978.

Deutscher, M. P., Methods Enzymol. 182:779-80, 1990.

Doolittle, R. F., OF URFS AND ORFs, University Science Books, CA, 1986.

Ellouz, S. et al., J. Chromatography 396:307, 1987.

Fields and Song, *Nature* 340:245-246, 1989.

Filho, et al. Can. J. Microbiol. 42:1-5, 1996.

Fliess, A., et al., Eur. J. Appl. Microbiol. Biotechnol. 17:314, 1983.

Freer, et al. J. Biol. Chem. 268:9337-9342, 1993.

Freshney, R. I., ed., ANIMAL CELL CULTURE, 1987.

Goyal, A. et al. Bioresource Technol. 36:37, 1991.

Halldorsdottir, S et al., Appl Microbiol Biotechnol. 49(3): 277-84, 1998.

Hu et al., Mol Cell Biol. 11:5792-9, 1991.

Hemmpel, W. H. ITB Dyeing/Printing/Finishing 3:5-14, 1991.

Herr et al., Appl. Microbiol. Biotechnol. 5:29-36, 1978.

Jakobovits, A, et al., Ann N Y Acad Sci 764:525-35, 1995.

Jakobovits, A, Curr Opin Biotechnol 6(5):561-6, 1995.

Jones et al., Nature 321:522-525, 1986.

Kawaguchi, T et al., Gene 173(2):287-8, 1996.

Knowles, J. et al., TIBTECH 5, 255-261, 1987.

Kohler and Milstein, Nature 256:495, 1975.

Krishna, S. et al., Bioresource Tech. 77:193-196, 2001.

Kumar, A., et al., Textile Chemist and Colorist 29:37-42, 1997.
Lehtio, J. et al., FEMS Microbiology Letters 195:197-204, 2001.
Li and Ljungdahl Appl. Environ. Microbiol. 62:209-213, 1996.
Linder, M. and Teeri, T. T., Biotechnol. 57:15-28, 1997.
Medve, J. et al., J. Chromatography A 808:153, 1998.
Ohmiya et al., Biotechnol. Gen. Engineer. Rev. 14:365-414, 1997.
Ooi et al., Nucleic Acids Res. 18(19):5884, 1990.
Ortega et al., International Biodeterioration and Biodegradation 47:7-14, 2001.
Penttila et al., Yeast 3:175-185, 1987.
Penttila et al., Gene 63: 103-112, 1988.
Pere, J., et al., In Proc. Tappi Pulping Conf., Nashville, Tenn., 27-31, pp. 693-696, 1996.
Riechmann et al., Nature 332:323-327, 1988.
Rothstein et al., Gene 55:353-356, 1987.
Saarilahti et al., Gene 90:9-14, 1990.
Sakamoto et al., Curr. Genet. 27:435-439, 1995.
Saloheimo M, et al., Gene 63:11-22, 1988.
Sambrook et al., Molecular Cloning: a Laboratory Manual (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Spilliaert R, et al., Eur J Biochem. 224(3):923-30, 1994.
Stahlberg, J. et al., Bio/Technol. 9:286-290, 1991.
Stahlberg et al., 1996, J. Mol. Biol. 264: 337-349
Strathern et al., eds. (1981) The Molecular Biology of the Yeast *Saccharomyces.*
Suurnakki, A. et al., Cellulose 7:189-209, 2000.
Te'o, J. et al., FEMS Microbiology Letters 190:13-19, 2000.
Tilbeurgh, H. et al., FEBS Lett. 16:215, 1984.
Timberlake et al., *Cell* 1:29-37, 1981.
Tomaz, C. and Queiroz, J., J. Chromatography A 865:123-128, 1999.
Tomme, P. et al., Eur. J. Biochem. 170:575-581, 1988.
Tormo, J. et al., EMBO J. 15:5739-5751, 1996.
Tyndall, R. M., Textile Chemist and Colorist 24:23-26, 1992.
Van Rensburg et al., Yeast 14:67-76, 1998.
Van Tilbeurgh, H. et al., FEBS Lett. 204:223-227, 1986.
Verhoeyen et al., Science 239:1534-1536, 1988.
Warrington, et al., *Genomics* 13:803-808, 1992.
Wells et al., Gene 34:315, 1985.
Wells et al., Philos. Trans. R. Soc. London SerA 317:415, 1986.
Wood, Biochem. Soc. Trans., 13, pp. 407-410, 1985.
Wood et al., methods in enzymology, 160, 25, p. 87 et seq., Academic Press, New York, 1988.
Zoller et al., Nucl. Acids Res. 10:6487, 1987.

What is claimed is:

1. A variant of a parent glucoamylase (GA) enzyme, where the GA variant has starch hydrolysis activity; has at least 90% amino acid sequence identity to SEQ ID NO:4; and has an amino acid substitution at position A491 where the position corresponds to SEQ ID NO: 3.

2. The variant of claim 1, wherein the parent GA polypeptide is a fungal GA.

3. The variant of claim 1, wherein the GA variant has at least 95% amino acid sequence identity to SEQ ID NO: 4.

4. A composition comprising a GA variant of claim 1.

5. A method for hydrolyzing a starch substrate, comprising contacting the starch substrate with a GA variant according to claim 1.

6. A polynucleotide comprising a polynucleotide sequence encoding a variant of a parent GA polypeptide according to claim 1.

7. A host cell comprising the polynucleotide of claim 6.

8. The host cell of claim 7, wherein the host cell is a fungal cell or a bacterial cell.

9. A method for hydrolyzing a starch substrate, comprising contacting the starch substrate with a host cell according to claim 8.

* * * * *

SEQUENCE LISTING

```
<160> NUMBER OF SEQ ID NOS: 4

<210> SEQ ID NO 1
<211> LENGTH: 2103
<212> TYPE: DNA
<213> ORGANISM: Humicola grisea
<220> FEATURE:
<221> NAME/KEY: misc_feature
<223> OTHER INFORMATION: Nucleotide sequence of genomic HgGA

<400> SEQUENCE: 1

atgcatacct tctccaagct cctcgtcctg ggctctgccg tccagtctgc cctcgggcgg      60

cctcacggct cttcgcgtct ccaggaacgc gctgccgttg ataccttcat caacaccgag     120

aagcccatcg catggaacaa gctgctcgcc aacatcggcc ctaacggcaa agccgctccc     180

ggtgccgccg ccggcgttgt gattgccagc ccttccagga cggaccctcc ttgtacgtgg     240

tggcatggaa tggacccaag agactggttt tagatgaaag agagtttctg ctaaccgcca     300

cacccagact tcttcacctg gacccgcgat gccgccctgg tcctcaccgg catcatcgag     360

tcccttggcc acaactacaa caccaccctg cagaccgtca tccagaacta cgtcgcgtcg     420

caggccaagc tgcagcaggt ctcgaacccc tcgggaacct tcgccgacgg ctcgggtctc     480

ggtgaggcca agttcaatgt cgacctcact gccttcactg gcgaatgggg tcgccctcag     540

agggacggcc cgcccctgcg cgccatcgct ctcatccagt acgccaagtg gctgatcgcc     600

aacggctaca agagcacggc caagagcgtc gtctggcccg tcgtcaagaa cgatctcgcc     660

tacacggccc agtactggaa cgagaccggc ttcgatctct gggaggaggt ccccggcagc     720

tcgttcttta ccatcgccag ctctcacagg ggtgagtcat ttattgttca gtgttttctc     780

attgaataat taccggaatg ccactgacgc caaacagctc tgactgaggg tgcttacctc     840

gccgctcagc tcgacaccga gtgccgcgcc tgcacgaccg tcgcccctca ggttctgtgc     900

ttccagcagg ccttctggaa ctccaagggc aactatgtcg tctccaacag taagatccct     960
```

```
acaccaacaa aaaaaatcga aaaggaacgt tagctgaccc ttctagtcaa cggcggcgag   1020

tatcgctccg gcaaggacgc caactcgatc ctggcgtcca tccacaactt cgaccctgag   1080

gccggctgcg acaacctgac cttccagccc tgcagcgagc gcgccctggc caaccacaag   1140

gcctatgtcg actcgttccg caacctctac gccatcaaca agggcatcgc ccagggcaag   1200

gccgttgccg tcggccgcta ctcggaggat gtctactaca acggcaaccc gtggtacctg   1260

gccaactttg ccgccgccga gcagctctac gacgccatct acgtgtggaa caagcagggc   1320

tccatcaccg tgacctcggt ctccctgccc ttcttccgcg accttgtctc gtcggtcagc   1380

accggcacct actccaagag cagctcgacc ttcaccaaca tcgtcaacgc cgtcaaggcc   1440

tacgccgacg gcttcatcga ggtggcggcc aagtacaccc cgtccaacgg cgcgctcgcc   1500

gagcagtacg accgcaacac gggcaagccc gactcggccg ccgacctgac gtggtcgtac   1560

tcggccttcc tctcggccat cgaccgccgc gcgggtctcg tcccccccgag ctggcgggcc   1620

agcgtggcca agagccagct gccgtccacc tgctcgcgca tcgaggtcgc cggcacctac   1680

gtcgccgcca cgagcacctc gttcccgtcc aagcagaccc cgaacccctc cgcggcgccc   1740

tccccgtccc cctacccgac cgcctgcgcg gacgctagcg aggtgtacgt caccttcaac   1800

gagcgcgtgt cgaccgcgtg ggcgagaccc atcaaggtgg tgggcaacgt gccggcgctg   1860

gggaactggg acacgtccaa ggcggtgacc ctgtcggcca gcgggtacaa gtcgaatgat   1920

cccctctgga gcatcacggt gcccatcaag gcgacgggct cggccgtgca gtacaagtat   1980

atcaaggtcg gcaccaacgg gaagattact tgggagtcgg accccaacag gagcattacc   2040

ctgcagacgg cgtcgtctgc gggcaagtgc gccgcgcaga cggtgaatga ttcgtggcgt   2100

taa                                                                  2103
```

```
<210> SEQ ID NO 2
<211> LENGTH: 1905
<212> TYPE: DNA
<213> ORGANISM: Artificial Sequence
<220> FEATURE:
<223> OTHER INFORMATION: Nucleotide sequence of the synthetic optimized
      cDNA sequence of HgGA

<400> SEQUENCE: 2

atgcatacct tctccaagct cctcgttctt ggatctgccg tccagtctgc cctcggacgg     60

cctcacggct cttcgcgtct ccaggaacgc gctgccgttg atacattcat caacaccgag    120

aagcccattg catggaacaa gctgcttgcc aacatcggcc ctaacggcaa ggccgctccc    180

ggtgccgccg ccggtgttgt cattgccagc ccttccagga cggacccccc ttacttcttt    240

acctggactc gcgatgccgc tctggtcctc accggcatca tcgagtccct tggccacaac    300

tacaacacca cgctgcagac cgtcatccag aactacgtcg cgtctcaagc aaagctgcag    360

caggtgtcta accccagcgg aacgttcgcc gacggttctg gtctcggtga agccaagttc    420

aatgtcgact tgactgcttt cactggcgaa tggggtcgcc ctcagcgaga cggcccgccc    480

ctgcgcgcca tcgctctcat ccagtacgcc aagtggctga tcgccaacgg ttacaagagc    540

acggccaaga gcgtcgtctg gccagtcgtc aagaacgatc tcgcctatac ggcacaatac    600

tggaacgaga ccggctttga tctctgggag gaggtccccg gcagctcctt ctttacaatc    660

gctagctctc acagggctct gactgagggt gcttacctcg ccgctcagct cgacaccgag    720

tgccgcgctt gcacgaccgt cgcccctcag gttctgtgct tccagcaggc cttctggaat    780

tccaagggca actatgtcgt ctcgaatatc aacggcggcg agtatcgctc cggaaaggac    840
```

```
gccaactcga tccttgcgtc tatccacaac ttcgaccctg aggcaggctg tgacaacctg    900

accttccagc cctgcagcga acgcgccctg gccaaccaca aggcttatgt cgactcgttc    960

cggaacctct acgccattaa caagggcatc gcccagggca aggctgttgc cgtcggacgc   1020

tactcggagg atgtctacta caacggcaac ccgtggtatc ttgccaactt tgccgccgca   1080

gaacaactct acgacgccat ctacgtttgg aataagcaag gctccatcac agtgacctcc   1140

gtctccttgc cctttttcag ggacttggtc tcgagcgtca gcaccggcac ttacagcaag   1200

agcagcagca cgttcaccaa cattgtcaac gccgtcaagg catacgccga cggcttcatt   1260

gaggtggcgg ccaagtacac cccgtccaac ggcgcgctcg ccgagcagta cgaccgtaac   1320

acgggcaagc ccgactcggc cgctgacctg acttggtcgt actctgcctt cctctctgcc   1380

attgaccgac gagcaggtct cgtccccccca tcctggcggg ccagcgttgc caagagccag   1440

ctgccatcca catgttctcg catcgaggtc gcaggcacat atgtcgccgc cacgagcacc   1500

tcgtttccgt ccaagcaaac cccaaacccc tccgcggcgc cctccccgtc cccctacccg   1560

accgcttgcg cggacgctag cgaggtctac gttaccttca acgagcgagt gtcgaccgcg   1620

tggggcgaga ctatcaaggt ggtgggcaac gtgccggcgt tgggaaactg ggacacgtcc   1680

aaggcggtga ccctgtccgc cagcggatac aagtcgaatg atcccctctg gagcatcacg   1740

gtgcccatca aggctacggg ctccgccgtg cagtacaagt atattaaggt cggcacaaac   1800

ggtaagatta cttgggagtc cgaccccaat aggagcatta ccctgcagac ggcgtcgagc   1860

gctggcaagt gcgcagcgca gacggtgaat gattcgtggc gttga                   1905
```

<210> SEQ ID NO 3
<211> LENGTH: 634
<212> TYPE: PRT
<213> ORGANISM: Humicola grisea
<220> FEATURE:
<221> NAME/KEY: misc_feature
<223> OTHER INFORMATION: Amino acid sequence of full-length HgGA
      glycoamylase

<400> SEQUENCE: 3

```
Met His Thr Phe Ser Lys Leu Leu Val Leu Gly Ser Ala Val Gln Ser
1               5                   10                  15

Ala Leu Gly Arg Pro His Gly Ser Ser Arg Leu Gln Glu Arg Ala Ala
            20                  25                  30

Val Asp Thr Phe Ile Asn Thr Glu Lys Pro Ile Ala Trp Asn Lys Leu
        35                  40                  45

Leu Ala Asn Ile Gly Pro Asn Gly Lys Ala Ala Pro Gly Ala Ala Ala
    50                  55                  60

Gly Val Val Ile Ala Ser Pro Ser Arg Thr Asp Pro Pro Tyr Phe Phe
65                  70                  75                  80

Thr Trp Thr Arg Asp Ala Ala Leu Val Leu Thr Gly Ile Ile Glu Ser
                85                  90                  95

Leu Gly His Asn Tyr Asn Thr Thr Leu Gln Thr Val Ile Gln Asn Tyr
            100                 105                 110

Val Ala Ser Gln Ala Lys Leu Gln Gln Val Ser Asn Pro Ser Gly Thr
        115                 120                 125

Phe Ala Asp Gly Ser Gly Leu Gly Glu Ala Lys Phe Asn Val Asp Leu
    130                 135                 140

Thr Ala Phe Thr Gly Glu Trp Gly Arg Pro Gln Arg Asp Gly Pro Pro
145                 150                 155                 160
```

```
Leu Arg Ala Ile Ala Leu Ile Gln Tyr Ala Lys Trp Leu Ile Ala Asn
                165                 170                 175

Gly Tyr Lys Ser Thr Ala Lys Ser Val Val Trp Pro Val Val Lys Asn
            180                 185                 190

Asp Leu Ala Tyr Thr Ala Gln Tyr Trp Asn Glu Thr Gly Phe Asp Leu
        195                 200                 205

Trp Glu Glu Val Pro Gly Ser Ser Phe Phe Thr Ile Ala Ser Ser His
    210                 215                 220

Arg Ala Leu Thr Glu Gly Ala Tyr Leu Ala Ala Gln Leu Asp Thr Glu
225                 230                 235                 240

Cys Arg Ala Cys Thr Thr Val Ala Pro Gln Val Leu Cys Phe Gln Gln
                245                 250                 255

Ala Phe Trp Asn Ser Lys Gly Asn Tyr Val Val Ser Asn Ile Asn Gly
            260                 265                 270

Gly Glu Tyr Arg Ser Gly Lys Asp Ala Asn Ser Ile Leu Ala Ser Ile
        275                 280                 285

His Asn Phe Asp Pro Glu Ala Gly Cys Asp Asn Leu Thr Phe Gln Pro
    290                 295                 300

Cys Ser Glu Arg Ala Leu Ala Asn His Lys Ala Tyr Val Asp Ser Phe
305                 310                 315                 320

Arg Asn Leu Tyr Ala Ile Asn Lys Gly Ile Ala Gln Gly Lys Ala Val
                325                 330                 335

Ala Val Gly Arg Tyr Ser Glu Asp Val Tyr Tyr Asn Gly Asn Pro Trp
            340                 345                 350

Tyr Leu Ala Asn Phe Ala Ala Ala Glu Gln Leu Tyr Asp Ala Ile Tyr
        355                 360                 365

Val Trp Asn Lys Gln Gly Ser Ile Thr Val Thr Ser Val Ser Leu Pro
    370                 375                 380

Phe Phe Arg Asp Leu Val Ser Ser Val Ser Thr Gly Thr Tyr Ser Lys
385                 390                 395                 400

Ser Ser Ser Thr Phe Thr Asn Ile Val Asn Ala Val Lys Ala Tyr Ala
                405                 410                 415

Asp Gly Phe Ile Glu Val Ala Ala Lys Tyr Thr Pro Ser Asn Gly Ala
            420                 425                 430

Leu Ala Glu Gln Tyr Asp Arg Asn Thr Gly Lys Pro Asp Ser Ala Ala
        435                 440                 445

Asp Leu Thr Trp Ser Tyr Ser Ala Phe Leu Ser Ala Ile Asp Arg Arg
    450                 455                 460

Ala Gly Leu Val Pro Pro Ser Trp Arg Ala Ser Val Ala Lys Ser Gln
465                 470                 475                 480

Leu Pro Ser Thr Cys Ser Arg Ile Glu Val Ala Gly Thr Tyr Val Ala
                485                 490                 495

Ala Thr Ser Thr Ser Phe Pro Ser Lys Gln Thr Pro Asn Pro Ser Ala
            500                 505                 510

Ala Pro Ser Pro Ser Pro Tyr Pro Thr Ala Cys Ala Asp Ala Ser Glu
        515                 520                 525

Val Tyr Val Thr Phe Asn Glu Arg Val Ser Thr Ala Trp Gly Glu Thr
    530                 535                 540

Ile Lys Val Val Gly Asn Val Pro Ala Leu Gly Asn Trp Asp Thr Ser
545                 550                 555                 560

Lys Ala Val Thr Leu Ser Ala Ser Gly Tyr Lys Ser Asn Asp Pro Leu
                565                 570                 575

Trp Ser Ile Thr Val Pro Ile Lys Ala Thr Gly Ser Ala Val Gln Tyr
```

```
            580                 585                 590

Lys Tyr Ile Lys Val Gly Thr Asn Gly Lys Ile Thr Trp Glu Ser Asp
        595                 600                 605

Pro Asn Arg Ser Ile Thr Leu Gln Thr Ala Ser Ser Ala Gly Lys Cys
    610                 615                 620

Ala Ala Gln Thr Val Asn Asp Ser Trp Arg
625                 630


<210> SEQ ID NO 4
<211> LENGTH: 604
<212> TYPE: PRT
<213> ORGANISM: Humicola grisea
<220> FEATURE:
<221> NAME/KEY: misc_feature
<223> OTHER INFORMATION: Amino acid sequence of mature HgGA glycoamylase

<400> SEQUENCE: 4

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65                  70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110

Asp Leu Thr Ala Phe Thr Gly Glu Trp Gly Arg Pro Gln Arg Asp Gly
        115                 120                 125

Pro Pro Leu Arg Ala Ile Ala Leu Ile Gln Tyr Ala Lys Trp Leu Ile
    130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205

Thr Glu Cys Arg Ala Cys Thr Thr Val Ala Pro Gln Val Leu Cys Phe
    210                 215                 220

Gln Gln Ala Phe Trp Asn Ser Lys Gly Asn Tyr Val Val Ser Asn Ile
225                 230                 235                 240

Asn Gly Gly Glu Tyr Arg Ser Gly Lys Asp Ala Asn Ser Ile Leu Ala
                245                 250                 255

Ser Ile His Asn Phe Asp Pro Glu Ala Gly Cys Asp Asn Leu Thr Phe
            260                 265                 270

Gln Pro Cys Ser Glu Arg Ala Leu Ala Asn His Lys Ala Tyr Val Asp
        275                 280                 285

Ser Phe Arg Asn Leu Tyr Ala Ile Asn Lys Gly Ile Ala Gln Gly Lys
    290                 295                 300
```

-continued

```
Ala Val Ala Val Gly Arg Tyr Ser Glu Asp Val Tyr Tyr Asn Gly Asn
305                 310                 315                 320

Pro Trp Tyr Leu Ala Asn Phe Ala Ala Ala Glu Gln Leu Tyr Asp Ala
                325                 330                 335

Ile Tyr Val Trp Asn Lys Gln Gly Ser Ile Thr Val Thr Ser Val Ser
            340                 345                 350

Leu Pro Phe Phe Arg Asp Leu Val Ser Ser Val Ser Thr Gly Thr Tyr
        355                 360                 365

Ser Lys Ser Ser Ser Thr Phe Thr Asn Ile Val Asn Ala Val Lys Ala
    370                 375                 380

Tyr Ala Asp Gly Phe Ile Glu Val Ala Ala Lys Tyr Thr Pro Ser Asn
385                 390                 395                 400

Gly Ala Leu Ala Glu Gln Tyr Asp Arg Asn Thr Gly Lys Pro Asp Ser
                405                 410                 415

Ala Ala Asp Leu Thr Trp Ser Tyr Ser Ala Phe Leu Ser Ala Ile Asp
            420                 425                 430

Arg Arg Ala Gly Leu Val Pro Pro Ser Trp Arg Ala Ser Val Ala Lys
        435                 440                 445

Ser Gln Leu Pro Ser Thr Cys Ser Arg Ile Glu Val Ala Gly Thr Tyr
    450                 455                 460

Val Ala Ala Thr Ser Thr Ser Phe Pro Ser Lys Gln Thr Pro Asn Pro
465                 470                 475                 480

Ser Ala Ala Pro Ser Pro Ser Pro Tyr Pro Thr Ala Cys Ala Asp Ala
                485                 490                 495

Ser Glu Val Tyr Val Thr Phe Asn Glu Arg Val Ser Thr Ala Trp Gly
            500                 505                 510

Glu Thr Ile Lys Val Val Gly Asn Val Pro Ala Leu Gly Asn Trp Asp
        515                 520                 525

Thr Ser Lys Ala Val Thr Leu Ser Ala Ser Gly Tyr Lys Ser Asn Asp
    530                 535                 540

Pro Leu Trp Ser Ile Thr Val Pro Ile Lys Ala Thr Gly Ser Ala Val
545                 550                 555                 560

Gln Tyr Lys Tyr Ile Lys Val Gly Thr Asn Gly Lys Ile Thr Trp Glu
                565                 570                 575

Ser Asp Pro Asn Arg Ser Ile Thr Leu Gln Thr Ala Ser Ser Ala Gly
            580                 585                 590

Lys Cys Ala Ala Gln Thr Val Asn Asp Ser Trp Arg
        595                 600
```